US007687616B1

(12) United States Patent
Bentwich et al.

(10) Patent No.: US 7,687,616 B1
(45) Date of Patent: Mar. 30, 2010

(54) SMALL MOLECULES MODULATING ACTIVITY OF MICRO RNA OLIGONUCLEOTIDES AND MICRO RNA TARGETS AND USES THEREOF

(75) Inventors: Itzhak Bentwich, Kfar Daniel (IL); Amir Avniel, Rishon leZion (IL)

(73) Assignee: Rosetta Genomics Ltd, Rehovot (IL)

( * ) Notice: Subject to any disclaimer, the term of this patent is extended or adjusted under 35 U.S.C. 154(b) by 1074 days.

(21) Appl. No.: 10/709,577

(22) Filed: May 14, 2004

(51) Int. Cl.
C07H 21/04 (2006.01)
(52) U.S. Cl. .................................. 536/24.5; 536/23.1
(58) Field of Classification Search .................. None
See application file for complete search history.

(56) References Cited

U.S. PATENT DOCUMENTS

| | | | |
|---|---|---|---|
| 6,432,639 B1 * | 8/2002 | Lichter et al. ............. | 435/6 |
| 6,573,099 B2 | 6/2003 | Graham | |
| 6,582,908 B2 * | 6/2003 | Fodor et al. ............... | 435/6 |
| 6,720,138 B2 | 4/2004 | Sharma et al. | |
| 2002/0086356 A1 | 7/2002 | Tuschl et al. | |
| 2003/0108923 A1 | 6/2003 | Tuschl et al. | |
| 2003/0228691 A1 | 12/2003 | Lewis et al. | |
| 2004/0053411 A1 | 3/2004 | Cullen et al. | |
| 2004/0086884 A1 | 5/2004 | Beach et al. | |
| 2005/0227934 A1 * | 10/2005 | Stoffel et al. .............. | 514/44 |

FOREIGN PATENT DOCUMENTS

| | | |
|---|---|---|
| WO | WO 01/68836 | 9/2001 |
| WO | WO 01/75164 | 10/2001 |
| WO | WO 02/44321 | 6/2002 |
| WO | WO 02/094185 | 11/2002 |
| WO | WO 03/029459 | 4/2003 |
| WO | WO 03/070884 | 8/2003 |
| WO | WO 03/070903 | 8/2003 |
| WO | WO 03/070918 | 8/2003 |
| WO | WO 03/074654 | 9/2003 |
| WO | WO 2004/009779 | 1/2004 |
| WO | WO 2004/031412 | 4/2004 |

OTHER PUBLICATIONS

Honda et al., 1998, J. Cell Biology 140:1383-1393.*
Krutzfeldt et al. (2006) Nature Genetics 38:514-19.*
Bentwich (2005) FEBS Lett. 5904-5910.*
New England Biolabs 1998/99 Catalog, cover page, p. 121 and 284.*
Bentwich et al. (2005) FEBS Lett. 579:5904-5910.*
Martin et al. (2007) J. Biosci. 32:1049-1052.*
Maziere et al. (2007) Drug Discovery Today 12:452-458.*
Smalheiser et al. (2006) Methods Mol. Biol. 342:115-127.*
GenBank Accession No. BD247503.1 "Maize DNA ligase I orthologue and uses thereof", as published online Jul. 17, 2003, retrieved from the Nation Center for Biotechnology Information [online] on Oct. 22, 2008 at ncbi.nlm.nih.gov/entrez.*
Kim et al. (1996) "Construction and characterization of a human bacterial artificial chromosome library" Genomics 34:213-218.*

The International Human Genome Sequencing Consortium (2001) "Initial sequencing and analysis of the human genome" Nature 409:860-921.*
Buck et al (BioTechniques 27: 528-536, 1999).*
GenBank Accession No. AC_096504.7 "Rattus norvegicus clone CH230-167O14, Working Draft Sequence", as published online May 10, 2003, retrieved from the Nation Center for Biotechnology Information [online] on Oct. 22, 2008 at ncbi.nlm.nih.gov/entrez.*
U.S. Appl. No. 10/293,338, filed Nov. 14, 2002.
U.S. Appl. No. 10/310,914, filed Dec. 6, 2002.
U.S. Appl. No. 10/321,503, filed Dec. 18, 2002.
U.S. Appl. No. 10/345,201, filed Jan. 16, 2003.
U.S. Appl. No. 10/604,985, filed Aug. 29, 2003.
U.S. Appl. No. 10/535,164, filed Nov. 16, 2003.
U.S. Appl. No. 10/707,975, filed Jan. 29, 2004.
U.S. Appl. No. 10/708,204, filed Feb. 16, 2004.
U.S. Appl. No. 10/708,953, filed Apr. 2, 2004.
U.S. Appl. No. 10/709,572, filed May 14, 2004.
Lee, R. C., R. L. Feinbaum and V. Ambros. The *C. elegans* heterochronic gene lin-4 encodes small RNAs with antisense complementarity to lin-14 Cell Dec. 3, 1993 843-854 75.
Wightman, B., I. Ha and G. Ruvkun. Posttranscriptional regulation of the heterochronic gene lin-14 by lin-4 mediates temporal pattern formation in *C. elegans* Cell Dec. 3, 1993 855-862 75.
Gallinaro, H., L. Domenjoud and M. Jacob. Structural study of the 5' end of a synthetic premessenger RNA from adenovirus. Evidence for a long-range exon-intron interaction J Mol Biol Jul. 15, 1994 205-225 240.
Lu, C. and R. Bablanian. Characterization of small nontranslated polyadenylylated RNAs in vaccinia virus-infected cells Proc Natl Acad Sci U S A Mar. 5, 1996 2037-2042 93.
Crawford, E. D., E. P. Deantoni, R. Etzioni, V. C. Schaefer, R. M. Olson and C. A. Ross. Serum prostate-specific antigen and digital rectal examination for early detection of prostate cancer in a national community-based program. The Prostate Cancer Education Council Urology Jun. 1996 863-869 47.

(Continued)

*Primary Examiner*—Louis Wollenberger
(74) *Attorney, Agent, or Firm*—Posinelli Shughart PC; Teddy C. Scott, Jr.

(57) ABSTRACT

The present invention describes a novel approach whereby small molecules may be used to modulate activity of microRNA and GAM oligonucleotides. This mode of therapy allows inter alia up regulation of a disease-related target gene of novel GAM oligonucleotides of the present invention, by countering the activity of a GAM oligonucleotides which naturally inhibits expression of that target gene. Nucleic acid molecules are provided respectively encoding 122,764 GAM oligonucleotides and their respective precursors, and 18602 GR polynucleotides, as are vectors and probes both comprising the nucleic acid molecules, and methods and systems for detecting GAM oligonucleotides and GR polynucleotides and specific functions and utilities thereof, for detecting expression of GAM oligonucleotides and GR polynucleotides, and for selectively enhancing and selectively inhibiting translation of the respective target genes thereof.

4 Claims, 42 Drawing Sheets

OTHER PUBLICATIONS

Engdahl HM, Hjalt TA, Wagner EG. A two unit antisense RNA cassette test system for silencing of target genes. Nucleic Acids Res. Aug. 15, 1997 3218-27 25.

Dsouza, M., N. Larsen and R. Overbeek. Searching for patterns in genomic data Trends Genet Dec. 1997 497-498 13.

Moss, E. G., R. C. Lee and V. Ambros. The cold shock domain protein LIN-28 controls developmental timing in *C. elegans* and is regulated by the lin-4 RNA Cell 1997 637 88.

Fire, A., S. Xu, M. K. Montgomery, S. A. Kostas, S. E. Driver and C. C. Mello. Potent and specific genetic interference by double-stranded RNA in *Caenorhabditis elegans* Nature Feb. 19, 1998 806-811 391.

Waterhouse, P. M., M. W. Graham and M. B. Wang. Virus resistance and gene silencing in plants can be induced by simultaneous expression of sense and antisense RNA Proc Natl Acad Sci U S A Nov. 10, 1998 13959-13964 95.

Ngo, H., C. Tschudi, K. Gull and E. Ullu. Double-stranded RNA induces mRNA degradation in *Trypanosoma brucei* Proc Natl Acad Sci U S A Dec. 8, 1998 14687-14692 95.

Verma, S. and F. Eckstein. Modified oligonucleotides: synthesis and strategy for users Annu Rev Biochem *No date in Pubmed* 1998 99-134 67.

Wuchty, S., W. Fontana, I. L. Hofacker and P. Schuster. Complete suboptimal folding of RNA and the stability of secondary structures Biopolymers Feb. 1999 145-165 49.

Mathews, D. H., J. Sabina, M. Zuker and D. H. Turner. Expanded sequence dependence of thermodynamic parameters improves prediction of RNA secondary structure J Mol Biol May 21, 1999 911-940 288.

Chang, P. L. Encapsulation for somatic gene therapy Ann N Y Acad Sci Jun. 18, 1999 146-158 875.

Zhang, M. Q. Large-scale gene expression data analysis: a new challenge to computational biologists Genome Res Aug. 1999 681-688 9.

Grisaru, D., M. Sternfeld, A. Eldor, D. Glick and H. Soreq. Structural roles of acetylcholinesterase variants in biology and pathology Eur J Biochem Sep. 1999 672-686 264.

Fire, A. RNA-triggered gene silencing Trends Genet Sep. 1999 358-363 15.

Tabara, H., M. Sarkissian, W. G. Kelly, J. Fleenor, A. Grishok, L. Timmons, A. Fire and C. C. Mello. The rde-1 gene, RNA interference, and transposon silencing in *C. elegans* Cell Oct. 15, 1999 123-132 99.

Ryo, A., Y. Suzuki, K. Ichiyama, T. Wakatsuki, N. Kondoh, A. Hada, M. Yamamoto and N. Yamamoto. Serial analysis of gene expression in HIV-1-infected T cell lines FEBS Lett Nov. 26, 1999 182-186 462.

Olsen, P. H. and V. Ambros. The lin-4 regulatory RNA controls developmental timing in *Caenorhabditis elegans* by blocking LIN-14 protein synthesis after the initiation of translation Dev Biol Dec. 15, 1999 671-680 216.

Tuschl, T., P. D. Zamore, R. Lehmann, D. P. Bartel and P. A. Sharp. Targeted mRNA degradation by double-stranded RNA in vitro Genes Dev Dec. 15, 1999 3191-3197 13.

Reinhart, B. J., F. J. Slack, M. Basson, A. E. Pasquinelli, J. C. Bettinger, A. E. Rougvie, H. R. Horvitz and G. Ruvkun. The 21-nucleotide let-7 RNA regulates developmental timing in *Caenorhabditis elegans* Nature Feb. 24, 2000 901-906 403.

Pitt, J. N., J. A. Schisa and J. R. Priess. P granules in the germ cells of *Caenorhabditis elegans* adults are associated with clusters of nuclear pores and contain RNA Dev Biol Mar. 15, 2000 315-333 219.

Hammond, S. M., E. Bernstein, D. Beach and G. J. Hannon. An RNA-directed nuclease mediates post-transcriptional gene silencing in *Drosophila* cells Nature Mar. 16, 2000 293-296 404.

Slack, F. J., M. Basson, Z. Liu, V. Ambros, H. R. Horvitz and G. Ruvkun. The lin-41 RBCC gene acts in the *C. elegans* heterochronic pathway between the let-7 regulatory RNA and the LIN-29 transcription factor Mol Cell Apr. 2000 659-669 5.

Fortier, E. and J. M. Belote. Temperature-dependent gene silencing by an expressed inverted repeat in *Drosophila* Genesis Apr. 2000 240-244 26.

Mourrain, P., C. Beclin, T. Elmayan, F. Feuerbach, C. Godon, J. B. Morel, D. Jouette, A. M. Lacombe, S. Nikic, N. Picault, K. Remoue, M. Sanial, T. A. Vo and H. Vaucheret. *Arabidopsis* SGS2 and SGS3 genes are required for posttranscriptional gene silencing and natural virus resistance Cell May 26, 2000 533-542 101.

Sijen, T. and J. M. Kooter. Post-transcriptional gene-silencing: RNAs on the attack or on the defense? Bioessays Jun. 2000 520-531 22.

Brenner, S., M. Johnson, J. Bridgham, G. Golda, D. H. Lloyd, D. Johnson, S. Luo, S. McCurdy, M. Foy, M. Ewan, R. Roth, D. George, S. Eletr, G. Albrecht, E. Vermaas, S. R. Williams, K. Moon, T. Burcham, M. Pallas, R. B. Dubridge, J. Kirchner, K. Fearon, J. Mao and K. Corcoran. Gene expression analysis by massively parallel signature sequencing (MPSS) on microbead arrays Nat Biotechnol Jun. 2000 630-634 18.

Ryo, A., Y. Suzuki, M. Arai, N. Kondoh, T. Wakatsuki, A. Hada, M. Shuda, K. Tanaka, C. Sato, M. Yamamoto and N. Yamamoto. Identification and characterization of differentially expressed mRNAs in HIV type 1-infected human T cells AIDS Res Hum Retroviruses Jul. 1, 2000 995 1005 16.

Nilsson, M., G. Barbany, D. O. Antson, K. Gertow and U. Landegren. Enhanced detection and distinction of RNA by enzymatic probe ligation Nat Biotechnol Jul. 2000 791-793 18.

Kent, W. J. and A. M. Zahler. Conservation, regulation, synteny, and introns in a large-scale *C. briggsae-C. elegans* genomic alignment Genome Res Aug. 2000 1115-1125 10.

Kennerdell, J. R. and R. W. Carthew. Heritable gene silencing in *Drosophila* using double-stranded RNA Nat Biotechnol Aug. 2000 896-898 18.

Smith, N. A., S. P. Singh, M. B. Wang, P. A. Stoutjesdijk, A. G. Green and P. M. Waterhouse. Total silencing by intron-spliced hairpin RNAs Nature Sep. 21, 2000 319-320 407.

Voinnet, O., C. Lederer and D. C. Baulcombe. A viral movement protein prevents spread of the gene silencing signal in *Nicotiana benthamiana* Cell Sep. 29, 2000 157-167 103.

Mette MF, Aufsatz W, van der Winden J, Matzke MA, Matzke AJ. Transcriptional silencing and promoter methylation triggered by double-stranded RNA. EMBO J. Oct. 2, 2000 5194-201 19.

Yang, D., H. Lu and J. W. Erickson. Evidence that processed small dsRNAs may mediate sequence-specific mRNA degradation during RNAi in *Drosophila* embryos Curr Biol Oct. 5, 2000 1191 1200 10.

Anandalakshmi, R., R. Marathe, X. Ge, J. M. Herr, Jr., C. Mau, A. Mallory, G. Pruss, L. Bowman and V. B. Vance. A calmodulin-related protein that suppresses posttranscriptional gene silencing in plants Science Oct. 6, 2000 142-144 290.

Fagard, M., S. Boutet, J. B. Morel, C. Bellini and H. Vaucheret. AGO1, QDE-2, and RDE-1 are related proteins required for post-transcriptional gene silencing in plants, quelling in fungi, and RNA interference in animals Proc Natl Acad Sci U S A Oct. 10, 2000 11650-11654 97.

Pasquinelli, A. E., B. J. Reinhart, F. Slack, M. Q. Martindale, M. I. Kuroda, B. Maller, D. C. Hayward, E. E. Ball, B. Degnan, P. Muller, J. Spring, A. Srinivasan, M. Fishman, J. Finnerty, J. Corbo, M. Levine, P. Leahy, E. Davidson and G. Ruvkun. Conservation of the sequence and temporal expression of let-7 heterochronic regulatory RNA Nature Nov. 2, 2000 86-89 408.

Llave, C., K. D. Kasschau and J. C. Carrington. Virus-encoded suppressor of posttranscriptional gene silencing targets a maintenance step in the silencing pathway Proc Natl Acad Sci U S A Nov. 21, 2000 13401-13406 9.

Cogoni, C. and G. Macino. Post-transcriptional gene silencing across kingdoms Curr Opin Genet Dev Dec. 2000 638-643 10.

Elbashir, S. M., W. Lendeckel and T. Tuschl. RNA interference is mediated by 21- and 22-nucleotide RNAs Genes Dev Jan. 15, 2001 188-200 15.

Bernstein, E., A. A. Caudy, S. M. Hammond and G. J. Hannon. Role for a bidentate ribonuclease in the initiation step of RNA interference Nature Jan. 18, 2001 363-366 409.

Vaucheret, H. and M. Fagard. Transcriptional gene silencing in plants: targets, inducers and regulators Trends Genet Jan. 2001 29-35 17.

Thomas, C. L., L. Jones, D. C. Baulcombe and A. J. Maule. Size constraints for targeting post-transcriptional gene silencing and for RNA-directed methylation in *Nicotiana benthamiana* using a potato virus X vector Plant J Feb. 2001 417-425 25.

Galyam, N., D. Grisaru, M. Grifman, N. Melamed-Book, F. Eckstein, S. Seidman, A. Eldor and H. Soreq. Complex host cell responses to antisense suppression of ACHE gene expression Antisense Nucleic Acid Drug Dev Feb. 2001 51-57 11.

Sharp, P. A. RNA interference—2001 Genes Dev Mar. 1, 2001 485-490 15.

Mallory, A. C., L. Ely, T. H. Smith, R. Marathe, R. Anandalakshmi, M. Fagard, H. Vaucheret, G. Pruss, L. Bowman and V. B. Vance. HC-Pro suppression of transgene silencing eliminates the small RNAs but not transgene methylation or the mobile signal Plant Cell Mar. 2001 571-583 13.

Matzke, M. A., A. J. Matzke, G. J. Pruss and V. B. Vance. RNA-based silencing strategies in plants Curr Opin Genet Dev Apr. 2001 221-227 11.

Schisa, J. A., J. N. Pitt and J. R. Priess. Analysis of RNA associated with P granules in germ cells of *C. elegans* adults Development Apr. 2001 1287-1298 128.

Di Serio, F., H. Schob, A. Iglesias, C. Tarina, E. Bouldoires and F. Meins, Jr. Sense- and antisense-mediated gene silencing in tobacco is inhibited by the same viral suppressors and is associated with accumulation of small RNAs Proc Natl Acad Sci U S A May 22, 2001 6506-6510 98.

Elbashir, S. M., J. Harborth, W. Lendeckel, A. Yalcin, K. Weber and T. Tuschl. Duplexes of 21-nucleotide RNAs mediate RNA interference in cultured mammalian cells Nature May 24, 2001 494-498 411.

Piccin, A., A. Salameh, C. Benna, F. Sandrelli, G. Mazzotta, M. Zordan, E. Rosato, C. P. Kyriacou and R. Costa. Efficient and heritable functional knock-out of an adult phenotype in *Drosophila* using a GAL4-driven hairpin RNA incorporating a heterologous spacer Nucleic Acids Res Jun. 15, 2001 E55-55 29.

Vance, V. and H. Vaucheret. RNA silencing in plants—defense and counterdefense Science Jun. 22, 2001 2277-2280 292.

Argaman, L., R. Hershberg, J. Vogel, G. Bejerano, E. G. Wagner, H. Margalit and S. Altuvia. Novel small RNA-encoding genes in the intergenic regions of *Escherichia coli* Curr Biol Jun. 26, 2001 941-950 11.

Grishok, A., A. E. Pasquinelli, D. Conte, N. Li, S. Parrish, I. Ha, D. L. Baillie, A. Fire, G. Ruvkun and C. C. Mello. Genes and mechanisms related to RNA interference regulate expression of the small temporal RNAs that control *C. elegans* developmental timing Cell Jul. 13, 2001 23-34 106.

Hutvagner, G., J. McLachlan, A. E. Pasquinelli, E. Balint, T. Tuschl and P. D. Zamore. A cellular function for the RNA-interference enzyme Dicer in the maturation of the let-7 small temporal RNA Science Aug. 3, 2001 834-838 293.

Hammond, S. M., S. Boettcher, A. A. Caudy, R. Kobayashi and G. J. Hannon. Argonaute2, a link between genetic and biochemical analyses of RNAi Science Aug. 10, 2001 1146-1150 293.

Vaucheret, H., C. Beclin and M. Fagard. Post-transcriptional gene silencing in plants J Cell Sci Sep. 2001 3083-3091 114.

Wesley, S. V., C. A. Helliwell, N. A. Smith, M. B. Wang, D. T. Rouse, Q. Liu, P. S. Gooding, S. P. Singh, D. Abbott, P. A. Stoutjesdijk, S. P. Robinson, A. P. Gleave, A. G. Green and P. M. Waterhouse. Construct design for efficient, effective and high-throughput gene silencing in plants Plant J Sep. 2001 581-590 27.

Mattick, J. S. and M. J. Gagen. The evolution of controlled multitasked gene networks: the role of introns and other noncoding RNAs in the development of complex organisms Mol Biol Evol Sep. 2001 1611-1630 18.

Carter, R. J., I. Dubchak and S. R. Holbrook. A computational approach to identify genes for functional RNAs in genomic sequences Nucleic Acids Res Oct. 1, 2001 3928-3938 29.

Moss, E. G. RNA interference: it's a small RNA world Curr Biol Oct. 2, 2001 R772-775 11.

Ketting, R. F., S. E. Fischer, E. Bernstein, T. Sijen, G. J. Hannon and R. H. Plasterk. Dicer functions in RNA interference and in synthesis of small RNA involved in developmental timing in *C. elegans* Genes Dev Oct. 15, 2001 2654-2659 15.

Ruvkun, G. Molecular biology. Glimpses of a tiny RNA world Science Oct. 26, 2001 797-799 294.

Lee, R. C. and V. Ambros. An extensive class of small RNAs in *Caenorhabditis elegans* Science Oct. 26, 2001 862-864 294.

Lau, N. C., L. P. Lim, E. G. Weinstein and D. P. Bartel. An abundant class of tiny RNAs with probable regulatory roles in *Caenorhabditis elegans* Science Oct. 26, 2001 858-862 294.

Lagos-Quintana, M., R. Rauhut, W. Lendeckel and T. Tuschl. Identification of novel genes coding for small expressed RNAs Science Oct. 26, 2001 853-858 294.

Itaya, A., A. Folimonov, Y. Matsuda, R. S. Nelson and B. Ding. Potato spindle tuber viroid as inducer of RNA silencing in infected tomato Mol Plant Microbe Interact Nov. 2001 1332-1334 14.

Mattick, J. S. Non-coding RNAs: the architects of eukaryotic complexity EMBO Rep Nov. 2001 986-991 2.

Elbashir, S. M., J. Martinez, A. Patkaniowska, W. Lendeckel and T. Tuschl. Functional anatomy of siRNAs for mediating efficient RNAi in *Drosophila melanogaster* embryo lysate Embo J Dec. 3, 2001 6877-6888 20.

Ambros, V. microRNAs: tiny regulators with great potential Cell Dec. 28, 2001 823-826 107.

Blaszczyk, J., J. E. Tropea, M. Bubunenko, K. M. Routzahn, D. S. Waugh, D. L. Court and X. Ji. Crystallographic and modeling studies of RNase III suggest a mechanism for double-stranded RNA cleavage Structure Dec. 2001 1225-1236 9.

Crete, P., S. Leuenberger, V. A. Iglesias, V. Suarez, H. Schob, H. Holtorf, S. Van Eeden and F. Meins. Graft transmission of induced and spontaneous post-transcriptional silencing of chitinase genes Plant J Dec. 2001 493-501 28.

Smallridge, R. A small fortune Nat Rev Mol Cell Biol Dec. 2001 867 2.

Eddy, S. R. Non-coding RNA genes and the modern RNA world Nat Rev Genet Dec. 2001 919-929 2.

Lu, C. M. miRNA bead detection Genaco Biomedical Products PHS 398 2001 1.

Matzke, M., A. J. Matzke and J. M. Kooter. RNA: guiding gene silencing 2001 1080 293.

Grosshans, H. and F. J. Slack. Micro-RNAs: small is plentiful J Cell Biol Jan. 7, 2002 17-21 156.

Meshorer, E., C. Erb, R. Gazit, L. Pavlovsky, D. Kaufer, A. Friedman, D. Glick, N. Benarie and H. Soreq. Alternative splicing and neuritic mRNA translocation under long-term neuronal hypersensitivity Science Jan. 18, 2002 508-512 295.

Paddison, P. J., A. A. Caudy and G. J. Hannon. Stable suppression of gene expression by RNAi in mammalian cells Proc Natl Acad Sci U S A Feb. 5, 2002 1443-1448 99.

Moss, E. G. MicroRNAs: hidden in the genome Curr Biol Feb. 19, 2002 R138-140 12.

Banerjee, D. and F. Slack. Control of developmental timing by small temporal RNAs: a paradigm for RNA-mediated regulation of gene expression Bioessays Feb. 2002 119-129 24.

Elbashir, S. M., J. Harborth, K. Weber and T. Tuschl. Analysis of gene function in somatic mammalian cells using small interfering RNAs Methods Feb. 2002 199-213 26.

Han, Y. and D. Grierson. Relationship between small antisense RNAs and aberrant RNAs associated with sense transgene mediated gene silencing in tomato Plant J Feb. 2002 509-519 29.

Nicholson, R. H. and A. W. Nicholson. Molecular characterization of a mouse cDNA encoding Dicer, a ribonuclease III ortholog involved in RNA interference Mamm Genome Feb. 2002 67-73 13.

Puerta-Fernandez, E., A. Barroso-Deljesus and A. Berzal-Herranz. Anchoring hairpin ribozymes to long target RNAs by loop-loop RNA interactions Antisense Nucleic Acid Drug Dev Feb. 2002 1-9 12.

Giordano, E., R. Rendina, I. Peluso and M. Furia. RNAi triggered by symmetrically transcribed transgenes in *Drosophila melanogaster* Genetics Feb. 2002 637-648 160.

Martens, H., J. Novotny, J. Oberstrass, T. L. Steck, P. Postlethwait and W. Nellen. RNAi in *Dictyostelium*: the role of RNA-directed RNA polymerases and double-stranded RNase Mol Biol Cell Feb. 2002 445-453 13.

Mourelatos, Z., J. Dostie, S. Paushkin, A. Sharma, B. Charroux, L. Abel, J. Rappsilber, M. Mann and G. Dreyfuss. miRNPs: a novel class of ribonucleoproteins containing numerous microRNAs Genes Dev Mar. 15, 2002 720-728 16.

Seggerson, K., L. Tang and E. G. Moss. Two genetic circuits repress the *Caenorhabditis elegans* heterochronic gene lin-28 after translation initiation Dev Biol Mar. 15, 2002 215-225 243.

Morel, J. B., C. Godon, P. Mourrain, C. Beclin, S. Boutet, F. Feuerbach, F. Proux and H. Vaucheret. Fertile hypomorphic ARGONAUTE (ago1) mutants impaired in post-transcriptional gene silencing and virus resistance Plant Cell Mar. 2002 629-639 14.

Catalanotto, C., G. Azzalin, G. Macino and C. Cogoni. Involvement of small RNAs and role of the qde genes in the gene silencing pathway in Neurospora Genes Dev Apr. 1, 2002 790-795 16.

Boutla, A., K. Kalantidis, N. Tavernarakis, M. Tsagris and M. Tabler. Induction of RNA interference in *Caenorhabditis elegans* by RNAs derived from plants exhibiting post-transcriptional gene silencing Nucleic Acids Res Apr. 1, 2002 1688-1694 30.

Pasquinelli, A. E. and G. Ruvkun. Control of developmental timing by micrornas and their targets Annu Rev Cell Dev Biol Epub 2002 Apr. 2, 2002 495-513 18.

Paddison, P. J., A. A. Caudy, E. Bernstein, G. J. Hannon and D. S. Conklin. Short hairpin RNAs (shRNAs) induce sequence-specific silencing in mammalian cells Genes Dev Apr. 15, 2002 948-958 16.

Beclin, C., S. Boutet, P. Waterhouse and H. Vaucheret. A branched pathway for transgene-induced RNA silencing in plants Curr Biol Apr. 16, 2002 684-688 12.

Eddy, S. R. Computational genomics of noncoding RNA genes Cell Apr. 19, 2002 137-140 109.

Lagos-Quintana, M., R. Rauhut, A. Yalcin, J. Meyer, W. Lendeckel and T. Tuschl. Identification of tissue-specific microRNAs from mouse Curr Biol Apr. 30, 2002 735-739 12.

Kent, W. J. BLAT—the Blast-like alignment tool Genome Res Apr. 2002 656-664 12.

Hutvagner, G. and P. D. Zamore. RNAi: nature abhors a double-strand Curr Opin Genet Dev Apr. 2002 225-232 12.

Nilsson, M., J. Baner, M. Mendel-Hartvig, F. Dahl, D. O. Antson, M. Gullberg and U. Landegren. Making ends meet in genetic analysis using padlock probes Hum Mutat Apr. 2002 410-415 19.

Pasquinelli, A. E. MicroRNAs: deviants no longer Trends Genet Apr. 2002 171-173 18.

Lai, E. C. Micro RNAs are complementary to 3' UTR sequence motifs that mediate negative post-transcriptional regulation Nat Genet Apr. 2002 363-364 30.

Schwarz, D. S. and P. D. Zamore. Why do miRNAs live in the miRNP? Genes Dev May 1, 2002 1025-1031 16.

Brantl, S. Antisense-RNA regulation and RNA interference Biochim Biophys Acta May 3, 2002 15-25 1575.

Li, H., W. X. Li and S. W. Ding. Induction and suppression of RNA silencing by an animal virus Science May 17, 2002 1319-1321 296.

Zamore, P. D. Ancient pathways programmed by small RNAs Science May 17, 2002 1265-1269 296.

Chen, S., E. A. Lesnik, T. A. Hall, R. Sampath, R. H. Griffey, D. J. Ecker and L. B. Blyn. A bioinformatics based approach to discover small RNA genes in the *Escherichia coli* genome Biosystems Mar.-May 2002 157-177 65.

Lee, N. S., T. Dohjima, G. Bauer, H. Li, M. J. Li, A. Ehsani, P. Salvaterra and J. Rossi. Expression of small interfering RNAs targeted against HIV-1 rev transcripts in human cells Nat Biotechnol May 2002 500-505 20.

Draghici, S. Statistical intelligence: effective analysis of high-density microarray data Drug Discov Today Jun. 1, 2002 S55-63 7.

Silhavy, D., A. Molnar, A. Lucioli, G. Szittya, C. Hornyik, M. Tavazza and J. Burgyan. A viral protein suppresses RNA silencing and binds silencing-generated, 21- to 25-nucleotide double-stranded RNAs Embo J Jun. 17, 2002 3070-3080 21.

Ayash-Rashkovsky, M., Z. Weisman, J. Diveley, R. B. Moss, Z. Bentwich and G. Borkow. Generation of Th1 immune responses to inactivated, gp120-depleted HIV-1 in mice with a dominant Th2 biased immune profile via immunostimulatory [correction of imunostimulatory] oligonucleotides—relevance to AIDS vaccines in developing countries Vaccine Jun. 21, 2002 2684-2692 20.

Tabara, H., E. Yigit, H. Siomi and C. C. Mello. The dsRNA binding protein RDE-4 interacts with RDE-1, DCR-1, and a DExH-box helicase to direct RNAi in *C. elegans* Cell Jun. 28, 2002 861-871 109.

Bettencourt, R., O. Terenius and I. Faye. Hemolin gene silencing by ds-RNA injected into *Cecropia pupae* is lethal to next generation embryos Insect Mol Biol Jun. 2002 267-271 11.

Hooper, N. M. and A. J. Turner. The search for alpha-secretase and its potential as a therapeutic approach to Alzheimer s disease Curr Med Chem Jun. 2002 1107-1119 9.

Liu, Q., S. Singh and A. Green. High-oleic and high-stearic cottonseed oils: nutritionally improved cooking oils developed using gene silencing J Am Coll Nutr Jun. 2002 205S-211S 21.

Zeng, Y., E. J. Wagner and B. R. Cullen. Both natural and designed micro RNAs can inhibit the expression of cognate mRNAs when expressed in human cells Mol Cell Jun. 2002 1327-1333 9.

McManus, M. T., C. P. Petersen, B. B. Haines, J. Chen and P. A. Sharp. Gene silencing using micro-RNA designed hairpins Rna Jun. 2002 842-850 8.

Reinhart, B. J., E. G. Weinstein, M. W. Rhoades, B. Bartel and D. P. Bartel. MicroRNAs in plants Genes Dev Jul. 1, 2002 1616-1626 16.

McCaffrey, A. P., L. Meuse, T. T. Pham, D. S. Conklin, G. J. Hannon and M. A. Kay. RNA interference in adult mice Nature Jul. 4, 2002 38-39 418.

Hannon, G. J. RNA interference Nature Jul. 11, 2002 244-251 418.

Dennis, C. The brave new world of RNA Nature Jul. 11, 2002 122-124 418.

Jacque, J. M., K. Triques and M. Stevenson. Modulation of HIV-1 replication by RNA interference Nature Jul. 25, 2002 435-438 418.

Cullen, B. R. RNA interference: antiviral defense and genetic tool Nat Immunol Jul. 2002 597-599 3.

Ma, C. and A. Mitra. Intrinsic direct repeats generate consistent post-transcriptional gene silencing in tobacco Plant J Jul. 2002 37-49 31.

Novina, C. D., M. F. Murray, D. M. Dykxhoorn, P. J. Beresford, J. Riess, S. K. Lee, R. G. Collman, J. Lieberman, P. Shankar and P. A. Sharp. siRNA-directed inhibition of HIV-1 infection Nat Med Jul. 2002 681-686 8.

Pomerantz, R. J. RNA interference meets HIV-1: will silence be golden? Nat Med Jul. 2002 659-660 8.

Zeng, Y. and B. R. Cullen. RNA interference in human cells is restricted to the cytoplasm Rna Jul. 2002 855-860 8.

Xiang, C. C., O. A. Kozhich, M. Chen, J. M. Inman, Q. N. Phan, Y. Chen and M. J. Brownstein. Amine-modified random primers to label probes for DNA microarrays Nat Biotechnol Jul. 2002 738-742 20.

Llave, C., K. D. Kasschau, M. A. Rector and J. C. Carrington. Endogenous and silencing-associated small RNAs in plants Plant Cell Jul. 2002 1605-1619 14.

Rhoades, M. W., B. J. Reinhart, L. P. Lim, C. B. Burge, B. Bartel and D. P. Bartel. Prediction of plant microRNA targets Cell Aug. 23, 2002 513-520 110.

Hipfner, D. R., K. Weigmann and S. M. Cohen. The bantam gene regulates *Drosophila* growth Genetics Aug. 2002 1527-1537 161.

Liu, Q., S. P. Singh and A. G. Green. High-stearic and High-oleic cottonseed oils produced by hairpin RNA-mediated post-transcriptional gene silencing Plant Physiol Aug. 2002 1732-1743 129.

Stoutjesdijk, P. A., S. P. Singh, Q. Liu, C. J. Hurlstone, P. A. Waterhouse and A. G. Green. hpRNA-mediated targeting of the *Arabidopsis* FAD2 gene gives highly efficient and stable silencing Plant Physiol Aug. 2002 1723-1731 129.

Suzuma, S., S. Asari, K. Bunai, K. Yoshino, Y. Ando, H. Kakeshita, M. Fujita, K. Nakamura and K. Yamane. Identification and characterization of novel small RNAs in the aspS-yrvM intergenic region of the *Bacillus subtilis* genome Microbiology Aug. 2002 2591-2598 148.

Milligan, L., T. Forne, E. Antoine, M. Weber, B. Hemonnot, L. Dandolo, C. Brunel and G. Cathala. Turnover of primary transcripts is a major step in the regulation of mouse H19 gene expression EMBO Rep Aug. 2002 774-779 3.

Hamilton, A., O. Voinnet, L. Chappell and D. Baulcombe. Two classes of short interfering RNA in RNA silencing Embo J Sep. 2, 2002 4671-4679 21.

Lee, Y., K. Jeon, J. T. Lee, S. Kim and V. N. Kim. MicroRNA maturation: stepwise processing and subcellular localization Embo J Sep. 2, 2002 4663-4670 21.

Klahre, U., P. Crete, S. A. Leuenberger, V. A. Iglesias and F. Meins, Jr. High molecular weight RNAs and small interfering RNAs induce systemic posttranscriptional gene silencing in plants Proc Natl Acad Sci U S A Sep. 3, 2002 11981-11986 99.

Park, W., J. Li, R. Song, J. Messing and X. Chen. Carpel Factory, a Dicer homolog, and HEN1, a novel protein, act in microRNA metabolism in *Arabidopsis thaliana* Curr Biol Sep. 3, 2002 1484-1495 12.

Jiang, M. and J. Milner. Selective silencing of viral gene expression in HPV-positive human cervical carcinoma cells treated with siRNA, a primer of RNA interference Oncogene Sep. 5, 2002 6041-6048 21.

Martinez, J., A. Patkaniowska, H. Urlaub, R. Luhrmann and T. Tuschl. Single-stranded antisense siRNAs guide target RNA cleavage in RNAi Cell Sep. 6, 2002 563-574 110.

Allshire, R. Molecular biology. RNAi and heterochromatin—a hushed-up affair Science Sep. 13, 2002 1818-1819 297.

Reinhart, B. J. and D. P. Bartel. Small RNAs correspond to centromere heterochromatic repeats Science Sep. 13, 2002 1831 297.

Volpe, T. A., C. Kidner, I. M. Hall, G. Teng, S. I. Grewal and R. A. Martienssen. Regulation of heterochromatic silencing and histone H3 lysine-9 methylation by RNAi Science Sep. 13, 2002 1833-1837 297.

Baulcombe, D. DNA events. An RNA microcosm Science Sep. 20, 2002 2002-2003 297.

Llave, C., Z. Xie, K. D. Kasschau and J. C. Carrington. Cleavage of Scarecrow-like mRNA targets directed by a class of *Arabidopsis* miRNA Science Sep. 20, 2002 2053-2056 297.

Mochizuki, K., N. A. Fine, T. Fujisawa and M. A. Gorovsky. Analysis of a piwi-related gene implicates small RNAs in genome rearrangement in tetrahymena Cell Sep. 20, 2002 689-699 110.

Hutvagner, G. and P. D. Zamore. A microRNA in a multiple-turnover RNAi enzyme complex Science Sep. 20, 2002 2056-2060 297.

Coburn, G. A. and B. R. Cullen. Potent and specific inhibition of human immunodeficiency virus type 1 replication by RNA interference J Virol Sep. 2002 9225-9231 76.

Caudy, A. A., M. Myers, G. J. Hannon and S. M. Hammond. Fragile X-related protein and VIG associate with the RNA interference machinery Genes Dev Oct. 1, 2002 2491-2496 16.

Ishizuka, A., M. C. Siomi and H. Siomi. A *Drosophila* fragile X protein interacts with components of RNAi and ribosomal proteins Genes Dev Oct. 1, 2002 2497-2508 16.

Voinnet, O. RNA silencing: small RNAs as ubiquitous regulators of gene expression Curr Opin Plant Biol Oct. 2002 444-451 5.

Golden, T. A., S. E. Schauer, J. D. Lang, S. Pien, A. R. Mushegian, U. Grossniklaus, D. W. Meinke and A. Ray. Short INTEGUMENTS1/SUSPENSOR1/Carpel Factory, a Dicer homolog, is a maternal effect gene required for embryo development in *Arabidopsis* Plant Physiol Oct. 2002 808-822 130.

Merkle, I., M. J. Van Ooij, F. J. Van Kuppeveld, D. H. Glaudemans, J. M. Galama, A. Henke, R. Zell and W. J. Melchers. Biological significance of a human enterovirus B-specific RNA element in the 3' nontranslated region J Virol Oct. 2002 9900-9909 76.

Froeyen, M. and P. Herdewijn. RNA as a target for drug design, the example of Tat-TAR interaction Curr Top Med Chem Oct. 2002 1123-1145 2.

Carmell, M. A., Z. Xuan, M. Q. Zhang and G. J. Hannon. The Argonaute family: tentacles that reach into RNAi, developmental control, stem cell maintenance, and tumorigenesis Genes Dev Nov. 1, 2002 2733-2742 16.

Provost, P., D. Dishart, J. Doucet, D. Frendewey, B. Samuelsson and O. Radmark. Ribonuclease activity and RNA binding of recombinant human Dicer Embo J Nov. 1, 2002 5864-5874 21.

Zhang, H., F. A. Kolb, V. Brondani, E. Billy and W. Filipowicz. Human Dicer preferentially cleaves dsRNAs at their termini without a requirement for ATP Embo J Nov. 1, 2002 5875-5885 21.

Mallory, A. C., B. J. Reinhart, D. Bartel, V. B. Vance and L. H. Bowman. A viral suppressor of RNA silencing differentially regulates the accumulation of short interfering RNAs and micro-RNAs in tobacco Proc Natl Acad Sci U S A Nov. 12, 2002 15228-15233 99.

Gottesman, S. Stealth regulation: biological circuits with small RNA switches Genes Dev Nov. 15, 2002 2829-2842 16.

Calin, G. A., C. D. Dumitru, M. Shimizu, R. Bichi, S. Zupo, E. Noch, H. Aldler, S. Rattan, M. Keating, K. Rai, L. Rassenti, T. Kipps, M. Negrini, F. Bullrich and C. M. Croce. Frequent deletions and downregulation of micro- RNA genes miR15 and miR16 at 13q14 in chronic lymphocytic leukemia Proc Natl Acad Sci U S A Nov. 26, 2002 15524-15529 99.

Gaudilliere, B., Y. Shi and A. Bonni. RNA interference reveals a requirement for myocyte enhancer factor 2A in activity-dependent neuronal survival J Biol Chem Nov. 29, 2002 46442-46446.

Jones, L. Revealing micro-RNAs in plants Trends Plant Sci Nov. 2002 473-475 7.

Schauer, S. E., S. E. Jacobsen, D. W. Meinke and A. Ray. DICER-LIKE1: blind men and elephants in *Arabidopsis* development Trends Plant Sci Nov. 2002 487-491 7.

Okazaki, Y., M. Furuno, T. Kasukawa, J. Adachi, H. Bono, S. Kondo, et al. Analysis of the mouse transcriptome based on functional annotation of 60,770 full-length cDNAs Nature Dec. 5, 2002 563-573 420.

Dennis, C. Small RNAs: the genome's guiding hand? Nature Dec. 19-26, 2002 732 420.

Uchida, N., S. Hoshino, H. Imataka, N. Sonenberg and T. Katada. A novel role of the mammalian GSPT/eRF3 associating with poly(A)-binding protein in Cap/Poly(A)-dependent translation J Biol Chem Dec. 27, 2002 50286-50292 277.

Huttenhofer, A., J. Brosius and J. P. Bachellerie. RNomics: identification and function of small, non-messenger RNAs Curr Opin Chem Biol Dec. 2002 835-843 6.

Wood, N. T. Unravelling the molecular basis of viral suppression of PTGS Trends Plant Sci 2002 384 7.

Cohen, O., C. Erb, D. Ginzberg, Y. Pollak, S. Seidman, S. Shoham, R. Yirmiya and H. Soreq. Neuronal overexpression of "readthrough" acetylcholinesterase is associated with antisense-suppressible behavioral impairments Mol Psychiatry *No date in pubmed* 2002 874-885 7.

Mlotshwa, S., O. Voinnet, M. F. Mette, M. Matzke, H. Vaucheret, S. W. Ding, G. Pruss and V. B. Vance. RNA silencing and the mobile silencing signal Plant Cell *No date in pubmed* 2002 S289-301 14 Suppl.

Tang, G., B. J. Reinhart, D. P. Bartel and P. D. Zamore. A biochemical framework for RNA silencing in plants Genes Dev Jan. 1, 2003 49-63 17.

Kawasaki, H. and K. Taira. Short hairpin type of dsRNAs that are controlled by tRNA(Val) promoter significantly induce RNAi-mediated gene silencing in the cytoplasm of human cells Nucleic Acids Res Jan. 15, 2003 700-707 31.

Ashrafi, K., F. Y. Chang, J. L. Watts, A. G. Fraser, R. S. Kamath, J. Ahringer and G. Ruvkun. Genome-wide RNAi analysis of *Caenorhabditis elegans* fat regulatory genes Nature Jan. 16, 2003 268-272 421.

Kamath, R. S., A. G. Fraser, Y. Dong, G. Poulin, R. Durbin, M. Gotta, A. Kanapin, N. Le Bot, S. Moreno, M. Sohrmann, D. P. Welchman, P. Zipperlen and J. Ahringer. Systematic functional analysis of the *Caenorhabditis elegans* genome using RNAi Nature Jan. 16, 2003 231-237 421.

Tuschl, T. Functional genomics: RNA sets the standard Nature Jan. 16, 2003 220-221 421.

Iyer, L. M., E. V. Koonin and L. Aravind. Evolutionary connection between the catalytic subunits of DNA-dependent RNA polymerases and eukaryotic RNA-dependent RNA polymerases and the origin of RNA polymerases BMC Struct Biol Jan. 28, 2003 1 3.

Shi, Y. Mammalian RNAi for the masses Trends Genet Jan. 2003 9-12 19.

Cerutti, H. RNA interference: traveling in the cell and gaining functions? Trends Genet Jan. 2003 39-46 19.

Zeng, Y. and B. R. Cullen. Sequence requirements for micro RNA processing and function in human cells Rna Jan. 2003 112-123 9.

Kawasaki, H., E. Suyama, M. Iyo and K. Taira. siRNAs generated by recombinant human Dicer induce specific and significant but target site-independent gene silencing in human cells Nucleic Acids Res Feb. 1, 2003 981-987 31.

Reiner, A., D. Yekutieli and Y. Benjamini. Identifying differentially expressed genes using false discovery rate controlling procedures Bioinformatics Feb. 12, 2003 368-375 19.

Doench, J. G., C. P. Petersen and P. A. Sharp. siRNAs can function as miRNAs Genes Dev Feb. 15, 2003 438-442 17.

Gupta, V., A. Cherkassky, P. Chatis, R. Joseph, A. L. Johnson, J. Broadbent, T. Erickson and J. Dimeo. Directly labeled mRNA produces highly precise and unbiased differential gene expression data Nucleic Acids Res Feb. 15, 2003 e13 31.

Boffelli, D., J. Mcauliffe, D. Ovcharenko, K. D. Lewis, I. Ovcharenko, L. Pachter and E. M. Rubin. Phylogenetic shadowing of primate sequences to find functional regions of the human genome Science Feb. 28, 2003 1391-1394 299.

Kasschau, K. D., Z. Xie, E. Allen, C. Llave, E. J. Chapman, K. A. Krizan and J. C. Carrington. P1/HC-Pro, a viral suppressor of RNA silencing, interferes with *Arabidopsis* development and miRNA unction Dev Cell Feb. 2003 205-217 4.

Carmell, M. A., L. Zhang, D. S. Conklin, G. J. Hannon and T. A. Rosenquist. Germline transmission of RNAi in mice Nat Struct Biol Feb. 2003 91-92 10.

Dostie, J., Z. Mourelatos, M. Yang, A. Sharma and G. Dreyfuss. Numerous microRNPs in neuronal cells containing novel microRNAs Rna Feb. 2003 180-186 9.

Lagos-Quintana, M., R. Rauhut, J. Meyer, A. Borkhardt and T. Tuschl. New microRNAs from mouse and human Rna Feb. 2003 175-179 9.

Wilson, J. A., S. Jayasena, A. Khvorova, S. Sabatinos, I. G. Rodrigue-Gervais, S. Arya, F. Sarangi, M. Harris-Brandts, S. Beaulieu and C. D. Richardson. RNA interference blocks gene expression and RNA synthesis from hepatitis C replicons propagated in human liver cells Proc Natl Acad Sci U S A Mar. 4, 2003 2783-2788 100.

Lim, L. P., M. E. Glasner, S. Yekta, C. B. Burge and D. P. Bartel. Vertebrate microRNA genes Science Mar. 7, 2003 1540 299.

Maniataki, E., A. E. Martinez De Alba, R. Sagesser, M. Tabler and M. Tsagris. Viroid RNA systemic spread may depend on the interaction of a 71-nucleotide bulged hairpin with the host protein VirP1 Rna Mar. 2003 346-354 9.

Ambros, V., B. Bartel, D. P. Bartel, C. B. Burge, J. C. Carrington, X. Chen, G. Dreyfuss, S. R. Eddy, S. Griffiths-Jones, M. Marshall, M. Matzke, G. Ruvkun and T. Tuschl. A uniform system for microRNA annotation Rna Mar. 2003 277-279 9.

Findley, S. D., M. Tamanaha, N. J. Clegg and H. Ruohola-Baker. Maelstrom, a *Drosophila* spindle-class gene, encodes a protein that colocalizes with Vasa and RDE1/AGO1 homolog, Aubergine, in nuage Development Mar. 2003 859-871 130.

Hershberg, R., S. Altuvia and H. Margalit. A survey of small RNA-encoding genes in *Escherichia coli* Nucleic Acids Res Apr. 1, 2003 1813-1820 31.

Zhou, A., S. Scoggin, R. B. Gaynor and N. S. Williams. Identification of NF-kappa B-regulated genes induced by TNFalpha utilizing expression profiling and RNA interference Oncogene Apr. 3, 2003 2054-2064 22.

Brennecke, J., D. R. Hipfner, A. Stark, R. B. Russell and S. M. Cohen. bantam encodes a developmentally regulated microRNA that controls cell proliferation and regulates the proapoptotic gene hid in *Drosophila* Cell Apr. 4, 2003 25-36 113.

Lim, L. P., N. C. Lau, E. G. Weinstein, A. Abdelhakim, S. Yekta, M. W. Rhoades, C. B. Burge and D. P. Bartel. The microRNAs of *Caenorhabditis elegans* Genes Dev Apr. 15, 2003 991-1008 17.

Xu, P., S. Y. Vernooy, M. Guo and B. A. Hay. The *Drosophila* microRNA Mir-14 suppresses cell death and is required for normal fat metabolism Curr Biol Apr. 29, 2003 790-795 13.

Xie, Z., K. D. Kasschau and J. C. Carrington. Negative feedback regulation of Dicer-Like1 in *Arabidopsis* by microRNA-guided mRNA degradation Curr Biol Apr. 29, 2003 784-789 13.

Carmichael, G. G. Antisense starts making more sense Nat Biotechnol Apr. 2003 371-372 21.

Yelin, R., D. Dahary, R. Sorek, E. Y. Levanon, O. Goldstein, A. Shoshan, A. Diber, S. Biton, Y. Tamir, R. Khosravi, S. Nemzer, E. Pinner, S. Walach, J. Bernstein, K. Savitsky and G. Rotman. Widespread occurrence of antisense transcription in the human genome Nat Biotechnol Apr. 2003 379-386 21.

Boutet, S., F. Vazquez, J. Liu, C. Beclin, M. Fagard, A. Gratias, J. B. Morel, P. Crete, X. Chen and H. Vaucheret. *Arabidopsis* HEN1: a genetic link between endogenous miRNA controlling development and siRNA controlling transgene silencing and virus resistance Curr Biol May 13, 2003 843-848 13.

Ambros, V., R. C. Lee, A. Lavanway, P. T. Williams and D. Jewell. MicroRNAs and other tiny endogenous RNAs in *C. elegans* Curr Biol May 13, 2003 807-818 13.

Liang, X. S., J. Q. Lian, Y. X. Zhou, Q. H. Nie and C. Q. Hao. A small yeast RNA inhibits HCV IRES mediated translation and inhibits replication of poliovirus in vivo World J Gastroenterol May 2003 1008-1013 9.

Grad, Y., J. Aach, G. D. Hayes, B. J. Reinhart, G. M. Church, G. Ruvkun and J. Kim. Computational and experimental identification of *C. elegans* microRNAs Mol Cell May 2003 1253-1263 11.

Abrahante, J. E., A. L. Daul, M. Li, M. L. Volk, J. M. Tennessen, E. A. Miller and A. E. Rougvie. The *Caenorhabditis elegans* hunchback-like gene lin-57/hbl-1 controls developmental time and is regulated by microRNAs Dev Cell May 2003 625-637 4.

Lin, S. Y., S. M. Johnson, M. Abraham, M. C. Vella, A. Pasquinelli, C. Gamberi, E. Gottlieb and F. J. Slack. The *C elegans* hunchback homolog, hbl-1, controls temporal patterning and is a probable microRNA target Dev Cell May 2003 639-650 4.

Zamvil, S. S. and L. Steinman. Diverse targets for intervention during inflammatory and neurodegenerative phases of multiple sclerosis Neuron Jun. 5, 2003 685-688 38.

Ambros, V. MicroRNA pathways in flies and worms: growth, death, fat, stress, and timing Cell Jun. 13, 2003 673-676 113.

Moss, E. G. and L. Tang. Conservation of the heterochronic regulator Lin-28, its developmental expression and microRNA complementary sites Dev Biol Jun. 15, 2003 432-442 258.

Smalheiser, N. R. EST analyses predict the existence of a population of chimeric microRNA precursor-mRNA transcripts expressed in normal human and mouse tissues Genome Biol Epub 2003 Jun. 18, 2003 403 4.

Kawasaki, H. and K. Taira. Hes1 is a target of microRNA-23 during retinoic-acid-induced neuronal differentiation of NT2 cells Nature Jun. 19, 2003 838-842 423.

Lai, E. C., P. Tomancak, R. W. Williams and G. M. Rubin. Computational identification of *Drosophila* microRNA genes Genome Biol Epub 2003 Jun. 30, 2003 R42 4.

No author listed. Whither RNAi? Nat Cell Biol Jun. 2003 489-490 5.

Bartel, B. and D. P. Bartel. MicroRNAs: at the root of plant development? Plant Physiol Jun. 2003 709-717 132.

Dykxhoorn, D. M., C. D. Novina and P. A. Sharp. Killing the messenger: short RNAs that silence gene expression Nat Rev Mol Cell Biol Jun. 2003 457-467 4.

Saunders, L. R. and G. N. Barber. The dsRNA binding protein family: critical roles, diverse cellular functions Faseb J Jun. 2003 961-983 17.

Steinman, L. and S. Zamvil. Transcriptional analysis of targets in multiple sclerosis Nat Rev Immunol Jun. 2003 483-492 3.

Qi, Y. and B. Ding. Inhibition of cell growth and shoot development by a specific nucleotide sequence in a noncoding viroid RNA Plant Cell Jun. 2003 1360-1374 15.

Jackson, A. L., S. R. Bartz, J. Schelter, S. V. Kobayashi, J. Burchard, M. Mao, B. Li, G. Cavet and P. S. Linsley. Expression profiling reveals off-target gene regulation by RNAi Nat Biotechnol Jun. 2003 635-637 21.

Bashirullah, A., A. E. Pasquinelli, A. A. Kiger, N. Perrimon, G. Ruvkun and C. S. Thummel. Coordinate regulation of small temporal RNAs at the onset of *Drosophila* metamorphosis Dev Biol Jul. 1, 2003 1-8 259.

Sempere, L. F., N. S. Sokol, E. B. Dubrovsky, E. M. Berger and V. Ambros. Temporal regulation of microRNA expression in *Drosophila melanogaster* mediated by hormonal signals and broad-Complex gene activity Dev Biol Jul. 1, 2003 9-18 259.

Heetebrij, R. J., E. G. Talman, M. A. V Velzen, R. P. Van Gijlswijk, S. S. Snoeijers, M. Schalk, J. Wiegant, F. V D Rijke, R. M. Kerkhoven, A. K. Raap, H. J. Tanke, J. Reedijk and H. J. Houthoff. Platinum(II)-based coordination compounds as nucleic acid labeling reagents: synthesis, reactivity, and applications in hybridization assays Chembiochem Jul. 7, 2003 573-583 4.

Borodina, T. A., H. Lehrach and A. V. Soldatov. Ligation-based synthesis of oligonucleotides with block structure Anal Biochem Jul. 15, 2003 309-313 318.

Johnson, S. M., S. Y. Lin and F. J. Slack. The time of appearance of the *C. elegans* let-7 microRNA is transcriptionally controlled utilizing a temporal regulatory element in its promoter Dev Biol Jul. 15, 2003 364-379 259.

Carrington, J. C. and V. Ambros. Role of microRNAs in plant and animal development Science Jul. 18, 2003 336-338 301.

Smale, S. T. The establishment and maintenance of lymphocyte identity through gene silencing Nat Immunol Jul. 2003 607-615 4.

Bridge, A. J., S. Pebernard, A. Ducraux, A. L. Nicoulaz and R. Iggo. Induction of an interferon response by RNAi vectors in mammalian cells Nat Genet Jul. 2003 263-264 34.

Seitz, H., N. Youngson, S. P. Lin, S. Dalbert, M. Paulsen, J. P. Bachellerie, A. C. Ferguson-Smith and J. Cavaille. Imprinted microRNA genes transcribed antisense to a reciprocally imprinted retrotransposon-like gene Nat Genet Jul. 2003 261-262 34.

Zeng, Y., R. Yi and B. R. Cullen. MicroRNAs and small interfering RNAs can inhibit mRNA expression by similar mechanisms Proc Natl Acad Sci U S A Aug. 19, 2003 9779-9784 100.

Schramke, V. and R. Allshire. Hairpin RNAs and retrotransposon LTRs effect RNAi and chromatin-based gene silencing Science Aug. 22, 2003 1069-1074 301.

Wiznerowicz, M. and D. Trono. Conditional suppression of cellular genes: lentivirus vector-mediated drug-inducible RNA interference J Virol Aug. 2003 8957-8961 77.

Lau, N. C. and D. P. Bartel. Censors of the genome Sci Am Aug. 2003 34-41 289.

Houbaviy, H. B., M. F. Murray and P. A. Sharp. Embryonic stem cell-specific MicroRNAs Dev Cell Aug. 2003 351-358 5.

Aravin, A. A., M. Lagos-Quintana, A. Yalcin, M. Zavolan, D. Marks, B. Snyder, T. Gaasterland, J. Meyer and T. Tuschl. The small RNA profile during *Drosophila melanogaster* development Dev Cell Aug. 2003 337-350 5.

McManus, M. T. MicroRNAs and cancer Semin Cancer Biol Aug. 2003 253-258 13.

Baner, J., A. Isaksson, E. Waldenstrom, J. Jarvius, U. Landegren and M. Nilsson. Parallel gene analysis with allele-specific padlock probes and tag microarrays Nucleic Acids Res Sep. 1, 2003 e103 31.

Boutla, A., C. Delidakis and M. Tabler. Developmental defects by antisense-mediated inactivation of micro-RNAs 2 and 13 in *Drosophila* and the identification of putative target genes Nucleic Acids Res Sep. 1, 2003 4973-4980 31.

Palatnik, J. F., E. Allen, X. Wu, C. Schommer, R. Schwab, J. C. Carrington and D. Weigel. Control of leaf morphogenesis by microRNAs Nature Sep. 18, 2003 257-263 425.

Klein, R. J. and S. R. Eddy. RSEARCH: finding homologs of single structured RNA sequences BMC Bioinformatics Sep. 22, 2003 44 4.

Caudy, A. A., R. F. Ketting, S. M. Hammond, A. M. Denli, A. M. Bathoorn, B. B. Tops, J. M. Silva, M. M. Myers, G. J. Hannon and R. H. Plasterk. A micrococcal nuclease homologue in RNAi effector complexes Nature Sep. 25, 2003 411-414 425.

Lee, Y., C. Ahn, J. Han, H. Choi, J. Kim, J. Yim, J. Lee, P. Provost, O. Radmark, S. Kim and V. N. Kim. The nuclear RNase III Drosha initiates microRNA processing Nature Sep. 25, 2003 415-419 425.

Sledz, C. A., M. Holko, M. J. De Veer, R. H. Silverman and B. R. Williams. Activation of the interferon system by short-interfering RNAs Nat Cell Biol Sep. 2003 834-839 5.

Bergmann, A. and M. E. Lane. HIDden targets of microRNAs for growth control Trends Biochem Sci Sep. 2003 461-463 28.

Khvorova, A., A. Reynolds and S. D. Jayasena. Functional siRNAs and miRNAs exhibit strand bias Cell Oct. 17, 2003 209-216 115.

Schwarz, D. S., G. Hutvagner, T. Du, Z. Xu, N. Aronin and P. D. Zamore. Asymmetry in the assembly of the RNAi enzyme complex Cell Oct. 17, 2003 199-208 115.

Abbott, A. L. Heterochronic genes Curr Biol Oct. 28, 2003 R824-825 13.

Hake, S. MicroRNAs: a role in plant development Curr Biol Oct. 28, 2003 R851-852 13.

Carthew, R. W. Making and breaking with nucleases and small RNAs Nat Struct Biol Oct. 2003 776-777 10.

Krichevsky, A. M., K. S. King, C. P. Donahue, K. Khrapko and K. S. Kosik. A microRNA array reveals extensive regulation of microRNAs during brain development Rna Oct. 2003 1274-1281 9.

Mattick, J. S. Challenging the dogma: the hidden layer of non-protein-coding RNAs in complex organisms Bioessays Oct. 2003 930-939 25.

Nelson, P., M. Kiriakidou, A. Sharma, E. Maniataki and Z. Mourelatos. The microRNA world: small is mighty Trends Biochem Sci Oct. 2003 534-540 28.

Michael, M. Z., O. C. SM, N. G. Van Holst Pellekaan, G. P. Young and R. J. James. Reduced accumulation of specific microRNAs in colorectal neoplasia Mol Cancer Res Oct. 2003 882-891 1.

Allinson, T. M., E. T. Parkin, A. J. Turner and N. M. Hooper. ADAMs family members as amyloid precursor protein alpha-secretases J Neurosci Res Nov. 1, 2003 342-352 74.

Kawasaki, H. and K. Taira. Retraction: Hes1 is a target of microRNA-23 during retinoic-acid-induced neuronal differentiation of NT2 cells Nature Nov. 6, 2003 100 426.

Saxena, S., Z. O. Jonsson and A. Dutta. Small RNAs with imperfect match to endogenous mRNA repress translation. Implications for off-target activity of small inhibitory RNA in mammalian cells J Biol Chem Nov. 7, 2003 44312-44319 278.

Basyuk, E., F. Suavet, A. Doglio, R. Bordonne and E. Bertrand. Human let-7 stem-loop precursors harbor features of RNase III cleavage products Nucleic Acids Res Nov. 15, 2003 6593-6597 31.

Stevenson, M. Dissecting HIV-1 through RNA interference Nat Rev Immunol Nov. 2003 851-858 3.

Wienholds, E., M. J. Koudijs, F. J. Van Eeden, E. Cuppen and R. H. Plasterk. The microRNA-producing enzyme Dicer1 is essential for zebrafish development Nat Genet Nov. 2003 217-218 35.

Gibbs, W. W. The unseen genome: gems among the junk Sci Am Nov. 2003 26-33 289.

Chang, J., P. Provost and J. M. Taylor. Resistance of human hepatitis delta virus RNAs to dicer activity J Virol Nov. 2003 11910-11917 77.

Wang, D., A. Urisman, Y. T. Liu, M. Springer, T. G. Ksiazek, D. D. Erdman, E. R. Mardis, M. Hickenbotham, V. Magrini, J. Eldred, J. P. Latreille, R. K. Wilson, D. Ganem and J. L. Derisi. Viral discovery and sequence recovery using DNA microarrays PLoS Biol Nov. 2003 E2 1.

Aukerman, M. J. and H. Sakai. Regulation of flowering time and floral organ identity by a MicroRNA and its APETALA2-like target genes Plant Cell Nov. 2003 2730-2741 15.

Finnegan, E. J. and M. A. Matzke. The small RNA world J Cell Sci Dec. 1, 2003 4689-4693 116.

Enright, A. J., B. John, U. Gaul, T. Tuschl, C. Sander and D. S. Marks. MicroRNA targets in *Drosophila* Genome Biol Epub 2003 Dec. 12, 2003 R1 5.

Rosok, O. and M. Sioud. Systematic identification of sense-antisense transcripts in mammalian cells Nat Biotechnol Jan (Epub Dec. 14, 2003) 2004 104-108 22.

Yi, R., Y. Qin, I. G. Macara and B. R. Cullen. Exportin-5 mediates the nuclear export of premicroRNAs and short hairpin RNAs Genes Dev Dec. 15, 2003 3011-3016 17.

Cao, X., W. Aufsatz, D. Zilberman, M. F. Mette, M. S. Huang, M. Matzke and S. E. Jacobsen. Role of the DRM and CMT3 methyltransferases in RNA-directed DNA methylation Curr Biol Dec. 16, 2003 2212-2217 13.

Ye, K., L. Malinina and D. J. Patel. Recognition of small interfering RNA by a viral suppressor of RNA silencing Nature Dec. 18, 2003 874-878 426.

Johnston, R. J. and O. Hobert. A microRNA controlling left/right neuronal asymmetry in *Caenorhabditis elegans* Nature Dec. 18, 2003 845-849 426.

Xayaphoummine, A., T. Bucher, F. Thalmann and H. Isambert. Prediction and statistics of pseudoknots in RNA structures using exactly clustered stochastic simulations Proc Natl Acad Sci U S A Dec. 23, 2003 15310-15315 100.

Lewis, B. P., I. H. Shih, M. W. Jones-Rhoades, D. P. Bartel and C. B. Burge. Prediction of mammalian microRNA targets Cell Dec. 26, 2003 787-798 115.

Robinson, W. H., P. J. Utz and L. Steinman. Genomic and proteomic analysis of multiple sclerosis. Opinion Curr Opin Immunol Dec. 2003 660-667 15.

Gibbs, W. W. The unseen genome: beyond DNA Sci Am Dec. 2003 106-113 289.

Stark, A., J. Brennecke, R. B. Russell and S. M. Cohen. Identification of *Drosophila* MicroRNA targets PLoS Biol Dec. 2003 E60 1.

Stein, T. D. and J. A. Johnson. Genetic programming by the proteolytic fragments of the amyloid precursor protein: somewhere between confusion and clarity Rev Neurosci *no date in pubmed* 2003 317-341 14.

Szymanski, M., M. Z. Barciszewska, M. Zywicki and J. Barciszewski. Noncoding RNA transcripts J Appl Genet *No Datein Pubmed* 2003 1-19 44.

Griffiths-Jones, S. The microRNA Registry Nucleic Acids Res Jan. 1, 2004 D109-111 32.

Chen, C. Z., L. Li, H. F. Lodish and D. P. Bartel. MicroRNAs modulate hematopoietic lineage differentiation Science Jan. 2, 2004 83-86 303.

Kim, J., A. Krichevsky, Y. Grad, G. D. Hayes, K. S. Kosik, G. M. Church and G. Ruvkun. Identification of many microRNAs that copurify with polyribosomes in mammalian neurons Proc Natl Acad Sci U S A Jan. 6, 2004 360-365 101.

Ohno, M., E. A. Sametsky, L. H. Younkin, H. Oakley, S. G. Younkin, M. Citron, R. Vassar and J. F. Disterhoft. BACE1 deficiency rescues memory deficits and cholinergic dysfunction in a mouse model of Alzheimer's disease Neuron Jan. 8, 2004 27-33 41.

Vella, M. C., E. Y. Choi, S. Y. Lin, K. Reinert and F. J. Slack. The *C. elegans* microRNA let-7 binds to imperfect let-7 complementary sites from the lin-41 3'UTR Genes Dev Jan. 15, 2004 132-137 18.

Kao, S. C., A. M. Krichevsky, K. S. Kosik and L. H. Tsai. BACE1 suppression by RNA interference in primary cortical neurons J Biol Chem Jan. 16, 2004 1942-1949 279.

Hofacker, I. L., B. Priwitzer and P. F. Stadler. Prediction of locally stable RNA secondary structures for genome-wide surveys Bioinformatics Jan. 22, 2004 186-190 20.

Ruvkun, G., B. Wightman and I. Ha. The 20 years it took to recognize the importance of tiny RNAs Cell Jan. 23, 2004 S93-96, 92 p following S96 116.

Bartel, D. P. MicroRNAs: genomics, biogenesis, mechanism, and function Cell Jan. 23, 2004 281-297 116.

Han, M. H., S. Goud, L. Song and N. Fedoroff. The *Arabidopsis* double-stranded RNA-binding protein HYL1 plays a role in microRNA-mediated gene regulation Proc Natl Acad Sci U S A Jan. 27, 2004 1093-1098 101.

Hartig, J. S., I. Grune, S. H. Najafi-Shoushtari and M. Famulok. Sequence-specific detection of MicroRNAs by signal-amplifying ribozymes J Am Chem Soc Jan. 28, 2004 722-723 126.

Nishitsuji, H., T. Ikeda, H. Miyoshi, T. Ohashi, M. Kannagi and T. Masuda. Expression of small hairpin RNA by lentivirus-based vector confers efficient and stable gene-suppression of HIV-1 on human cells including primary non-dividing cells Microbes Infect Jan. 2004 76-85 6.

Ota, T., Y. Suzuki, T. Nishikawa, T. Otsuki, T. Sugiyama, R. Irie, A., et al. Complete sequencing and characterization of 21,243 full-length human cDNAs Nat Genet Jan. 2004 40-45 36.

Colciaghi, F., E. Marcello, B. Borroni, M. Zimmermann, C. Caltagirone, F. Cattabeni, A. Padovani and M. Di Luca. Platelet APP, ADAM 10 and BACE alterations in the early stages of Alzheimer disease Neurology Feb. 10, 2004 498-501 62.

Boden, D., O. Pusch, R. Silbermann, F. Lee, L. Tucker and B. Ramratnam. Enhanced gene silencing of HIV-1 specific siRNA using microRNA designed hairpins Nucleic Acids Res Feb. 13, 2004 1154-1158 32.

Sempere, L. F., S. Freemantle, I. Pitha-Rowe, E. Moss, E. Dmitrovsky and V. Ambros. Expression profiling of mammalian microRNAs uncovers a subset of brain-expressed microRNAs with possible roles in murine and human neuronal differentiation Genome Biol Epub 2004 Feb. 16, 2004 R13 5.

Scacheri, P. C., O. Rozenblatt-Rosen, N. J. Caplen, T. G. Wolfsberg, L. Umayam, J. C. Lee, C. M. Hughes, K. S. Shanmugam, A. Bhattacharjee, M. Meyerson and F. S. Collins. Short interfering RNAs can induce unexpected and divergent changes in the levels of untargeted proteins in mammalian cells Proc Natl Acad Sci U S A Feb. 17, 2004 1892-1897 101.

Xie, Z., L. K. Johansen, A. M. Gustafson, K. D. Kasschau, A. D. Lellis, D. Zilberman, S. E. Jacobsen and J. C. Carrington. Genetic and functional diversification of small RNA pathways in plants PLoS Biol May (Epub Feb. 18, 2004) 2004 E104 2.

Cawley, S., S. Bekiranov, H. H. Ng, P. Kapranov, E. A. Sekinger, D. Kampa, A. Piccolboni, V. Sementchenko, J. Cheng, A. J. Williams, R. Wheeler, B. Wong, J. Drenkow, M. Yamanaka, S. Patel, S. Brubaker, H. Tammana, G. Helt, K. Struhl and T. R. Gingeras. Unbiased mapping of transcription factor binding sites along human chromosomes 21 and 22 points to widespread regulation of noncoding RNAs Cell Feb. 20, 2004 499-509 116.

Dandekar, D. H., K. N. Ganesh and D. Mitra. HIV-1 Tat directly binds to NFkappaB enhancer sequence: role in viral and cellular gene expression Nucleic Acids Res Feb. 23, 2004 1270-1278 32.

Hutvagner, G., M. J. Simard, C. C. Mello and P. D. Zamore. Sequence-specific inhibition of small RNA function PLoS Biol Apr (Epub Feb. 24, 2004) 2004 E98 2.

Schmittgen, T. D., J. Jiang, Q. Liu and L. Yang. A high-throughput method to monitor the expression of microRNA precursors Nucleic Acids Res Feb. 25, 2004 e43 32.

Stremlau, M., C. M. Owens, M. J. Perron, M. Kiessling, P. Autissier and J. Sodroski. The cytoplasmic body component TRIM5alpha restricts HIV-1 infection in Old World monkeys Nature Feb. 26, 2004 848-853 427.

Bohnsack, M. T., K. Czaplinski and D. Gorlich. Exportin 5 is a RanGTP-dependent dsRNA-binding protein that mediates nuclear export of pre-miRNAs Rna Feb. 2004 185-191 10.

Demidov, V. V. and M. D. Frank-Kamenetskii. Two sides of the coin: affinity and specificity of nucleic acid interactions Trends Biochem Sci Feb. 2004 62-71 29.

Maquat, L. E. Nonsense-mediated mRNA decay: splicing, translation and mRNP dynamics Nat Rev Mol Cell Biol Feb. 2004 89-99 5.

Nijholt, I., N. Farchi, M. Kye, E. H. Sklan, S. Shoham, B. Verbeure, D. Owen, B. Hochner, J. Spiess, H. Soreq and T. Blank. Stress-induced alternative splicing of acetylcholinesterase results in enhanced fear memory and long-term potentiation Mol Psychiatry Feb. 2004 174-183 9.

Sengupta, P. Taking sides in the nervous system with miRNA Nat Neurosci Feb. 2004 100-102 7.

Zerhouni, B., J. A. Nelson and K. Saha. Isolation of CD4-independent primary human immunodeficiency virus type 1 isolates that are syncytium inducing and acutely cytopathic for CD8+ lymphocytes J Virol Feb. 2004 1243-1255 78.

Jin, P., D. C. Zarnescu, S. Ceman, M. Nakamoto, J. Mowrey, T. A. Jongens, D. L. Nelson, K. Moses and S. T. Warren. Biochemical and genetic interaction between the fragile X mental retardation protein and the microRNA pathway Nat Neurosci Feb. 2004 113-117 7.

Lai, E. C., C. Wiel and G. M. Rubin. Complementary miRNA pairs suggest a regulatory role for miRNA:miRNA duplexes Rna Feb. 2004 171-175 10.

Metzler, M., M. Wilda, K. Busch, S. Viehmann and A. Borkhardt. High expression of precursor microRNA-155/BIC RNA in children with Burkitt lymphoma Genes Chromosomes Cancer Feb. 2004 167-169 39.

Doench, J. G. and P. A. Sharp. Specificity of microRNA target selection in translational repression Genes Dev Mar. 1, 2004 504-511 18.

Liang, X. S., J. Q. Lian, Y. X. Zhou and M. B. Wan. Inhibitor RNA blocks the protein translation mediated by hepatitis C virus internal ribosome entry site in vivo World J Gastroenterol Mar. 1, 2004 664-667 10.

Calin, G. A., C. Sevignani, C. D. Dumitru, T. Hyslop, E. Noch, S. Yendamuri, M. Shimizu, S. Rattan, F. Bullrich, M. Negrini and C. M. Croce. Human microRNA genes are frequently located at fragile sites and genomic regions involved in cancers Proc Natl Acad Sci U S A Mar. 2, 2004 2999-3004 101.

Juarez, M. T., J. S. Kui, J. Thomas, B. A. Heller and M. C. Timmermans. microRNA-mediated repression of rolled leaf1 specifies maize leaf polarity Nature Mar. 4, 2004 84-88 428.

Kidner, C. A. and R. A. Martienssen. Spatially restricted microRNA directs leaf polarity through ARGONAUTE1 Nature Mar. 4, 2004 81-84 428.

Zamore, P. D. Plant RNAi: How a viral silencing suppressor inactivates siRNA Curr Biol Mar. 9, 2004 R198-200 14.

Wang, J. F., H. Zhou, Y. Q. Chen, Q. J. Luo and L. H. Qu. Identification of 20 microRNAs from Oryza sativa Nucleic Acids Res Mar. 12, 2004 1688-1695 32.

Jack, T. Molecular and genetic mechanisms of floral control Plant Cell Epub 2004 Mar. 12, 2004 S1-17 16 Suppl.

Roth, M. E., L. Feng, K. J. McConnell, P. J. Schaffer, C. E. Guerra, J. P. Affourtit, K. R. Piper, L. Guccione, J. Hariharan, M. J. Ford, S. W. Powell, H. Krishnaswamy, J. Lane, L. Guccione, G. Intrieri, J. S.

Merkel, C. Perbost, A. Valerio, B. Zolla, C. D. Graham, J. Hnath, C. Michaelson, R. Wang, B. Ying, C. Halling, C. E. Parman, D. Raha, B. Orr, B. Jedrzkiewicz, J. Liao, A. Tevelev, M. J. Mattessich, D. M. Kranz, M. Lacey, J. C. Kaufman, J. Kim, D. R. Latimer and P. M. Lizardi. Expression profiling using a hexamer-based universal microarray Nat Biotechnol Apr (Epub Mar. 14, 2004) 2004 418-426 22.

Rajewsky, N. and N. D. Socci. Computational identification of microRNA targets Dev Biol Mar. 15, 2004 529-535 267.

Winkler, W. C., A. Nahvi, A. Roth, J. A. Collins and R. R. Breaker. Control of gene expression by a natural metabolite-responsive ribozyme Nature Mar. 18, 2004 281-286 428.

Kuwabara, T., J. Hsieh, K. Nakashima, K. Taira and F. H. Gage. A small modulatory dsRNA specifies the fate of adult neural stem cells Cell Mar. 19, 2004 779-793 116.

Chen, X. A microRNA as a translational repressor of APETALA2 in *Arabidopsis* flower development Science Mar. 26, 2004 2022-2025 303.

Carmell, M. A. and G. J. Hannon. RNase III enzymes and the initiation of gene silencing Nat Struct Mol Biol Mar. 2004 214-218 11.

Davidson, B. L. and H. L. Paulson. Molecular medicine for the brain: silencing of disease genes with RNA interference Lancet Neurol Mar. 2004 145-149 3.

Kawasaki, H., R. Wadhwa and K. Taira. World of small RNAs: from ribozymes to siRNA and miRNA Differentiation Mar. 2004 58-64 72.

Meister, G., M. Landthaler, Y. Dorsett and T. Tuschl. Sequence-specific inhibition of microRNA- and siRNA-induced RNA silencing Rna Mar. 2004 544-550 10.

Nelson, P. T., A. G. Hatzigeorgiou and Z. Mourelatos. miRNP:mRNA association in polyribosomes in a human neuronal cell line Rna Mar. 2004 387-394 10.

Floyd, S. K. and J. L. Bowman. Gene regulation: ancient microRNA target sequences in plants Nature Apr. 1, 2004 485-486 428.

Lee, Y. S., K. Nakahara, J. W. Pham, K. Kim, Z. He, E. J. Sontheimer and R. W. Carthew. Distinct roles for *Drosophila* Dicer-1 and Dicer-2 in the siRNA/miRNA silencing pathways Cell Apr. 2, 2004 69-81 117.

Tijsterman, M. and R. H. Plasterk. Dicers at RISC; the mechanism of RNAi Cell Apr. 2, 2004 1 3 117.

Macdiarmid, R. RNA Silencing in Productive Virus Infections Annu Rev Phytopathol Apr. 12, 2004.

Chen, J., W. X. Li, D. Xie, J. R. Peng and S. W. Ding. Viral virulence protein suppresses RNA silencing-mediated defense but upregulates the role of microrna in host gene expression Plant Cell May (Epub Apr. 20, 2004) 2004 1302-1313 16.

Yekta, S., I. H. Shin and D. P. Bartel. MicroRNA-directed cleavage of HOXB8 mRNA Science Apr. 23, 2004 594-596 304.

Lamontagne, B., R. N. Hannoush, M. J. Damha and S. Abou Elela. Molecular requirements for duplex recognition and cleavage by eukaryotic RNase III: discovery of an RNA-dependent DNA cleavage activity of yeast Rnt1p J Mol Biol Apr. 23, 2004 401-418 338.

Barrick, J. E., K. A. Corbino, W. C. Winkler, A. Nahvi, M. Mandal, J. Collins, M. Lee, A. Roth, N. Sudarsan, I. Jona, J. K. Wickiser and R. R. Breaker. New RNA motifs suggest an expanded scope for riboswitches in bacterial genetic control Proc Natl Acad Sci U S A Apr. 27, 2004 6421-6426 101.

Pfeffer, S., M. Zavolan, F. A. Grasser, M. Chien, J. J. Russo, J. Ju, B. John, A. J. Enright, D. Marks, C. Sander and T. Tuschl. Identification of virus-encoded microRNAs Science Apr. 30, 2004 734-736 304.

Dorsett, Y. and T. Tuschl. siRNAs: applications in functional genomics and potential as therapeutics Nat Rev Drug Discov Apr. 2004 318-329 3.

Mallory, A. C. and H. Vaucheret. MicroRNAs: something important between the genes Curr Opin Plant Biol Apr. 2004 120-125 7.

Ogita, S., H. Uefuji, M. Morimoto and H. Sano. Application of RNAi to confirm theobromine as the major intermediate for caffeine biosynthesis in coffee plants with potential for construction of decaffeinated varieties Plant Mol Biol Apr. 2004 931-941 54.

Storz, G., J. A. Opdyke and A. Zhang. Controlling mRNA stability and translation with small, noncoding RNAs Curr Opin Microbiol Apr. 2004 140-144 7.

Kim, V. N. MicroRNA precursors in motion: exportin-5 mediates their nuclear export Trends Cell Biol Apr. 2004 156-159 14.

Jabri, E. RISCy business Nat Struct Mol Biol Apr. 2004 300 11.

Nakahara, K. and R. W. Carthew. Expanding roles for miRNAs and siRNAs in cell regulation Curr Opin Cell Biol Apr. 2004 127-133 16.

Ota, A., H. Tagawa, S. Karnan, S. Tsuzuki, A. Karpas, S. Kira, Y. Yoshida and M. Seto. Identification and characterization of a novel gene, C13orf25, as a target for 13q31-q32 amplification in malignant lymphoma Cancer Res May 1, 2004 3087-3095 64.

Marillonnet, S., A. Giritch, M. Gils, R. Kandzia, V. Klimyuk and Y. Gleba. In planta engineering of viral RNA replicons: efficient assembly by recombination of DNA modules delivered by *Agrobacterium* Proc Natl Acad Sci U S A May 4, 2004 6852-6857 101.

Pooggin, M. and T. Hohn. Fighting geminiviruses by RNAi and vice versa Plant Mol Biol May 2004 149-152 55.

Bartel, D. P. and C. Z. Chen. Micromanagers of gene expression: the potentially widespread influence of metazoan microRNAs Nat Rev Genet May 2004 396-400 5.

Dunoyer, P., C. H. Lecellier, E. A. Parizotto, C. Himber and O. Voinnet. Probing the microRNA and small interfering RNA pathways with virus-encoded suppressors of RNA silencing Plant Cell May (Epub Apr. 14, 2004(2004 1235-1250 16.

Doench JG and Sharp PA. Specificity of microRNA target selection in translational repression. Genes Dev, 2004;18(5):504-11.

Lai EC. Micro RNAs are complementary to 3' UTR sequence motifs that mediate negative post-transcriptional regulation. Nature Genetics 2002;30:363-4.

Stark A. Identification of *Drosophila* MicroRNA Targets. PLoS Biology 2003;1(3):397-409.

Lai EC. Predicting and validating microRNA targets. Genome Biology 2004;5:115.

Vella MC. Architecture of a Validated MicroRNA::Target Interaction. Chemistry & Biology 2004;11:1619-23.

Brennecke J. Principles of MicroRNA—Target Recognition. PLoS Biology 2005;3(3):e85.

Lewis BP. Prediction of Mammalian MicroRNA Targets. Cell 2003;115:787-98.

Enright AJ. MicroRNA targets in *Drosophila*. Genome Biology 2003;5: R1.

Taniyama Y et al. Role of p38 MAPK and MAPKAPK-2 in angiotensin II-induced Akt activation in vascular smooth muscle cells. Am J Physiol Cell Physiol 2004;287:C494-9.

Li M et al. The Myeloid Leukemia-associated Protein SET Is a Potent Inhibitor of Protein Phosphatase 2A. Jo Biol Chem 1996;271(19):11059-62.

Al-Murrani SWK et al. Expression of I2PP2A, an inhibitor of protein phosphatase 2A, induces c-Jun and AP-1 activity. Biochem J 1999;341:293-8.

* cited by examiner

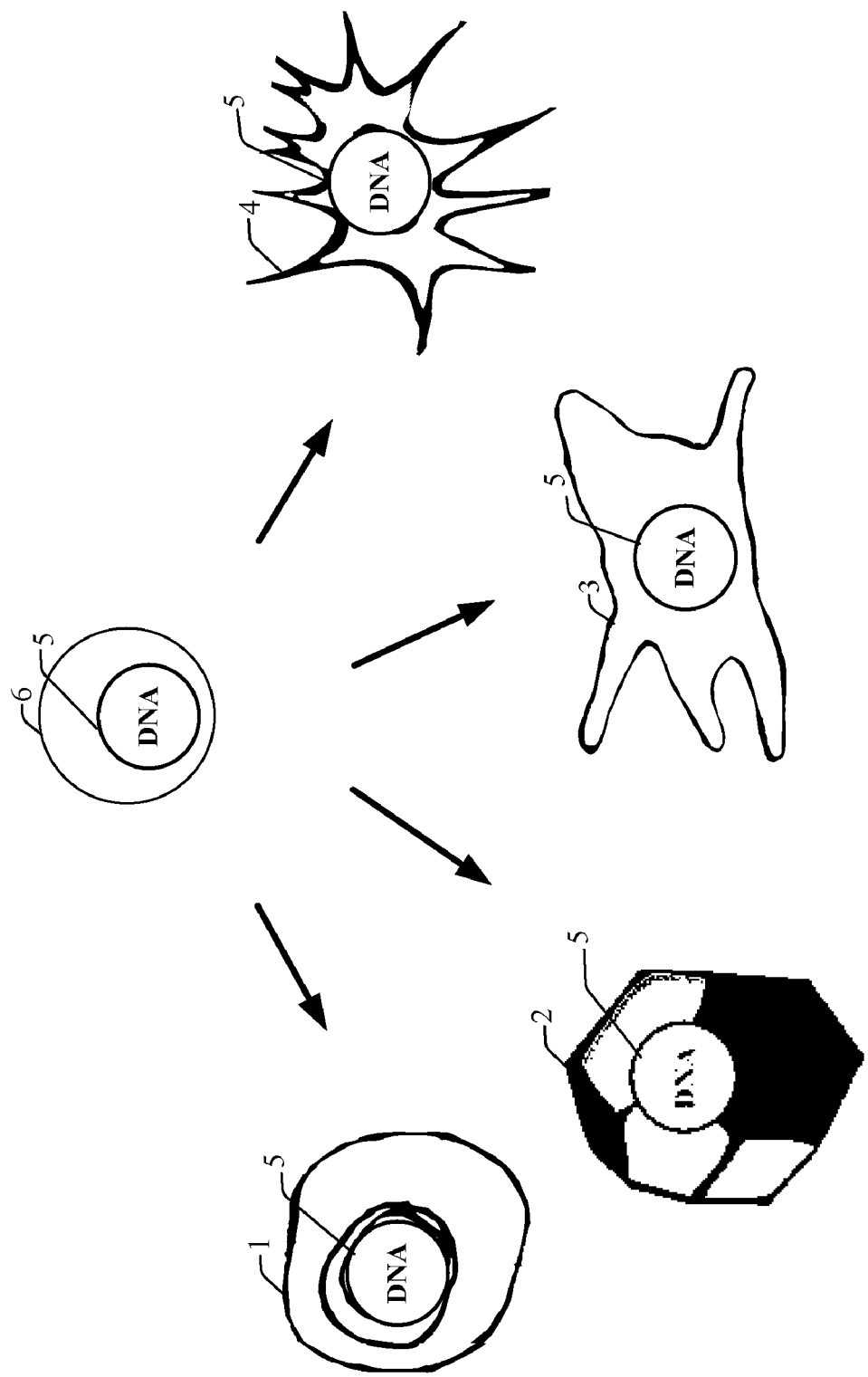

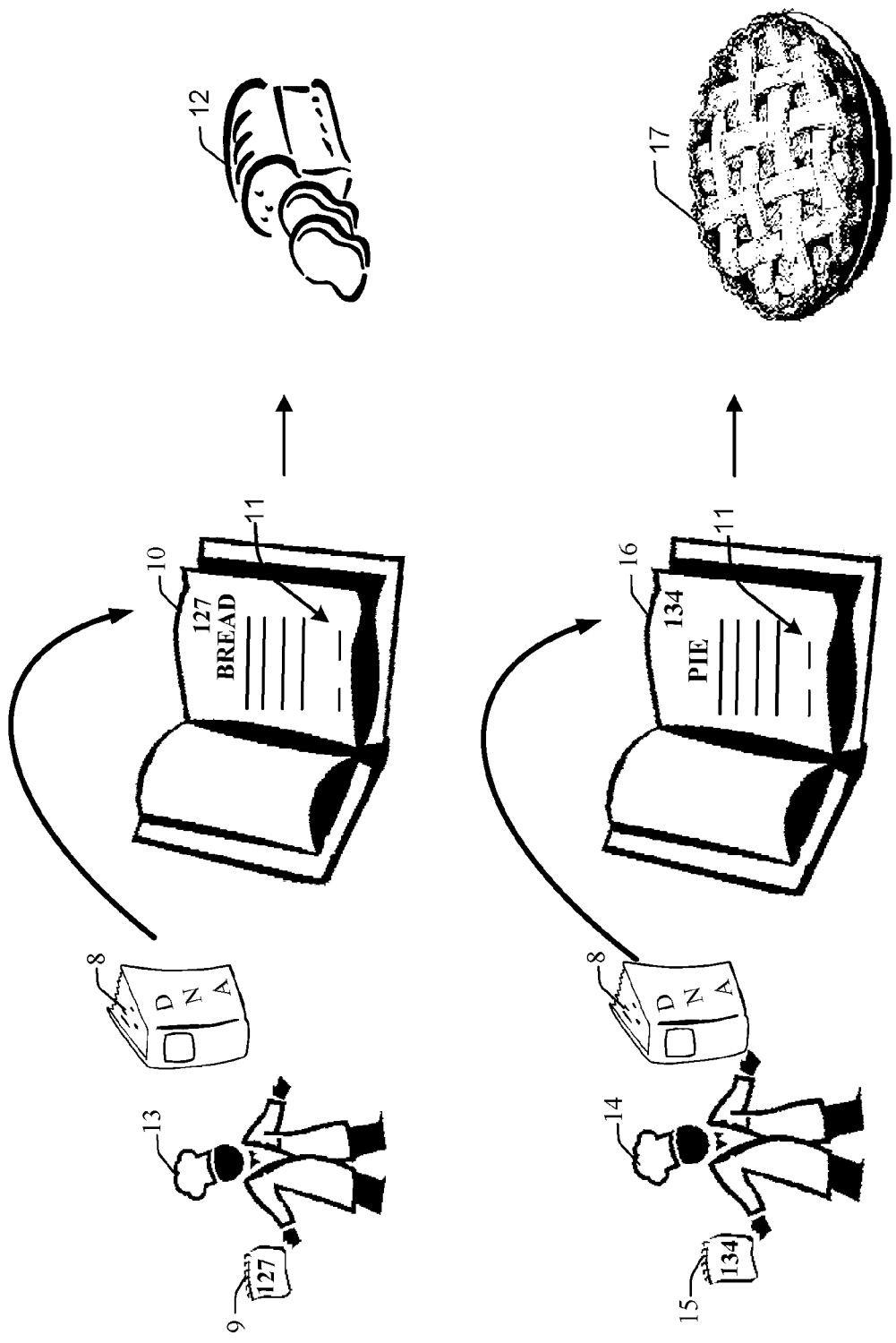

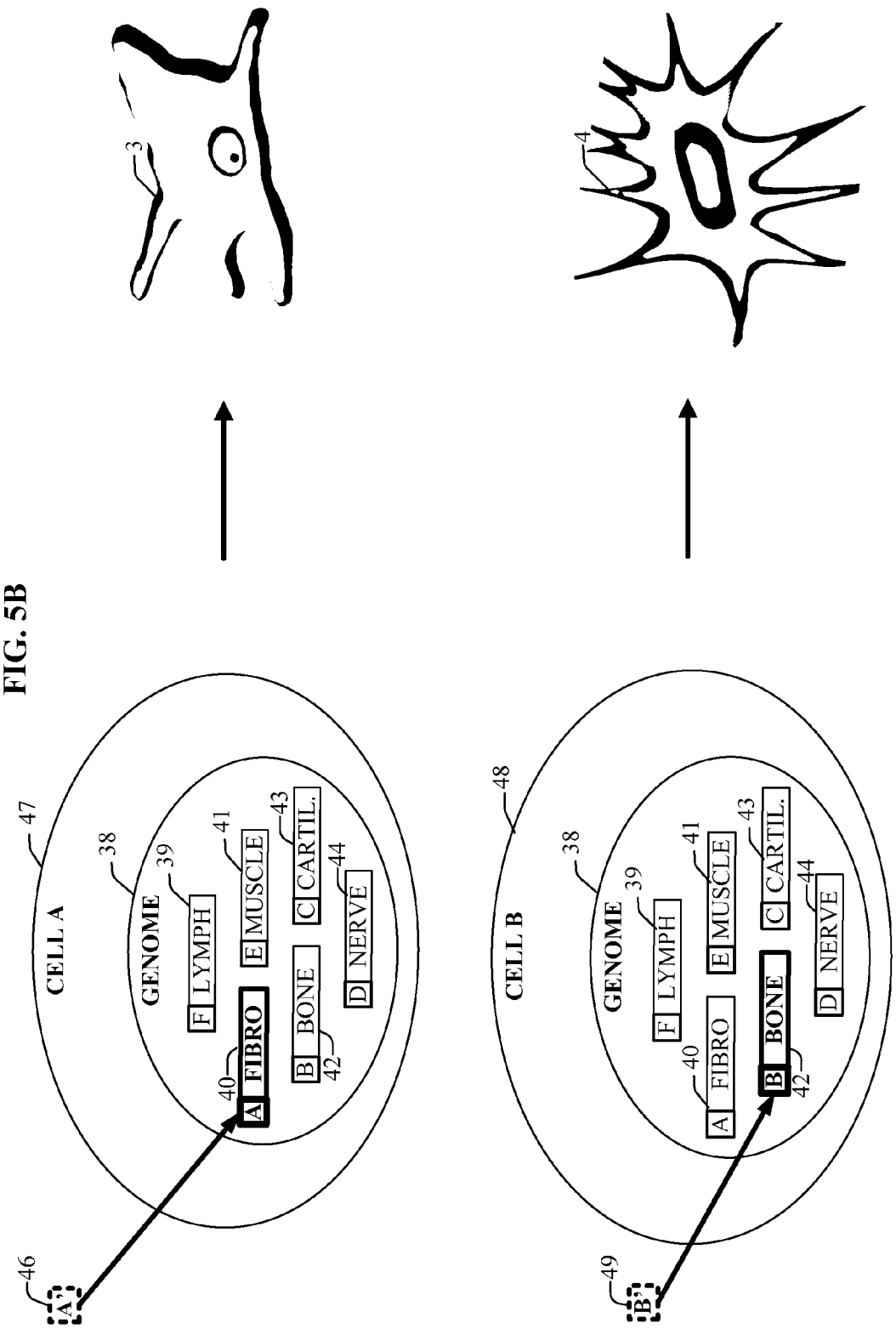

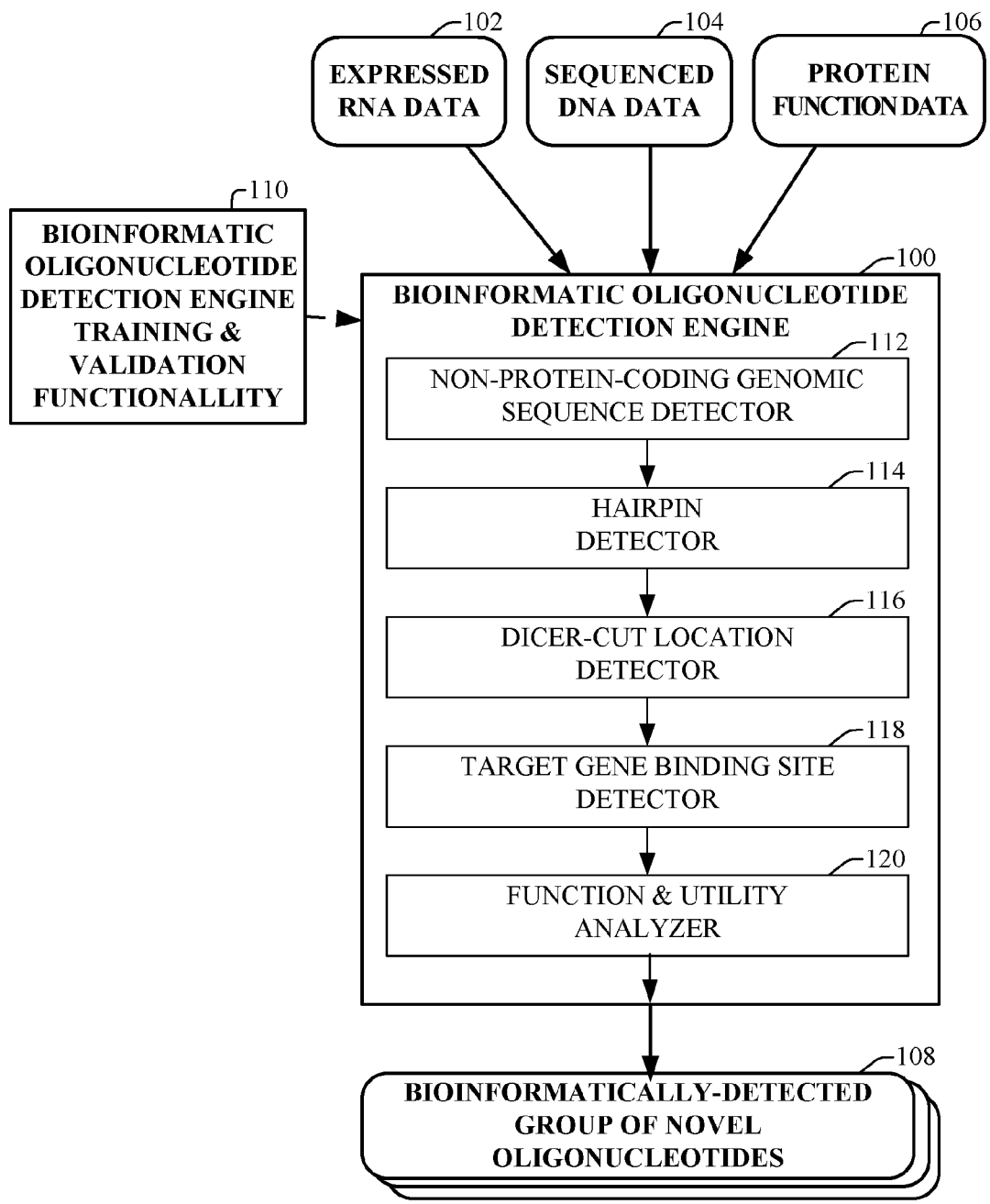

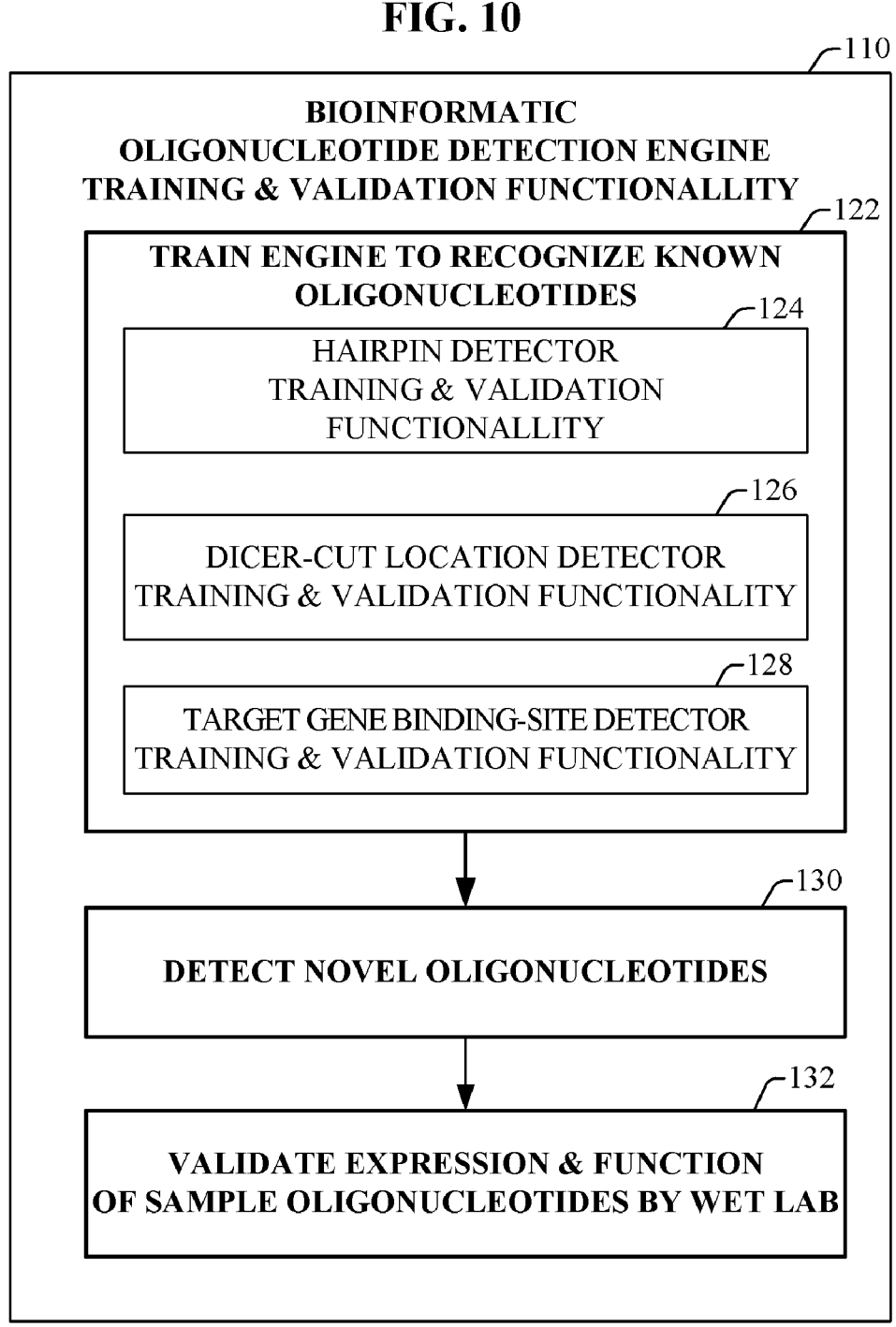

FIG. 22

| ROW | PRIMER SEQUENCE | SEQ ID NO | SEQUENCED SEQENCE | SEQ ID NO | PREDICTED GAM RNA | SEQ ID NO | DIST-ANCE | GAM NAME |
|---|---|---|---|---|---|---|---|---|
| 1* | AATTGCTTGAAC | 10,068,194 | CCAGGAAGTGGA | 10,068,223 | AATTGCTTGAACCCAGGAAGTGGA | 10,068,252 | 0 | 25-A |
| 2* | ACTGCACTCC | 10,068,195 | AGCCTGGGC | 10,068,224 | ACTGCACTCCAGCCTGGGCTAC | 10,068,253 | 0 | 351661-A |
| 3 | CACTGCACTC | 10,068,196 | CAGCCCGAGCAACA | 10,068,225 | CACTGCACTCCAGCCCGAGCAA | 10,068,254 | 0 | 351946-A |
| 4 | CTAGACTGAAG | 10,068,197 | CTCCTTGAGGAC | 10,068,226 | CTAGACTGAAGCTCCTTGAGGA | 10,068,255 | 0 | 352759-A |
| 5 | GAAGTTTGAAG | 10,068,198 | CCTGTTGTTCA | 10,068,227 | GAAGTTTGAAGCCTGTTGTTCA | 10,068,256 | 0 | 4426-A |
| 6 | TCACTGCAAC | 10,068,199 | CTCCACCA | 10,068,228 | (TCACTGCAACCTCCACCACGTG), (TCACTGCAACCTCCACCAGCCT) | 10,068,257 | 0 | (357950-A),(352721-A) |
| 7* | TCTAAGAGAAAG | 10,068,200 | GAAGTTCAGA | 10,068,229 | TCTAAGAGAAAGGAAGTTCAGA | 10,068,258 | 0 | 337950-A |
| 8 | GGGCAGTGGA | 10,068,201 | GCTGGAA | 10,068,230 | GGGCGTGGAGCTGGAATGATGT | 10,068,259 | 1 | 351996-A |
| 9 | AATTGCTTGAAC | 10,068,202 | CCAAGAAGTGGA | 10,068,231 | AATCACTTGAACCCAAGAAGTG | 10,068,260 | 2 | 351874-A |
| 10 | AGCAGCCCA | 10,068,203 | GGGTTTTGT | 10,068,232 | AGCAAGACCAGGGTTTTGTGTT | 10,068,261 | 2 | 352083-A |
| 11 | AGGCAAGACG | 10,068,204 | GACCAGA | 10,068,233 | AGGCAGAGGAGGACCAGAGACT | 10,068,262 | 2 | 351944-A |
| 12 | AGGGAAAGAAT | 10,068,205 | TAATGTGAA | 10,068,234 | GGGAAATAATTAATGTGAAGTC | 10,068,263 | 2 | 353325-A |
| 13 | AGGGAAAGAAT | 10,068,206 | TAATGTGAG | 10,068,235 | AGGAAAAAAATTAATGTGAGTC | 10,068,264 | 2 | 352649-A |
| 14 | ATTCAGTTG | 10,068,207 | CCCATGTTT | 10,068,236 | (ATTCATTGCCCATGTTTG), (TATTCATGCCCATGGTGA) | 10,068,265 | 2 | A),(352957-A,352960-A) |
| 15 | CTAGACTGAAG | 10,068,208 | CTCCTTGAGG | 10,068,237 | CTGGACTGAGCTCCTTGAGGCC | 10,068,266 | 2 | 352288-A |
| 16 | TTCAGAGTGGT | 10,068,209 | TAAGTTCTG | 10,068,238 | TTCTGATGGTTAAGTTCTGTCA | 10,068,267 | 2 | 353875-A |
| 17 | TTCAGAGTGGT | 10,068,210 | TAAGTTCTGC | 10,068,239 | TTCAAGTGTTTAAGTTCTGCTT | 10,068,268 | 2 | 351940-A |
| 18 | AGCAGCCCA | 10,068,211 | GAAGGAAGC | 10,068,240 | AGGCCAAGAAGGAAGCAGAGG | 10,068,269 | 3 | 352496-A |
| 19 | AGTTTGCCTTG | 10,068,212 | TAAGAAAAG | 10,068,241 | AGTTTGTGTAAGAAAAGC | 10,068,270 | 3 | 352518-A |
| 20 | ATCAGAGGGTG | 10,068,213 | GGTGCTAA | 10,068,242 | ATTAGGAGAGTGGGTGCTAAGT | 10,068,271 | 3 | 352511-A |
| 21 | ATGGTGGGAG | 10,068,214 | AGTTTGTCAGT | 10,068,243 | TGGAGGAGAGTTTGTCAGTATAG | 10,068,272 | 3 | 353484-A |
| 22 | CCCAGGAAG | 10,068,215 | TGGAGCCTGGGC | 10,068,244 | CCCGGGTGGAGCCTGGGCTGTG | 10,068,273 | 3 | 351990-A |
| 23 | GGGCAGTGGA | 10,068,216 | GGTCCGT | 10,068,245 | AGGGACAGGAGGTCCGTCCCTTC | 10,068,274 | 3 | 353880-A |
| 24 | GGGCAGTGGA | 10,068,217 | TCTAGAC | 10,068,246 | GTGACAGTGAATCTAGACAGAC | 10,068,275 | 3 | 352810-A |
| 25 | TCAAGCTCATTC | 10,068,218 | CACTAAA | 10,068,247 | CTCAGCTCATCCACTAAATACCC | 10,068,276 | 3 | 353184-A |
| 26 | TGGAAAGTT | 10,068,219 | GGTTGTATGGTT | 10,068,248 | GGAATGGTGGTTGTATGGTTG | 10,068,277 | 3 | 353855-A |
| 27 | TGGAGAGTT | 10,068,220 | CCATATTTTG | 10,068,249 | TGATAGATCCATATTTTGGTAA | 10,068,278 | 3 | 352004-A |
| 28 | TGGAGAGTT | 10,068,221 | GTTTGTACAGT | 10,068,250 | TGGGTTTTGTTTGTACAGTGTA | 10,068,279 | 3 | 353160-A |
| 29 | TCACTGCAAC | 10,068,222 | CTCCACC | 10,068,251 | TCACTGCAACCTCCACCTTCCG | 10,068,280 | 0 | 353856-A |

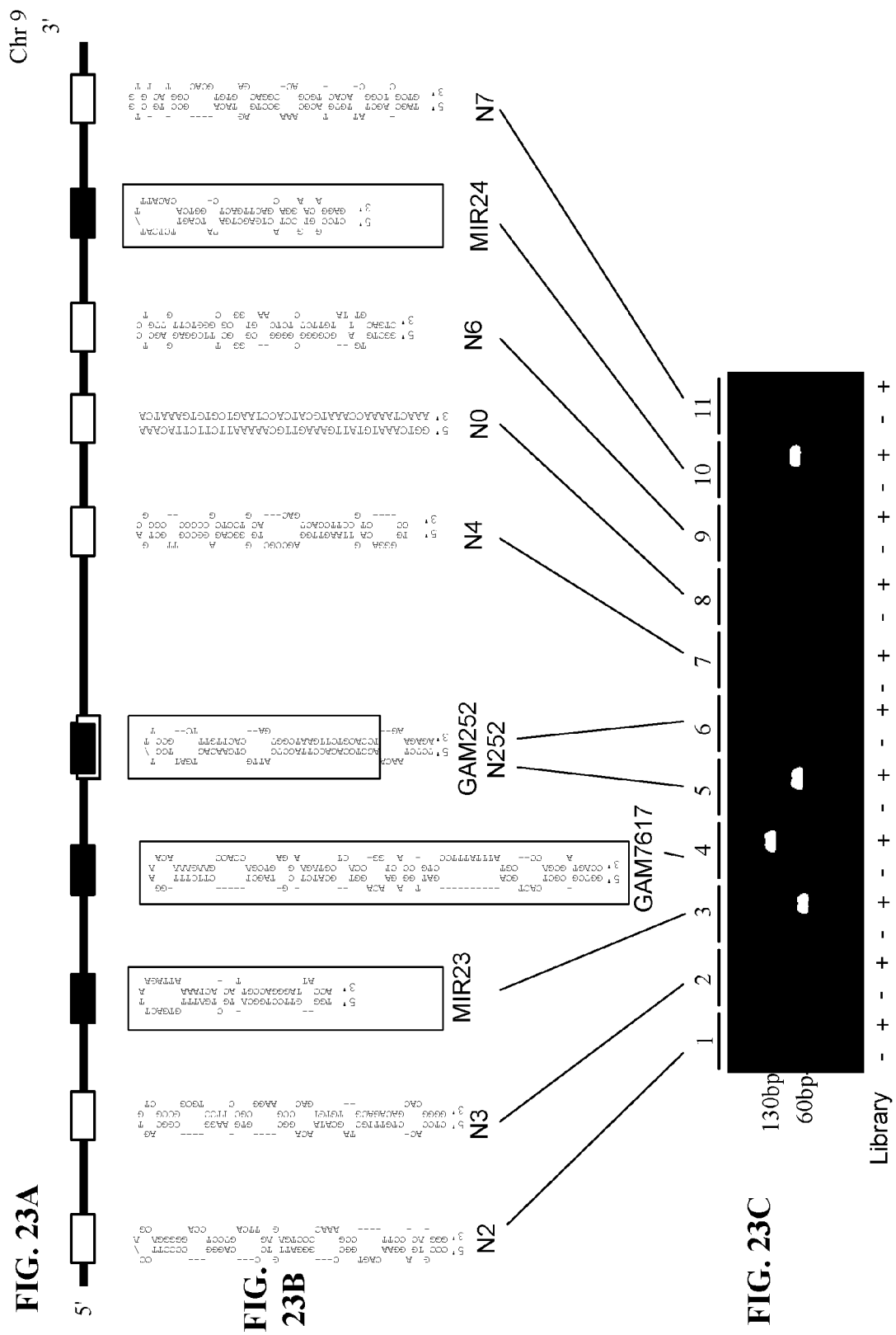

FIG. 24A

EST72223 (705 nt.)

Chr.X

5'─────▭──────────────────────────▭─────3'
     MIR98                                              GAM25

EST72223 sequence:

CCCTTATTAGAGGATTCTGCTCATGCCAGG**GTGAGGTAGTAAGTTGTATTG
TTGTGGGGTAGGGATATTAGGCCCCAATTAGAAGATAACTATACAACT** MIR98
TACTACTTTCCCTGGTGTGTGGCATATTCACACTTAGTCTTAGCAGTGTTGCC
TCCATCAGACAAAGTTGTAGATGTTCCTTGGATAATTTGGACTGGAAGAAAAGA
GACATGGAAGGGGACAGATGGTGTTTAGGGTGAGGCAGATGTCATTATAAAGT
GACTTGTCTTTCATTAATTGGAGCATATAATTATTTTACCTTTGGGCATGAACTC
ATTTTGCTATTCTTCAACTGTGTAATGATTGCATTTTATTAGTAATAGAACAGGA
ATGTGTGCAAGGGAATGGAAAGCATACTTTAAGAATTTTGGGCCAGGCGCGGT
GGTTCATGCCTGTAATCCCAGCATTTTTGGGAGGCCGAGGCGGGTGGATCAC
CTGAGGTCAGGAGTTCGAGACCAACCTGGCCAACACGGCGAAACCCCGCCTC
TACTCAAATACAAAAATTAGCCAGGCTTGGTGACACTCGCCTGTGGTCCCAGC
TACTCAGGAGGCTGAGGCAGGAGAATTGCTTGAACCCAGGAAGTGGAG GAM25
**GCTTCAGTGAGCTGAGAACACGCCACTGCACTCCAGTCCTGGGCAAC
AGAGCAAGACTCTGTCTC**AGGAAAAAAAAAG

FIG. 24B

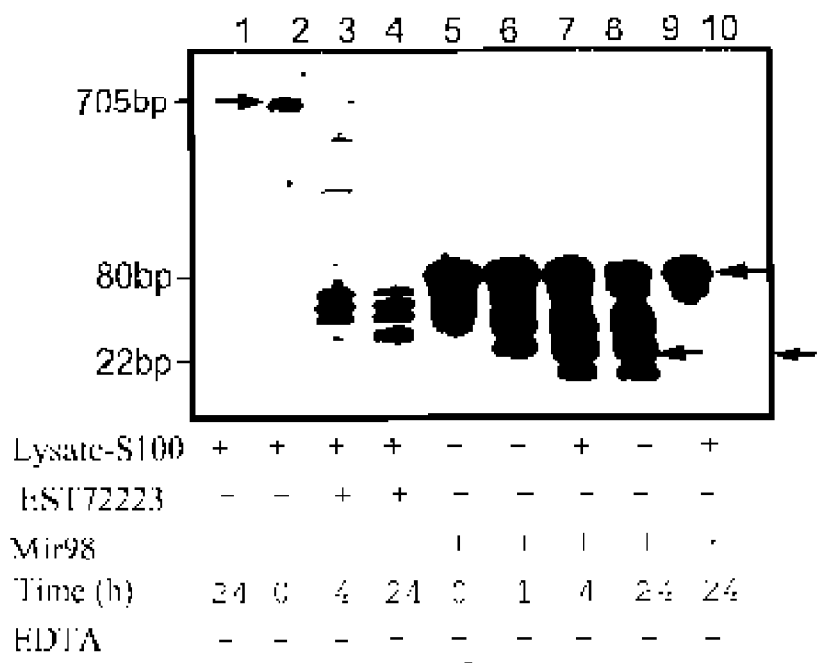

FIG. 25D

| P R E # | PREDICTED PRECURSOR SEQUENCE | SEQ ID | PRIMER 1 TYPE/NAME | PRIMER 1 SEQUENCE | SEQ ID | PRIMER 2 TYPE/NAME | PRIMER 2 SEQUENCE | SEQ ID | METHOD | OBSERVED SEQUENCE | GAM NAME |
|---|---|---|---|---|---|---|---|---|---|---|---|
| 1 | AATGCTGAGTCCT GTGAGTCTTCCTA GCAAATCAAATCT GGAAGGGGTCTTG AGGACTCCAGCATT | 10,068,297 | F STEM 1 3 | GAGTCCTG TGAGTCTT CCTAGC | 10,068,300 | R STEM 1 3 | TGCTGGAGT CCTCAAGA CC | 10,068,303 | A | | |
| 2 | TGAGCCCTCAGCC CTCATGGCTTTCC CGATGCTCACCGG TGCAGAGGAGCC AGCTGGGGAGCCT CTGT | 10,068,298 | R LOOP 2 1 | AAAGCCAT GAGGGCTG AGG | 10,068,301 | R STEM 2 1 | GTGAGCAT CGGGAAAG CCA | 10,068,304 | B | | |
| 3 | ACTGTTGGTCTTC TGTTTAGCCATTA TTCTCAGTTCTGT GCAGGAGTGAGCT GAAACAAAGTTGT ATAGCCCAGAGA GTGAGAAGCTGCA TTTCATGTCTCCC AACAGT | 10,068,299 | F STEM 3 3 | TTCTCAGT TCTGTGTCA GGAGTG | 10,068,302 | R STEM 3 3 | CTTCTCACT CTCTGGGC TATAC | 10,068,305 | A | | |

FIG. 27C

| MIRNA NAME | HELA | BRAIN | LIVER | THYMUS | TESTES | PLACENTA | REFERENCE |
|---|---|---|---|---|---|---|---|
| HSA-MIR-124A | 1879 | 65517 | 7025 | 3099 | 2672 | 2498 | 1,3 |
| HSA-MIR-9 | 642 | 42659 | 3504 | 4455 | 4485 | 2313 | 2,3 |
| HSA-MIR-128A | 2015 | 27701 | 4940 | 4876 | 5166 | 2495 | 3 |
| HSA-MIR-129 | 503 | 22573 | 1175 | 2213 | 5364 | 2017 | 3 |
| HSA-MIR-128B | 1168 | 21969 | 3954 | 4819 | 5383 | 2027 | |
| HSA-MIR-122A | 1051 | 447 | 65518 | 2644 | 617 | 570 | 1,3 |
| HSA-MIR-194 | 501 | 910 | 65518 | 4737 | 2342 | 7952 | 3 |
| HSA-MIR-148 | 413 | 620 | 38436 | 5250 | 6204 | 2711 | |
| HSA-MIR-192 | 452 | 606 | 20650 | 1628 | 1263 | 2607 | |
| HSA-MIR-96 | 887 | 3100 | 1477 | 44800 | 2266 | 5466 | |
| HSA-MIR-150 | 648 | 1463 | 5295 | 65518 | 29728 | 5280 | |
| HSA-MIR-205 | 551 | 615 | 1646 | 65518 | 2645 | 39072 | |
| HSA-MIR-182 | 662 | 1944 | 1091 | 25771 | 2034 | 3683 | |
| HSA-MIR-183 | 1026 | 1123 | 1286 | 8754 | 1681 | 2138 | |
| HSA-MIR-204 | 525 | 3898 | 1757 | 6535 | 64859 | 6233 | |
| HSA-MIR-10B | 410 | 433 | 477 | 3871 | 23083 | 738 | |
| HSA-MIR-154 | 438 | 733 | 1914 | 3309 | 14750 | 9637 | |
| HSA-MIR-134 | 448 | 617 | 698 | 763 | 2250 | 997 | |
| HSA-MIR-224 | 3233 | 11061 | 7684 | 32305 | 5377 | 65518 | |
| HSA-MIR-210 | 844 | 2280 | 10703 | 6864 | 15288 | 62452 | |
| HSA-MIR-221 | 625 | 9325 | 3520 | 20212 | 10608 | 54287 | |
| HSA-MIR-141 | 696 | 805 | 1220 | 4063 | 2000 | 46845 | |
| HSA-MIR-23A | 1312 | 3492 | 2990 | 6021 | 11173 | 40076 | |
| HSA-MIR-200C | 556 | 595 | 1027 | 10636 | 1478 | 33532 | |
| HSA-MIR-136 | 465 | 725 | 709 | 776 | 3100 | 8840 | |

1 LAGOS-QUINTANA ET AL., CURRENT BIOLOGY 12:735 (2002)
2 KRICHEVSKY ET AL., RNA 9:1274 (2003)
3 SEMPERE ET AL., GENOME BIOLOGY 5:R13 (2004)

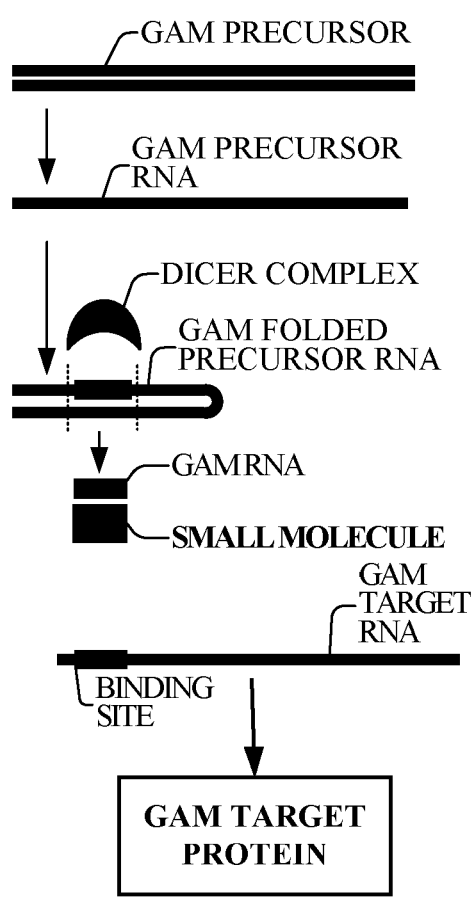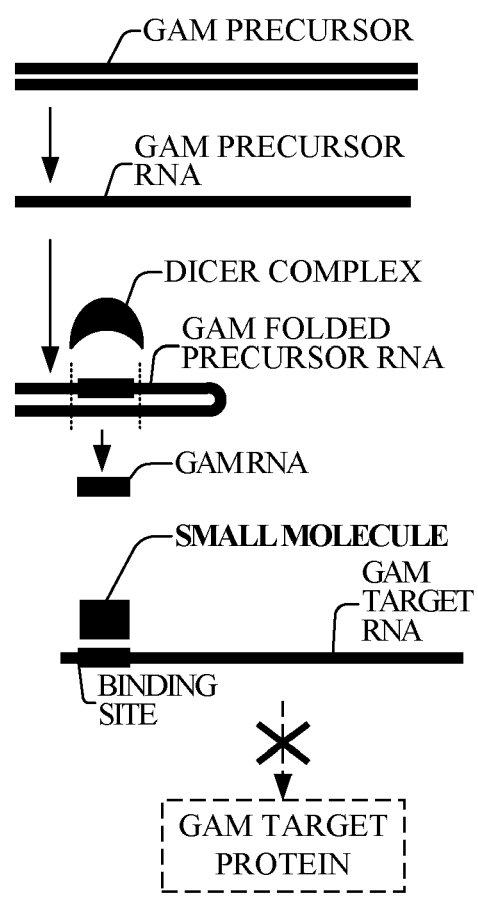

SMALL MOLECULES MODULATING ACTIVITY OF MICRO RNA OLIGONUCLEOTIDES AND MICRO RNA TARGETS AND USES THEREOF

REFERENCES CITED

Altschul, S. F., Gish, W., Miller, W., Myers, E. W., and Lipman, D. J. (1990). Basic local alignment search tool. J. Mol. Biol. 215, 403-410.

Dan Gusfield, Algorithms on strings, trees, and sequences: computer science and computational biology, Cambridge University Press, 1997.

Elbashir, S. M., Lendeckel, W., and Tuschl, T. (2001). RNA interference is mediated by 21- and 22-nucleotide RNAs. Genes Dev. 15, 188-200.

Gussow, D. and Clackson, T. (1989). Direct clone characterization from plaques and colonies by the polymerase chain reaction. Nucleic Acids Res. 17, 4000.

Hamosh A, Scott A F, Amberger J, Bocchini C, Valle D and McKusick V A. (2002). Online Mendelian Inheritance in Man (OMIM), a knowledgebase of human genes and genetic disorders. Nucleic Acids Res. 30: 52-55.

Jenuth J. P. (2000). The NCBI. Publicly available tools and resources on the Web. Methods Mol. Biol. 132, 301-312.

Kirkness, E. F. and Kerlavage, A. R. (1997). The TIGR human cDNA database. Methods Mol. Biol. 69, 261-268.

Lagos-Quintana, M., Rauhut, R., Lendeckel, W., and Tuschl, T. (2001). Identification of novel genes coding for small expressed RNAs. Science 294, 853-858.

Lau, N. C., Lim, L. P., Weinstein, E. G., and Bartel, D. P. (2001). An abundant class of tiny RNAs with probable regulatory roles in Caenorhabditis elegans. Science 294, 858-862.

Mathews, D. H., Sabina, J., Zuker, M., and Turner, D. H. (1999). Expanded sequence dependence of thermodynamic parameters improves prediction of RNA secondary structure. J. Mol. Biol. 288, 911-940.

Reinhart, B. J., Slack, F. J., Basson, M., Pasquinelli, A. E., Bettinger J. C., Rougvie, A. E., Horvitz, H. R., and Ruvkun, G. (2000). The 21-nucleotide let-7 RNA regulates developmental timing in Caenorhabditis elegans. Nature 403, 901-906.

Southern, E. M. (1992). Detection of specific sequences among DNA fragments separated by gel electrophoresis. 1975. Biotechnology 24, 122-139.

Tom M. Mitchell, Machine Learning, McGraw Hill, 1997.

Wightman, B., Ha, I., and Ruvkun, G. (1993). Posttranscriptional regulation of the heterochronic gene lin-14 by lin-4 mediates temporal pattern formation in C. elegans. Cell 75, 855-862.

BACKGROUND OF THE INVENTION

1. Field of the Invention

The present invention relates to a group of bioinformatically detectable novel human oligonucleotides, here identified as "Genomic Address Messenger" (GAM) oligonucleotides.

All of abovementioned oligonucleotides are believed to be related to the microRNA (miRNA) group of oligonucleotides.

2. Description of Prior Art miRNA oligonucleotides are short ~22 nucleotide (nt) long, non-coding, regulatory RNA oligonucleotides that are found in a wide range of species. miRNA oligonucleotides are believed to function as specific gene translation repressors and are sometimes involved in cell differentiation.

The ability to detect novel miRNA oligonucleotides is limited by the methodologies used to detect such oligonucleotides. All miRNA oligonucleotides identified so far either present a visibly discernable whole body phenotype, as do Lin-4 and Let-7 (Wightman, B., Ha, I., and Ruvkun, G., Cell 75: 855-862 (1993); Reinhart et al. Nature 403: 901-906 (2000)), or produce sufficient quantities of RNA so as to be detected by standard molecular biological techniques.

Ninety-three miRNA oligonucleotides have been discovered in several species (Lau et al., Science 294: 858-862 (2001), Lagos-Quintana et al., Science 294: 853-858 (2001)) by sequencing a limited number of clones (300 by Lau and 100 by Lagos-Quintana) of size-fractionated small segments of RNA. miRNAs that were detected in these studies therefore represent the more prevalent among the miRNA oligonucleotide family and cannot be much rarer than 1% of all small ~20 nt-long RNA oligonucleotides.

The aforementioned studies provide no basis for the detection of miRNA oligonucleotides which either do not present a visually discernable whole body phenotype, or are rare (e.g. rarer than 0.1% of all of the size-fractionated, ~20 nt-long RNA segments that were expressed in the tissues examined), and therefore do not produce large enough quantities of RNA to be detected by standard biological techniques.

The following U.S. Patents relate to bioinformatic detection of genes: U.S. patent Ser. No. 10/348,935, entitled "Statistical algorithms for folding and target accessibility prediction and design of nucleic acids", U.S. Pat. No. 6,369,195, entitled "Prostate-specific gene for diagnosis, prognosis and management of prostate cancer", and U.S. Pat. No. 6,291,666 entitled "Spike tissue-specific promoter", each of which is hereby incorporated by reference herein.

BRIEF DESCRIPTION OF SEQUENCE LISTING, TABLES AND COMPUTER PROGRAM LISTING

Reference is made to the appendix submitted herein. The appendix contains the following:

"Patent25_US_10_709577_Sequence_Listing_Jan_2007_Amended_tmp_1001.txt" (550,001 KB), "Patent25_US_10_709577_Sequence_Listing_Jan_2007_Amended_tmp_1002.txt" (550,000 KB), "Patent25_US_10_709577_Sequence_Listing_Jan_2007_Amended_tmp_1003.txt" (439,301 KB), which were created Jul. 27, 2008, which altogether are a sequence listing in accordance with 37 C.F.R. §§ 1.821-1.825, the contents of which are incorporated by reference herein.

Tables relating to genomic sequences are attached to the present application, appear in 21 files (size, creation date), incorporated herein: TABLE_1.txt (572 MB, 13-May-04), TABLE_2_A.txt (619 MB, 13-May-04), TABLE_2_B.txt (619 MB, 13-May-04), TABLE_2_C.txt (111 MB, 13-May-04), TABLE_3.txt (22.1 MB, 13-May-04); TABLE_4.txt (62.3 MB, 13-May-04), TABLE_5.txt (27.4 MB, 13-May-04), TABLE_6_A.txt (619 MB, 13-May-04), TABLE_6_B.txt (50.3 MB, 13-May-04), TABLE_7_A.txt (619 MB, 13-May-04), TABLE_7_B.txt (571 MB, 13-May-04), TABLE_8_A.txt (619 MB, 13-May-04), TABLE_8_B.txt (619 MB, 13-May-04), TABLE_9.txt (10.2 MB, 13-May-04), TABLE_10.txt (123 MB, 13-May-04), TABLE_11.txt (79.8 MB, 13-May-04), TABLE_12.txt (75 KB, 13-May-04), TABLE_13.txt (285 KB, 14-May-04), TABLE_14.txt (68 KB, 13-May-04) and TABLE_15.txt (75 KB, 13-May-04) all of which are incorporated by reference herein.

LENGTHY TABLES

The patent contains a lengthy table section. A copy of the table is available in electronic form from the USPTO web site (http://seqdata.uspto.gov/?pageRequest=docDetail&DocID=US07687616B1). An electronic copy of the table will also be available from the USPTO upon request and payment of the fee set forth in 37 CFR 1.19(b)(3).

A computer program listing constructed and operative in accordance with a preferred embodiment of the present invention is enclosed on an electronic medium in computer readable form, and is hereby incorporated by reference herein. The computer program listing is contained in 6 files, the name, sizes and creation date of which are as follows: AUXILARY_FILES.txt (117K, 14-Nov-03); EDIT_DIS-TANCE.txt (144K, 24-Nov-03); FIRST-K.txt (96K, 24-Nov-03); HAIRPIN_PREDICTION.txt (19K, 25-Mar-04); TWO_PHASED_SIDE_SELECTOR.txt (4K, 14-Nov-03); TWO_PHASED_PREDICTOR.txt (74K, 14-Nov-03), and BS_CODE.txt (118K, 11-May-04).

SUMMARY OF THE INVENTION

The present invention discloses 122,764 novel human regulatory microRNA-like (miRNA) oligonucleotides referred to here as Genomic Address Messenger (GAM) oligonucleotides, which GAM oligonucleotides are detectable using a novel bioinformatic approach, and go undetected by conventional molecular biology methods. Each GAM oligonucleotide specifically inhibits translation of one of more target genes by hybridization of an RNA transcript encoded by the GAM, to a site located in an untranslated region (UTR) of the mRNA of one or more of the target genes. Also disclosed are 18,602 novel microRNA-cluster like polynucleotides, referred to here as Genomic Record (GR) polynucleotides.

Accordingly, the invention provides several substantially pure nucleic acids (e.g., genomic DNA, cDNA or synthetic DNA) each comprising a novel human GAM oligonucleotide, vectors comprising the DNAs, probes comprising the DNAs, a method and system for bioinformatic detection of GAM oligonucleotides and their respective targets, laboratory methods for validating expression of GAM oligonucleotides, and a method and system for selectively modulating translation of known target genes of the GAM oligonucleotides.

The present invention describes a novel approach whereby small molecules may be used to modulate activity of microRNA and GAM oligonucleotides. This mode of therapy allows inter alia up regulation of a disease-related target gene of novel GAM oligonucleotides of the present invention, by countering the activity of a GAM oligonucleotides which naturally inhibits expression of that target gene.

The present invention further represents a scientific breakthrough, disclosing novel miRNA-like oligonucleotides the number of which is dramatically larger than previously believed existed. Prior-art studies reporting miRNA oligonucleotides ((Lau et al., Science 294:858-862 (2001), Lagos-Quintana et al., Science 294: 853-858 (2001)) discovered 93 miRNA oligonucleotides in several species, including 21 in human, using conventional molecular biology methods, such as cloning and sequencing.

Molecular biology methodologies employed by these studies are limited in their ability to detect rare miRNA oligonucleotides, since these studies relied on sequencing of a limited number of clones (300 clones by Lau and 100 clones by Lagos-Quintana) of small segments (i.e. size-fractionated) of RNA. miRNA oligonucleotides detected in these studies therefore, represent the more prevalent among the miRNA oligonucleotide family, and are typically not be much rarer than 1% of all small ~20 nt-long RNA oligonucleotides present in the tissue from the RNA was extracted.

Recent studies state the number of miRNA oligonucleotides to be limited, and describe the limited sensitivity of available methods for detection of miRNA oligonucleotides: "The estimate of 255 human miRNA oligonucleotides is an upper bound implying that no more than 40 miRNA oligonucleotides remain to be identified in mammals" (Lim et al., Science, 299:1540 (2003)); "Estimates place the total number of vertebrate miRNA genes at about 200-250" (Ambros et al. Curr. Biol. 13:807-818 (2003)); and "Confirmation of very low abundance miRNAs awaits the application of detection methods more sensitive than Northern blots" (Ambros et al. Curr. Biol. 13:807-818 (2003)).

The oligonucleotides of the present invention represent a revolutionary new dimension of genomics and of biology: a dimension comprising a huge number of non-protein-coding oligonucleotides which modulate expression of thousands of proteins and are associated with numerous major diseases. This new dimension disclosed by the present invention dismantles a central dogma that has dominated life-sciences during the past 50 years, a dogma which has emphasized the importance of protein-coding regions of the genome, holding non-protein-coding regions to be of little consequence, often dubbing them "junk DNA".

Indeed, only in November, 2003 has this long held belief as to the low importance of non-protein-coding regions been vocally challenged. As an example, an article titled "The Unseen Genome—Gems in the Junk" (Gibbs, W. W. Sci. Am. 289:46-53 (2003)) asserts that the failure to recognize the importance of non-protein-coding regions "may well go down as one of the biggest mistakes in the history of molecular biology". Gibbs further asserts that "what was damned as junk because it was not understood, may in fact turn out to be the very basis of human complexity. The present invention provides a dramatic leap in understanding specific important roles of non-protein-coding regions.

An additional scientific breakthrough of the present invention is a novel conceptual model disclosed by the present invention, which conceptual model is preferably used to encode in a genome the determination of cell-differentiation, utilizing oligonucleotides and polynucleotides of the present invention.

Using the bioinformatic engine of the present invention, 122,764 GAM oligonucleotides and their respective precursors and targets have been detected. These bioinformatic predictions are supported by robust biological studies. Microarray experiments validated expression of 2,534 GAM oligonucleotides out of a sample of 8,244 tested. Of these, 1,114 GAM oligonucleotides scored extremely highly: over six standard deviations higher than the background noise of the microarray, and over two standard deviations above their individual mismatch control probes. Thirty eight GAM oligonucleotides were sequenced.

In various preferred embodiments, the present invention seeks to provide an improved method and system for specific modulation of the expression of specific target genes involved in significant human diseases. It also provides an improved method and system for detection of the expression of novel oligonucleotides of the present invention, which modulate these target genes. In many cases, the target genes may be known and fully characterized, however in alternative embodiments of the present invention, unknown or less well characterized genes may be targeted.

A "Nucleic acid" is defined as a ribonucleic acid (RNA) molecule, or a deoxyribonucleic acid (DNA) molecule, or complementary deoxyribonucleic acid (cDNA), comprising either naturally occurring nucleotides or non-naturally occurring nucleotides.

"Substantially pure nucleic acid", "Isolated Nucleic Acid", "Isolated Oligoucleotide" and "Isolated Polynucleotide" are defined as a nucleic acid that is free of the genome of the organism from which the nucleic acid is derived, and include, for example, a recombinant nucleic acid which is incorporated into a vector, into an autonomously replicating plasmid or virus, or into the genomic nucleic acid of a prokaryote or eukaryote at a site other than its natural site; or which exists as a separate molecule (e.g., a cDNA or a genomic or cDNA fragment produced by PCR or restriction endonuclease digestion) independent of other nucleic acids.

An "Oligonucleotide" is defined as a nucleic acid comprising 2-139 nts, or preferably 16-120 nts. A "Polynucleotide" is defined as a nucleic acid comprising 140-5000 nts, or preferably 140-1000 nts.

A "Complementary" sequence is defined as a first nucleotide sequence which reverses complementary of a second nucleotide sequence: the first nucleotide sequence is reversed relative to a second nucleotide sequence, and wherein each nucleotide in the first nucleotide sequence is complementary to a corresponding nucleotide in the second nucleotide sequence (e.g. ATGGC is the complementary sequence of GCCAT).

"Hybridization", "Binding" and "Annealing" are defined as hybridization, under in-vivo physiological conditions, of a first nucleic acid to a second nucleic acid, which second nucleic acid is at least partially complementary to the first nucleic acid.

A "Hairpin Structure" is defined as an oligonucleotide having a nucleotide sequence that is 50-140 nts in length, the first half of which nucleotide sequence is at least partially complementary to the second part thereof, thereby causing the nucleic acid to fold onto itself, forming a secondary hairpin structure.

A "Hairpin-Shaped Precursor" is defined as a Hairpin Structure which is processed by a Dicer enzyme complex, yielding an oligonucleotide which is about 19 to about 24 nts in length.

"Inhibiting translation" is defined as the ability to prevent synthesis of a specific protein encoded by a respective gene by means of inhibiting the translation of the mRNA of this gene. For example, inhibiting translation may include the following steps: (1) a DNA segment encodes an RNA, the first half of whose sequence is partially complementary to the second half thereof; (2) the precursor folds onto itself forming a hairpin-shaped precursor; (3) a Dicer enzyme complex cuts the hairpin-shaped precursor yielding an oligonucleotide that is approximately 22 nt in length; (4) the oligonucleotide binds complementarily to at least one binding site, having a nucleotide sequence that is at least partially complementary to the oligonucleotide, which binding site is located in the mRNA of a target gene, preferably in the untranslated region (UTR) of a target gene, such that the binding inhibits translation of the target protein.

A "Translation inhibitor site" is defined as the minimal nucleotide sequence sufficient to inhibit translation.

The present invention describes novel miRNA oligonucleotides, detected using a bioinformatic engine described hereinabove. The ability of this detection engine has been demonstrated using stringent algorithmic criteria, showing that the engine has both high sensitivity, indicated by the high detection rate of published miRNAs and their targets, as well as high specificity, indicated by the low amount of "background" hairpin candidates passing its filters. Laboratory tests, based both on sequencing of predicted miRNA oligonucleotides and on microarray experiments, validated 2534 of the miRNA oligonucleotides in the present invention. Further, at least one of these validated miRNA oligonucleotides binds to 1953 of the 2031 target genes described in the present invention.

There is thus provided in accordance with a preferred embodiment of the present invention a bioinformatically detectable isolated oligonucleotide which is endogenously processed from a hairpin-shaped precursor, and anneals to a portion of a mRNA transcript of a target gene, wherein binding of the oligonucleotide to the mRNA transcript represses expression of the target gene, and wherein the oligonucleotide has at least 80% sequence identity with a nucleotide sequence selected from the group consisting of SEQ ID NOs: 1-380 and 6894883-7033873.

There is further provided in accordance with another preferred embodiment of the present invention a bioinformatically detectable isolated oligonucleotide which is endogenously processed from a hairpin-shaped precursor, and anneals to a portion of a mRNA transcript of a target gene selected from the group consisting of genes shown in Table 12, Row 1, wherein binding of the oligonucleotide to the mRNA transcript represses expression of the target gene, and wherein the oligonucleotide has at least 80% sequence identity with a nucleotide sequence selected from the group consisting of SEQ ID NOs: 1-380 and 6894883-7033873.

There is still further provided in accordance with another preferred embodiment of the present invention a bioinformatically detectable isolated oligonucleotide having a nucleotide sequence selected from the group consisting of SEQ ID NOs: 1-380 and 6894883-7033873.

There is additionally provided in accordance with another preferred embodiment of the present invention a bioinformatically detectable first oligonucleotide which is a portion of a mRNA transcript of a target gene, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs: 1-380 and 6894883-7033873.

There is moreover provided in accordance with another preferred embodiment of the present invention a bioinformatically detectable first oligonucleotide which is a portion of a mRNA transcript of a target gene selected from the group consisting of genes shown in Table 12 row 1, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs: 1-380 and 6894883-7033873.

There is further provided in accordance with another preferred embodiment of the present invention a bioinformatically detectable oligonucleotide having a nucleotide sequence selected from the group consisting of SEQ ID NOs: 5054808-6757247.

There is still further provided in accordance with another preferred embodiment of the present invention a bioinformatically detectable isolated oligonucleotide which anneals to a portion of a mRNA transcript of a target gene associated with Multiple Sclerosis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 2.

There is additionally provided in accordance with another preferred embodiment of the present invention a bioinformatically detectable isolated oligonucleotide which anneals to a portion of a mRNA transcript of a target gene associated with Alzheimer, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 3.

There is moreover provided in accordance with another preferred embodiment of the present invention a bioinformatically detectable isolated oligonucleotide which anneals to a portion of a mRNA transcript of a target gene associated with Prostate cancer, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 4.

There is further provided in accordance with another preferred embodiment of the present invention a bioinformatically detectable isolated oligonucleotide which anneals to a portion of a mRNA transcript of a target gene associated with Respiratory Syncytial Virus, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 5.

There is still further provided in accordance with another preferred embodiment of the present invention a bioinformatically detectable isolated oligonucleotide which anneals to a portion of a mRNA transcript of a target gene associated with Inflammatory Bowel Diseases, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 6.

There is additionally provided in accordance with another preferred embodiment of the present invention a bioinformatically detectable isolated oligonucleotide which anneals to a portion of a mRNA transcript of a target gene associated with Chronic obstructive pulmonary disease, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 7.

There is moreover provided in accordance with another preferred embodiment of the present invention a bioinformatically detectable isolated oligonucleotide which anneals to a portion of a mRNA transcript of a target gene associated with Myasthenia Gravis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 8.

There is further provided in accordance with another preferred embodiment of the present invention a bioinformatically detectable isolated oligonucleotide which anneals to a portion of a mRNA transcript of a target gene associated with Nephrogenic diabetes insipidus, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 9.

There is still further provided in accordance with another preferred embodiment of the present invention a bioinformatically detectable isolated oligonucleotide which anneals to a portion of a mRNA transcript of a target gene associated with Carcinoid, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 10.

There is additionally provided in accordance with another preferred embodiment of the present invention a bioinformatically detectable isolated oligonucleotide which anneals to a portion of a mRNA transcript of a target gene associated with Esophageal cancer, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 11.

There is moreover provided in accordance with another preferred embodiment of the present invention a bioinformatically detectable isolated oligonucleotide which anneals to a portion of a mRNA transcript of a target gene associated with Polyposis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 12.

There is further provided in accordance with another preferred embodiment of the present invention a bioinformatically detectable isolated oligonucleotide which anneals to a portion of a mRNA transcript of a target gene associated with Allergic contact dermatitis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 13.

There is still further provided in accordance with another preferred embodiment of the present invention a bioinformatically detectable isolated oligonucleotide which anneals to a portion of a mRNA transcript of a target gene associated with Myopathy, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 14.

There is additionally provided in accordance with another preferred embodiment of the present invention a bioinformatically detectable isolated oligonucleotide which anneals to a portion of a mRNA transcript of a target gene associated with Otitis Media, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 15.

There is moreover provided in accordance with another preferred embodiment of the present invention a bioinformatically detectable isolated oligonucleotide which anneals to a portion of a mRNA transcript of a target gene associated with Lung cancer, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 16.

There is further provided in accordance with another preferred embodiment of the present invention a bioinformatically detectable isolated oligonucleotide which anneals to a portion of a mRNA transcript of a target gene associated with Enterovirus, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 18.

There is still further provided in accordance with another preferred embodiment of the present invention a bioinformatically detectable isolated oligonucleotide which anneals to a portion of a mRNA transcript of a target gene associated with Stroke, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 19.

There is additionally provided in accordance with another preferred embodiment of the present invention a bioinformatically detectable isolated oligonucleotide which anneals to a portion of a mRNA transcript of a target gene associated with Hodgkin Disease, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 20.

There is moreover provided in accordance with another preferred embodiment of the present invention a bioinformatically detectable isolated oligonucleotide which anneals to a portion of a mRNA transcript of a target gene associated with Amyloidosis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 21.

There is further provided in accordance with another preferred embodiment of the present invention a bioinformatically detectable isolated oligonucleotide which anneals to a portion of a mRNA transcript of a target gene associated with Depressive Disorder, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 22.

There is still further provided in accordance with another preferred embodiment of the present invention a bioinformatically detectable isolated oligonucleotide which anneals to a portion of a mRNA transcript of a target gene associated with Clostridium, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 23.

There is additionally provided in accordance with another preferred embodiment of the present invention a bioinformatically detectable isolated oligonucleotide which anneals to a portion of a mRNA transcript of a target gene associated with HIV, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 24.

There is moreover provided in accordance with another preferred embodiment of the present invention a bioinformatically detectable isolated oligonucleotide which anneals to a portion of a mRNA transcript of a target gene associated with Ventricular Fibrillation, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 25.

There is further provided in accordance with another preferred embodiment of the present invention a bioinformatically detectable isolated oligonucleotide which anneals to a portion of a mRNA transcript of a target gene associated with Hyperlipidemia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 26.

There is still further provided in accordance with another preferred embodiment of the present invention a bioinformatically detectable isolated oligonucleotide which anneals to a portion of a mRNA transcript of a target gene associated with Lymphoma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 27.

There is additionally provided in accordance with another preferred embodiment of the present invention a bioinformatically detectable isolated oligonucleotide which anneals to a portion of a mRNA transcript of a target gene associated with Atopic dermatitis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 28.

There is moreover provided in accordance with another preferred embodiment of the present invention a bioinformatically detectable isolated oligonucleotide which anneals to a portion of a mRNA transcript of a target gene associated with Pagets Disease, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 29.

There is further provided in accordance with another preferred embodiment of the present invention a bioinformatically detectable isolated oligonucleotide which anneals to a portion of a mRNA transcript of a target gene associated with Emphysema, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 30.

There is still further provided in accordance with another preferred embodiment of the present invention a bioinformatically detectable isolated oligonucleotide which anneals to a portion of a mRNA transcript of a target gene associated with Ventricular tachycardia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 31.

There is additionally provided in accordance with another preferred embodiment of the present invention a bioinformatically detectable isolated oligonucleotide which anneals to a portion of a mRNA transcript of a target gene associated with Hepatocellular carcinoma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 32.

There is moreover provided in accordance with another preferred embodiment of the present invention a bioinformatically detectable isolated oligonucleotide which anneals to a portion of a mRNA transcript of a target gene associated with Kidney Failure, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 33.

There is further provided in accordance with another preferred embodiment of the present invention a bioinformatically detectable isolated oligonucleotide which anneals to a portion of a mRNA transcript of a target gene associated with Addisons disease, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 34.

There is still further provided in accordance with another preferred embodiment of the present invention a bioinformatically detectable isolated oligonucleotide which anneals to a portion of a mRNA transcript of a target gene associated with Herpes, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 35.

There is additionally provided in accordance with another preferred embodiment of the present invention a bioinformatically detectable isolated oligonucleotide which anneals to a portion of a mRNA transcript of a target gene associated with Malaria, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 36.

There is moreover provided in accordance with another preferred embodiment of the present invention a bioinformatically detectable isolated oligonucleotide which anneals to a portion of a mRNA transcript of a target gene associated with Breast cancer, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 37.

There is further provided in accordance with another preferred embodiment of the present invention a bioinformatically detectable isolated oligonucleotide which anneals to a portion of a mRNA transcript of a target gene associated with Leukemia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 38.

There is still further provided in accordance with another preferred embodiment of the present invention a bioinformatically detectable isolated oligonucleotide which anneals to a portion of a mRNA transcript of a target gene associated with Alopecia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 39.

There is additionally provided in accordance with another preferred embodiment of the present invention a bioinformatically detectable isolated oligonucleotide which anneals to a portion of a mRNA transcript of a target gene associated with Hepatitis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 40.

There is moreover provided in accordance with another preferred embodiment of the present invention a bioinformatically detectable isolated oligonucleotide which anneals to a portion of a mRNA transcript of a target gene associated with Cataract, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 41.

There is further provided in accordance with another preferred embodiment of the present invention a bioinformatically detectable isolated oligonucleotide which anneals to a portion of a mRNA transcript of a target gene associated with Encephalitis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 42.

There is still further provided in accordance with another preferred embodiment of the present invention a bioinformatically detectable isolated oligonucleotide which anneals to a portion of a mRNA transcript of a target gene associated with Cholestasis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 43.

There is additionally provided in accordance with another preferred embodiment of the present invention a bioinformatically detectable isolated oligonucleotide which anneals to a portion of a mRNA transcript of a target gene associated with Schizophrenia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 44.

There is moreover provided in accordance with another preferred embodiment of the present invention a bioinformatically detectable isolated oligonucleotide which anneals to a portion of a mRNA transcript of a target gene associated with Hyperglycemia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 45.

There is further provided in accordance with another preferred embodiment of the present invention a bioinformatically detectable isolated oligonucleotide which anneals to a portion of a mRNA transcript of a target gene associated with Megaloblastic anemia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 46.

There is still further provided in accordance with another preferred embodiment of the present invention a bioinformatically detectable isolated oligonucleotide which anneals to a portion of a mRNA transcript of a target gene associated with Endometrial carcinoma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 47.

There is additionally provided in accordance with another preferred embodiment of the present invention a bioinformatically detectable isolated oligonucleotide which anneals to a portion of a mRNA transcript of a target gene associated with Burkitt lymphoma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 48.

There is moreover provided in accordance with another preferred embodiment of the present invention a bioinformatically detectable isolated oligonucleotide which anneals to a portion of a mRNA transcript of a target gene associated with Crohn disease, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 49.

There is further provided in accordance with another preferred embodiment of the present invention a bioinformatically detectable isolated oligonucleotide which anneals to a portion of a mRNA transcript of a target gene associated with Osteoarthritis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 50.

There is still further provided in accordance with another preferred embodiment of the present invention a bioinformatically detectable isolated oligonucleotide which anneals to a portion of a mRNA transcript of a target gene associated with Pancreatitis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 51.

There is additionally provided in accordance with another preferred embodiment of the present invention a bioinformatically detectable isolated oligonucleotide which anneals to a portion of a mRNA transcript of a target gene associated with Fragile X Syndrome, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 52.

There is moreover provided in accordance with another preferred embodiment of the present invention a bioinformatically detectable isolated oligonucleotide which anneals to a portion of a mRNA transcript of a target gene associated with Anorexia Nervosa, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 53.

There is further provided in accordance with another preferred embodiment of the present invention a bioinformatically detectable isolated oligonucleotide which anneals to a portion of a mRNA transcript of a target gene associated with Bladder cancer, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 54.

There is still further provided in accordance with another preferred embodiment of the present invention a bioinformatically detectable isolated oligonucleotide which anneals to a portion of a mRNA transcript of a target gene associated with Insulin-Dependent Diabetes Mellitus, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 55.

There is additionally provided in accordance with another preferred embodiment of the present invention a bioinformatically detectable isolated oligonucleotide which anneals to a portion of a mRNA transcript of a target gene associated with Sideroblastic anemia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 56.

There is moreover provided in accordance with another preferred embodiment of the present invention a bioinformatically detectable isolated oligonucleotide which anneals to a portion of a mRNA transcript of a target gene associated with Celiac Disease, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 57.

There is further provided in accordance with another preferred embodiment of the present invention a bioinformatically detectable isolated oligonucleotide which anneals to a portion of a mRNA transcript of a target gene associated with Diabetes Mellitus, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 58.

There is still further provided in accordance with another preferred embodiment of the present invention a bioinformatically detectable isolated oligonucleotide which anneals to a portion of a mRNA transcript of a target gene associated with Basal cell carcinoma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 59.

There is additionally provided in accordance with another preferred embodiment of the present invention a bioinformatically detectable isolated oligonucleotide which anneals to a portion of a mRNA transcript of a target gene associated with Cytomegalovirus, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 60.

There is moreover provided in accordance with another preferred embodiment of the present invention a bioinformatically detectable isolated oligonucleotide which anneals to a portion of a mRNA transcript of a target gene associated with Aids, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 61.

There is further provided in accordance with another preferred embodiment of the present invention a bioinformatically detectable isolated oligonucleotide which anneals to a portion of a mRNA transcript of a target gene associated with Small cell carcinoma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 62.

There is still further provided in accordance with another preferred embodiment of the present invention a bioinformatically detectable isolated oligonucleotide which anneals to a portion of a mRNA transcript of a target gene associated with Diabetic Nephropathy, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 63.

There is additionally provided in accordance with another preferred embodiment of the present invention a bioinformatically detectable isolated oligonucleotide which anneals to a portion of a mRNA transcript of a target gene associated with Adrenal cortical carcinoma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 65.

There is moreover provided in accordance with another preferred embodiment of the present invention a bioinformatically detectable isolated oligonucleotide which anneals to a portion of a mRNA transcript of a target gene associated with Toxoplasmosis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 66.

There is further provided in accordance with another preferred embodiment of the present invention a bioinformatically detectable isolated oligonucleotide which anneals to a portion of a mRNA transcript of a target gene associated with Bundle-Branch Block, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 67.

There is still further provided in accordance with another preferred embodiment of the present invention a bioinformatically detectable isolated oligonucleotide which anneals to a portion of a mRNA transcript of a target gene associated with Thyroiditis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 68.

There is additionally provided in accordance with another preferred embodiment of the present invention a bioinformatically detectable isolated oligonucleotide which anneals to a portion of a mRNA transcript of a target gene associated with Urethral neoplasms, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 69.

There is moreover provided in accordance with another preferred embodiment of the present invention a bioinformatically detectable isolated oligonucleotide which anneals to a portion of a mRNA transcript of a target gene associated with Adenovirus, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 70.

There is further provided in accordance with another preferred embodiment of the present invention a bioinformatically detectable isolated oligonucleotide which anneals to a portion of a mRNA transcript of a target gene associated with Atherosclerosis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 71.

There is still further provided in accordance with another preferred embodiment of the present invention a bioinformatically detectable isolated oligonucleotide which anneals to a portion of a mRNA transcript of a target gene associated with Infectious Mononucleosis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 72.

There is additionally provided in accordance with another preferred embodiment of the present invention a bioinformatically detectable isolated oligonucleotide which anneals to a portion of a mRNA transcript of a target gene associated with Non-Insulin-Dependent Diabetes Mellitus, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 73.

There is moreover provided in accordance with another preferred embodiment of the present invention a bioinformatically detectable isolated oligonucleotide which anneals to a portion of a mRNA transcript of a target gene associated with Virus Diseases, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 74.

There is further provided in accordance with another preferred embodiment of the present invention a bioinformatically detectable isolated oligonucleotide which anneals to a portion of a mRNA transcript of a target gene associated with Hypertrophic cardiomyopathy, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 75.

There is still further provided in accordance with another preferred embodiment of the present invention a bioinformatically detectable isolated oligonucleotide which anneals to a portion of a mRNA transcript of a target gene associated with Syphilis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 76.

There is additionally provided in accordance with another preferred embodiment of the present invention a bioinformatically detectable isolated oligonucleotide which anneals to a portion of a mRNA transcript of a target gene associated with Thrombocytopenia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 77.

There is moreover provided in accordance with another preferred embodiment of the present invention a bioinformatically detectable isolated oligonucleotide which anneals to a portion of a mRNA transcript of a target gene associated with Cerebrovascular Accident, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 78.

There is further provided in accordance with another preferred embodiment of the present invention a bioinformatically detectable isolated oligonucleotide which anneals to a portion of a mRNA transcript of a target gene associated with Skin Neoplasms, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 79.

There is still further provided in accordance with another preferred embodiment of the present invention a bioinformatically detectable isolated oligonucleotide which anneals to a portion of a mRNA transcript of a target gene associated with Cleft Palate, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 80.

There is additionally provided in accordance with another preferred embodiment of the present invention a bioinformatically detectable isolated oligonucleotide which anneals to a portion of a mRNA transcript of a target gene associated with Obesity, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 81.

There is moreover provided in accordance with another preferred embodiment of the present invention a bioinformatically detectable isolated oligonucleotide which anneals to a portion of a mRNA transcript of a target gene associated with Picornaviridae, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 82.

There is further provided in accordance with another preferred embodiment of the present invention a bioinformatically detectable isolated oligonucleotide which anneals to a portion of a mRNA transcript of a target gene associated with Nonsmall cell lung cancer, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 83.

There is still further provided in accordance with another preferred embodiment of the present invention a bioinformatically detectable isolated oligonucleotide which anneals to a portion of a mRNA transcript of a target gene associated with Dermatomyositis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 84.

There is additionally provided in accordance with another preferred embodiment of the present invention a bioinformatically detectable isolated oligonucleotide which anneals to a portion of a mRNA transcript of a target gene associated with Migraine, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 85.

There is moreover provided in accordance with another preferred embodiment of the present invention a bioinformatically detectable isolated oligonucleotide which anneals to a portion of a mRNA transcript of a target gene associated with Meningitis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 86.

There is further provided in accordance with another preferred embodiment of the present invention a bioinformatically detectable isolated oligonucleotide which anneals to a portion of a mRNA transcript of a target gene associated with Renal Tubular Acidosis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 87.

There is still further provided in accordance with another preferred embodiment of the present invention a bioinformatically detectable isolated oligonucleotide which anneals to a portion of a mRNA transcript of a target gene associated with Pancreatic cancer, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 88.

There is additionally provided in accordance with another preferred embodiment of the present invention a bioinformatically detectable isolated oligonucleotide which anneals to a portion of a mRNA transcript of a target gene associated with Ulcerative colitis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 89.

There is moreover provided in accordance with another preferred embodiment of the present invention a bioinformatically detectable isolated oligonucleotide which anneals to a portion of a mRNA transcript of a target gene associated with Epilepsy, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 90.

There is further provided in accordance with another preferred embodiment of the present invention a bioinformatically detectable isolated oligonucleotide which anneals to a portion of a mRNA transcript of a target gene associated with Cholelithiasis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 91.

There is still further provided in accordance with another preferred embodiment of the present invention a bioinformatically detectable isolated oligonucleotide which anneals to a portion of a mRNA transcript of a target gene associated with Intestinal Neoplasms, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 92.

There is additionally provided in accordance with another preferred embodiment of the present invention a bioinformatically detectable isolated oligonucleotide which anneals to a portion of a mRNA transcript of a target gene associated with Renal cell carcinoma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 93.

There is moreover provided in accordance with another preferred embodiment of the present invention a bioinformatically detectable isolated oligonucleotide which anneals to a portion of a mRNA transcript of a target gene associated with Cirrhosis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 94.

There is further provided in accordance with another preferred embodiment of the present invention a bioinformatically detectable isolated oligonucleotide which anneals to a portion of a mRNA transcript of a target gene associated with Peritonitis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 95.

There is still further provided in accordance with another preferred embodiment of the present invention a bioinformatically detectable isolated oligonucleotide which anneals to a portion of a mRNA transcript of a target gene associated with Appendicitis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 96.

There is additionally provided in accordance with another preferred embodiment of the present invention a bioinformatically detectable isolated oligonucleotide which anneals to a portion of a mRNA transcript of a target gene associated with Papilloma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 97.

There is moreover provided in accordance with another preferred embodiment of the present invention a bioinformatically detectable isolated oligonucleotide which anneals to a portion of a mRNA transcript of a target gene associated with Down Syndrome, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 98.

There is further provided in accordance with another preferred embodiment of the present invention a bioinformatically detectable isolated oligonucleotide which anneals to a portion of a mRNA transcript of a target gene associated with Nephrolithiasis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 99.

There is still further provided in accordance with another preferred embodiment of the present invention a bioinformatically detectable isolated oligonucleotide which anneals to a portion of a mRNA transcript of a target gene associated with Aortic Aneurysm, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 100.

There is additionally provided in accordance with another preferred embodiment of the present invention a bioinformatically detectable isolated oligonucleotide which anneals to a portion of a mRNA transcript of a target gene associated with Vascular dementia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 101.

There is moreover provided in accordance with another preferred embodiment of the present invention a bioinformatically detectable isolated oligonucleotide which anneals to a portion of a mRNA transcript of a target gene associated with Infertility, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 102.

There is further provided in accordance with another preferred embodiment of the present invention a bioinformatically detectable isolated oligonucleotide which anneals to a portion of a mRNA transcript of a target gene associated with Thyroid carcinoma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 103.

There is still further provided in accordance with another preferred embodiment of the present invention a bioinformatically detectable isolated oligonucleotide which anneals to a portion of a mRNA transcript of a target gene associated with Thrombosis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 104.

There is additionally provided in accordance with another preferred embodiment of the present invention a bioinformatically detectable isolated oligonucleotide which anneals to a portion of a mRNA transcript of a target gene associated with Asthma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 105.

There is moreover provided in accordance with another preferred embodiment of the present invention a bioinformatically detectable isolated oligonucleotide which anneals to a portion of a mRNA transcript of a target gene associated with Diverticulitis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 106.

There is further provided in accordance with another preferred embodiment of the present invention a bioinformatically detectable isolated oligonucleotide which anneals to a portion of a mRNA transcript of a target gene associated with Tuberculosis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 108.

There is still further provided in accordance with another preferred embodiment of the present invention a bioinformatically detectable isolated oligonucleotide which anneals to a portion of a mRNA transcript of a target gene associated with Multiinfarct dementia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 109.

There is additionally provided in accordance with another preferred embodiment of the present invention a bioinformatically detectable isolated oligonucleotide which anneals to a portion of a mRNA transcript of a target gene associated with Cervical cancer, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 110.

There is moreover provided in accordance with another preferred embodiment of the present invention a bioinformatically detectable isolated oligonucleotide which anneals to a portion of a mRNA transcript of a target gene associated with Beta Thalassemia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 111.

There is further provided in accordance with another preferred embodiment of the present invention a bioinformatically detectable isolated oligonucleotide which anneals to a portion of a mRNA transcript of a target gene associated with Hepatocellular carcinoma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 112.

There is still further provided in accordance with another preferred embodiment of the present invention a bioinformatically detectable isolated oligonucleotide which anneals to a portion of a mRNA transcript of a target gene associated with Psoriasis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 113.

There is additionally provided in accordance with another preferred embodiment of the present invention a bioinformatically detectable isolated oligonucleotide which anneals to a portion of a mRNA transcript of a target gene associated with Diphtheria, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 114.

There is moreover provided in accordance with another preferred embodiment of the present invention a bioinformatically detectable isolated oligonucleotide which anneals to a portion of a mRNA transcript of a target gene associated with Bronchiectasis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 115.

There is further provided in accordance with another preferred embodiment of the present invention a bioinformatically detectable isolated oligonucleotide which anneals to a portion of a mRNA transcript of a target gene associated with EBV, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 116.

There is still further provided in accordance with another preferred embodiment of the present invention a bioinformatically detectable isolated oligonucleotide which anneals to a portion of a mRNA transcript of a target gene associated with Coronary disease, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 117.

There is additionally provided in accordance with another preferred embodiment of the present invention a bioinformatically detectable isolated oligonucleotide which anneals to a portion of a mRNA transcript of a target gene associated with Polyposis coli, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 118.

There is moreover provided in accordance with another preferred embodiment of the present invention a bioinformatically detectable isolated oligonucleotide which anneals to a portion of a mRNA transcript of a target gene associated with Influenza, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 119.

There is further provided in accordance with another preferred embodiment of the present invention a bioinformatically detectable isolated oligonucleotide which anneals to a portion of a mRNA transcript of a target gene associated with Parkinson, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 120.

There is still further provided in accordance with another preferred embodiment of the present invention a bioinformatically detectable isolated oligonucleotide which anneals to a portion of a mRNA transcript of a target gene associated with Hemolytic anemia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 121.

There is additionally provided in accordance with another preferred embodiment of the present invention a bioinformatically detectable isolated oligonucleotide which anneals to a portion of a mRNA transcript of a target gene associated with Medullary thyroid carcinoma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 122.

There is moreover provided in accordance with another preferred embodiment of the present invention a bioinformatically detectable isolated oligonucleotide which anneals to a portion of a mRNA transcript of a target gene associated with Sickle cell anemia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 123.

There is further provided in accordance with another preferred embodiment of the present invention a bioinformatically detectable isolated oligonucleotide which anneals to a portion of a mRNA transcript of a target gene associated with Deafness, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 124.

There is still further provided in accordance with another preferred embodiment of the present invention a bioinformatically detectable isolated oligonucleotide which anneals to a portion of a mRNA transcript of a target gene associated with Diabetic Neuropathies, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 125.

There is additionally provided in accordance with another preferred embodiment of the present invention a bioinformatically detectable isolated oligonucleotide which anneals to a portion of a mRNA transcript of a target gene associated with Psoriatic arthritis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 126.

There is moreover provided in accordance with another preferred embodiment of the present invention a bioinformatically detectable isolated oligonucleotide which anneals to a portion of a mRNA transcript of a target gene associated with Barrett Esophagus, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 127.

There is further provided in accordance with another preferred embodiment of the present invention a bioinformatically detectable isolated oligonucleotide which anneals to a portion of a mRNA transcript of a target gene associated with Cerebral Hemorrhage, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 128.

There is still further provided in accordance with another preferred embodiment of the present invention a bioinformatically detectable isolated oligonucleotide which anneals to a portion of a mRNA transcript of a target gene associated with Cerebral Infarction, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 129.

There is additionally provided in accordance with another preferred embodiment of the present invention a bioinformatically detectable isolated oligonucleotide which anneals to a portion of a mRNA transcript of a target gene associated with *E. coli*, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 130.

There is moreover provided in accordance with another preferred embodiment of the present invention a bioinformatically detectable isolated oligonucleotide which anneals to a portion of a mRNA transcript of a target gene associated with Urticaria, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 131.

There is further provided in accordance with another preferred embodiment of the present invention a bioinformatically detectable isolated oligonucleotide which anneals to a portion of a mRNA transcript of a target gene associated with Attention Deficit Disorder, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 132.

There is still further provided in accordance with another preferred embodiment of the present invention a bioinformatically detectable isolated oligonucleotide which anneals to a portion of a mRNA transcript of a target gene associated with Pituitary tumor, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 133.

There is additionally provided in accordance with another preferred embodiment of the present invention a bioinformatically detectable isolated oligonucleotide which anneals to a portion of a mRNA transcript of a target gene associated with Enuresis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 134.

There is moreover provided in accordance with another preferred embodiment of the present invention a bioinformatically detectable isolated oligonucleotide which anneals to a portion of a mRNA transcript of a target gene associated with Osteoporosis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 135.

There is further provided in accordance with another preferred embodiment of the present invention a bioinformatically detectable isolated oligonucleotide which anneals to a portion of a mRNA transcript of a target gene associated with Urinary calculi, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 136.

There is still further provided in accordance with another preferred embodiment of the present invention a bioinformatically detectable isolated oligonucleotide which anneals to a portion of a mRNA transcript of a target gene associated with Multiple Myeloma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 137.

There is additionally provided in accordance with another preferred embodiment of the present invention a bioinformatically detectable isolated oligonucleotide which anneals to a portion of a mRNA transcript of a target gene associated with Aplastic anemia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 138.

There is moreover provided in accordance with another preferred embodiment of the present invention a bioinformatically detectable isolated oligonucleotide which anneals to a portion of a mRNA transcript of a target gene associated with Gestational Diabetes, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 139.

There is further provided in accordance with another preferred embodiment of the present invention a bioinformatically detectable isolated oligonucleotide which anneals to a portion of a mRNA transcript of a target gene associated with Rheumatoid arthritis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 140.

There is still further provided in accordance with another preferred embodiment of the present invention a bioinformatically detectable isolated oligonucleotide which anneals to a portion of a mRNA transcript of a target gene associated with Duodenal Neoplasms, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 141.

There is additionally provided in accordance with another preferred embodiment of the present invention a bioinformatically detectable isolated oligonucleotide which anneals to a portion of a mRNA transcript of a target gene associated with Hypertrophic Cardiomopathy, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 142.

There is moreover provided in accordance with another preferred embodiment of the present invention a bioinformatically detectable isolated oligonucleotide which anneals to a portion of a mRNA transcript of a target gene associated with Myocardial Infarction, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 143.

There is further provided in accordance with another preferred embodiment of the present invention a bioinformatically detectable isolated oligonucleotide which anneals to a portion of a mRNA transcript of a target gene associated with Left Ventricular Dysfunction, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 144.

There is still further provided in accordance with another preferred embodiment of the present invention a bioinformatically detectable isolated oligonucleotide which anneals to a portion of a mRNA transcript of a target gene associated with Postpartum depression, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 145.

There is additionally provided in accordance with another preferred embodiment of the present invention a bioinformatically detectable isolated oligonucleotide which anneals to a portion of a mRNA transcript of a target gene associated with Colorectal cancer, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 146.

There is moreover provided in accordance with another preferred embodiment of the present invention a bioinformatically detectable isolated oligonucleotide which anneals to a portion of a mRNA transcript of a target gene associated with Transitional cell carcinoma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 147.

There is further provided in accordance with another preferred embodiment of the present invention a bioinformatically detectable isolated oligonucleotide which anneals to a portion of a mRNA transcript of a target gene associated with Alpha thalassemia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 148.

There is still further provided in accordance with another preferred embodiment of the present invention a bioinformatically detectable isolated oligonucleotide which anneals to a portion of a mRNA transcript of a target gene associated with Cleft Lip, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 149.

There is additionally provided in accordance with another preferred embodiment of the present invention a bioinformatically detectable isolated oligonucleotide which anneals to a portion of a mRNA transcript of a target gene associated with Hypercholesterolemia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 150.

There is moreover provided in accordance with another preferred embodiment of the present invention a bioinformatically detectable isolated oligonucleotide which anneals to a portion of a mRNA transcript of a target gene associated with Sudden cardiac death, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 151.

There is further provided in accordance with another preferred embodiment of the present invention a bioinformatically detectable isolated oligonucleotide which anneals to a portion of a mRNA transcript of a target gene associated with Atrial fibrillation, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 152.

There is still further provided in accordance with another preferred embodiment of the present invention a bioinformatically detectable isolated oligonucleotide which anneals to a portion of a mRNA transcript of a target gene associated with Hypertension, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 153.

There is additionally provided in accordance with another preferred embodiment of the present invention a bioinformatically detectable isolated oligonucleotide which anneals to a portion of a mRNA transcript of a target gene associated with Ovarian cancer, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 154.

There is moreover provided in accordance with another preferred embodiment of the present invention a bioinformatically detectable isolated oligonucleotide which anneals to a portion of a mRNA transcript of a target gene associated with Coronary spasm, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 155.

There is further provided in accordance with another preferred embodiment of the present invention a bioinformatically detectable isolated oligonucleotide which anneals to a portion of a mRNA transcript of a target gene associated with Hemophilia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 157.

There is still further provided in accordance with another preferred embodiment of the present invention a bioinformatically detectable isolated oligonucleotide which anneals to a portion of a mRNA transcript of a target gene associated with Peripheral Vascular Diseases, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 158.

There is additionally provided in accordance with another preferred embodiment of the present invention a bioinformatically detectable isolated oligonucleotide which anneals to a portion of a mRNA transcript of a target gene associated with Bacillary Dysentery, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 159.

There is moreover provided in accordance with another preferred embodiment of the present invention a bioinformatically detectable isolated oligonucleotide which anneals to a portion of a mRNA transcript of a target gene associated with Macular Degeneration, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 160.

There is further provided in accordance with another preferred embodiment of the present invention a bioinformatically detectable isolated oligonucleotide which anneals to a portion of a mRNA transcript of a target gene associated with *Mycobacterium*, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 161.

There is still further provided in accordance with another preferred embodiment of the present invention a bioinformatically detectable isolated oligonucleotide which anneals to a portion of a mRNA transcript of a target gene associated with Cushing Syndrome, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 162.

There is additionally provided in accordance with another preferred embodiment of the present invention a bioinformatically detectable isolated oligonucleotide which anneals to a portion of a mRNA transcript of a target gene associated with Melanoma, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 163.

There is moreover provided in accordance with another preferred embodiment of the present invention a bioinformatically detectable isolated oligonucleotide which anneals to a portion of a mRNA transcript of a target gene associated with Bipolar Disorder, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 164.

There is further provided in accordance with another preferred embodiment of the present invention a bioinformatically detectable isolated oligonucleotide which anneals to a portion of a mRNA transcript of a target gene associated with Coronary artery disease, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 166.

There is still further provided in accordance with another preferred embodiment of the present invention a bioinformatically detectable isolated oligonucleotide which anneals to a portion of a mRNA transcript of a target gene associated with Dementia, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 167.

There is additionally provided in accordance with another preferred embodiment of the present invention a bioinformatically detectable isolated oligonucleotide which anneals to a portion of a mRNA transcript of a target gene associated with Lupus Erythematosus, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 168.

There is moreover provided in accordance with another preferred embodiment of the present invention a bioinformatically detectable isolated oligonucleotide which anneals to a portion of a mRNA transcript of a target gene associated with Rhinitis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 169.

There is further provided in accordance with another preferred embodiment of the present invention a bioinformatically detectable isolated oligonucleotide which anneals to a portion of a mRNA transcript of a target gene associated with Peptic Ulcer, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 170.

There is still further provided in accordance with another preferred embodiment of the present invention a bioinformatically detectable isolated oligonucleotide which anneals to a portion of a mRNA transcript of a target gene associated with Cystic fibrosis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 171.

There is additionally provided in accordance with another preferred embodiment of the present invention a bioinformatically detectable isolated oligonucleotide which anneals to a portion of a mRNA transcript of a target gene associated with Autism, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 172.

There is moreover provided in accordance with another preferred embodiment of the present invention a bioinformatically detectable isolated oligonucleotide which anneals to a portion of a mRNA transcript of a target gene associated with HTLV, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 173.

There is further provided in accordance with another preferred embodiment of the present invention a bioinformatically detectable isolated oligonucleotide which anneals to a portion of a mRNA transcript of a target gene associated with Sinusitis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 174.

There is still further provided in accordance with another preferred embodiment of the present invention a bioinformatically detectable isolated oligonucleotide which anneals to a portion of a mRNA transcript of a target gene associated with Diabetic Retinopathy, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 176.

There is additionally provided in accordance with another preferred embodiment of the present invention a bioinformatically detectable isolated oligonucleotide which anneals to a portion of a mRNA transcript of a target gene associated with Antisocial Personality Disorder, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 177.

There is moreover provided in accordance with another preferred embodiment of the present invention a bioinformatically detectable isolated oligonucleotide which anneals to a portion of a mRNA transcript of a target gene associated with Amyotrophic Lateral Sclerosis, wherein binding of the oligonucleotide to the mRNA transcript represses expression of the target gene, and wherein the oligonucleotide has at least 80% sequence identity with a nucleotide sequence selected from the group consisting of SEQ ID NOs shown in Table 14 row 178.

There is further provided in accordance with another preferred embodiment of the present invention a method for treatment of a disease involving a tissue in which a protein is pathologically expressed to an undesirable extent, the protein having a messenger RNA, the method including: providing a material which modulates activity of a microRNA oligonucleotide which binds complementarily to a segment of the messenger RNA, and introducing the material into the tissue, causing modulation of the activity of the microRNA oligonucleotide and thereby modulating expression of the protein in a desired manner.

There is still further provided in accordance with another preferred embodiment of the present invention a method for treatment of a disease involving tissue in which a protein is pathologically expressed to an undesirable extent, the protein having a messenger RNA, the method including: providing a material which at least partially binds a segment of the messenger RNA that is bound complementarily by a microRNA oligonucleotide, thereby modulating expression of the protein, and introducing the material into the tissue, thereby modulating expression of the protein.

There is additionally provided in accordance with another preferred embodiment of the present invention a method for treatment of a disease involving a tissue in which a protein is pathologically over-expressed, the protein having a messenger RNA, the method including: providing a microRNA oligonucleotide which binds complementarily to a segment of the messenger RNA, and introducing the microRNA oligonucleotide into the tissue, causing the microRNA oligonucleotide to bind complementarily to a segment of the messenger RNA and thereby inhibit expression of the protein.

There is moreover provided in accordance with another preferred embodiment of the present invention a method for treatment of a disease involving a tissue in which a protein is pathologically over-expressed, the protein having a messenger RNA, the method including: providing a chemically-modified microRNA oligonucleotide which binds complementarily to a segment of the messenger RNA, and introducing the chemically-modified microRNA oligonucleotide into the tissue, causing the microRNA oligonucleotide to bind complementarily to a segment of the messenger RNA and thereby inhibit expression of the protein.

There is further provided in accordance with another preferred embodiment of the present invention a method for treatment of a disease involving a tissue in which a protein is pathologically under-expressed, the protein having a messenger RNA, the method including: providing an oligonucleotide that inhibits activity of a microRNA oligonucleotide which binds complementarily to a segment of the messenger RNA, and introducing the oligonucleotide into the tissue, causing inhibition of the activity of the microRNA oligonucleotide and thereby promotion of translation of the protein.

There is still further provided in accordance with another preferred embodiment of the present invention a method for treatment of a disease involving a tissue in which a protein is pathologically under-expressed, the protein having a messenger RNA, the method including: providing a chemically-modified oligonucleotide that inhibits activity of a microRNA oligonucleotide which binds complementarily to a segment of the messenger RNA, and introducing the chemically-modified oligonucleotide into the tissue, causing inhibition of the activity of the microRNA oligonucleotide and thereby promotion of translation of the protein.

There is additionally provided in accordance with another preferred embodiment of the present invention a method for diagnosis of a disease involving a tissue in which a protein is expressed to abnormal extent, the protein having a messenger RNA, the method including: assaying a microRNA oligonucleotide which at least partially binds a segment of the messenger RNA and modulates the expression of the protein, thereby providing an indication of at least one parameter of the disease.

There is moreover provided in accordance with another preferred embodiment of the present invention a method for detection of expression of an oligonucleotide, the method including: determining a first nucleotide sequence of a first oligonucleotide, which first nucleotide sequence is not complementary to a genome of an organism, receiving a second nucleotide sequence of a second oligonucleotide whose expression is sought to be detected, designing a third nucleotide sequence that is complementary to the second nucleotide sequence of the second oligonucleotide, and a fourth nucleotide sequence that is complementary to a fifth nucleotide sequence which is different from the second nucleotide sequence of the second oligonucleotide by at least one nucleotide, synthesizing a first oligonucleotide probe having a sixth nucleotide sequence including the third nucleotide sequence followed by the first nucleotide sequence of the first oligonucleotide, and a second oligonucleotide probe having a seventh nucleotide sequence including the fourth nucleotide sequence followed by the first nucleotide sequence of the first oligonucleotide, locating the first oligonucleotide probe and the second oligonucleotide probe on a microarray platform, receiving an RNA test sample from at least one tissue of the organism, obtaining size-fractionated RNA from the RNA test sample, amplifying the size-fractionated RNA, hybridizing the adaptor-linked RNA with the first and second oligonucleotide probes on the microarray platform, and determining expression of the first oligonucleotide in the at least one tissue of the organism, based at least in part on the hybridizing.

There is further provided in accordance with another preferred embodiment of the present invention a bioinformatically detectable isolated polynucleotide which is endogenously processed into a plurality of hairpin-shaped precursor oligonucleotides, each of which is endogenously processed into a respective oligonucleotide, which in turn anneals to a portion of a mRNA transcript of a target gene, wherein binding of the oligonucleotide to the mRNA transcript represses expression of the target gene.

There is still further provided in accordance with another preferred embodiment of the present invention a bioinformatically detectable isolated oligonucleotide which is endogenously processed from a hairpin-shaped precursor, and anneals to a portion of a mRNA transcript of a target gene, wherein binding of the oligonucleotide to the mRNA transcript represses expression of the target gene, and wherein the target gene does not encode a protein.

There is additionally provided in accordance with another preferred embodiment of the present invention a bioinformatically detectable isolated oligonucleotide which is endogenously processed from a hairpin-shaped precursor, and anneals to a portion of a mRNA transcript of a target gene, wherein binding of the oligonucleotide to the mRNA transcript represses expression of the target gene, and wherein a function of the oligonucleotide includes modulation of cell type.

There is moreover provided in accordance with another preferred embodiment of the present invention a bioinformatically detectable isolated oligonucleotide which is endogenously processed from a hairpin-shaped precursor, and anneals to a portion of a mRNA transcript of a target gene, wherein binding of the oligonucleotide to the mRNA transcript represses expression of the target gene, and wherein the oligonucleotide is maternally transferred by a cell to at least one daughter cell of the cell, and a function of the oligonucleotide includes modulation of cell type of the daughter cell.

There is further provided in accordance with another preferred embodiment of the present invention a method for bioinformatic detection of microRNA oligonucleotides, the method including: bioinformatically detecting a hairpin-shaped precursor oligonucleotide, bioinformatically detecting an oligonucleotide which is endogenously processed from the hairpin-shaped precursor oligonucleotide, and bioinformatically detecting a target gene of the oligonucleotide wherein the oligonucleotide anneals to at least one portion of a mRNA transcript of the target gene, and wherein the binding represses expression of the target gene, and the target gene is associated with a disease.

BRIEF DESCRIPTION OF DRAWINGS

FIG. 1 is a simplified diagram illustrating a genomic differentiation enigma that the present invention addresses;

FIGS. 5A and 5B are schematic diagrams which, when taken together, illustrate a "genomic records" concept of the conceptual model of the present invention, addressing the genomic differentiation enigma;

FIG. 9 is a simplified block diagram illustrating a bioinformatic oligonucleotide detection system capable of detecting oligonucleotides of the novel group of oligonucleotides of the present invention, which system is constructed and operative in accordance with a preferred embodiment of the present invention;

FIG. 10 is a simplified flowchart illustrating operation of a mechanism for training of a computer system to recognize the novel oligonucleotides of the present invention, which mechanism is constructed and operative in accordance with a preferred embodiment of the present invention;

FIG. 22 is a summary table of laboratory results validating expression of novel human oligonucleotides detected by a bioinformatic oligonucleotide detection engine constructed and operative in accordance with a preferred embodiment of the present invention, thereby validating its efficacy;

FIG. 23A is a schematic representation of an "operon-like" cluster of novel human hairpin sequences detected by a bioinformatic oligonucleotide detection engine constructed and operative in accordance with a preferred embodiment of the present invention, and non-GAM hairpin sequences used as negative controls thereto. The hairpins shown are as follows: N2 (SEQ ID NO: 10068286), N3 (SEQ ID NO: 10068287), MIR23 (SEQ ID NO: 10068288), GAM252 (SEQ ID NO: 10068289), GAM7617 (SEQ ID NO: 10068290), N252 (SEQ ID NO: 10068291), N4 (SEQ ID NO: 10068292), N0 (SEQ ID NO: 10068293), N6 (SEQ ID NO: 10068294), MIR24 (SEQ ID NO: 10068295), and N7 (SEQ ID NO: 10068296).

FIG. 23B is a schematic representation of secondary folding of hairpins of the operon-like cluster of FIG. 23A;

FIG. 23C is a photograph of laboratory results demonstrating expression of novel oligonucleotides of FIGS. 23A and 23B and lack of expression of the negative controls, thereby validating efficacy of bioinformatic detection of GAM oligonucleotides and GR polynucleotides detected by a bioinformatic oligonucleotide detection engine, constructed and operative in accordance with a preferred embodiment of the present invention;

FIG. 24A is an annotated sequence of EST72223 (SEQ ID NO: 10068281) comprising known human miRNA oligonucleotide MIR98 and novel human oligonucleotide GAM25 PRECURSOR detected by the oligonucleotide detection system of the present invention. Additionally annotated in EST72223 are the miRNA-98 hairpin in bold (SEQ ID NO: 10068282), the sequence of the mature miRNA-98 in bold and underline (SEQ ID NO: 10068283), the sequence of the GAM25 hairpin in bold (SEQ ID NO: 10068284), and the sequence of the mature miRNA of GAM25 in bold and underline (SEQ ID NO: 10068285).

FIGS. 24B, 24C and 24D are pictures of laboratory results demonstrating laboratory confirmation of expression of known human oligonucleotide MIR98 and of novel bioinformatically-detected human GAM25 RNA respectively, both of FIG. 24A, thus validating the bioinformatic oligonucleotide detection system of the present invention;

FIG. 25D is a table of exemplary specific hairpin oligonucleotides identified and sequenced by the specific primers designed and used under the methods of FIG. 25A, 25B, and 25C.

FIG. 27C is a summary table demonstrating detection of known microRNA oligonucleotides using a microarray constructed and operative in accordance with a preferred embodiment of the present invention.

FIGS. 28A-28D are simplified diagrams which when taken together illustrate different modes by which small molecules may be uses as therapeutic agents related to microRNA oligonucleotides, in accordance with a preferred embodiment of the present invention.

BRIEF DESCRIPTION OF SEQUENCES

Figure 2A:
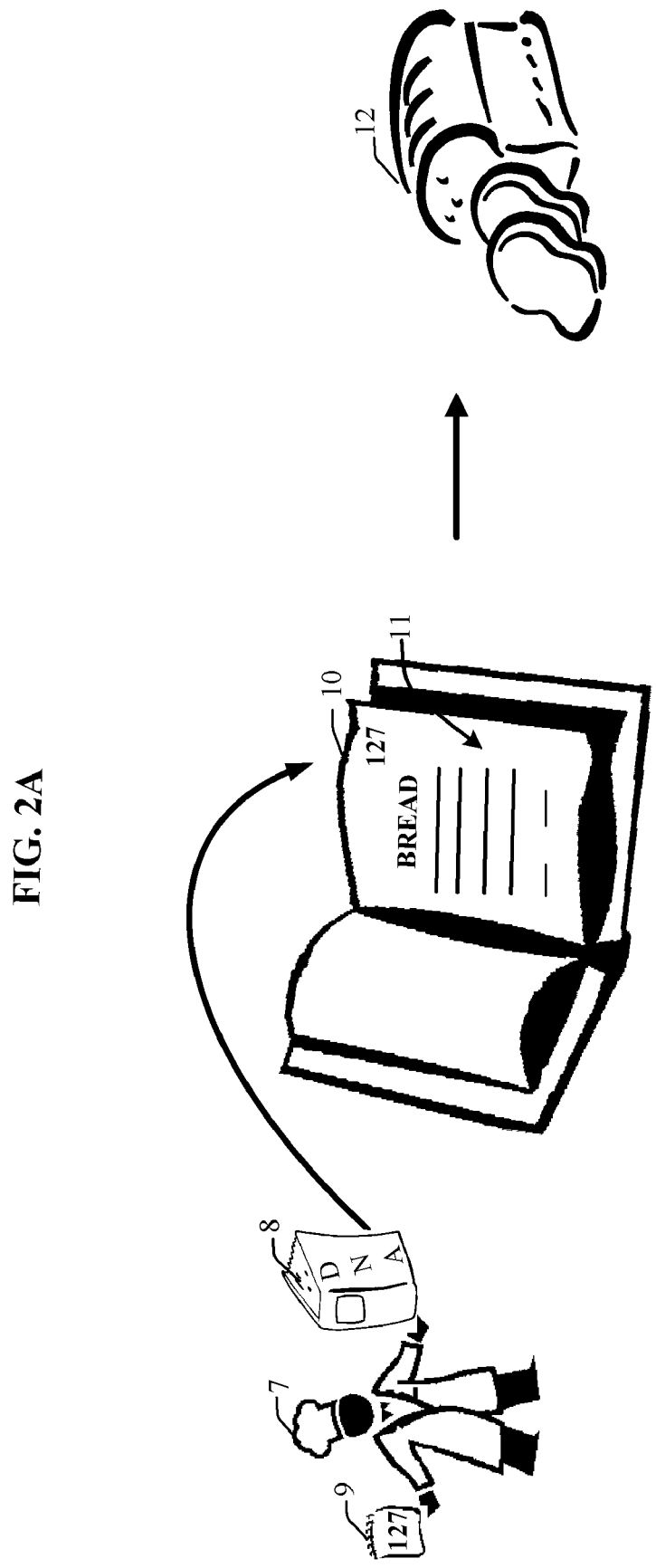
FIGS. 2, 3 and 4 are schematic diagrams which, when taken together, provide an analogy that illustrates a conceptual model of the present invention, addressing the genomic differentiation enigma.

A Sequence Listing of genomic sequences of the present invention designated SEQ ID NO:1 through SEQ ID: 10068177 is attached to this application, and is hereby incorporated herein. The genomic listing comprises the following nucleotide sequences: nucleotide sequences of 122764 GAM precursors of respective novel oligonucleotides of the present invention; nucleotide sequences of 139368 GAM RNA oligonucleotides of respective novel oligonucleotides of the present invention; and nucleotide sequences of 1709460 target gene binding sites of respective novel oligonucleotides of the present invention.

DETAILED DESCRIPTION

Reference is now made to FIG. 1, which is a simplified diagram providing a conceptual explanation of a genomic differentiation enigma, which the present invention addresses, inter alia.

FIG. 1 depicts various types of cells in an organism, such as a cartilage cell designated by reference numeral 1, a liver cell designated by reference numeral 2, a fibroblast cell designated by reference numeral 3, and a bone cell designated by reference numeral 4, all containing identical DNA designated by reference numeral 5. Notwithstanding that the various types of cells are all derived from a common initial fertilized egg cell designated by reference numeral 6, each of these cells expresses different proteins and accordingly acquire a different shape and function.

The present invention proposes inter alia that the inevitable conclusion from the foregoing is strikingly simple: the genome must contain a modular differentiation coding system. In other words, the genome of each cell must include multiple modules or records, possibly a different one for each cell type, as well as a mechanism by which each cell at its inception is instructed which one of the multiple records will govern its behavior.

This modular code concept may be somewhat difficult to grasp, since most persons are accustomed to view things from an external viewpoint. An architect, for example, looks at a plan of a building, which details exactly where each element (block, window, door, electrical switch, etc.) is to be placed relative to all other elements. Using the plan, the architect instructs the builders to place these elements in their designated places. This is an example of an external viewpoint: the architect is external to the plan, which itself is external with respect to the physical building, and with respect to its various elements. The architect may therefore act as an "external organizing agent" who can see the full picture and the relationships between all of the elements and is able to instruct from the outside where to place each of them.

According to a preferred embodiment of the present invention, genomic differentiation coding, in contrast to architectural building, functions without any external organizing agent. It comprises a smart block (the first cell), which is the architect and the plan. This smart block continuously duplicates itself, somehow knowing when to manifest itself as a block and when as a window, door, or electrical switch.

Reference is now made to FIGS. 2A-4 which are schematic diagrams which, when taken together, provide an analogy that illustrates a conceptual model of the present invention, which conceptual model addresses the genomic differentiation enigma.

Reference is now made to FIG. 2A. A hypothetical talented chef, designated by reference numeral 7, is capable of preparing any dish provided that he is given specific written cooking instructions. The chef 7 is equipped with two items: (a) a recipe book 8, designated by reference numeral 8, and (b) a small note, designated by reference numeral 9, having a number scribbled on it. The recipe book 8 comprises multiple pages, each page detailing how to prepare a specific dish. The small note 9 indicates the page to be opened, and therefore the dish to be prepared. The chef looks at the page number written on the note, opens the recipe book 8 to the appropriate page, and prepares the dish according to the written instructions on this page. In the example shown in FIG. 2A, the chef 7 is holding a small note 9 bearing the number 127. He therefore opens the recipe book 8 to page 127, designated by reference numeral 10. Since this page contains the recipe for preparing bread, the chef 7 prepares a loaf of bread, designated by reference numeral 12. Pages of the recipe book 8, such as page 127 (designated by reference numeral 10) in the example shown in FIG. 2A, contain additional information, designated by reference numeral 11. The nature of the additional information 11 is further elaborated hereinbelow with reference to FIGS. 3 and 4.

Reference is now made to FIG. 2B, which depicts two identical chefs, a first chef, designated by reference numeral 13, and a second chef, designated by reference numeral 14, both holding an identical recipe book 8. Although the first chef 13 and the second chef 14 are identical and hold identical recipe books 8, they differ in that they hold different small notes. The first chef 13 holds a small note designated by reference numeral 9, having the number 127 written on it, whereas the second chef 14 holds a small note designated by reference numeral 15, having the number 134 written on it. Accordingly, the first chef 13 opens the recipe book 8 to page 127, as designated by reference numeral 10 and, based on the instructions written on page 127 prepares a loaf of bread, designated by reference numeral 12. The second chef 14 opens the recipe book 8 to page 134, as designated by reference numeral 16 and, based on the instructions written on page 134, prepares a pie, designated by reference numeral 17. Pages in the recipe book 8, such as pages 127 and 134 designated by reference numerals 10 and 16 respectively in the examples shown in FIG. 2B, contain additional information, designated by reference numeral 11. The nature of the additional information 11 is further elaborated hereinbelow with reference to FIGS. 3 and 4.

Figure 3:
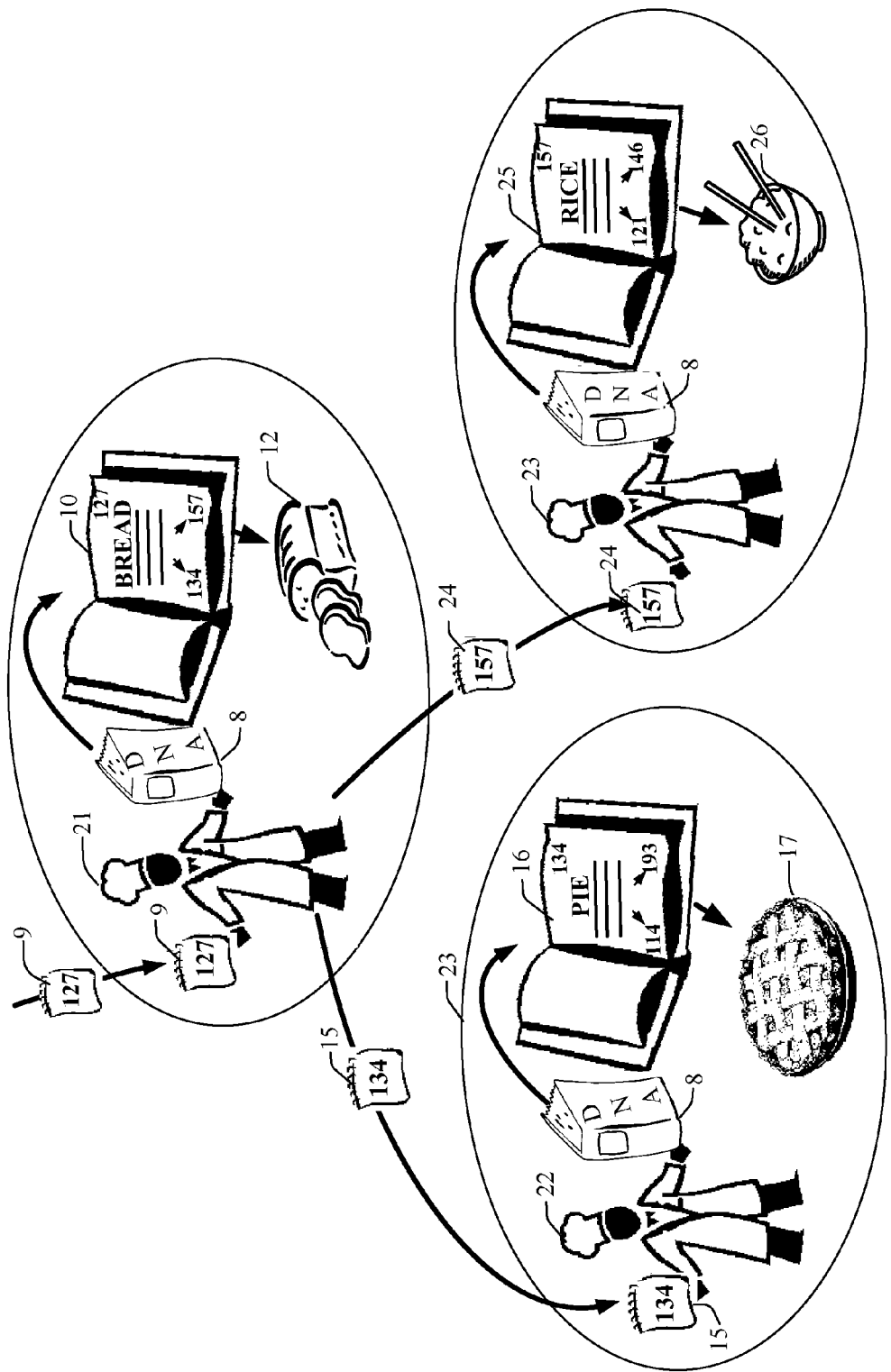

Reference is now made to FIG. 3, which illustrates a mode by which an imaginary chef can duplicate himself yielding two identical chefs, instructing each of the identical duplicate chefs to prepare a different dish. As an example, FIG. 3 shows a chef, designated by reference numeral 21, duplicating himself to yield two duplicate chefs: a first duplicate chef, designated by reference numeral 22, and a second duplicate chef, designated by reference numeral 23. The duplicate chefs are identical to each other and to chef 21.

Like chef 7 and chef 13 of FIGS. 2A and 2B, FIG. 3 shows chef 21 holding a recipe book 8 and receiving a note 9 bearing the number 127. Chef 21 therefore opens the recipe book 8 to page 127, designated by reference numeral 10, and prepares a loaf of bread 12. However, FIG. 3 also elaborates some of the additional information 11 (FIGS. 2A and 2B) found on page 127, designated by reference numeral 10: the bottom of page 127 bears two numbers 134 and 157.

Chef 21 is trained to perform the following three actions when he is finished preparing a dish: (a) Duplicate himself yielding two duplicate chefs, the first duplicate chef 22 and the second duplicate chef 23; (b) Duplicate his recipe book 8, handing an identical copy to each of the duplicate chefs 22 and 23; and (c) Write down on each of two notes one of the numbers that is found at the bottom of the page to which he was instructed to open. In the example illustrated by FIG. 3, chef 21 is instructed to open the recipe book 8 to page 127, designated by reference numeral 10, write the numbers 134 and 157 on two respective notes, a first note designated by reference numeral 15 and the second note designated by reference numerals 24. Chef 21 is further trained to hand the first note 15 bearing the number 134, to the first duplicate chef 22 and the second note 24 bearing the number 157, to the second duplicate chef 23.

Accordingly, the first duplicate chef 22 receives note 15 bearing the number 134 and therefore opens the recipe book 8 to page 134, designated by reference numeral 16, and prepares a pie, designated by reference numeral 17. The second duplicate chef 23 receives note 24 bearing the number 157 and therefore opens the recipe book 8 to page 157, designated by reference numeral 25, and prepares rice, designated by reference numeral 26.

It is appreciated that while chef 21 and duplicate chefs 22 and 23 are identical and hold identical recipe books 8, they each prepare a different dish. It is also appreciated that the dishes prepared by the first duplicate chef 22 and the second duplicate chef 23 are determined by chef 21 and are mediated by the differently numbered notes 15 and 24 passed on from chef 21 to duplicate chefs 22 and 23, respectively.

Further, it is appreciated that the mechanism illustrated by FIG. 3 enables an unlimited lineage of chefs to divide into duplicate, identical chefs and to determine the dishes those duplicate chefs would prepare. As an example, since the first duplicate chef 22 is directed to page 134, as designated by reference numeral 16, when he duplicates himself (not shown), he will instruct his two duplicate chefs to prepare dishes specified on particular pages, the numbers of which are written at the bottom of page 134, i.e. pages 114 and 193, respectively. Similarly, the second duplicate chef 23 will instruct its duplicate chefs to prepare dishes specified on pages 121 and 146, respectively, etc.

Figure 4:
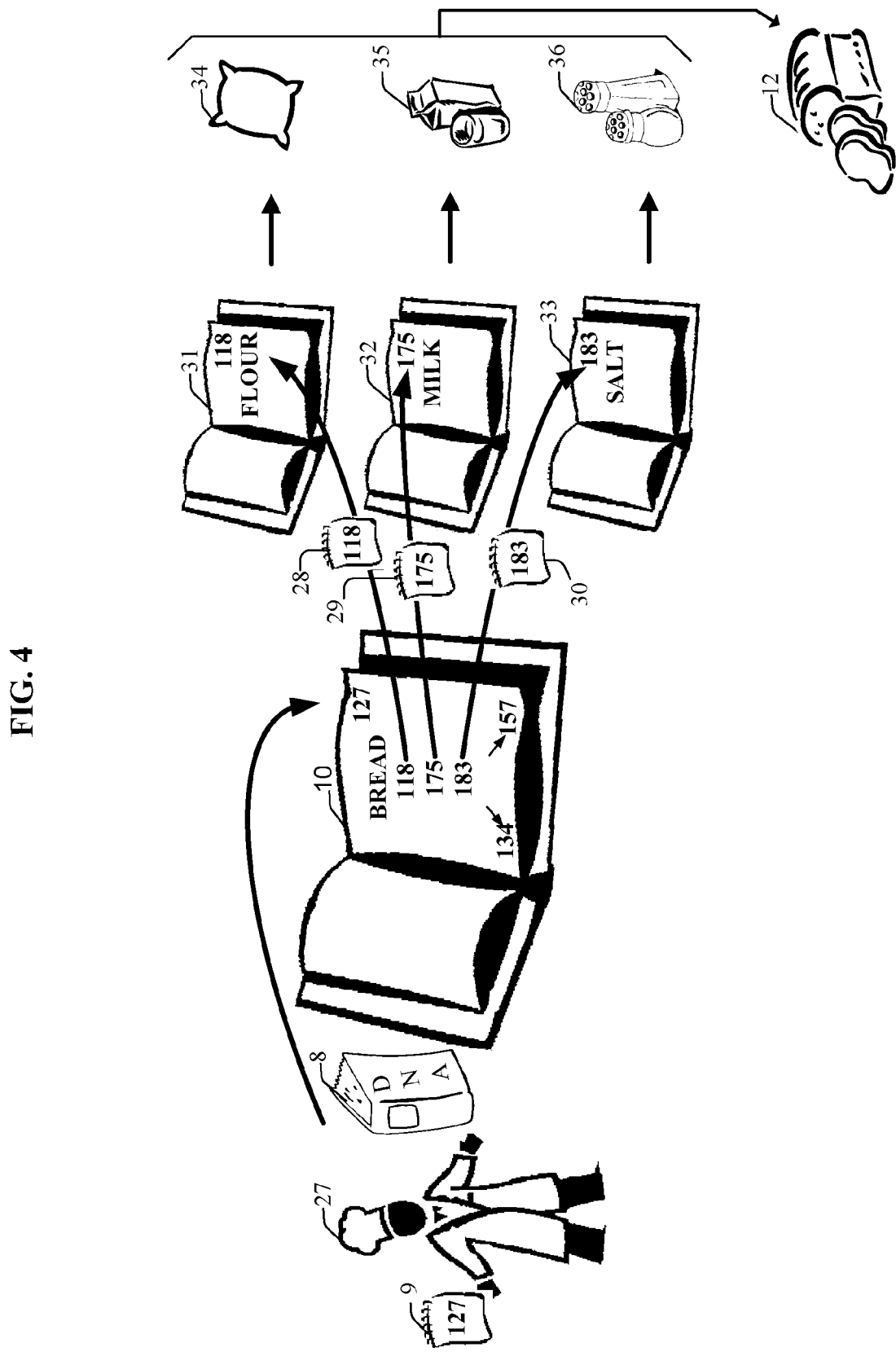

Reference is now made to FIG. 4, which illustrates a mode by which a chef can prepare a dish based on instructions written in a shorthand format: The page to which a chef is directed by a small note he is given merely contains a list of numbers which further direct him to other pages, each specifying how to prepare an ingredient of the dish to be prepared.

To illustrate this shorthand format, FIG. 4 shows a chef, designated by reference numeral 27, holding the recipe book 8 and the note 9 which bears the number 127. Chef 27 accordingly opens the recipe book 8 to page 127, designated by reference numeral 10, and based on instructions on this page, prepares bread 12. This is similar to chefs 7, 13 and 21 of FIGS. 2A, 2B and 3, respectively.

However, FIG. 4 also further elaborates on some of the additional information 11 (FIGS. 2A and 2B) that is written on page 127, designated by reference numeral 10. The cooking instructions found on page 127, designated by reference numeral 10, for making bread 12 are written in a shorthand format, comprising only three numbers: 118, 175 and 183. Chef 27 writes these numbers on three respective notes designated by reference numerals 28-30. The notes 28-30 are then used to turn to corresponding pages 118, 175 and 183, designated by reference numerals 31-33 of the recipe book 8, which pages provide instructions for the preparation of ingredients required for making bread 12: flour 34, milk 35 and salt 36.

The analogy provided by FIGS. 2A-4 illustrates the conceptual model of the present invention addressing the genomic differentiation enigma, and may be explained as follows: The chefs and duplicate chefs 7, 13, 14, 21-23 and 27 (FIGS. 2A-4) in the analogy represent cells. The recipe book 8 represents the DNA 5 (FIG. 1). Preparing dishes such as bread 12, pie 17 or rice 26 (all of FIG. 3) represent the cell manifesting itself as a specific cell type, such as cartilage cell 1, liver cell 2, fibroblast cell 3, or bone cell 4 (all of FIG. 1). Ingredients of a dish, such as flour 34, milk 35 and salt 36 (all of 4), represent proteins typically expressed by a particular cell type, such as 1-4. In the same way that the different chefs of the analogy have the same recipe book 8 yet prepare different dishes, so do different cells in an organism contain the same DNA 5 yet manifest themselves as different cell types 1-4 by expressing proteins typical of these respective cell types. Application of the analogy illustrated in FIGS. 2A-4 to the field of cell biology is further described hereinbelow with reference to FIGS. 5A-7.

Figure 5A:
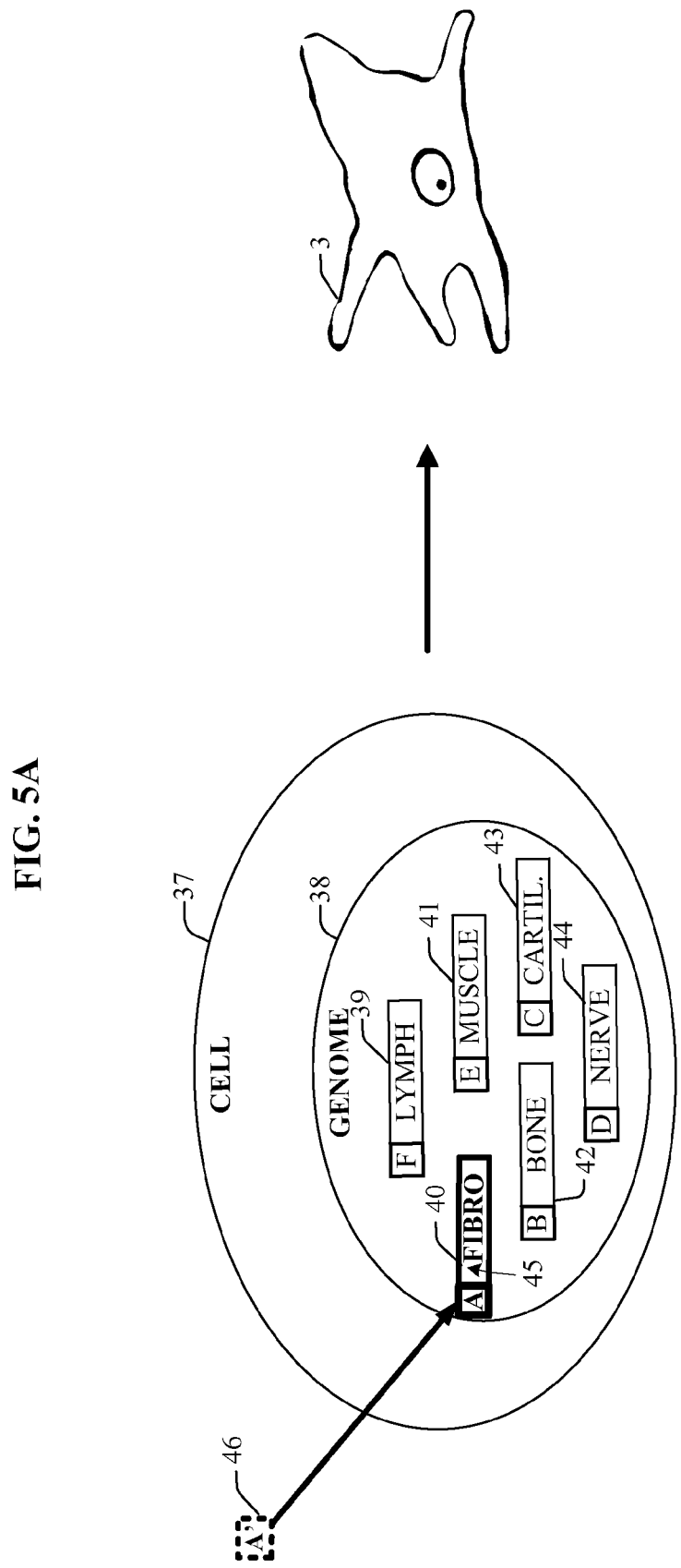

Reference is now made to FIGS. 5A and 5B which are schematic diagrams that, when taken together, illustrate a Genomic Records concept of the present invention, addressing the genomic differentiation enigma. FIGS. 5A and 5B correspond to FIGS. 2A and 2B of the chef analogy described hereinabove.

An important aspect of the present invention is the Genomic Records concept. According to a preferred embodiment of the present invention, the DNA (the recipe book 8 in analogy) comprises a very large number of Genomic Records (analogous to pages in the recipe book 8, such as pages 127, 134, and 157, designated by reference numerals 10, 16 and 25, respectively) containing instructions for differentiation of various different cell types or developmental process. Each Genomic Record comprises at least one very short genomic sequence, which functions as a "Genomic Address" of that Genomic Record (analogous to a page number, such as the numbers 127, 134 and 157 (reference numerals 10, 16 and 25) that appear in the recipe book 8 of FIG. 3). At its inception, each cell receives a short RNA segment (analogous to the scribbled short note, such as 9, 15 and 24 of FIG. 3) in addition to the DNA (analogous to the recipe book 8). This short RNA segment binds complementarily to a "Genomic Address" sequence of one of the Genomic Records, thereby modulating expression of that Genomic Record, and, accordingly, determining the cell's fate (analogous to opening the recipe book 8 to a page corresponding to a number on the scribbled note, thereby determining the dish to be prepared). A Genomic Record may also comprise multiple short RNA segments, each of which binds complementarily to a target protein-coding gene, thus modulating expression of this target gene. The Genomic Records concept is analogous to the shorthand format illustrated by FIG. 4 whereby a page, such as page 127, designated by reference numeral 10, points to other pages, such as pages 118, 175 and 183, designated by reference numerals 31-33 respectively, encoding various ingredients, such as flour 34, milk 35 and salt 36, all of FIG. 4.

Reference is now made to FIG. 5A. FIG. 5A illustrates a cell 37 having a genome 38. The genome 38 comprises a plurality of Genomic Records, some of which correspond to specific cell types. As an example, six such genomic records are shown, corresponding to six cell types: lymphocyte (LYMPH) genomic record 39, fibroblast (FIBRO) genomic record 40, muscle genomic record 41, bone genomic record 42, cartilage (CARTIL.) genomic record 43 and nerve genomic record 44. Each genomic record comprises genomic instructions on differentiation into a specific cell type, as further elaborated hereinbelow with reference to FIG. 7. At its inception, cell 37 receives a material short RNA segment 46, which activates one of the genomic records, causing the cell to differentiate according to the instructions this genomic record comprises. As an example, FIG. 5A illustrates cell 37 reception of a maternal short RNA segment, designated by reference numeral 46 and outlined by a broken line, having a nucleotide sequence herein symbolically represented by A'.

The fibroblast genomic record 40 contains a binding site having a nucleotide sequence symbolically represented by A, which is complementary to the nucleotide sequence of A', and therefore the short RNA segment 46 binds to the fibroblast genomic record 40. This binding activates the fibroblast genomic record, causing cell 37 to differentiate into a fibroblast cell 3 (FIG. 1). Other genomic records, designated by reference numerals 39 and 41-44, comprise binding sites having nucleotide sequences that are symbolically represented by F, E, B, C and D respectively, which are not complementary to the nucleotide sequence of the short RNA segment 46 symbolically represented by A' and are therefore not activated by it. Genomic Records, such as the fibroblast genomic record 40, contain additional information, designated by reference numeral 45, which is further elaborated hereinbelow with reference to FIGS. 6 and 7.

Reference is now made to FIG. 5B, which is a simplified schematic diagram that illustrates a concept of cellular differentiation that is mediated by Genomic Records. FIG. 5B depicts two cells in an organism, cell A designated by reference numeral 47 and cell B designated by reference numeral 48, each having a genome 38. It is appreciated that since cell A 47 and cell B 48 are cells in the same organism, the genome 38 of cells 47 and 48 is identical. Despite having an identical genome 38, cell A 47 differentiates differently from cell B 48 due to the activation of different genomic records in these two cells. In cell A 47, the fibroblast genomic record 40 is activated, causing cell A 47 to differentiate into a fibroblast cell 3, whereas in cell B 48, the bone genomic record 42 is activated, causing cell B 48 to differentiate into a bone cell 4 (FIG. 1). The activation of different genomic records in these two cells is due to the different maternal short RNA segments which each received. Cell A 47 received a maternal short RNA segment designated 46 bearing a nucleotide sequence represented by A' that activates the fibroblast genomic record 40, whereas cell B 48 received a maternal short RNA segment designated 49 bearing a nucleotide sequence represented by B' that activates the bone genomic record 42.

Figure 6:
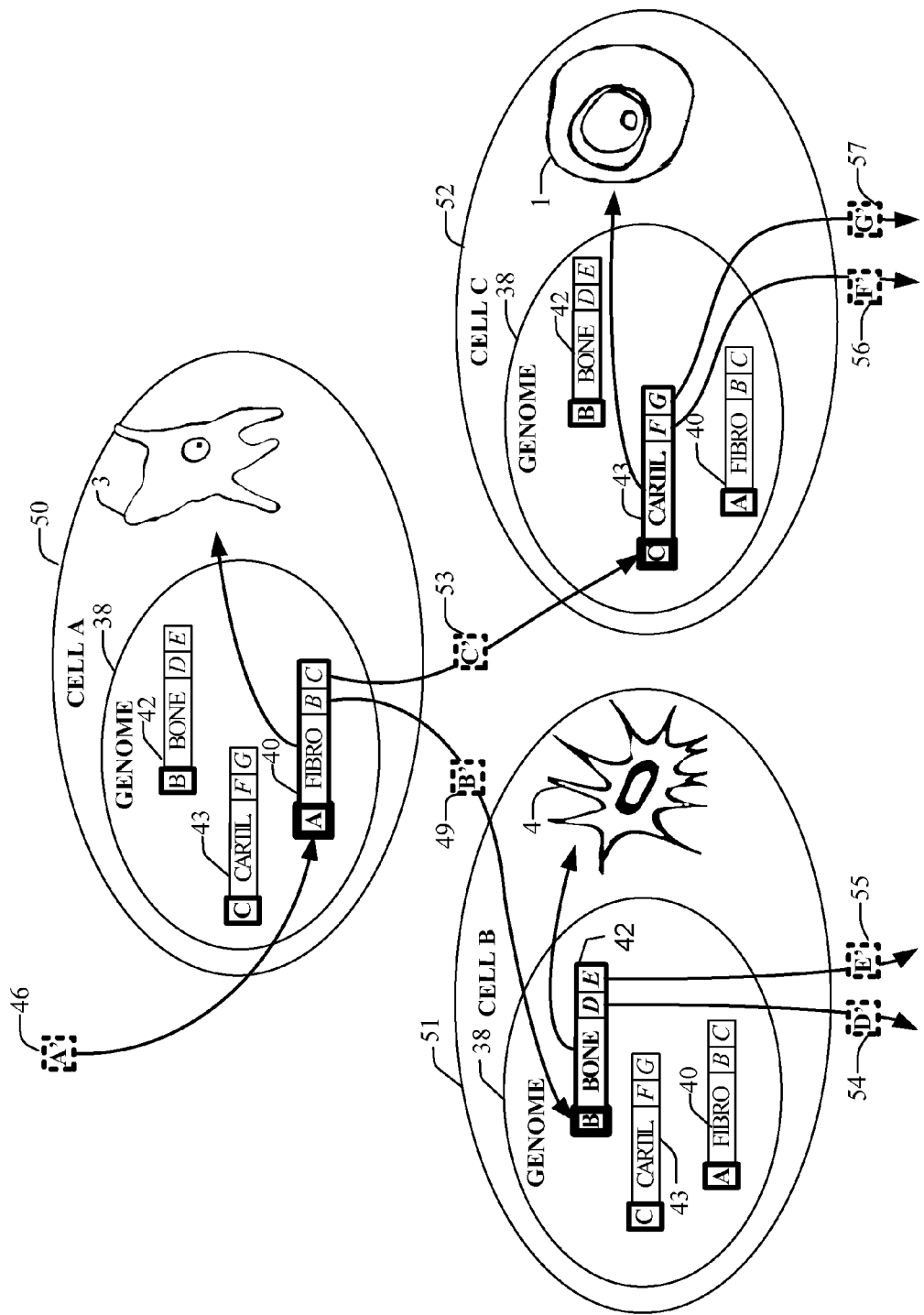
FIG. 6 is a schematic diagram illustrating a "genomically programmed cell differentiation" concept of the conceptual model of the present invention, addressing the genomic differentiation enigma.

Reference is now made to FIG. 6 which is a schematic diagram illustrating a "genomically programmed cell differentiation" concept of the conceptual model of the present invention, addressing the genomic differentiation enigma.

A cell designated cell A 50 divides into 2 cells designated cell B 51 and cell C 52. Cell A 50, cell B 51 and cell C 52 each comprise a genome 38. Each genome 38 comprises a plurality of genomic records, herein exemplified by reference numerals 40, 42 and 43. It is appreciated that since cell A 50, cell B 51 and cell C 52 are cells in the same organism, the genome 38 of these cells, and the genomic records of these cells, exemplified by 40, 42 and 43, are identical.

As described above with reference to FIG. 5B, at its inception, cell A 50 receives a maternal short RNA segment, designated by reference numeral 46 and outlined by a broken line, having nucleotide sequence represented by A'. This short RNA sequence activates the fibroblast genomic record 40, thereby causing cell A 50 to differentiate into a fibroblast cell 3. However, FIG. 6 elaborates on some of the additional information 45 of FIG. 5A of the genomic records. Specifically, a genomic record may also comprise two short genomic sequences, referred to here as Daughter Cell Genomic Addresses. Blocks designated B and C within the fibroblast genomic record in cell A 50 are Daughter Cell Genomic Addresses of the fibroblast genomic record. At cell division, each parent cell transcribes two short RNA segments, corresponding to the two Daughter Cell Genomic Addresses of the genomic record of that parent cell. The parent cell then transfers one of the Daughter Cell Genomic Addresses to each of its two daughter cells. As an example, cell A 50 transcribes and transfers to its two daughter cells 51 and 52 two short RNA segments, designated by reference numerals 49 and 53 and outlined by a broken line. The nucleotide sequences of these two short RNA segments, represented by B' and C' respectively, are complementary to the daughter cell genomic addresses designated B and C comprised in the fibroblast genomic record 40.

Cell B 51 therefore receives the abovementioned maternal short RNA segment designated 49, having a nucleotide sequence represented by B', which binds complementarily to the genomic address B of the bone genomic record 42. The binding of the nucleotide sequence B' to the genomic address B activates this genomic record, which in turn causes cell B 51 to differentiate into a bone cell 4. Similarly, cell C 52 receives the abovementioned maternal short RNA segment designated 53 having a nucleotide sequence represented by C', which binds complementarily to the genomic address C of the cartilage genomic record 43. The binding of the nucleotide sequence C' to the genomic address C activates this genomic record, which in turn causes cell C 52 to differentiate into a cartilage cell 1 (FIG. 1).

It is appreciated that the mechanism illustrated by FIG. 6 enables the determination of the cell fate of an unlimited lineage of daughter cells containing the same DNA 5 (FIG. 1). For example, when cell B 51 and cell C 52 divide into their respective daughter cells (not shown), they transfer the short RNA segments designated by reference numerals 54-57 to their respective daughter cells. The genomic record that is activated in each of these daughter cells is affected by the identity of the maternal short RNA segments 54-57 that they each receive, which in turn determines their cell fate.

Figure 7:
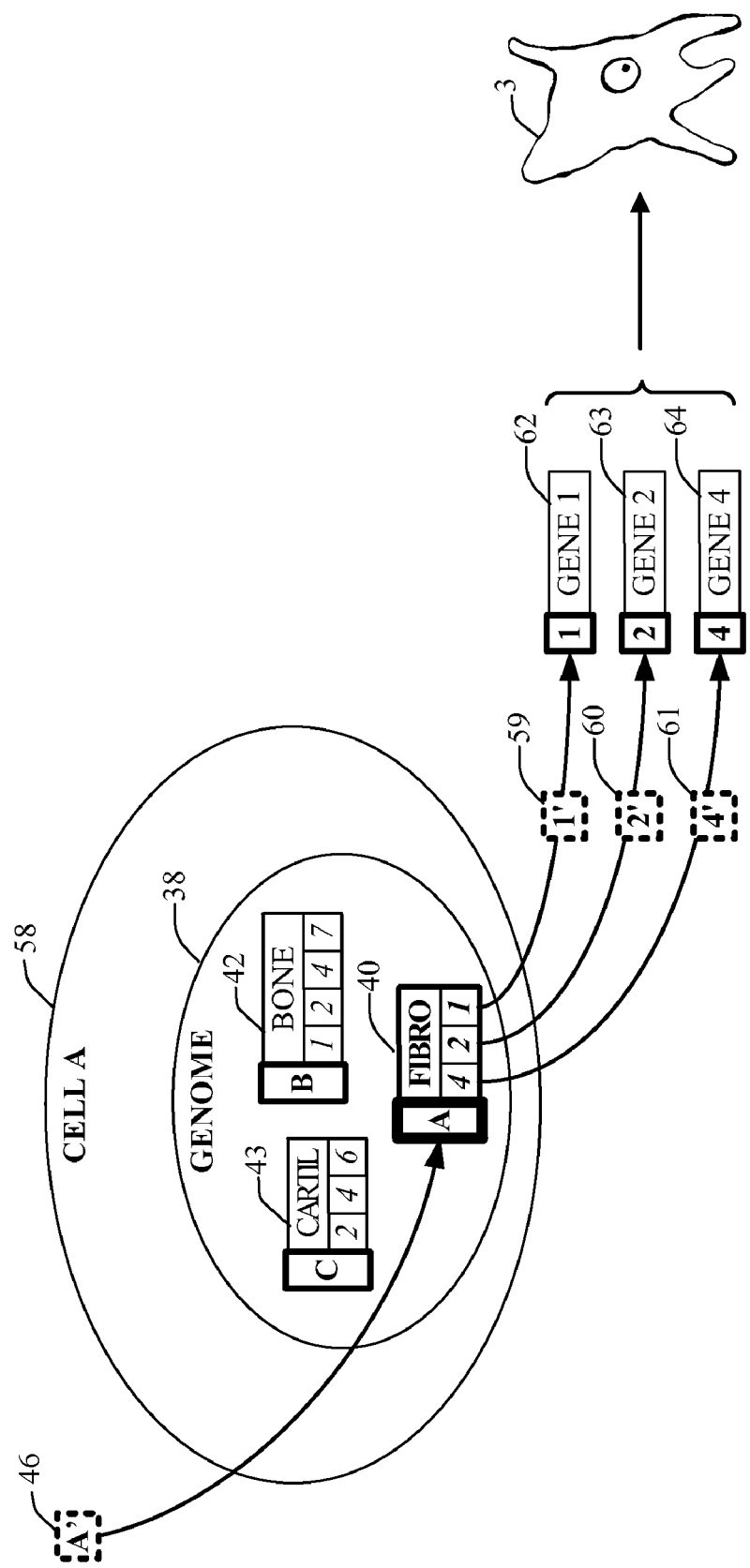
FIG. 7 is a schematic diagram illustrating a "genomically programmed cell-specific protein expression modulation" concept of the conceptual model of the present invention, addressing the genomic differentiation enigma.

Reference is now made to FIG. 7 which is a schematic diagram illustrating a "genomically programmed cell-specific protein expression modulation" concept of the conceptual model of the present invention, addressing the genomic differentiation enigma.

Cell A 58 receives a maternal short RNA segment designated 46 having a nucleotide sequence represented by A'. This maternal short RNA segment 46 activates the fibroblast genomic record 40 by complementarily binding to a binding site in the fibroblast genomic record, whose nucleotide sequence is designated A, and is complementary to the nucleotide sequence represented by A'. This is similar to the process shown in FIG. 5A. However, FIG. 7 further elaborates on some of the additional information 45 (FIG. 5A). The fibroblast genomic record 40 comprises three short nucleotide segments, whose nucleotide sequences are symbolically represented by 1, 2 and 4 respectively. These short nucleotide segments encode three respective short RNA oligonucleotides, designated by reference numerals 59-61. Each of these short RNA oligonucleotides modulates expression of a respective one of the target genes GENE 1, GENE 2 and GENE 4, designated by reference numerals 62-64 respectively, by complementarily binding to a binding site sequence associated with that target gene. In a preferred embodiment of the present invention, the translation inhibition of target genes by complementarily binding to binding sites located in UTRs of the target genes modulates the expression of target genes such as 62-64. Cell A 58 thus differentiates into a fibroblast cell 3 (see also FIG. 1) because the expression of genes 1, 2 and 4 was modulated.

It is appreciated that the concept of genomic records is compatible with features of miRNA-like oligonucleotides of the present invention. A genomic record may comprise a cluster of short RNA segments that modulates the expression of target genes and thus influences differentiation. These features of genomic records are similar to the clusters of miRNA-like oligonucleotides of the present invention, which inhibit the translation of their respective target genes by complementarily binding to binding sites located in the of mRNA of these target genes.

Figure 8:
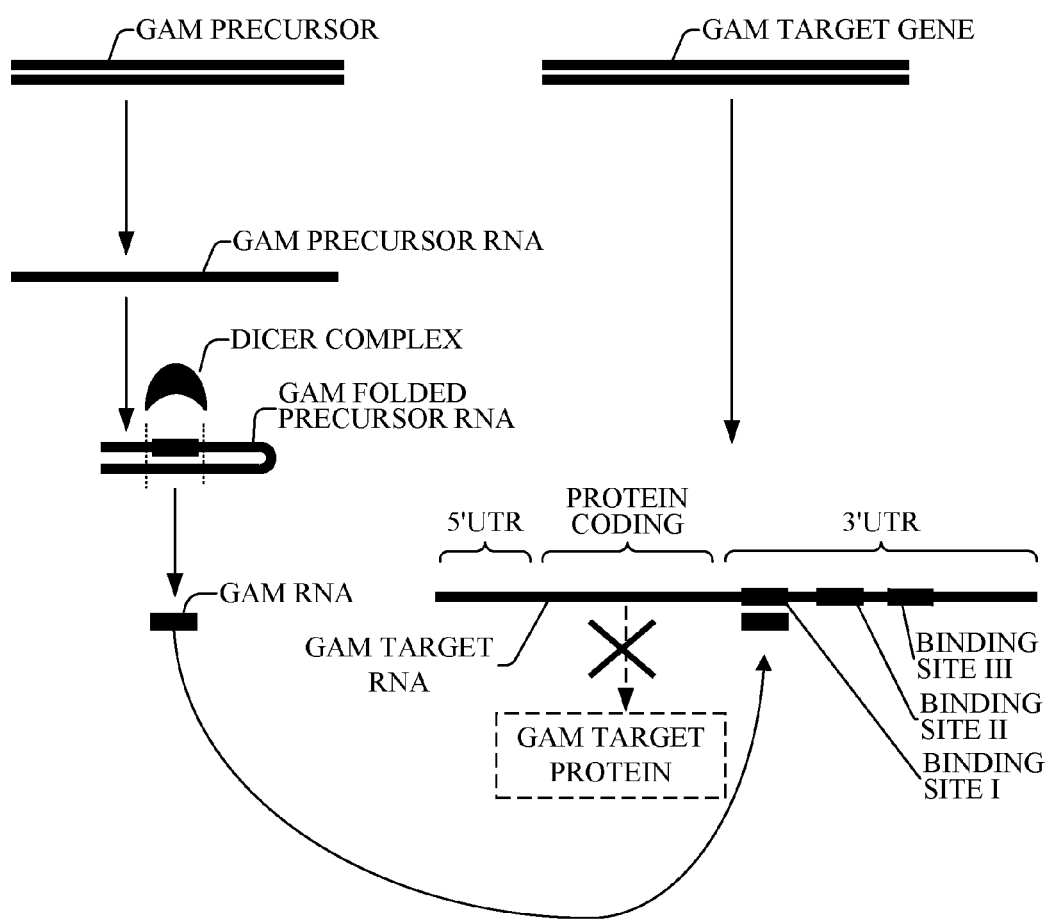
FIG. 8 is a simplified diagram illustrating a mode by which an oligonucleotide of a novel group of oligonucleotides of the present invention modulates expression of known target genes.

Reference is now made to FIG. 8, which is a simplified diagram describing a plurality of novel bioinformatically-detected oligonucleotide of the present invention referred to here as the Genomic Address Messenger (GAM) oligonucleotide, which modulates the expression of respective target genes whose function and utility are known in the art.

GAM is a novel bioinformatically detectable regulatory, non-protein-coding, miRNA-like oligonucleotide. The method by which GAM is detected is described with additional reference to FIGS. 8-15.

The GAM PRECURSOR is encoded by the human genome. The GAM TARGET GENE is a gene encoded by the human genome.

The GAM PRECURSOR encodes a GAM PRECURSOR RNA. Similar to other miRNA oligonucleotides, the GAM PRECURSOR RNA does not encode a protein.

GAM PRECURSOR RNA folds onto itself, forming GAM FOLDED PRECURSOR RNA, which has a two-dimensional "hairpin" structure. GAM PRECURSOR RNA folds onto itself, forming GAM FOLDED PRECURSOR RNA, which has a two-dimensional "hairpin structure". As is well-known in the art, this "hairpin structure" is typical of RNA encoded by known miRNA precursor oligonucleotides and is due to the full or partial complementarity of the nucleotide sequence of the first half of an miRNA precursor to the RNA that is encoded by a miRNA oligonucleotide to the nucleotide sequence of the second half thereof.

A complementary sequence is a sequence which is reversed and wherein each nucleotide is replaced by a complementary nucleotide, as is well known in the art (e.g. ATGGC is the complementary sequence of GCCAT).

An enzyme complex designated DICER COMPLEX, an enzyme complex composed of Dicer RNaseIII together with other necessary proteins, cuts the GAM FOLDED PRECURSOR RNA yielding a single-stranded ~22 nt-long RNA segment designated GAM RNA.

GAM TARGET GENE encodes a corresponding messenger RNA, designated GAM TARGET RNA. As is typical of mRNA of a protein-coding gene, each GAM TARGET RNAs of the present invention comprises three regions, as is typical of mRNA of a protein-coding gene: a 5' untranslated region, a protein-coding region and a 3' untranslated region, designated 5'UTR, PROTEIN-CODING and 3'UTR, respectively.

GAM RNA binds complementarily to one or more target binding sites located in the untranslated regions of each of the GAM TARGET RNAs of the present invention. This complementary binding is due to the partial or full complementarity between the nucleotide sequence of GAM RNA and the nucleotide sequence of each of the target binding sites. As an illustration, FIG. 8 shows three such target binding sites, designated BINDING SITE I, BINDING SITE II and BINDING SITE III, respectively. It is appreciated that the number of target binding sites shown in FIG. 8 is only illustrative and that any suitable number of target binding sites may be present. It is further appreciated that although FIG. 8 shows target binding sites only in the 3'UTR region, these target binding sites may instead be located in the 5'UTR region or in both the 3'UTR and 5'UTR regions.

The complementary binding of GAM RNA to target binding sites on GAM TARGET RNA, such as BINDING SITE I, BINDING SITE II and BINDING SITE III, inhibits the translation of each of the GAM TARGET RNAs of the present invention into respective GAM TARGET PROTEIN, shown surrounded by a broken line.

It is appreciated that the GAM TARGET GENE in fact represents a plurality of GAM target genes. The mRNA of each one of this plurality of GAM target genes comprises one or more target binding sites, each having a nucleotide sequence which is at least partly complementary to GAM RNA and which when bound by GAM RNA causes inhibition of translation of the GAM target mRNA into a corresponding GAM target protein.

The mechanism of the translational inhibition that is exerted by GAM RNA on one or more GAM TARGET GENEs may be similar or identical to the known mechanism of translational inhibition exerted by known miRNA oligonucleotides.

The nucleotide sequences of each of a plurality of GAM oligonucleotides that are described by FIG. 8 and their respective genomic sources and genomic locations are set forth in Tables 1-3, hereby incorporated herein.

The nucleotide sequences of GAM PRECURSOR RNAs, and a schematic representation of a predicted secondary folding of GAM FOLDED PRECURSOR RNAs, of each of a plurality of GAM oligonucleotides that are described by FIG. 8 are set forth in Table 4, hereby incorporated herein.

The nucleotide sequences of "diced" GAM RNAs of each of a plurality of GAM oligonucleotides that are described by FIG. 8 are set forth in Table 5, hereby incorporated herein.

The nucleotide sequences of target binding sites, such as BINDING SITE I, BINDING SITE II and BINDING SITE III that are found on GAM TARGET RNAs of each of a plurality of GAM oligonucleotides that are described by FIG. 8, and a schematic representation of the complementarity of each of these target binding sites to each of a plurality of GAM RNAs that are described by FIG. 8 are set forth in Tables 6-7, hereby incorporated herein.

It is appreciated that the specific functions and accordingly the utilities of each of a plurality of GAM oligonucleotides that are described by FIG. 8 are correlated with and may be deduced from the identity of the GAM TARGET GENES inhibited thereby, and whose functions are set forth in Table 8, hereby incorporated herein.

Studies documenting the well known correlations between each of a plurality of GAM TARGET GENEs that are described by FIG. 8 and the known gene functions and related diseases are listed in Table 9, hereby incorporated herein.

The present invention discloses a novel group of human oligonucleotides, belonging to the miRNA-like oligonucleotide group, here termed GAM oligonucleotides, for which a specific complementary binding has been determined bioinformatically.

Reference is now made to FIG. 9 which is a simplified block diagram illustrating a bioinformatic oligonucleotide detection system and method constructed and operative in accordance with a preferred embodiment of the present invention.

An important feature of the present invention is a bioinformatic oligonucleotide detection engine 100, which is capable of bioinformatically detecting oligonucleotides of the present invention.

The functionality of the bioinformatic oligonucleotide detection engine 100 includes receiving expressed RNA data 102, sequenced DNA data 104, and PROTEIN FUNCTION DATA 106; performing a complex process of analysis of this data as elaborated hereinbelow, and based on this analysis provides information, designated by reference numeral 108, identifying and describing features of novel oligonucleotides.

Expressed RNA data 102 comprises published expressed sequence tags (EST) data, published mRNA data, as well as other published RNA data. Sequenced DNA data 104 comprises alphanumeric data representing genomic sequences and preferably including annotations such as information indicating the location of known protein-coding regions relative to the genomic sequences.

PROTEIN FUNCTION DATA 106 comprises information from scientific publications e.g. physiological functions of known proteins and their connection, involvement and possible utility in treatment and diagnosis of various diseases.

Expressed RNA data 102 and sequenced DNA data 104 may preferably be obtained from data published by the National Center for Biotechnology Information (NCBI) at the National Institute of Health (NIH) (Jenuth, J. P. (2000). Methods Mol. Biol. 132:301-312 (2000), herein incorporated by reference) as well as from various other published data sources. PROTEIN FUNCTION DATA 106 may preferably be obtained from any one of numerous relevant published data sources, such as the Online Mendelian Inherited Disease In Man (OMIM™, Hamosh et al., Nucleic Acids Res. 30: 52-55 (2002)) database developed by John Hopkins University, and also published by NCBI (2000).

Prior to or during actual detection of BIOINFORMATICALLY-DETECTED GROUP OF NOVEL OLIGONUCLE- OTIDES 108 by the bioinformatic oligonucleotide detection engine 100, bioinformatic oligonucleotide detection engine training & validation functionality 110 is operative. This functionality uses one or more known miRNA oligonucleotides as a training set to train the bioinformatic oligonucleotide detection engine 100 to bioinformatically recognize miRNA-like oligonucleotides, and their respective potential target binding sites. BIOINFORMATIC OLIGONUCLEOTIDE DETECTION ENGINE TRAINING &VALIDATION FUNCTIONALITY 110 is further described hereinbelow with reference to FIG. 10.

The bioinformatic oligonucleotide detection engine 100 preferably comprises several modules which are preferably activated sequentially, and are described as follows:

A NON-CODING GENOMIC SEQUENCE DETECTOR 112 operative to bioinformatically detect non-protein-coding genomic sequences. The non-protein-coding genomic sequence detector 112 is further described herein below with reference to FIGS. 11A and 11B.

A hairpin detector 114 operative to bioinformatically detect genomic "hairpin-shaped" sequences, similar to GAM FOLDED PRECURSOR RNA (FIG. 8). The hairpin detector 114 is further described herein below with reference to FIGS. 12A and 12B.

A Dicer-cut location detector 116 operative to bioinformatically detect the location on a GAM FOLDED PRECURSOR RNA which is enzymatically cut by DICER COMPLEX (FIG. 8), yielding "diced" GAM RNA. The Dicer-cut location detector 116 is further described herein below with reference to FIGS. 13A-13C.

A target gene binding site detector 118 operative to bioinformatically detect target genes having binding sites, the nucleotide sequence of which is partially complementary to that of a given genomic sequence, such as a nucleotide sequence cut by DICER COMPLEX. The target gene binding site detector 118 is further described hereinbelow with reference to FIGS. 14A and 14B.

A function & utility analyzer, designated by reference numeral 120, is operative to analyze the function and utility of target genes in order to identify target genes which have a significant clinical function and utility. The function & utility analyzer 120 is further described hereinbelow with reference to FIG. 15

According to an embodiment of the present invention, the bioinformatic oligonucleotide detection engine 100 may employ a cluster of 40 personal computers (PCs; XEON®, 2.8 GHz, with 80 GB storage each) connected by Ethernet to eight servers (2-CPU, XEON™ 1.2-2.2 GHz, with ~200 GB storage each) and combined with an 8-processor server (8-CPU, Xeon 550 Mhz w/8 GB RAM) connected via 2 HBA fiber-channels to an EMC CLARIION™ 100-disks, 3.6 Terabyte storage device. A preferred embodiment of the present invention may also preferably comprise software that utilizes a commercial database software program, such as MICROSOFT™ SQL Server 2000.

According to a preferred embodiment of the present invention, the bioinformatic oligonucleotide detection engine 100 may employ a cluster of 80 Servers (XEON®, 2.8 GHz, with 80 GB storage each) connected by Ethernet to eight servers (2-CPU, XEON™ 1.2-2.2 GHz, with ~200 GB storage each) and combined with storage device (Promise Technology Inc., RM8000) connected to an 8-disks, 2 Terabytes total. A preferred embodiment of the present invention may also preferably comprise software that utilizes a commercial database software program, such as MICROSOFT™ SQL Server 2000. It is appreciated that the abovementioned hardware configuration is not meant to be limiting and is given as an illustration only. The present invention may be implemented in a wide variety of hardware and software configurations.

The present invention discloses 122764 novel oligonucleotides of the GAM group of oligonucleotides, which have been detected bioinformatically and 18602 novel polynucleotides of the GR group of polynucleotides, which have been detected bioinformatically. Laboratory confirmation of bioinformatically predicted oligonucleotides of the GAM group of oligonucleotides, and several bioinformatically predicted polynucleotides of the GR group of polynucleotides, is described hereinbelow with reference to FIGS. 21-24D. FIG. 27 and TABLE_13.txt.

Reference is now made to FIG. 10 which is a simplified flowchart illustrating operation of a preferred embodiment of the bioinformatic oligonucleotide detection engine training & validation functionality 110 described hereinabove with reference to FIG. 9.

bioinformatic oligonucleotide detection engine training & validation functionality 110 begins by training the bioinformatic oligonucleotide detection engine 100 (FIG. 9) to recognize one or more known miRNA oligonucleotides, as designated by reference numeral 122. This training step comprises hairpin detector training & validation functionality 124, further described hereinbelow with reference to FIG. 12A, Dicer-cut location detector training & validation functionality 126, further described hereinbelow with reference to FIGS. 13A and 13B, and target gene binding site detector training & validation functionality 128, further described hereinbelow with reference to FIG. 14A.

Next, the bioinformatic oligonucleotide detection engine training & validation functionality 110 is operative bioinformatically detect novel oligonucleotides, using bioinformatic oligonucleotide detection engine 100 (FIG. 9), as designated by reference numeral 130. Wet lab experiments are preferably conducted in order to validate expression and preferably function of some samples of the novel oligonucleotides detected by the bioinformatic oligonucleotide detection engine 100, as designated by reference numeral 132. FIGS. 22A-24D and Table 13 illustrate examples of wet lab validation of sample novel human oligonucleotides bioinformatically-detected in accordance with a preferred embodiment of the present invention.

Figure 11A:
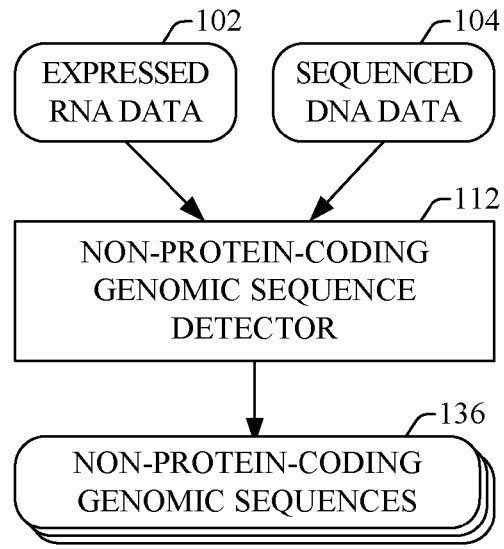
FIG. 11A is a simplified block diagram of a non-coding genomic sequence detector constructed and operative in accordance with a preferred embodiment of the present invention.

Reference is now made to FIG. 11A which is a simplified block diagram of a preferred implementation of the non-protein-coding genomic sequence detector 112 described hereinabove with reference to FIG. 9. The non-protein-coding genomic sequence detector 112 preferably receives at least two types of published genomic data: Expressed RNA data 102 and sequenced DNA data 104. The expressed RNA data 102 may include, inter alia, EST data, EST clusters data, EST genome alignment data and mRNA data. Sources for expressed RNA data 102 include NCBI dbEST, NCBI UniGene clusters and mapping data, and TIGR gene indices (Kirkness F. and Kerlavage, A. R., Methods Mol. Biol. 69:261-268 (1997)). Sequenced DNA data 104 may include sequence data (FASTA format files), and feature annotations (GenBank file format) mainly from NCBI databases. Based on the above mentioned input data, the non-protein-coding genomic sequence detector 112 produces a plurality of non-protein-coding genomic sequences 136. Preferred operation of the non-protein-coding genomic sequence detector 112 is described hereinbelow with reference to FIG. 11B.

Figure 11B:
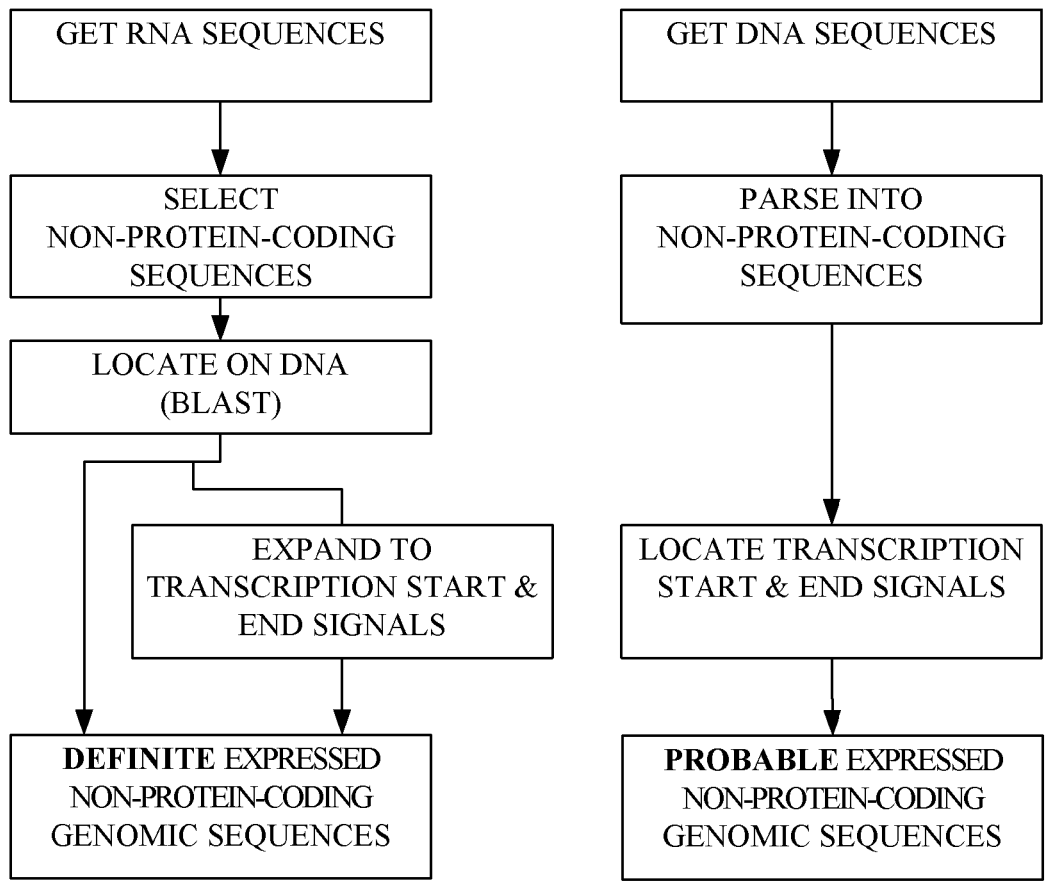
FIG. 11B is a simplified flowchart illustrating operation of a non-coding genomic sequence detector constructed and operative in accordance with a preferred embodiment of the present invention.

Reference is now made to FIG. 11B which is a simplified flowchart illustrating a preferred operation of the non-protein-coding genomic sequence detector 112 of FIG. 9. Detection of non-protein-coding genomic sequences 136, generally preferably progresses along one of the following two paths:

A first path for detecting non-protein-coding genomic sequences 136 (FIG. 11A) begins with receipt of a plurality of known RNA sequences, such as EST data. Each RNA sequence is first compared with known protein-coding DNA sequences, in order to select only those RNA sequences which are non-protein-coding, i.e. intergenic or intronic sequences. This can preferably be performed by using one of many alignment algorithms known in the art, such as BLAST (Altschul et al., J. Mol. Biol. 215:403-410 (1990)). This sequence comparison preferably also provides localization of the RNA sequence on the DNA sequences.

Alternatively, selection of non-protein-coding RNA sequences and their localization on the DNA sequences can be performed by using publicly available EST cluster data and genomic mapping databases, such as the UNIGENE database published by NCBI or the TIGR database. Such databases, map expressed RNA sequences to DNA sequences encoding them, find the correct orientation of EST sequences, and indicate mapping of ESTs to protein-coding DNA regions, as is well known in the art. Public databases, such as TIGR, may also be used to map an EST to a cluster of ESTs, known in the art as Tentative Human Consensus and assumed to be expressed as one segment. Publicly available genome annotation databases, such as NCBI's GenBank, may also be used to deduce expressed intronic sequences.

Optionally, an attempt may be made to "expand" the non-protein RNA sequences thus found, by searching for transcription start and end signals, respectively upstream and downstream of the location of the RNA on the DNA, as is well known in the art.

A second path for detecting non-protein-coding genomic sequences 136 (FIG. 11A) begins with receipt of DNA sequences. The DNA sequences are parsed into non-protein-coding sequences, using published DNA annotation data, by extracting those DNA sequences which are between known protein-coding sequences. Next, transcription start and end signals are sought. If such signals are found, and depending on their robustness, probable expressed non-protein-coding genomic sequences are obtained. Such approach is especially useful for identifying novel GAM oligonucleotides which are found in proximity to other known miRNA oligonucleotides, or other wet lab validated GAM oligonucleotides. Since, as described hereinbelow with reference to FIG. 16, GAM oligonucleotides are frequently found in clusters; sequences located near known miRNA oligonucleotides are more likely to contain novel GAM oligonucleotides. Optionally, sequence orthology, i.e. sequence conservation in an evolutionary related species, may be used to select genomic sequences having a relatively high probability of containing expressed novel GAM oligonucleotides.

Figure 12A:
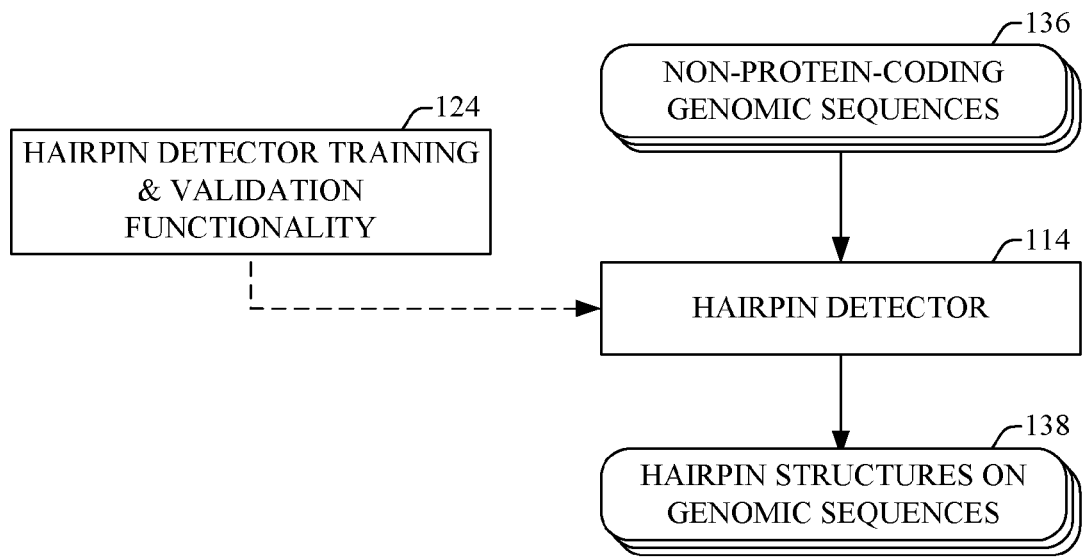
FIG. 12A is a simplified block diagram of a hairpin detector constructed and operative in accordance with a preferred embodiment of the present invention.

Reference is now made to FIG. 12A which is a simplified block diagram of a preferred implementation of the hairpin detector 114 described hereinabove with reference to FIG. 9.

The goal of the hairpin detector 114 is to detect hairpin-shaped genomic sequences, similar to those of known miRNA oligonucleotides. A hairpin-shaped genomic sequence is a genomic sequence, having a first half which is at least partially complementary to a second half thereof, which causes the halves to folds onto themselves, thereby forming a hairpin structure, as mentioned hereinabove with reference to FIG. 8.

The hairpin detector 114 (FIG. 9) receives a plurality of non-protein-coding genomic sequences 136 (FIG. 11A). Following operation of hairpin detector training & validation functionality 124 (FIG. 10), the hairpin detector 114 is operative to detect and output hairpin-shaped sequences, which are found in the non-protein-coding genomic sequences 136. The hairpin-shaped sequences detected by the hairpin detector 114 are designated hairpin structures on genomic sequences 138. A preferred mode of operation of the hairpin detector 114 is described hereinbelow with reference to FIG. 12B.

hairpin detector training & validation functionality 124 includes an iterative process of applying the hairpin detector 114 to known hairpin-shaped miRNA precursor sequences, calibrating the hairpin detector 114 such that it identifies a training set of known hairpin-shaped miRNA precursor sequences, as well as other similarly hairpin-shaped sequences. In a preferred embodiment of the present invention, the hairpin detector training & validation functionality 124 trains the hairpin detector 114 and validates each of the steps of operation thereof described hereinbelow with reference to FIG. 12B

The hairpin detector training & validation functionality 124 preferably uses two sets of data: the aforesaid training set of known hairpin-shaped miRNA precursor sequences, such as hairpin-shaped miRNA precursor sequences of 440 miRNA oligonucleotides of *H. sapiens, M. musculus, C. elegans, C. Brigssae* and *D. Melanogaster*, annotated in the RFAM database (Griffiths-Jones 2003), and a background set of about 1000 hairpin-shaped sequences found in expressed non-protein-coding human genomic sequences. The background set is expected to comprise some valid, previously undetected hairpin-shaped miRNA-like precursor sequences, and many hairpin-shaped sequences which are not hairpin-shaped miRNA-like precursors.

In a preferred embodiment of the present invention the efficacy of the hairpin detector 114 (FIG. 9) is confirmed. For example, when a similarity threshold is chosen such that 87% of the known hairpin-shaped miRNA precursors are successfully predicted, only 21.8% of the 1000 background set of hairpin-shaped sequences are predicted to be hairpin-shaped miRNA-like precursors.

Figure 12B:
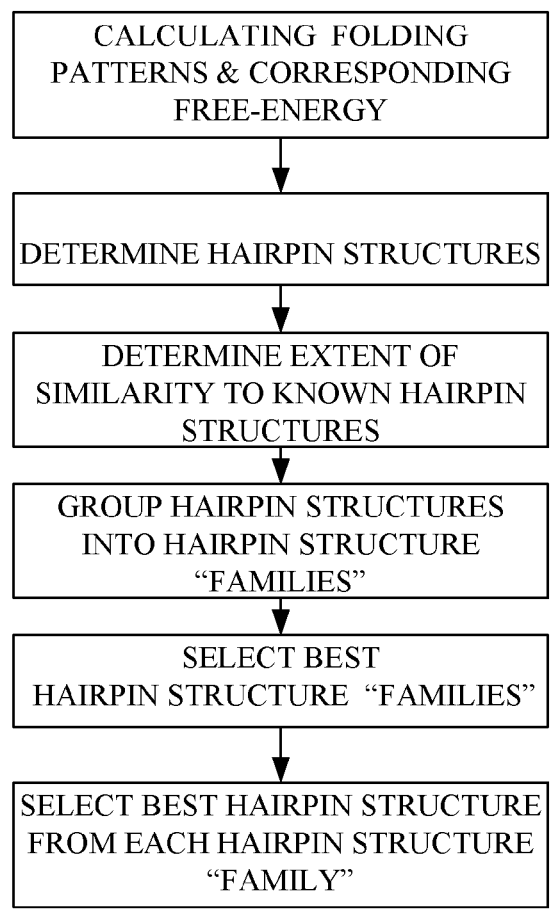
FIG. 12B is a simplified flowchart illustrating operation of a hairpin detector constructed and operative in accordance with a preferred embodiment of the present invention.

Reference is now made to FIG. 12B which is a simplified flowchart illustrating preferred operation of the hairpin detector 114 of FIG. 9. The hairpin detector 114 preferably initially uses a secondary structure folding algorithm based on free-energy minimization, such as the MFOLD algorithm, described in Mathews et al. J. Mol. Biol. 288:911-940 (1999) and Zuker, M. Nucleic Acids Res. 31: 3406-3415 (2003), the disclosure of which is hereby incorporated by reference. This algorithm is operative to calculate probable secondary structure folding patterns of the non-protein-coding genomic sequences 136 (FIG. 11A) as well as the free-energy of each of these probable secondary folding patterns. The secondary structure folding algorithm, such as the MFOLD algorithm (Mathews, 1997; Zuker 2003), typically provides a listing of the base-pairing of the folded shape, i.e. a listing of each pair of connected nucleotides in the sequence.

Next, the hairpin detector 114 analyzes the results of the secondary structure folding patterns, in order to determine the presence and location of hairpin folding structures. The goal of this second step is to assess the base-pairing listing provided by the secondary structure folding algorithm, in order to determine whether the base-pairing listing describes one or more hairpin type bonding pattern. Preferably, sequence segment corresponding to a hairpin structure is then separately analyzed by the secondary structure folding algorithm in order to determine its exact folding pattern and free-energy.

The hairpin detector 114 then assesses the hairpin structures found by the previous step, comparing them to hairpin structures of known miRNA precursors, using various characteristic hairpin structure features such as its free-energy and its thermodynamic stability, the amount and type of mismatched nucleotides and the existence of sequence repeat-elements, number of mismatched nucleotides in positions 18-22 counting from loop, and Percent of G nucleotide. Only hairpins that bear statistically significant resemblance to the training set of hairpin structures of known miRNA precursors, according to the abovementioned parameters, are accepted.

In a preferred embodiment of the present invention, similarity to the training set of hairpin structures of known miRNA precursors is determined using a "similarity score" which is calculated using a multiplicity of terms, where each term is a function of one of the above-mentioned hairpin structure features. The parameters of each function are found heuristically from the set of hairpin structures of known miRNA precursors, as described hereinabove with reference to hairpin detector training & validation functionality 124 (FIG. 10). The selection of the features and their function parameters is optimized so as to achieve maximized separation between the distribution of similarity scores validated miRNA precursor hairpin structures, and the distribution of similarity scores of hairpin structures detected in the background set mentioned hereinabove with reference to FIG. 12B.

In an alternative preferred embodiment of the present invention, the step described in the preceding paragraph may be split into two stages. A first stage implements a simplified scoring method, typically based on thresholding a subset of the hairpin structure features described hereinabove, and may employ a minimum threshold for hairpin structure length and a maximum threshold for free energy. A second stage is preferably more stringent, and preferably employs a full calculation of the weighted sum of terms described hereinabove. The second stage preferably is performed only on the subset of hairpin structures that survived the first stage.

The hairpin detector 114 also attempts to select hairpin structures whose thermodynamic stability is similar to that of hairpin structures of known miRNA precursors. This may be achieved in various ways. A preferred embodiment of the present invention utilizes the following methodology, preferably comprising three logical steps:

First, the hairpin detector 114 attempts to group hairpin structures into "families" of closely related hairpin structures. As is known in the art, a secondary structure folding algorithm typically provides multiple alternative folding patterns, for a given genomic sequence and indicates the free energy of each alternative folding pattern. It is a particular feature of the present invention that the hairpin detector 114 preferably assesses the various hairpin structures appearing in the various alternative folding patterns and groups' hairpin structures which appear at identical or similar sequence locations in various alternative folding patterns into common sequence location based "families" of hairpins. For example, all hairpin structures whose center is within 7 nucleotides of each other may be grouped into a "family". Hairpin structures may also be grouped into a "family" if their nucleotide sequences are identical or overlap to a predetermined degree.

It is also a particular feature of the present invention that the hairpin structure "families" are assessed in order to select only those families which represent hairpin structures that are as thermodynamically stable as those of hairpin structures of known miRNA precursors. Preferably only families which are represented in at least a selected majority of the alternative secondary structure folding patterns, typically 65%, 80% or 100% are considered to be sufficiently stable. Our tests suggest that only about 50% of the hairpin structures, predicted by the MFOLD algorithm with default parameters, are members of sufficiently stable families, comparing to about 90% of the hairpin structures that contain known miRNAs. This percent depends on the size of the fraction that was fold. In an alternative embodiment of the present invention we use fractions of size 1000 nts as preferable size. Different embodiment uses other sizes of genomics sequences, more or less strict demand for representation in the alternative secondary structure folding patterns.

It is an additional particular feature of the present invention that the most suitable hairpin structure is selected from each selected family. For example, a hairpin structure which has the greatest similarity to the hairpin structures appearing in alternative folding patterns of the family may be preferred. Alternatively or additionally, the hairpin structures having relatively low free energy may be preferred.

Alternatively or additionally considerations of homology to hairpin structures of other organisms and the existence of clusters of thermodynamically stable hairpin structures located adjacent to each other along a sequence may be important in selection of hairpin structures. The tightness of the clusters in terms of their location and the occurrence of both homology and clusters may be of significance.

Figure 13A:
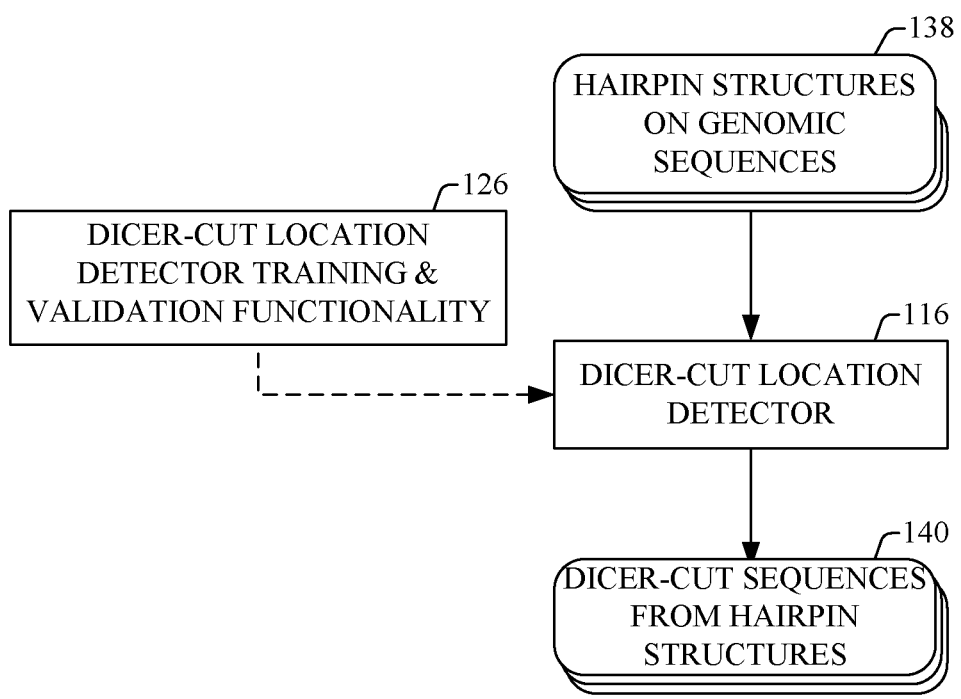
FIG. 13A is a simplified block diagram of a Dicer-cut location detector constructed and operative in accordance with a preferred embodiment of the present invention.
Figure 13B:
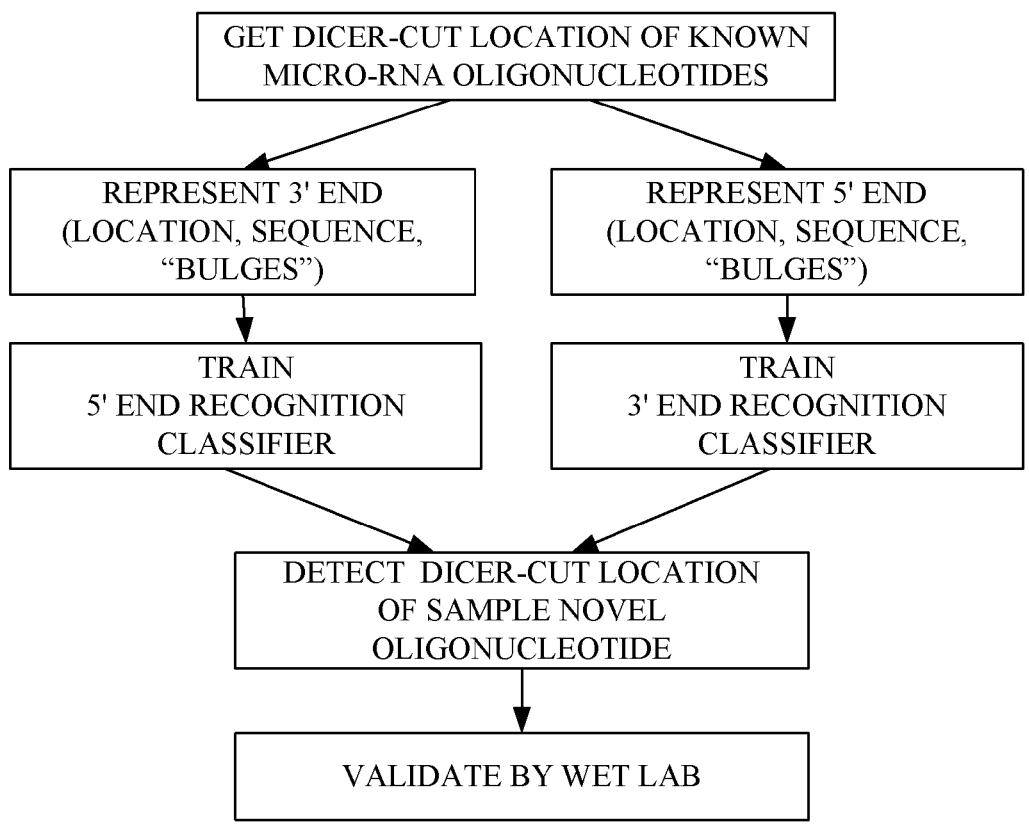
FIG. 13B is a simplified flowchart illustrating training of a Dicer-cut location detector constructed and operative in accordance with a preferred embodiment of the present invention.
Figure 13C:
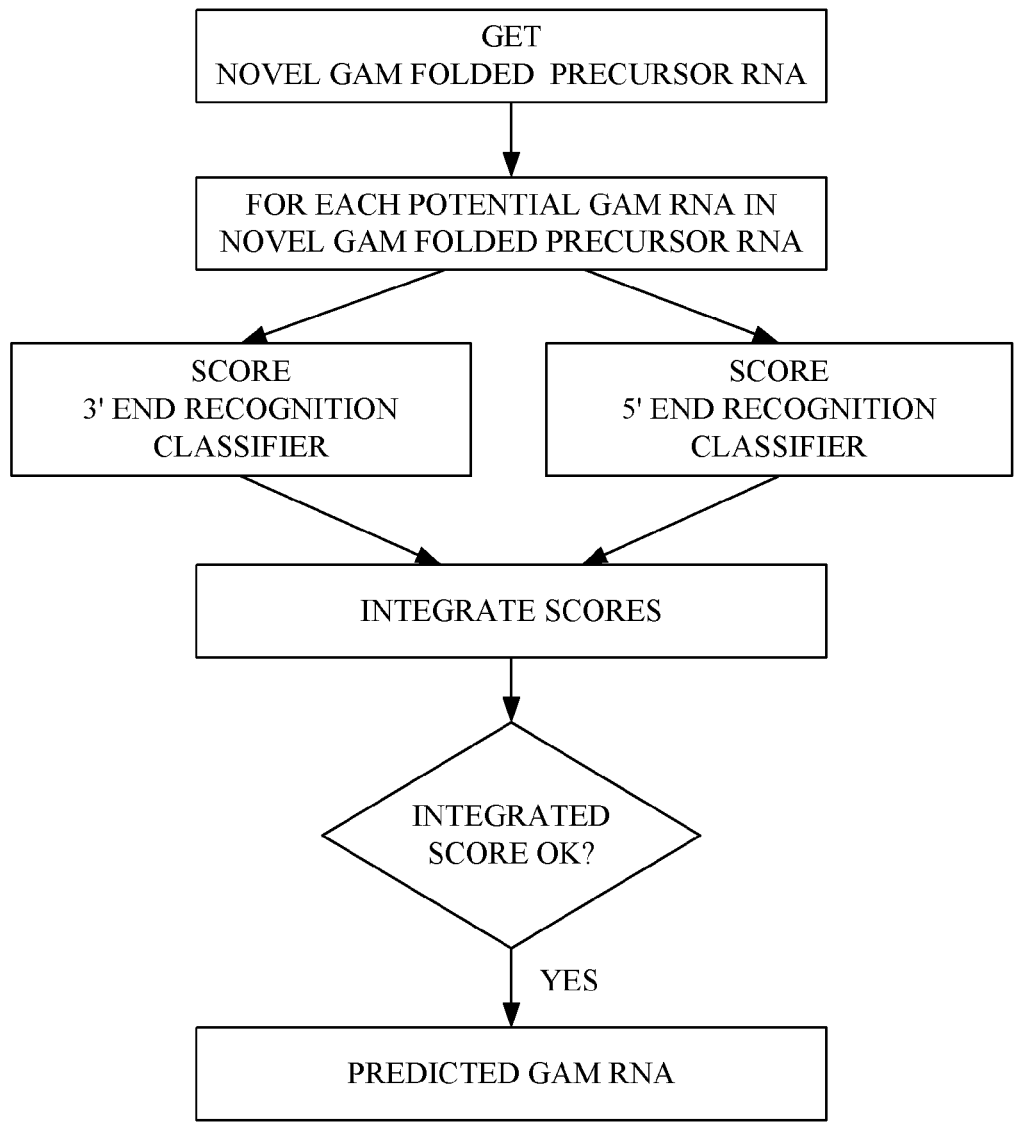
FIG. 13C is a simplified flowchart illustrating operation of a Dicer-cut location detector constructed and operative in accordance with a preferred embodiment of the present invention.

Reference is now made to FIGS. 13A-13C, which together describe the structure and operation of the Dicer-cut location detector 116, described hereinabove with reference to FIG. 9.

Reference is now made to FIG. 13A, which is a simplified block diagram of a preferred implementation of the Dicer-cut location detector 116. The goal of the Dicer-cut location detector 116 is to detect the location in which the DICER COMPLEX, described hereinabove with reference to FIG. 8, dices GAM FOLDED PRECURSOR RNA, yielding GAM RNA.

The Dicer-cut location detector 116 therefore receives a plurality of hairpin structures on genomic sequences, designated by reference numeral 138 (FIG. 12A), and following operation of Dicer-cut location detector training & validation functionality 126 (FIG. 10), is operative to detect a plurality of Dicer-cut sequences from hairpin structures, designated by reference numeral 140.

Reference is now made to FIG. 13B, which is a simplified flowchart illustrating a preferred implementation of Dicer-cut location detector training & validation functionality 126.

A general goal of the Dicer-cut location detector training & validation functionality 126 is to analyze the Dicer-cut locations of known diced miRNA on respective hairpin-shaped miRNA precursors in order to determine a common pattern in these locations, which can be used to predict Dicer-cut locations on GAM folded precursor RNAs.

The Dicer-cut locations of known miRNA precursors are obtained and studied. Locations of the 5' and/or 3' ends of the known diced miRNA oligonucleotides are preferably represented by their respective distances from the 5' end of the corresponding hairpin-shaped miRNA precursor. Additionally or alternatively, the 5' and/or 3' ends of the known diced miRNA oligonucleotides are preferably represented by the relationship between their locations and the locations of one or more nucleotides along the hairpin-shaped miRNA precursor. Additionally or alternatively, the 5' and/or 3' ends of the known diced miRNA oligonucleotides are preferably represented by the relationship between their locations and the locations of one or more bound nucleotide pairs along the hairpin-shaped miRNA precursor. Additionally or alternatively, the 5' and/or 3' ends of the known diced miRNA oligonucleotides are preferably represented by the relationship between their locations and the locations of one or more mismatched nucleotide pairs along the hairpin-shaped miRNA precursor. Additionally or alternatively, the 5' and/or 3' ends of the known diced miRNA oligonucleotides are preferably represented by the relationship between their locations and the locations of one or more unmatched nucleotides along the hairpin-shaped miRNA precursor. Additionally or alternatively, locations of the 5' and/or 3' ends of the known diced miRNA oligonucleotides are preferably represented by their respective distances from the loop located at the center of the corresponding hairpin-shaped miRNA precursor.

One or more of the foregoing location metrics may be employed in the Dicer-cut location detector training & validation functionality 126. Additionally, metrics related to the nucleotide content of the diced miRNA and/or of the hairpin-shaped miRNA precursor may be employed.

In a preferred embodiment of the present invention, Dicer-cut location detector training & validation functionality 126 preferably employs standard machine learning techniques known in the art of machine learning to analyze existing patterns in a given "training set" of examples. Standard machine learning techniques are capable, to a certain degree, of detecting patterns in examples to which they have not been previously exposed that are similar to those in the training set. Such machine learning techniques include, but are not limited to neural networks, Bayesian Modeling, Bayesian Networks, Support Vector Machines (SVM), Genetic Algorithms, Markovian Modeling, Maximum Likelihood Modeling, Nearest Neighbor Algorithms, Decision Trees and other techniques, as is well-known in the art.

In accordance with an embodiment of the present invention, two or more classifiers or predictors based on the abovementioned machine learning techniques are separately trained on the abovementioned training set, and are used jointly in order to predict the Dicer-cut location. As an example, FIG. 13B illustrates operation of two classifiers, a 3' end recognition classifier and a 5' end recognition classifier. Most preferably, the Dicer-cut location detector training & validation functionality 126 implements a "best-of-breed" approach employing a pair of classifiers based on the abovementioned Bayesian Modeling and Nearest Neighbor Algorithms, and accepting only "potential GAM RNAs" that score highly on one of these predictors. In this context, "high scores" means scores that have been demonstrated to have low false positive value when scoring known miRNA oligonucleotides. Alternatively, the Dicer-cut location detector training & validation functionality 126 may implement operation of more or less than two classifiers.

Predictors used in a preferred embodiment of the present invention are further described hereinbelow with reference to FIG. 13C. A computer program listing of a computer program implementation of the Dicer-cut location detector training & validation functionality 126 is enclosed on an electronic medium in computer-readable form, and is hereby incorporated by reference herein.

When evaluated on the abovementioned validation set of 440 published miRNA oligonucleotides using k-fold cross validation (Mitchell, 1997) with k=3, the performance of the resulting predictors is as follows: In 70% of known miRNA oligonucleotides, a 5' end location is correctly determined by a Support Vector Machine predictor within up to two nucleotides; a Nearest Neighbor (EDIT DISTANCE) predictor achieves 56% accuracy (247/440); and a Two-Phased Predictor that uses Bayesian modeling (TWO PHASED) achieves 80% accuracy (352/440) when only the first phase is used. When the second phase (strand choice) is implemented by a naive Bayesian model, the accuracy is 55% (244/440), and when the K-nearest-neighbor modeling is used for the second phase, 374/440 decisions are made and the accuracy is 65% (242/374). A K-nearest-neighbor predictor (FIRST-K) achieves 61% accuracy (268/440). The accuracies of all predictors are considerably higher on top-scoring subsets of published miRNA oligonucleotides.

Finally, in order to validate the efficacy and accuracy of the Dicer-cut location detector 116, a sample of novel oligonucleotides detected thereby is preferably selected, and validated by wet lab experiments. Laboratory results validating the efficacy of the Dicer-cut location detector 116 are described hereinbelow with reference to FIGS. 22-24D, FIG. 27 and also in the enclosed file "TABLE__13.txt".

Reference is now made to FIG. 13C, which is a simplified flowchart illustrating an operation of a Dicer-cut location detector 116 (FIG. 9), constructed and operative in accordance with a preferred embodiment of the present invention. The Dicer-cut location detector 116 preferably comprises a machine learning computer program module, which is trained to recognize Dicer-cut locations on known hairpin-shaped miRNA precursors, and based on this training, is operable to detect Dicer-cut locations of novel GAM RNA (FIG. 8) on GAM FOLDED PRECURSOR RNA (FIG. 8). In a preferred embodiment of the present invention, the Dicer-cut location module preferably utilizes machine learning algorithms, including but not limited to Support Vector Machine, Bayesian modeling, Nearest Neighbors, and K-nearest-neighbor algorithms that are known in the art.

When initially assessing a novel GAM FOLDED PRECURSOR RNA, each 19-24 nt-long segment thereof is considered to be a potential GAM RNA, because the Dicer-cut location is initially unknown.

For each such potential GAM RNA, the location of its 5' end or the locations of its 5' and 3' ends are scored by at least one recognition classifier or predictor, operating on features such as the following: Locations of the 5' and/or 3' ends of the known diced miRNA oligonucleotides, which are preferably represented by their respective distances from the 5' end of the corresponding hairpin-shaped miRNA precursor. Additionally or alternatively, the 5' and/or 3' ends of the known diced miRNA oligonucleotides, which are preferably represented by the relationship between their locations and the locations of one or more nucleotides along the hairpin-shaped miRNA precursor. Additionally or alternatively, the 5' and/or 3' ends of the known diced miRNA oligonucleotides, which are preferably represented by the relationship between their locations and the locations of one or more bound nucleotide pairs along the hairpin-shaped miRNA precursor. Additionally or alternatively, the 5' and/or 3' ends of the known diced miRNA oligonucleotides, which are preferably represented by the relationship between their locations and the locations of one or more mismatched nucleotide pairs along the hairpin-shaped miRNA precursor. Additionally or alternatively, the 5' and/or 3' ends of the known diced miRNA oligonucleotides, which are preferably represented by the relationship between their locations and the locations of one or more unmatched nucleotides along the hairpin-shaped miRNA precursor. Additionally or alternatively, locations of the 5' and/or 3' ends of the known diced miRNA oligonucleotides, which are preferably represented by their respective distances from the loop located at the center of the corresponding hairpin-shaped miRNA precursor. Additionally or alternatively, metrics related to the nucleotide content of the diced miRNA and/or of the hairpin-shaped miRNA precursor.

In a preferred embodiment of the present invention, the Dicer-cut location detector 116 (FIG. 9) may use a Support Vector Machine predictor.

In another preferred embodiment of the present invention, the Dicer-cut location detector 116 (FIG. 9) preferably employs an "EDIT DISTANCE" predictor, which seeks sequences that are similar to those of known miRNA oligonucleotides, utilizing a Nearest Neighbor algorithm, where a similarity metric between two sequences is a variant of the Edit Distance algorithm (Gusfield, 1997). The EDIT DISTANCE predictor is based on an observation that miRNA oligonucleotides tend to form clusters, the members of which show marked sequence similarity.

In yet another preferred embodiment of the present invention, the Dicer-cut location detector 116 (FIG. 9) preferably uses a "TWO PHASE" predictor, which predicts the Dicer-cut location in two distinct phases: (a) selecting a double-stranded segment of the GAM FOLDED PRECURSOR RNA (FIG. 8) comprising the GAM RNA by naive Bayesian modeling and (b) detecting which strand of the double-stranded segment contains GAM RNA (FIG. 8) by employing either naive or K-nearest-neighbor modeling. K-nearest-neighbor modeling is a variant of the "FIRST-K" predictor described hereinbelow, with parameters optimized for this specific task. The "TWO PHASE" predictor may be operated in two modes: either utilizing only the first phase and thereby producing two alternative Dicer-cut location predictions, or utilizing both phases and thereby producing only one final Dicer-cut location.

In still another preferred embodiment of the present invention, the Dicer-cut location detector 116 preferably uses a "FIRST-K" predictor, which utilizes a K-nearest-neighbor algorithm. The similarity metric between any two sequences is 1-E/L, where L is a parameter, preferably 8-10 and E is the edit distance between the two sequences, taking into account only the first L nucleotides of each sequence. If the K-nearest-neighbor scores of two or more locations on the GAM FOLDED PRECURSOR RNA (FIG. 8) are not significantly different, these locations are further ranked by a Bayesian model, similar to the one described hereinabove.

In accordance with an embodiment of the present invention, scores of two or more of the abovementioned classifiers or predictors are integrated, yielding an integrated score for each potential GAM RNA. As an example, FIG. 13C illustrates an integration of scores from two classifiers, a 3' end recognition classifier and a 5' end recognition classifier, the scores of which are integrated to yield an integrated score. Most preferably, the INTEGRATED SCORE of FIG. 13C preferably implements a "best-of-breed" approach employing a pair of classifiers and accepting only "potential GAM RNAs" that score highly on one of the abovementioned "EDIT DISTANCE", or "TWO PHASE" predictors. In this context, "high scores" means scores that have been demonstrated to have low false positive value when scoring known miRNA oligonucleotides. Alternatively, the INTEGRATED SCORE may be derived from operation of more or less than two classifiers.

The INTEGRATED SCORE is evaluated as follows: (a) the "potential GAM RNA" having the highest score is preferably taken to be the most probable GAM RNA, and (b) if the integrated score of this most probable GAM RNA is higher than a pre-defined threshold, then the most probable GAM RNA is accepted as a PREDICTED GAM RNA. Preferably, this evaluation technique is not limited to the highest scoring potential GAM RNA.

In a preferred embodiment of the present invention, PREDICTED GAM RNAs comprising a low complexity nucleotide sequence (e.g., ATATATA) may optionally be filtered out, because there is a high probability that they are part of a repeated element in the DNA, and are therefore not functional, as is known in the art. For each PREDICTED GAM RNA sequence, the number of occurrences of each two nt combination (AA, AT, AC) comprised in that sequence is counted. PREDICTED GAM RNA sequences where the sum of the two most probable combinations is higher than a threshold, preferably 8-10, are filtered out. As an example, when the threshold is set such that 2% of the known miRNA oligonucleotides are filtered out, 30% of the predicted GAM RNAs are filtered out.

Figure 14A:
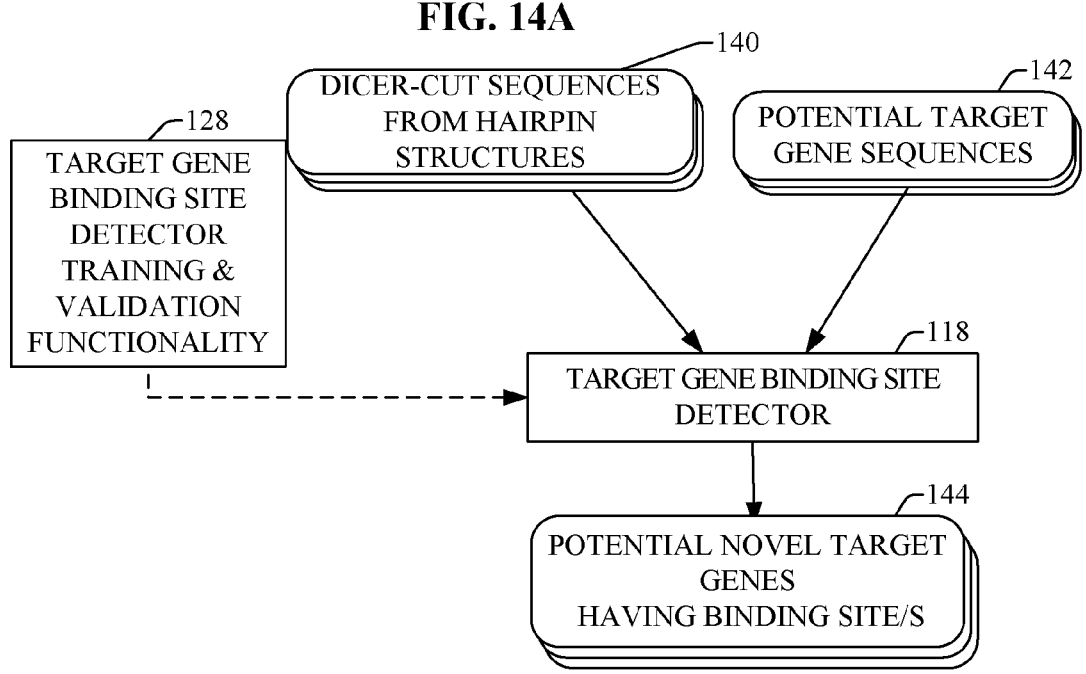
FIG. 14A is a simplified block diagram of a target gene binding site detector constructed and operative in accordance with a preferred embodiment of the present invention.

Reference is now made to FIG. 14A, which is a simplified block diagram of a preferred implementation of the target gene binding site detector 118 described hereinabove with reference to FIG. 9. The goal of the target gene binding site detector 118 is to detect one or more binding sites located in 3'UTRs of the mRNA of a known gene, such as BINDING SITE I, BINDING SITE II and BINDING SITE III (FIG. 8), the nucleotide sequence of which binding sites is partially or fully complementary to a GAM RNA, thereby determining that the abovementioned known gene is a target gene of the GAM RNA.

The target gene binding site detector 118 (FIG. 9) receives a plurality of Dicer-cut sequences from hairpin structures 140 (FIG. 13A) and a plurality of potential target gene sequences 142, which are derived from sequenced DNA data 104 (FIG. 9).

The target gene binding site detector training & validation functionality 128 (FIG. 10) is operative to train the target gene binding site detector 118 on known miRNA oligonucleotides and their respective target genes and to build a background model for an evaluation of the probability of achieving similar results randomly (P value) for the target gene binding site detector 118 results. The target gene binding site detector training & validation functionality 128 constructs the model by analyzing both heuristically and computationally the results of the target gene binding site detector 118.

Following operation of target gene binding site detector training & validation functionality 128 (FIG. 10), the target gene binding site detector 118 is operative to detect a plurality of potential novel target genes having binding site/s 144, the nucleotide sequence of which is partially or fully complementary to that of each of the plurality of Dicer-cut sequences from hairpin structures 140. Preferred operation of the target gene binding site detector 118 is further described hereinbelow with reference to FIG. 14B.

Figure 14B:
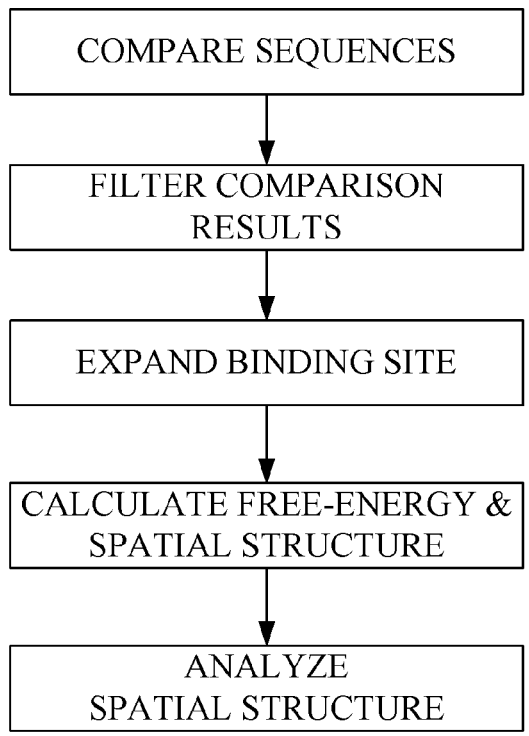
FIG. 14B is a simplified flowchart illustrating operation of a target gene binding site detector constructed and operative in accordance with a preferred embodiment of the present invention.

Reference is now made to FIG. 14B, which is a simplified flowchart illustrating a preferred operation of the target gene binding site detector 118 of FIG. 9.

In an embodiment of the present invention, the target gene binding site detector 118 first compares nucleotide sequences of each of the plurality of Dicer-cut sequences from hairpin structures 140 (FIG. 13A) to the potential target gene sequences 142 (FIG. 14A), such as 3' side UTRs of known mRNAs, in order to find crude potential matches. This step may be performed using a simple alignment algorithm such as BLAST.

Then, the target gene binding site detector 118 filters these crude potential matches, to find closer matches, which more closely resemble published miRNA oligonucleotide binding sites.

Next, the target gene binding site detector 118 expands the nucleotide sequences of the 3'UTR binding site found by the sequence comparison algorithm (e.g. BLAST or EDIT DISTANCE). A determination is made whether any subsequence of the expanded sequence may improve the match. The best match is considered the alignment.

Free-energy and spatial structure are computed for the resulting binding sites. Calculation of spatial structure may be performed by a secondary structure folding algorithm based on free-energy minimization, such as the MFOLD algorithm described in Mathews et al. (J. Mol. Biol. 288: 911-940 (1999)) and Zuker (Nucleic Acids Res. 31: 3406-3415

(2003)), the disclosure of which is hereby incorporated by reference. Free energy, spatial structure and the above preferences are reflected in scoring. The resulting scores are compared with scores characteristic of known binding sites of published miRNA oligonucleotides, and each binding site is given a score that reflects its resemblance to these known binding sites.

Finally, the target gene binding site detector 118 analyzes the spatial structure of the binding site. Each 3'UTR-GAM oligonucleotide pair is given a score. Multiple binding sites of the same GAM oligonucleotides to a 3'UTR are given higher scores than those that bind only once to a 3'UTR.

In a preferred embodiment of the present invention, performance of the target gene binding site detector 118 may be improved by integrating several of the abovementioned logical steps, using the methodology described hereinbelow.

For each of the dicer-cut sequence from hairpin structures 140, its starting segment, e.g. a segment comprising the first 8 nts from its 5' end, is obtained. For each starting segment, all of the 9 nt segments that are highly complementary to the starting segment are calculated. These calculated segments are referred to here as "potential binding site end segments". In a preferred embodiment of the present invention, for each 8 nt starting segment, the potential binding site end segments are all 9 nt segments whose complementary sequence contains a 7-9 nt sub-sequence that is not different from the starting segment by more than an insertion, deletion or replacement of one nt. Calculation of potential binding site end segments is preferably performed by a pre-processing tool that maps all possible 8 nt segments to their respective 9 nt segments.

Next, the mRNAs 3'UTRs is parsed into all the segments, with the same length as the potential binding site end segments, preferably 9 nt segments, comprised in the 3'UTR. Location of each such segment is noted, stored in a performance-efficient data structure and compared to the potential binding site end segments calculated in the previous step.

The target gene binding site detector 118 then expands the binding site sequence, preferably in the binding site 5' direction (i.e. immediately upstream), assessing the degree of its alignment to the dicer-cut sequence from hairpin structures 140. Preferably, an alignment algorithm is implemented which uses specific weighting parameters based on an analysis of known miRNA oligonucleotide binding sites. As an example, it is apparent that a good match of the 3' end of the binding site is critically important, a match of the 5' end is less important but can compensate for a small number of mismatches at the 3' end of the binding site, and a match of the middle portion of the binding site is much less important.

Next, the number of binding sites found in a specific 3'UTR, the degree of alignment of each of these binding sites, and their proximity to each other are assessed and compared to these properties found in known binding sites of published miRNA oligonucleotides. In a preferred embodiment, the fact that many of the known binding sites are clustered is used to evaluate the P value of obtaining a cluster of a few binding sites on the same target gene 3'UTR in the following way. It scans different score thresholds and calculates for each threshold the number and positions of possible binding sites with a score above the threshold. It then gets a P value for each threshold from a preprocessed calculated background matrix, described hereinbelow, and a number and positions of binding sites combination. The output score for each Dicer-cut sequences from hairpin structures 140 and potential target gene sequences 142 is the minimal P value, normalized with the number of threshold trails using a Bernoulli distribution. A preference of low P value pairs is made.

As mentioned hereinabove, for each target gene, a preprocessed calculated background matrix is built. The matrix includes rows for each number of miRNA oligonucleotide binding sites (in the preferred embodiment, the matrix includes 7 rows to accommodate 0 to 6 binding sites), and columns for each different score threshold (in the preferred embodiment, the matrix includes 5 columns for 5 different thresholds). Each matrix cell, corresponding to a specific number of binding sites and thresholds, is set to be the probability of getting equal or higher number binding sites and an equal or higher score using random 22 nt-long sequences with the same nucleotide distribution as known miRNA oligonucleotides (29.5% T, 24.5% A, 25% G and 21% C). Those probabilities are calculated by running the above procedure for 10000 random sequences that preserved the known miRNA nucleotide distribution (these sequence will be also referred to as miRNA oligonucleotide random sequences). The P value can be estimated as the number of random sequences that obeys the matrix cell requirement divided by the total number of random sequences (10000). In the preferred embodiment, 2 matrices are calculated. The P values of the second matrix are calculated under a constraint that at least two of the binding site positions are under a heuristically-determined constant value. The values of the second matrix are calculated without this constraint. The target gene binding site detector 118 uses the second matrix if the binding site positions agree with the constraint. Otherwise, it uses the first. In an alternative embodiment, only one matrix is calculated without any constraint on the binding sites positions.

A test performed using the target gene binding site detector 118 shows that all of the known miRNA oligonucleotide target genes are found using this algorithm with a P value of less than 0.5%. Running known miRNA oligonucleotides against 3400 potential 3'UTR of target gene sequences yields on average 32 target genes for each miRNA oligonucleotide with a P value less than 0.5%, while background sequences, as well as inverse or complement sequence of known miRNA oligonucleotide (which preserve their high order sequence statistics) found, as expected, 17 target genes on average. This result reflects that the algorithm has the ability to detect real target genes with 47% accuracy.

Finally, orthology data may optionally be used to further prefer binding sites based on their conservation. Preferably, this may be used in cases such as (a) where both the target mRNA and miRNA oligonucleotide have orthologues in another organism, e.g. Human-Mouse orthology, or (b) where a miRNA oligonucleotide (e.g. viral miRNA oligonucleotide) targets two mRNAs in orthologous organisms. In such cases, binding sites that are conserved are preferred.

In accordance with another preferred embodiment of the present invention, binding sites may be searched by a reverse process. Sequences of K (preferably 22) nucleotides in a UTR of a target gene are assessed as potential binding sites. A sequence comparison algorithm, such as BLAST or EDIT DISTANCE variant, is then used to search elsewhere in the genome for partially or fully complementary sequences that are found in known miRNA oligonucleotides or computationally-predicted GAM oligonucleotides. Only complementary sequences that meet predetermined spatial structure and free-energy criteria as described hereinabove, are accepted. Clustered binding sites are strongly preferred and potential binding sites and potential GAM oligonucleotides that occur in evolutionarily-conserved genomic sequences are also preferred. Scoring of candidate binding sites takes into account free-energy and spatial structure of the binding site complexes, as well as the aforesaid preferences.

Figure 15:
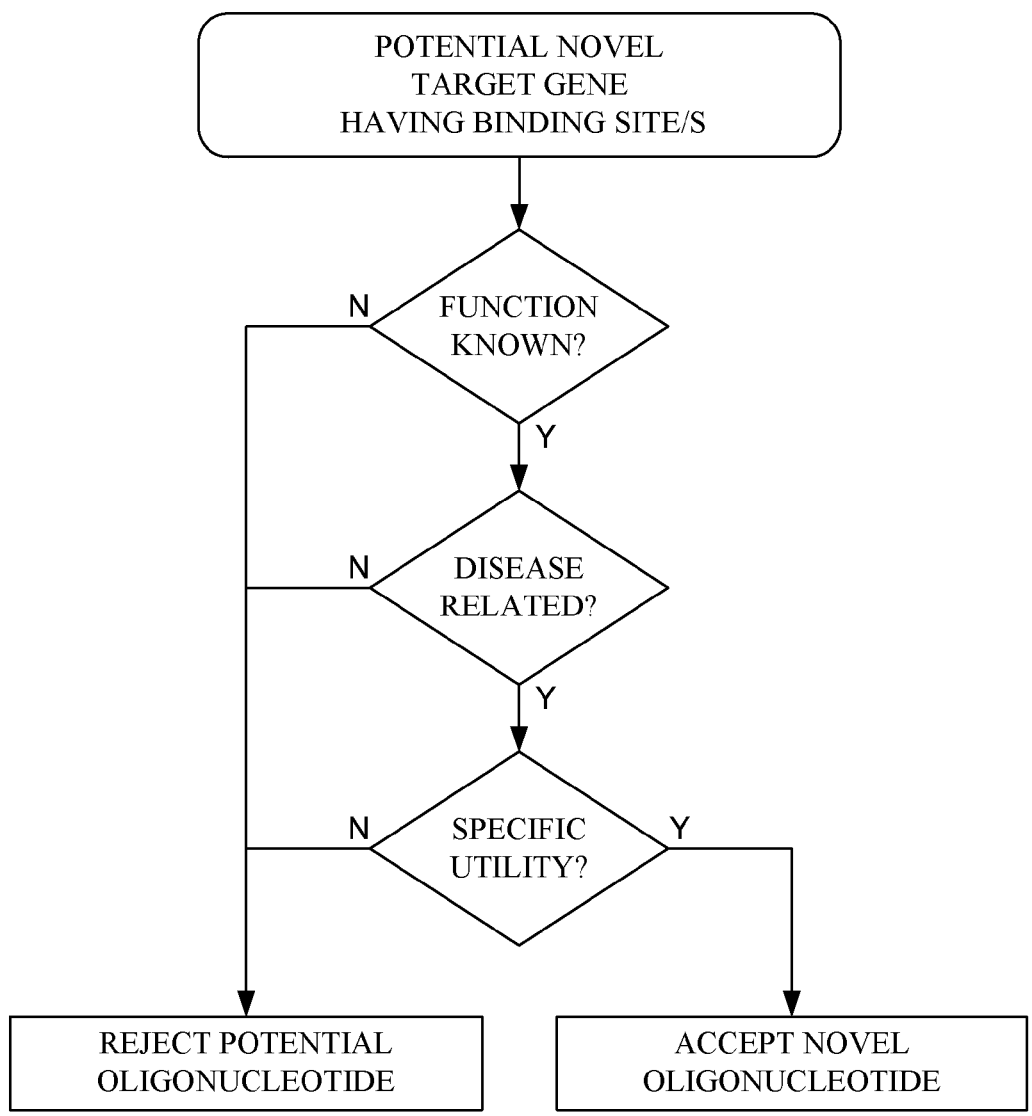
FIG. 15 is a simplified flowchart illustrating operation of a function and utility analyzer constructed and operative in accordance with a preferred embodiment of the present invention.

Reference is now made to FIG. 15 which is a simplified flowchart illustrating a preferred operation of the function & utility analyzer 120 described hereinabove with reference to FIG. 9. The goal of the function & utility analyzer 120 is to determine if a potential target gene is in fact a valid clinically useful target gene. Since a potential novel GAM oligonucleotide binding a binding site in the UTR of a target gene is understood to inhibit expression of that target gene, and if that target gene is shown to have a valid clinical utility, then in such a case it follows that the potential novel oligonucleotide itself also has a valid useful function which is the opposite of that of the target gene.

The function & utility analyzer 120 preferably receives as input a plurality of potential novel target genes having binding site/s 144 (FIG. 14A), generated by the target gene binding site detector 118 (FIG. 9). Each potential oligonucleotide is evaluated as follows: First, the system checks to see if the function of the potential target gene is scientifically well established. Preferably, this can be achieved bioinformatically by searching various published data sources presenting information on known function of proteins. Many such data sources exist and are published as is well known in the art. Next, for those target genes the function of which is scientifically known and is well documented, the system then checks if scientific research data exists which links them to known diseases. For example, a preferred embodiment of the present invention utilizes the OMIM™ (Hamosh et al, 2002) database published by NCBI, which summarizes research publications relating to genes which have been shown to be associated with diseases. Finally, the specific possible utility of the target gene is evaluated. While this process too may be facilitated by bioinformatic means, it might require manual evaluation of published scientific research regarding the target gene, in order to determine the utility of the target gene to the diagnosis and or treatment of specific disease. Only potential novel oligonucleotides, the target genes of which have passed all three examinations, are accepted as novel oligonucleotide.

Figure 16:
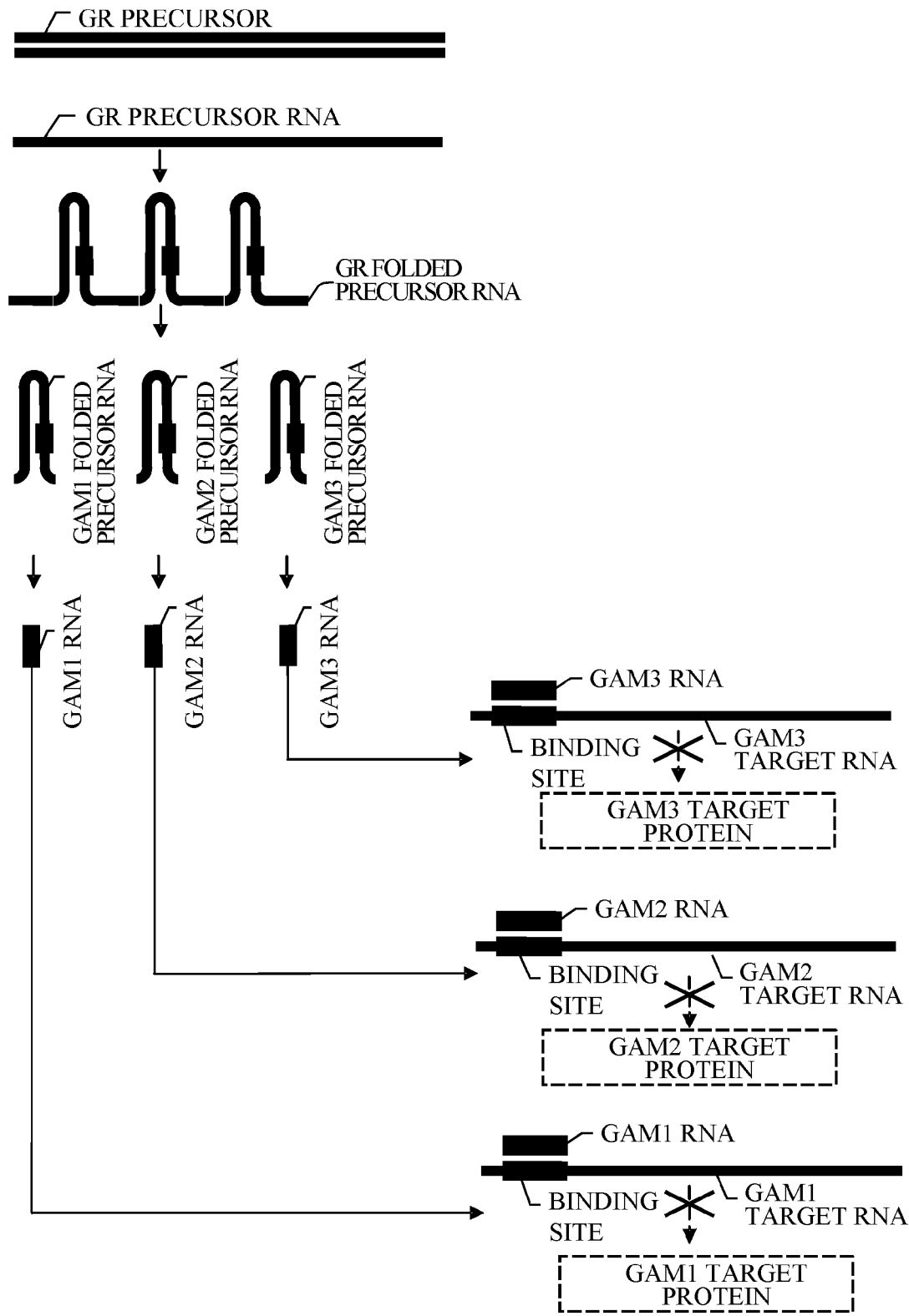
FIG. 16 is a simplified diagram describing a novel bioinformatically-detected group of regulatory polynucleotides, referred to here as Genomic Record (GR) polynucleotides, each of which encodes an "operon-like" cluster of novel miRNA-like oligonucleotides, which in turn modulate expression of one or more target genes.

Reference is now made to FIG. 16, which is a simplified diagram describing each of a plurality of novel bioinformatically-detected regulatory polynucleotide referred to in this Table as the Genomic Record (GR) polynucleotide. GR encodes an operon-like cluster of novel miRNA-like oligonucleotides, each of which in turn modulates the expression of at least one target gene. The function and utility of at least one target gene is known in the art.

The GR PRECURSOR is a novel, bioinformatically-detected, regulatory, non-protein-coding polynucleotide. The method by which the GR PRECURSOR is detected is described hereinabove with additional reference to FIGS. 9-18.

The GR PRECURSOR encodes GR PRECURSOR RNA that is typically several hundred to several thousand nts long. The GR PRECURSOR RNA folds spatially, forming the GR FOLDED PRECURSOR RNA. It is appreciated that the GR FOLDED PRECURSOR RNA comprises a plurality of what is known in the art as hairpin structures. Hairpin structures result from the presence of segments of the nucleotide sequence of GR PRECURSOR RNA in which the first half of each such segment has a nucleotide sequence which is at least a partial, and sometimes an accurate, reverse-complement sequence of the second half thereof, as is well known in the art.

The GR FOLDED PRECURSOR RNA is naturally processed by cellular enzymatic activity into a plurality of separate GAM precursor RNAs herein schematically represented by GAM1 FOLDED PRECURSOR RNA through GAM3 FOLDED PRECURSOR RNA. Each GAM folded precursor RNA is a hairpin-shaped RNA segment, corresponding to GAM FOLDED PRECURSOR RNA of FIG. 8.

The abovementioned GAM folded precursor RNAs are diced by DICER COMPLEX of FIG. 8, yielding short RNA segments of about 22 nts in length schematically represented by GAM1 RNA through GAM3 RNA. Each GAM RNA corresponds to GAM RNA of FIG. 8. GAM1 RNA, GAM2 RNA and GAM3 RNA each bind complementarily to binding sites located in the untranslated regions of their respective target genes, designated GAM1 TARGET RNA, GAM2 TARGET RNA and GAM3 TARGET RNA, respectively. These target binding sites correspond to BINDING SITE I, BINDING SITE II and BINDING SITE III of FIG. 8. The binding of each GAM RNA to its target RNA inhibits the translation of its respective target proteins, designated GAM1 TARGET PROTEIN, GAM2 TARGET PROTEIN and GAM3 TARGET PROTEIN, respectively.

It is appreciated that the specific functions, and accordingly the utilities, of the GR polynucleotide are correlated with and may be deduced from the identity of the target genes that are inhibited by GAM RNAs that are present in the operon-like cluster of the polynucleotide. Thus, for the GR polynucleotide, schematically represented by GAM1 TARGET PROTEIN through GAM3 TARGET PROTEIN that are inhibited by the GAM RNA. The function of these target genes is elaborated in Table 8, hereby incorporated herein.

Figure 17:
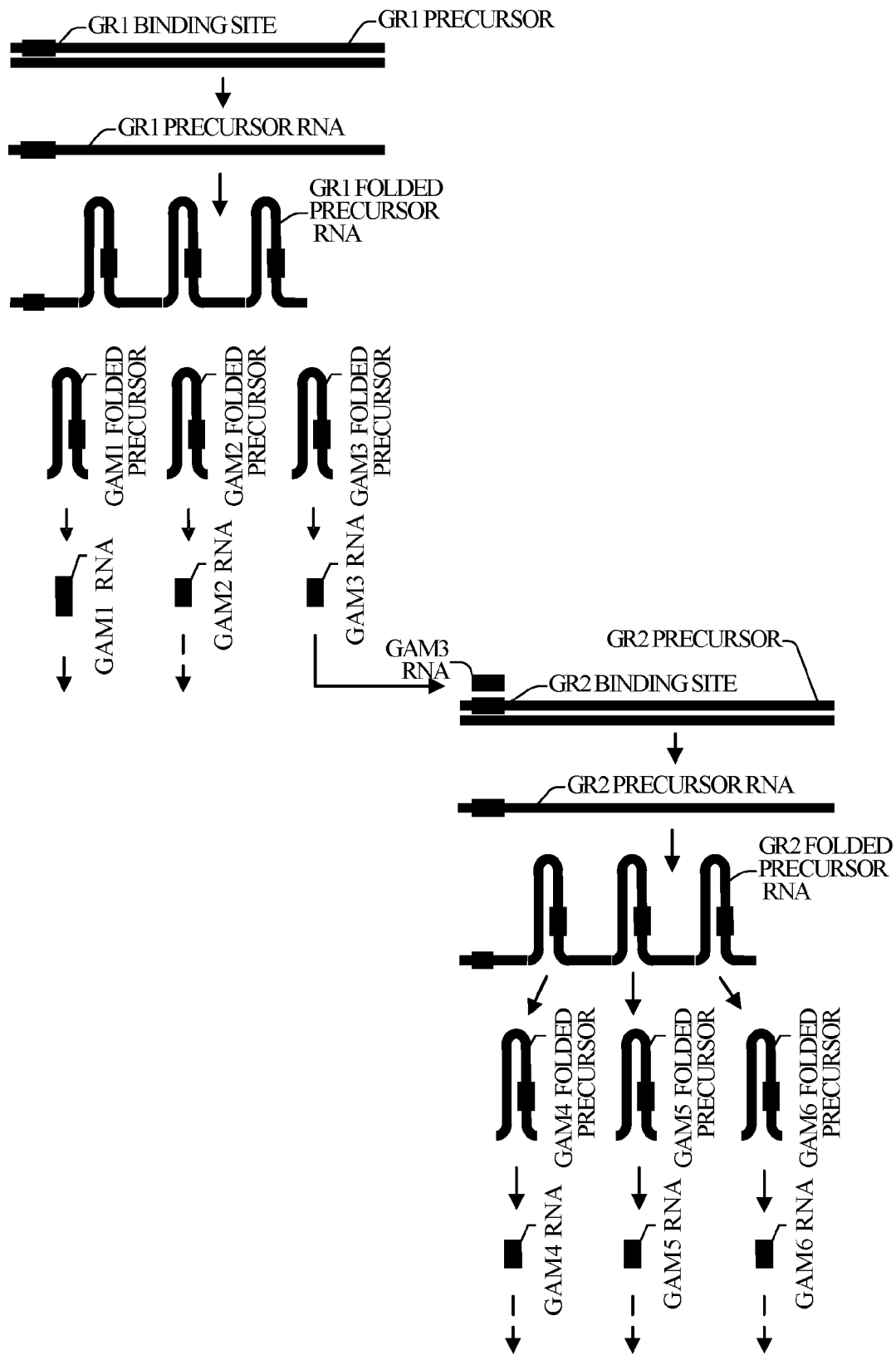
FIG. 17 is a simplified diagram illustrating a mode by which human oligonucleotides of a novel group of operon-like polynucleotides of the present invention, modulate expression of other such polynucleotides, in a cascading manner.

Reference is now made to FIG. 17 which is a simplified diagram illustrating a mode by which oligonucleotides of a novel group of operon-like polynucleotide described hereinabove with reference to FIG. 16 of the present invention, modulate expression of other such polynucleotide, in a cascading manner. GR1 PRECURSOR and GR2 PRECURSOR are two polynucleotides of the novel group of operon-like polynucleotides designated GR PRECURSOR (FIG. 16). As is typical of polynucleotides of the GR group of polynucleotides GR1 PRECURSOR and GR2 PRECURSOR, each encode a long RNA precursor, which in turn folds into a folded RNA precursor comprising multiple hairpin shapes, and is cut into respective separate hairpin-shaped RNA segments, each of which RNA segments being diced to yield an oligonucleotide of a group of oligonucleotides designated GAM RNA. In this manner GR1 yields GAM1 RNA, GAM2 RNA and GAM3 RNA, and GR2 yields GAM4 RNA, GAM5 RNA and GAM6 RNA. As FIG. 17 shows, GAM3 RNA, which derives from GR1, binds a binding site located adjacent to GR2 GPRECURSOR thus modulating expression of GR2, thereby invoking expression of GAM4 RNA, GAM5 RNA and GAM6 RNA which derive from GR2. It is appreciated that the mode of modulation of expression presented by FIG. 17 enables an unlimited "cascading effect" in which a GR polynucleotide comprises multiple GAM oligonucleotides each of which may modulate expression of other GR polynucleotides each such GR polynucleotides comprising additional GAM oligonucleotide etc., whereby eventually certain GAM oligonucleotides modulate expression of target proteins.

This mechanism is in accord with the conceptual model of the present invention addressing the differentiation enigma, described hereinabove with specific reference to FIGS. 6-7.

Figure 18:
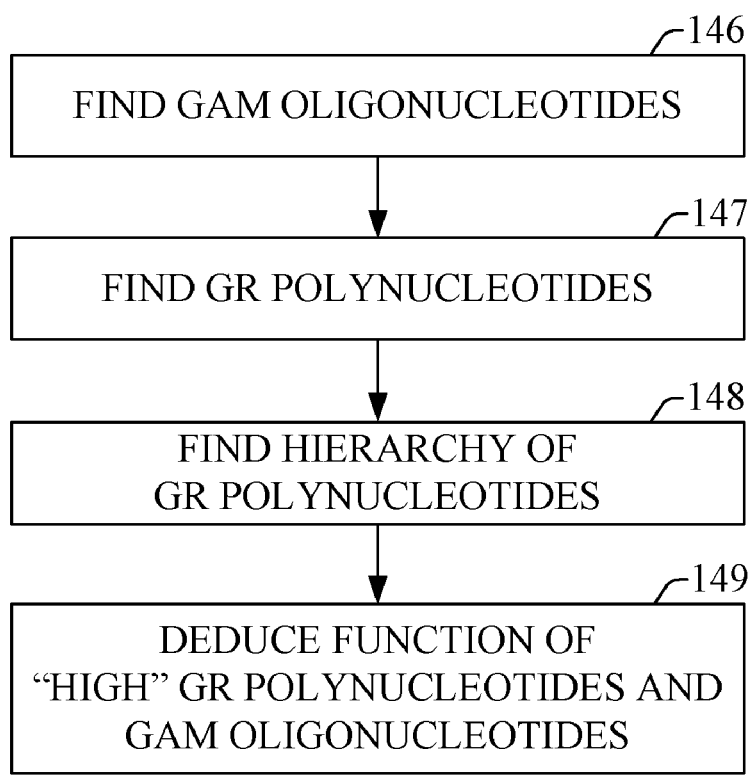
FIG. 18 is a block diagram illustrating an overview of a methodology for finding novel human oligonucleotides and novel operon-like human polynucleotides of the present invention, and their respective functions.

Reference is now made to FIG. 18 which is a block diagram illustrating an overview of a methodology for finding novel oligonucleotides and operon-like polynucleotides of the present invention, and their respective functions. According to a preferred embodiment of the present invention, the methodology to finding novel oligonucleotides of the present invention and their function comprises of the following major steps: First, FIND GAM OLIGONUCLEOTIDES 146 is used to detect, oligonucleotide of the novel group of oligonucleotide of the present invention, referred to here as GAM oligonucleotide. GAM oligonucleotides are located and their function elicited by detecting target proteins they bind and the function of those target proteins, as described hereinabove with reference to FIGS. 9-15. Next, FIND GR POLYNUCLEOTIDES 147 is used to detect polynucleotide of a novel group of operon-like polynucleotide of the present invention, referred to here as GR polynucleotide. GR polynucleotides are located, by locating clusters of proximally located GAM oligonucleotide, based on the previous step. Consequently, FIND HIERARCHY OF GR POLYNUCLEOTIDES 148 elicits the hierarchy of GR and GAM: binding sites for non-protein-binding GAM oligonucleotide comprised in each GR polynucleotide found are sought adjacent to other GR polynucleotides. When found, such a binding site indicates that the connection between the GAM and the GR the expression of which it modulates, and thus the hierarchy of the GR polynucleotides and the GAM oligonucleotides they comprise. Lastly, DEDUCE FUNCTION OF "HIGH" GR POLYNUCLEOTIDES AND GAM OLIGONUCLEOTIDES 149 is used to deduce the function of GR polynucleotides and GAM oligonucleotides which are "high" in the hierarchy, i.e. GAM oligonucleotides which modulate expression of other GR polynucleotides rather than directly modulating expression of target proteins. A preferred approach is as follows: The function of protein-modulating GAM oligonucleotides is deducible from the proteins which they modulate, provided that the function of these target proteins is known. The function of "higher" GAM oligonucleotides may be deduced by comparing the function of protein-modulating GAM oligonucleotides with the hierarchical relationships by which the "higher" GAM oligonucleotides are connected to the protein-modulating GAM oligonucleotides. For example, given a group of several protein-modulating GAM oligonucleotides which collectively cause a protein expression pattern typical of a certain cell-type, then a "higher" GAM oligonucleotide is sought which modulates expression of GR polynucleotides which perhaps modulate expression of other GR polynucleotides which eventually modulate expression of the given group of protein-modulating GAM oligonucleotide. The "higher" GAM oligonucleotide found in this manner is taken to be responsible for differentiation of that cell-type, as per the conceptual model of the invention described hereinabove with reference to FIG. 6.

Figure 19:
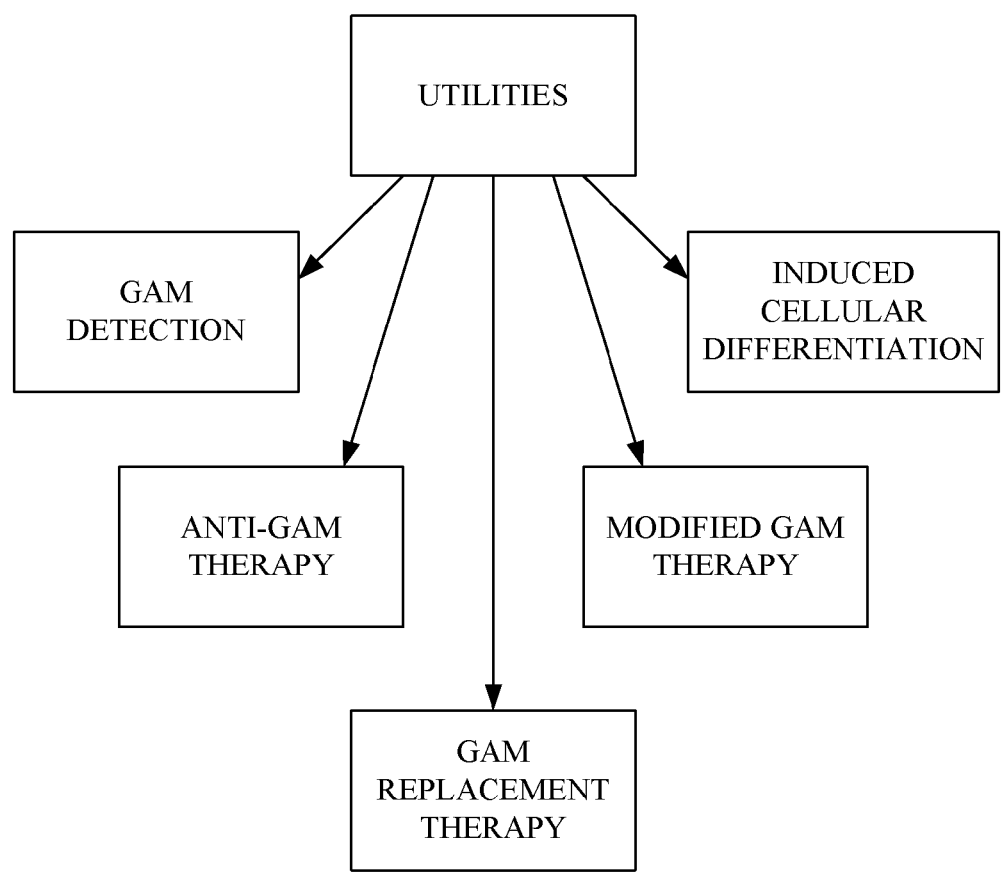
FIG. 19 is a block diagram illustrating different utilities of novel oligonucleotides and novel operon-like polynucleotides, both of the present invention.

Reference is now made to FIG. 19 which is a block diagram illustrating different utilities of oligonucleotide of the novel group of oligonucleotides of the present invention referred to here as GAM oligonucleotides and GR polynucleotides. The present invention discloses a first plurality of novel oligonucleotides referred to here as GAM oligonucleotides and a second plurality of operon-like polynucleotides referred to here as GR polynucleotides, each of the GR polynucleotide encoding a plurality of GAM oligonucleotides. The present invention further discloses a very large number of known target genes, which are bound by, and the expression of which is modulated by each of the novel oligonucleotides of the present invention. Published scientific data referenced by the present invention provides specific, substantial, and credible evidence that the above mentioned target genes modulated by novel oligonucleotides of the present invention, are associated with various diseases. Specific novel oligonucleotides of the present invention, target genes thereof and diseases associated therewith, are described hereinbelow with reference to Tables 1 through 13. It is therefore appreciated that a function of GAM oligonucleotides and GR polynucleotides of the present invention is modulation of expression of target genes related to known diseases, and that therefore utilities of novel oligonucleotides of the present invention include diagnosis and treatment of the above mentioned diseases.

FIG. 19 describes various types of diagnostic and therapeutic utilities of novel oligonucleotides of the present invention. A utility of novel oligonucleotide of the present invention is detection of GAM oligonucleotides and of GR polynucleotides. It is appreciated that since GAM oligonucleotides and GR polynucleotides modulate expression of disease related target genes, that detection of expression of GAM oligonucleotides in clinical scenarios associated with said diseases is a specific, substantial and credible utility. Diagnosis of novel oligonucleotides of the present invention may preferably be implemented by RNA expression detection techniques, including but not limited to biochips, as is well known in the art. Diagnosis of expression of oligonucleotides of the present invention may be useful for research purposes, in order to further understand the connection between the novel oligonucleotides of the present invention and the above mentioned related diseases, for disease diagnosis and prevention purposes, and for monitoring disease progress.

Another utility of novel oligonucleotides of the present invention is anti-GAM therapy, a mode of therapy which allows up regulation of a disease-related target gene of a novel GAM oligonucleotide of the present invention, by lowering levels of the novel GAM oligonucleotide which naturally inhibits expression of that target gene. This mode of therapy is particularly useful with respect to target genes which have been shown to be under-expressed in association with a specific disease. Anti-GAM therapy is further discussed hereinbelow with reference to FIGS. 20A and 20B and 28A-29.

A further utility of novel oligonucleotides of the present invention is GAM replacement therapy, a mode of therapy which achieves down regulation of a disease related target gene of a novel GAM oligonucleotide of the present invention, by raising levels of the GAM which naturally inhibits expression of that target gene. This mode of therapy is particularly useful with respect to target genes which have been shown to be over-expressed in association with a specific disease. GAM replacement therapy involves introduction of supplementary GAM products into a cell, or stimulation of a cell to produce excess GAM products. GAM replacement therapy may preferably be achieved by transfecting cells with an artificial DNA molecule encoding a GAM which causes the cells to produce the GAM product, as is well known in the art. Replacement therapy may also be performed by means of a suitable small molecule as further described hereinbelow with reference to FIG. 28D.

Yet a further utility of novel oligonucleotides of the present invention is modified GAM therapy. Disease conditions are likely to exist, in which a mutation in a binding site of a GAM RNA prevents natural GAM RNA to effectively bind inhibit a disease related target gene, causing up regulation of that target gene, and thereby contributing to the disease pathology. In such conditions, a modified GAM oligonucleotides is designed which effectively binds the mutated GAM binding site, i.e. is an effective anti-sense of the mutated GAM binding site, and is introduced in disease effected cells. Modified GAM therapy may be achieved by transfecting cells with an artificial DNA molecule encoding the modified GAM which causes the cells to produce the modified GAM product. It may also be achieved by introducing an appropriate small molecule into the cell, which acts similarly to the endogenous GAM oligonucleotide, as elaborated hereinbelow with reference to FIG. 28D.

The present invention may also be used to modulate differentiation, as conceptually described hereinabove with reference to FIGS. 1-7, using either oligonucleotides that specifically inhibit or enhance GAM oligonucleotide activity, or small molecules that do the same.

An additional utility of novel GAM of the present invention is induced cellular differentiation therapy. An aspect of the present invention is finding oligonucleotides which determine cellular differentiation, as described hereinabove with reference to FIG. 18. Induced cellular differentiation therapy comprises transfection of cell with such GAM oligonucleotides thereby determining their differentiation as desired. It is appreciated that this approach may be widely applicable, inter alia as a means for auto trans-plantation harvesting cells of one cell-type from a patient, modifying their differentiation as desired, and then trans-planting them back into the patient. It is further appreciated that this approach may also be utilized to modify cell differentiation in-vivo, by transfecting cells in a genetically diseased tissue with a cell-differentiation determining GAM thus stimulating these cells to differentiate appropriately.

Figure 20A:
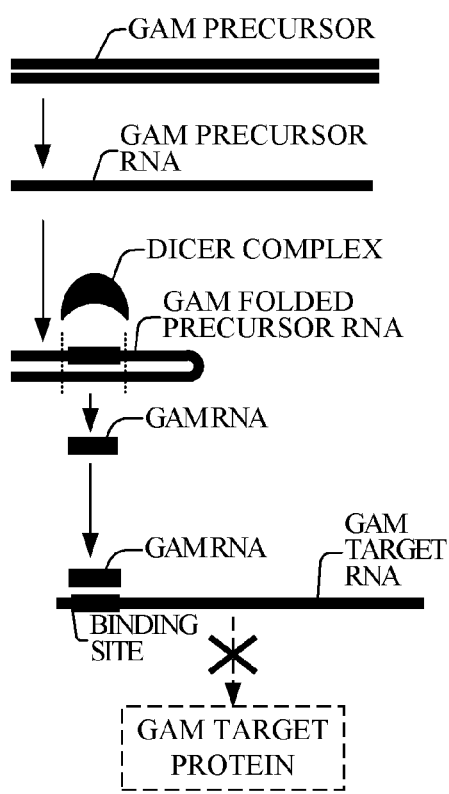
FIGS. 20A and 20B are simplified diagrams which, when taken together, illustrate a mode of oligonucleotide therapy applicable to novel oligonucleotides of the present invention.
Figure 20B:
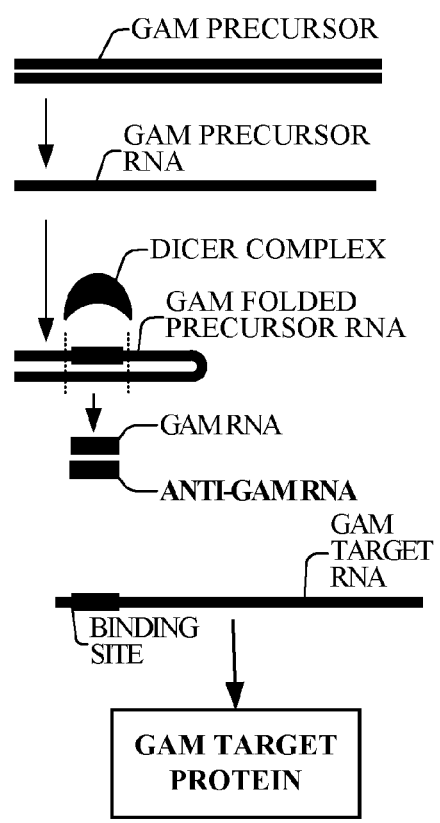

Reference is now made to FIGS. 20A and 20B, simplified diagrams which when taken together illustrate anti-GAM therapy mentioned hereinabove with reference to FIG. 19. A utility of novel GAMs of the present invention is anti-GAM therapy, a mode of therapy which allows up regulation of a disease-related target gene of a novel GAM of the present invention, by lowering levels of the novel GAM which naturally inhibits expression of that target gene. FIG. 20A shows a normal GAM inhibiting translation of a target gene by binding of GAM RNA to a BINDING SITE found in an untranslated region of GAM TARGET RNA, as described hereinabove with reference to FIG. 8.

FIG. 20B shows an example of anti-GAM therapy. ANTI-GAM RNA is short artificial RNA molecule the sequence of which is an anti-sense of GAM RNA. Anti-GAM treatment comprises transfecting diseased cells with ANTI-GAM RNA, or with a DNA encoding thereof. The ANTI-GAM RNA binds the natural GAM RNA, thereby preventing binding of natural GAM RNA to its BINDING SITE. This prevents natural translation inhibition of GAM TARGET RNA by GAM RNA, thereby up regulating expression of GAM TARGET PROTEIN.

It is appreciated that anti-GAM therapy is particularly useful with respect to target genes which have been shown to be under-expressed in association with a specific disease.

Furthermore, anti-GAM therapy is particularly useful, since it may be used in situations in which technologies known in the art as RNAi and siRNA can not be utilized. As in known in the art, RNAi and siRNA are technologies which offer means for artificially inhibiting expression of a target protein, by artificially designed short RNA segments which bind complementarily to mRNA of said target protein. However, RNAi and siRNA can not be used to directly up regulate translation of target proteins.

Figure 21A:
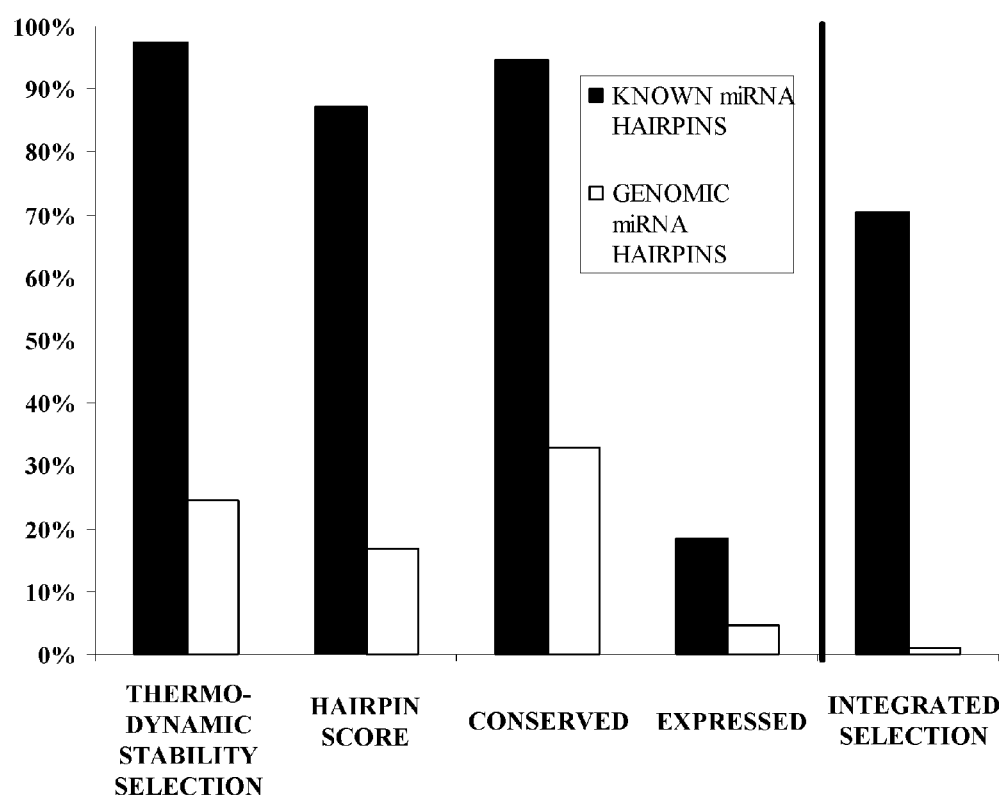
FIG. 21A is a bar graph illustrating performance results of a hairpin detector constructed and operative in accordance with a preferred embodiment of the present invention.

Reference is now made to FIG. 21A, which is a bar graph illustrating performance results of the hairpin detector 114 (FIG. 9) constructed and operative in accordance with a preferred embodiment of the present invention.

FIG. 21A illustrates efficacy of several features used by the hairpin detector 114 to detect GAM FOLDED PRECURSOR RNAs (FIG. 8). The values of each of these features is compared between a set of published miRNA precursor oligonucleotides, represented by shaded bars, and a set of random hairpins folded from the human genome denoted hereinbelow as a hairpin background set, represented by white bars. The published miRNA precursor oligonucleotides set is taken from RFAM database, Release 2.1 and includes 148 miRNA oligonucleotides from *H. Sapiens*. The background set comprises a set of 10,000 hairpins folded from the human genome.

It is appreciated that the hairpin background set is expected to comprise some valid, previously undetected hairpin-shaped miRNA precursor-like GAM FOLDED PRECURSOR RNAs of the present invention, and many hairpin-shaped sequences that are not hairpin-shaped miRNA-like precursors.

For each feature, the bars depict the percent of known miRNA hairpin precursors (shaded bars) and the percent of background hairpins (white bars) that pass the threshold for that feature. The percent of known miRNA oligonucleotides that pass the threshold indicates the sensitivity of the feature, while the corresponding background percent implies the specificity of the feature, although not precisely, because the background set comprises both true and false examples.

The first bar pair, labeled Thermodynamic Stability Selection, depicts hairpins that have passed the selection of "families" of closely related hairpin structures, as described hereinabove with reference to FIG. 12B.

The second bar pair, labeled Hairpin Score, depicts hairpins that have been selected by hairpin detector 114 (FIG. 12B), regardless of the families selection.

The third bar pair, labeled Conserved, depicts hairpins that are conserved in human, mouse and rat, (UCSC Goldenpath™ HG16 database).

The fourth bar pair, labeled Expressed, depicts hairpins that are found in EST blocks.

The fifth bar pair, labeled Integrated Selection, depicts hairpin structures predicted by a preferred embodiment of the present invention to be valid GAM PRECURSORs. In a preferred embodiment of the present invention, a hairpin may be considered to be a GAM PRECURSOR if its hairpin detector score is above 0, and it is in one of the following groups: a) in an intron and conserved or b) in an intergenic region and conserved or c) in an intergenic region and expressed, as described below. Further filtering of GAM precursor may be obtained by selecting hairpins with a high score of Dicer-cut location detector 116 as described hereinabove with reference to FIGS. 13A-13C, and with predicted miRNA oligonucleotides, which pass the low complexity filter as described hereinabove, and whose targets are selected by the target gene binding site detector 118 as described hereinabove with reference to FIGS. 14A-14B.

It is appreciated that these results validate the sensitivity and specificity of the hairpin detector 114 (FIG. 9) in identifying novel GAM FOLDED PRECURSOR RNAs, and in effectively distinguishing them from the abundant hairpins found in the genome.

Figure 21B:
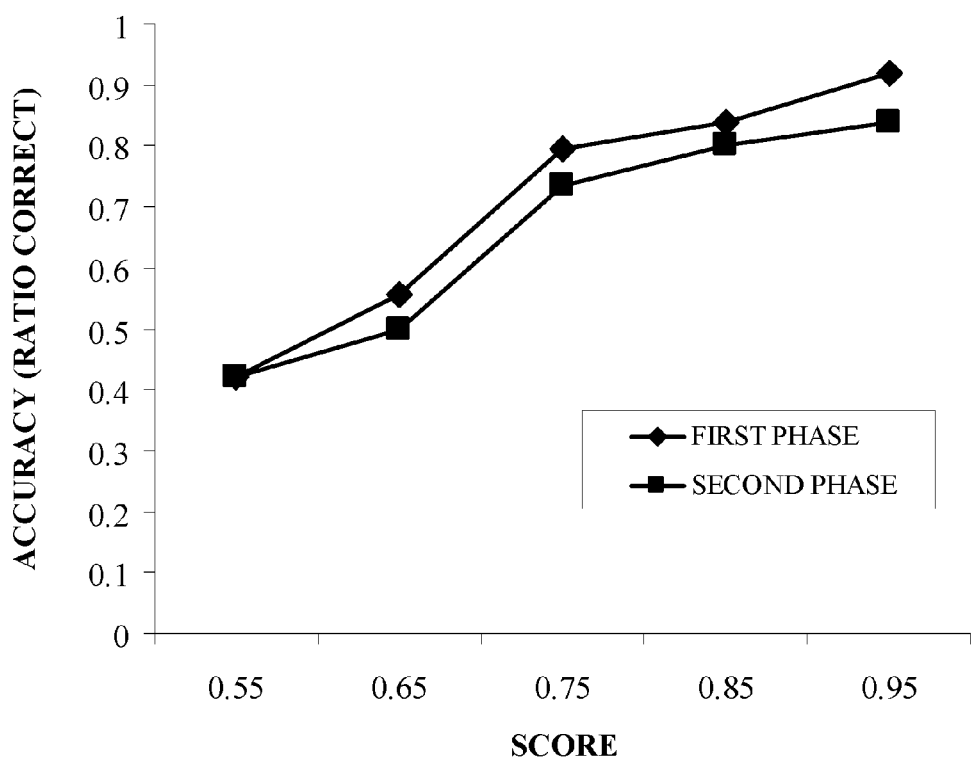
FIG. 21B is a line graph illustrating accuracy of a Dicer-cut location detector constructed and operative in accordance with a preferred embodiment of the present invention.

Reference is now made to FIG. 21B, which is a line graph illustrating accuracy of a Dicer-cut location detector 116 (FIG. 9) constructed and operative in accordance with a preferred embodiment of the present invention.

To determine the accuracy of the Dicer-cut location detector 116, a stringent training and test set was chosen from the abovementioned set of 440 known miRNA oligonucleotides, such that no two miRNA oligonucleotides in the set are homologous. This was performed to get a lower bound on the accuracy and avoid effects of similar known miRNA oligonucleotides appearing in both the training and test sets. On this stringent set of size 204, mfold cross validation with k=3 was performed to determine the percent of known miRNA oligonucleotides in which the dicer-cut location detector 116 described hereinabove predicted the correct miRNA oligonucleotide up to two nucleotides from the correct location.

The accuracy of the TWO PHASED predictor is depicted in the graph. The accuracy of the first phase of the TWO PHASED predictor is depicted by the upper line, and that of both phases of the TWO PHASED predictor is depicted by the lower line. Both are binned by the predictor score, where the score is the score of the first stage.

It is appreciated that these results validate the accuracy of the Dicer-cut location detector 116.

Figure 21C:
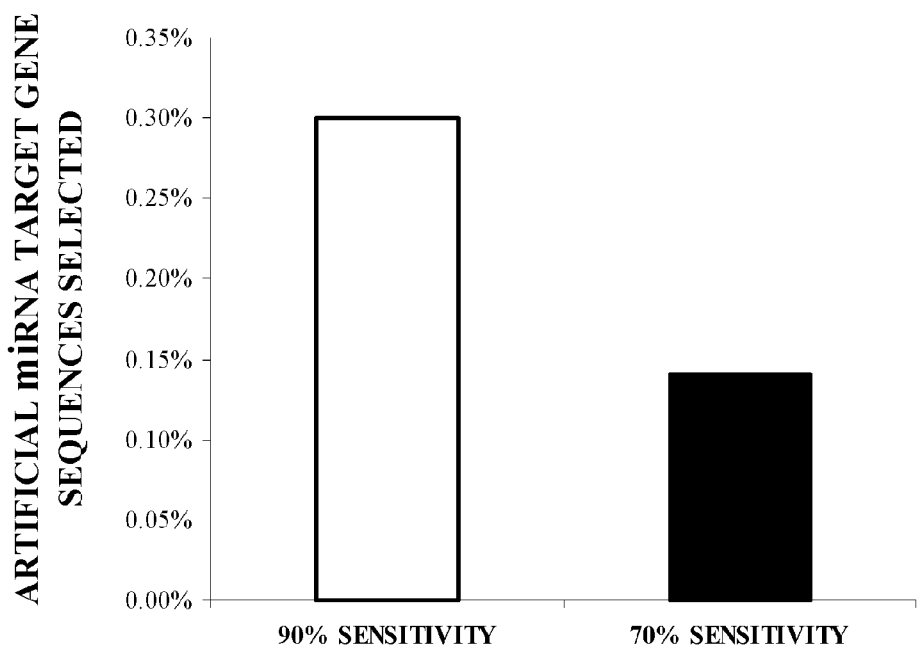
FIG. 21C is a bar graph illustrating performance results of the target gene binding site detector 118, constructed and operative in accordance with a preferred embodiment of the present invention.

Reference is now made to FIG. 21C, which is a bar graph illustrating the performance results of the target gene binding site detector 118 (FIG. 14A) constructed and operative in accordance with a preferred embodiment of the present invention.

FIG. 21C illustrates specificity and sensitivity of the target gene binding site detector 118. The values presented are the result of testing 10000 artificial miRNA oligonucleotide sequences (random 22 nt sequences with the same base composition as published miRNA oligonucleotide sequence). Adjusting the threshold parameters to fulfill 90% sensitivity of validated, published miRNA-3'UTR pairs, requires the P VAL of potential target gene sequences-Dicer-cut sequences to be less than 0.01 and also the P VAL of potential target ortholog gene sequences-Dicer-cut sequences to be less than 0.05. The target gene binding site detector 118 can filter out 99.7% of potential miRNA/gene pairs, leaving only the 0.3% that contain the most promising potential miRNA/gene pairs. Limiting the condition for the P VAL of potential target ortholog gene sequences-Dicer-cut sequences to be less than 0.01 reduces the sensitivity ratio to 70% but filters out more then 50% of the remaining 0.3%, to a final ratio of less than 0.15%.

It is appreciated that these results validate the sensitivity and specificity of the target gene binding site detector 118.

Reference is now made to FIG. 22, which is a summary table of laboratory results validating the expression of 29 novel human GAM RNA oligonucleotides in HeLa cells or, alternatively, in liver or thymus tissues detected by the bioinformatic oligonucleotide detection engine 100 (FIG. 9).

As a positive control, we used a reference set of eight known human miRNA oligonucleotides: hsa-MIR-21; hsa-MIR-27b; hsa-MIR-186; hsa-MIR-93; hsa-MIR-26a; hsa-MIR-191; hsa-MIR-31; and hsa-MIR-92. All positive controls were successfully validated by sequencing.

The table of FIG. 22 lists all GAM RNA predictions whose expression was validated. The field "Primer Sequence" contains the "specific" part of the primer; the field "Sequenced sequence" represents the nucleotide sequence detected by cloning (excluding the hemispecific primer sequence); the field "Predicted GAM RNA" contains the GAM RNA predicted sequence; the field "Distance indicate the distance from Primer; the number of mismatches between the "specific" region of the primer and the corresponding part of the GAM RNA sequence; the field "GAM Name" contains GAM RNA PRECURSOR ID followed by "A" or "B", which represents the GAM RNA position on the precursor as elaborated in the attached Tables.

A primer was designed such that its first half, the 5' region, is complementary to the adaptor sequence and its second half, the 3' region, anneals to the 5' terminus of GAM RNA sequence, yielding a hemispecific primer (as elaborated hereinbelow in the Methods section). A sample of 13 predicted GAM RNA sequences was examined by PCR using hemispecific primers and a primer specific to the 3' adaptor. PCR products were cloned into plasmid vectors and then sequenced. For all 13 predicted GAM RNA sequences, the GAM RNA sequence found in the hemispecific primer plus the sequence observed between the hemispecific primer and the 3' adaptor was completely included in the expected GAM RNA sequence (rows 1-7, and 29). The rest are GAM RNA predictions that were verified by cloning and sequencing, yet, by using a primer that was originally designed for a slightly different prediction.

It is appreciated that failure to detect a predicted oligonucleotide in the lab does not necessarily indicate a mistaken bioinformatic prediction. Rather, it may be due to technical sensitivity limitation of the lab test, or because the predicted oligonucleotides are not expressed in the tissue examined, or at the development phase tested. The observed GAM RNAs may be strongly expressed in HeLa cells while the original GAM RNAs are expressed at low levels in HeLa cells or not expressed at all. Under such circumstances, primer sequences containing up to three mismatches from a specific GAM RNA sequence may amplify it. Thus, we also considered cases in which differences of up to 3 mismatches in the hemispecific primer occur.

The 3' terminus of observed GAM RNA sequences is often truncated or extended by one or two nucleotides. Cloned sequences that were sequenced from both 5' and 3' termini have an asterick appended to the row number.

Interestingly, the primer sequence followed by the observed cloned sequence is contained within five GAM RNA sequences of different lengths, and belong to 24 precursors derived from distinct loci (Row 29). Out of these, one precursor appears four times in the genome and its corresponding GAM Names are 351973-A, 352169-A, 352445-A and 358164-A.

The sequence presented in Row 29 is a representative of the group of five GAM RNAs. The full list of GAM RNA sequences and their corresponding precursors is as follows (each GAM RNA sequence is followed by the GAM Name): TCACTGCAACCTCCACCTCCCA (352092, 352651, 355761), TCACTGCAACCTCCACCTCCCG (351868, 352440, 351973, 352169, 352445, 358164, 353737, 352382, 352235, 352232, 352268, 351919, 352473, 352444, 353638, 353004, 352925, 352943), TCACTGCAACCTCCACCTC-CTG (358311), TCACTGCAACCTCCACCTTCAG (353323), and TCACTGCAACCTCCACCTTCCG (353856).

Method Section

Cell Lines

Three common human cell lines, obtained from Dr. Yonat Shemer at Soroka Medical Center, Be'er Sheva, Israel, were used for RNA extraction; Human Embryonic Kidney HEK-293 cells, Human Cervix Adenocarcinoma HeLa cells and Human Prostate Carcinoma PC3 cells.

RNA Purification

Several sources of RNA were used to prepare libraries:

Total HeLa S100 RNA was prepared from HeLa S100 cellular fraction (4C Biotech, Belgium) through an SDS (1%)-Proteinase K (200 g/ml) 30 minute incubation at 37 C followed by an acid Phenol-Chloroform purification and isopropanol precipitation (Sambrook et al; Molecular Cloning—A Laboratory Manual).

Total HeLa, HEK-293 and PC3 cell RNA was prepared using the standard Tri-Reagent protocol (Sigma) according to the manufacturer's instructions, except that 1 volume of isopropanol was substituted with 3 volumes of ethanol.

Nuclear and Cytoplasmic RNA was prepared from HeLa or HEK-293 cells in the following manner:

Cell were washed and harvested in ice-cold PBS and precipitated in a swing-out rotor at 1200 rpm at 4 C for 5 minutes. Pellets were loosened by gentle vortexing. 4 ml of "NP40 lysis buffer" (10 mM TrisHCl, 5 mM MgCl2, 10 mM NaCl, 0.5% Nonidet P40, 1 mM Spermidine, 1 mM DTT, 140 U/ml rRnasine) was then added per 5*10^7 cells. Cells and lysis buffer were incubated for 5 minutes on ice and centrifuged in a swing-out rotor at 500×g at 4 C for 5 minutes. Supernatant, termed cytoplasm, is carefully removed to a tube containing SDS (1% final) and proteinase-K (200 g/ml final). Pellet, termed nuclear fraction, is re-washed and incubated with a similar amount of fresh lysis buffer. Lysis is monitored visually under a microscope at this stage, typically for 5 minutes. Nuclei are pelleted in a swing-out rotor at 500×g at 4 C for 5 minutes. Supernatant is pooled, incubated at 37 C for 30 minutes, Phenol/Chloroform-extracted, and RNA is alcohol-precipitated (Sambrook et al). Nuclei are loosened and then homogenized immediately in >10 volumes of Tri-Reagent (Sigma). Nuclear RNA is then prepared according to the manufacturer's instructions.

Total Tissue RNA

Total tissue RNA was obtained from Ambion USA, and included Human Liver, Thymus, Placenta, Testes and Brain.

RNA Size Fractionation

RNA used for libraries was always size-fractionated. Fractionation was done by loading up to 500 g RNA per YM100 Amicon Microcon column (Millipore) followed by a 500×g centrifugation for 40 minutes at 4 C. Flow-through "YM100" RNA is about one quarter of the total RNA and was used for library preparation or fractionated further by loading onto a YM30 Amicon Microcon column (Millipore) followed by a 13,500×g centrifugation for 25 minutes at 4 C. Flow-through "YM30" was used for library preparation "as is" and consists of less than 0.5% of total RNA. Additional size fractionation was achieved during library preparation.

Library Preparation

Two types of cDNA libraries, designated "One-tailed" and "Ligation", were prepared from the one of the abovementioned fractionated RNA samples. RNA was dephosphorylated and ligated to an RNA (designated with lowercase letters)-DNA (designated with UPPERCASE letters) hybrid 5'-phosphorylated, 3' idT blocked 3'-adapter (5'-P-uuuAAC-CGCATCCTTCTC-idT-3' Dharmacon #P-002045-01-05) (as elaborated in Elbashir et al., Genes Dev. 15:188-200 (2001)) resulting in ligation only of RNase III type cleavage products. 3'-Ligated RNA was excised and purified from a half 6%, half 13% polyacrylamide gel to remove excess adapter with a Nanosep 0.2M centrifugal device (Pall) according to instructions, and precipitated with glycogen and 3 volumes of ethanol. Pellet was resuspended in a minimal volume of water.

For the "Ligation" library, a DNA (UPPERCASE)-RNA (lowercase) hybrid 5'-adapter (5'-TACTAATACGACTCAC-Taaa-3' Dharmacon #P-002046-01-05) was ligated to the 3'-adapted RNA, reverse transcribed with "EcoRI-RT": (5'-GACTAGCTGGAATTCAAGGATGCGGTTAAA-3'), PCR amplified with two external primers essentially as in Elbashir et al. (2001), except that primers were "EcoRI-RT" and "PstI Fwd" (5'-CAGCCAACGCTGCAGATACGACTCAC-TAAA-3'). This PCR product was used as a template for a second round of PCR with one hemispecific and one external primer or with two hemispecific primers.

For the "One-tailed" library, the 3'-adapted RNA was annealed to 20 pmol primer "EcoRI RT" by heating to 70 C and cooling 0.1 C/sec to 30 C and then reverse-transcribed with Superscript II RT (according to manufacturer's instructions, Invitrogen) in a 20 l volume for 10 alternating 5 minute cycles of 37 C and 45 C. Subsequently, RNA was digested with 1 1 2M NaOH and 2 mM EDTA at 65 C for 10 minutes. cDNA was loaded on a polyacrylamide gel, excised and gel-purified from excess primer as above (invisible, judged by primer run alongside) and resuspended in 13 L of water. Purified cDNA was then oligo-dC tailed with 400 U of recombinant terminal transferase (Roche Molecular Biochemicals), 1 1 100M dCTP, 1 1 15 mM CoCl2, and 4 l reaction buffer, to a final volume of 20 l for 15 minutes at 37 C. Reaction was stopped with 2 l 0.2M EDTA and 15 l 3M NaOAc pH 5.2. Volume was adjusted to 150 l with water, Phenol:Bromochloropropane 10:1 extracted and subsequently precipitated with glycogen and 3 volumes of ethanol. C-tailed cDNA was used as a template for PCR with the external primers "T3-PstBsg (G/I)18" (5'-AATTAACCCTCACTAAAGGCTGCAG GTGCAGGIGGGIIGGGIIGGGIIGN-3' where I stands for Inosine and N for any of the 4 possible deoxynucleotides), and with "EcoRI Nested" (5'-GGAATTCAAGGATGCG-GTTA-3'). This PCR product was used as a template for a second round of PCR with one hemispecific and one external primer or with two hemispecific primers.

Primer Design and PCR

Hemispecific primers were constructed for each predicted GAM RNA oligonucleotide by an in-house program designed to choose about half of the 5' or 3' sequence of the GAM RNA corresponding to a TM of about 30-34 C constrained by an optimized 3' clamp, appended to the cloning adapter sequence (for "One-tailed" libraries, 5'-GGN-NGGGNNG on the 5' end or TTTAACCGCATC-3' on the 3' end of the GAM RNA; for "Ligation" libraries, the same 3' adapter and 5'-CGACTCACTAAA on the 5' end of the GAM RNA). Consequently, a fully complementary primer of a TM higher than 60 C was created covering only one half of the GAM RNA sequence permitting the unbiased elucidation by sequencing of the other half.

For each primer, the following criteria were used: Primers were graded according to the TM of the primer half and the nucleotide content of 3 nucleotides of the 3' clamp from worst to best, roughly: GGG-3'<CCC-3'<TTT-3'/AAA-3'<GG-3'<CC-3'<a TM lower than 30<a TM higher than 34<TT-3'/AA-3'<3G/C nucleotide combination <3 A/T nucleotide combination <any combination of two/three different nucleotides <any combination of three/three different nucleotides.

Validation PCR Product by Southern Blot

GAM RNA oligonucleotides were validated by hybridization of Polymerase Chain Reaction (PCR)-product Southern blots with a probe to the predicted GAM RNA.

PCR product sequences were confirmed by Southern blot (Southern E. M., Biotechnology 1992, 24:122-139 (1975)) and hybridization with DNA oligonucleotide probes synthesized as complementary (antisense) to predicted GAM RNA oligonucleotides. Gels were transferred onto a Bio-dyne PLUS 0.45 m (Pall) positively charged nylon membrane and UV cross-linked. Hybridization was performed overnight with DIG-labeled probes at 42?C in DIG Easy-Hyb buffer (Roche). Membranes were washed twice with 2×SSC and 0.1% SDS for 10 minutes at 42?C and then washed twice with 0.5×SSC and 0.1% SDS for 5 min at 42?C. The membrane was then developed by using a DIG luminescent detection kit (Roche) using anti-DIG and CSPD reaction, according to the manufacturer's protocol. All probes were prepared according to the manufacturer's (Roche Molecular Biochemicals) protocols: Digoxigenin (DIG) labeled antisense transcripts were prepared from purified PCR products using a DIG RNA labeling kit with T3 RNA polymerase. DIG-labeled PCR was prepared by using a DIG PCR labeling kit. 3'-DIG-tailed oligo ssDNA anti-sense probes, containing DIG-dUTP and dATP at an average tail length of 50 nts were prepared from 100 pmole oligonucleotides with the DIG Oligonucleotide Labeling Kit. Control reactions contained all of the components of the test reaction except library template.

Validation of PCR Product by Nested PCR on the Ligation

To further validate predicted GAM PCR product sequence derived from hemi-primers, a PCR-based diagnostic technique was devised to amplify only those products containing at least two additional nucleotides of the non hemi-primer defined part of the predicted GAM RNA oligonucleotide. In essence, a diagnostic primer was designed so that its 3' end, which is the specificity determining side, was identical to the desired GAM RNA oligonucleotide, 2-10 nts (typically 4-7, chosen for maximum specificity) further into its 3' end than the nucleotide stretch primed by the hemi-primer. The hemi-primer PCR product was first ligated into a T-cloning vector (pTZ57/T or pGEM-T) as described hereinabove. The ligation reaction mixture was used as template for the diagnostic PCR under strict annealing conditions with the new diagnostic primer in conjunction with a general plasmid-homologous primer, resulting in a distinct ~200 base-pair product. This PCR product can be directly sequenced, permitting the elucidation of the remaining nucleotides up to the 3' of the mature GAM RNA oligonucleotide adjacent to the 3' adapter. Alternatively, following analysis of the diagnostic PCR reaction on an agarose gel, positive ligation reactions (containing a band of the expected size) were transformed into E. coli. Using this same diagnostic technique and as an alternative to screening by Southern blot colony hybridization, transformed bacterial colonies were screened by colony-PCR (Gussow, D. and Clackson, T, Nucleic Acids Res. 17:4000 (1989)) with the nested primer and the vector primer, prior to plasmid purification and sequencing.

Validation of PCR Product by Cloning and Sequencing

CLONE SEQUENCING: PCR products were inserted into pGEM-T (Promega) or pTZ57/T (MBI Fermentas), heat-shock transformed into competent JM109 E. coli (Promega) and seeded on LB-Ampicilin plates with IPTG and Xgal. White and light blue colonies were transferred to duplicate gridded plates, one of which was blotted onto a membrane (Biodyne Plus, Pall) for hybridization with DIG tailed oligo probes (according to instructions, Roche) complementary to the expected GAM. Plasmid DNA from positive colonies was sequenced.

It is appreciated that the results summarize in FIG. 22 validate the efficacy of the bioinformatic oligonucleotide detection engine 100 of the present invention.

Reference is now made to FIG. 23A, which is a schematic representation of a novel human GR polynucleotide, located on chromosome 9, comprising 2 known human MIR oligonucleotides—MIR24 and MIR23, and 2 novel GAM oligonucleotides, herein designated GAM7617 and GAM252 (later discovered by other researchers as hsa-mir-27b), all marked by solid black boxes. FIG. 23A also schematically illustrates 6 non-GAM hairpin sequences, and one non-hairpin sequence, all marked by white boxes, and serving as negative controls. By "non-GAM hairpin sequences" is meant sequences of a similar length to known MIR PRECURSOR sequences, which form hairpin secondary folding pattern similar to MIR PRECURSOR hairpins, and yet which are assessed by the bioinformatic oligonucleotide detection engine 100 not to be valid GAM PRECURSOR hairpins. It is appreciated that FIG. 23A is a simplified schematic representation, reflecting only the order in which the segments of interest appear relative to one another, and not a proportional distance between the segments.

Reference is now made to FIG. 23B, which is a schematic representation of secondary folding of each of the MIRs and GAMs of the GR MIR24, MIR23, GAM7617 and GAM252, and of the negative control non-GAM hairpins, herein designated N2, N3, N252, N4, N6 and N7. N0 is a non-hairpin control, of a similar length to that of known MIR PRECURSOR hairpins. It is appreciated that the negative controls are situated adjacent to and in between real MIR oligonucleotides and GAM predicted oligonucleotides and demonstrates similar secondary folding patterns to that of known MIRs and GAMs.

Reference is now made to FIG. 23C, which is a picture of laboratory results of a PCR test upon a YM100 size-fractionated "ligation"-library, utilizing a set of specific primer pairs located directly inside the boundaries of the hairpins. Due to the nature of the library the only PCR amplifiable products can result from RNaseIII type enzyme cleaved RNA, as expected for legitimate hairpin precursors presumed to be produced by DROSHA (Lee et al, Nature 425 415-419, 2003). FIG. 23C demonstrates expression of hairpin precursors of known MIR oligonucleotides hsa-mir23 and hsa-mir24, and of novel bioinformatically-detected GAM7617 and GAM252 hairpins predicted bioinformatically by a system constructed and operative in accordance with a preferred embodiment of the present invention. FIG. 23C also shows that none of the 7 controls (6 hairpins designated N2, N3, N23, N4, N6 and N7 and 1 non-hairpin sequence designated N0) were expressed. N252 is a negative control sequence partially overlapping GAM252.

In the picture, test lanes including template are designated "+" and the control lane is designated "−". The control reaction contained all the components of the test reaction except library template. It is appreciated that for each of the tested hairpins, a clear PCR band appears in the test ("+") lane, but not in the control ("−") lane.

FIGS. 23A through 23C, when taken together validate the efficacy of the bioinformatic oligonucleotide detection engine in: (a) detecting known MIR oligonucleotides; (b) detecting novel GAM PRECURSOR hairpins which are found adjacent to these MIR oligonucleotides, and which despite exhaustive prior biological efforts and bioinformatic detection efforts, went undetected; (c) discerning between GAM (or MIR) PRECURSOR hairpins, and non-GAM hairpins.

It is appreciated that the ability to discern GAM-hairpins from non-GAM-hairpins is very significant in detecting GAM oligonucleotides since hairpins are highly abundant in the genome. Other MIR prediction programs have not been able to address this challenge successfully.

Reference is now made to FIG. 24A which is an annotated sequence of an EST comprising a novel GAM oligonucleotides detected by the oligonucleotide detection system of the present invention. FIG. 24A shows the nucleotide sequence of a known human non-protein-coding EST (Expressed Sequence Tag), identified as EST72223. The EST72223 clone obtained from TIGR database (Kirkness and Kerlavage, 1997) was sequenced to yield the above 705 bp transcript with a polyadenyl tail. It is appreciated that the sequence of this EST comprises sequences of one known miRNA oligonucleotide, identified as hsa-MIR98, and of one novel GAM oligonucleotide referred to here as GAM25, detected by the bioinformatic oligonucleotide detection engine 100 (FIG. 9) of the present invention.

The sequences of the precursors of the known MIR98 and of the predicted GAM25 precursors are marked in bold, the sequences of the established miRNA 98 and of the predicted miRNA-like oligonucleotide GAM25 are underlined.

Figure 24D:
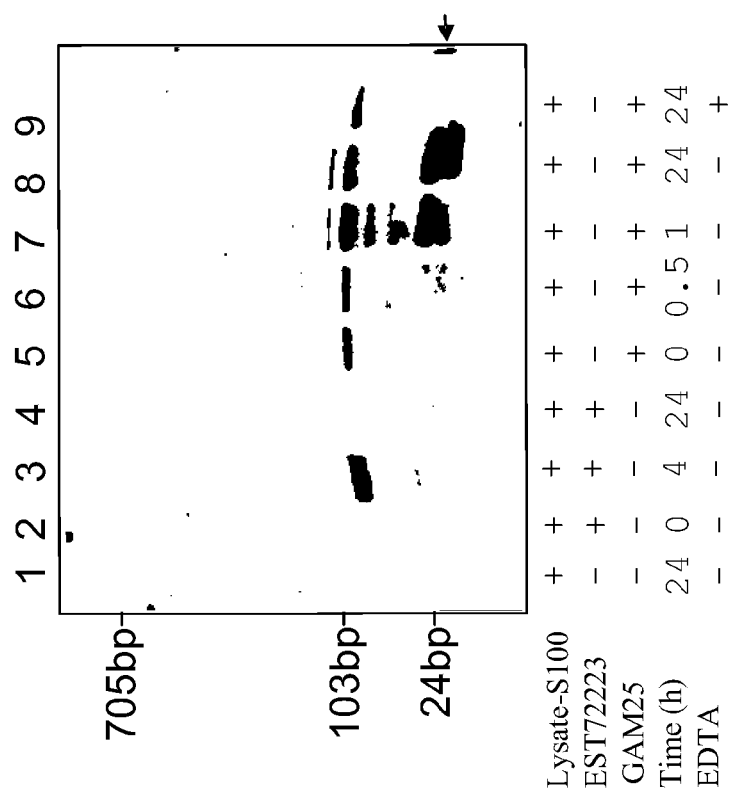
Figure 24C:
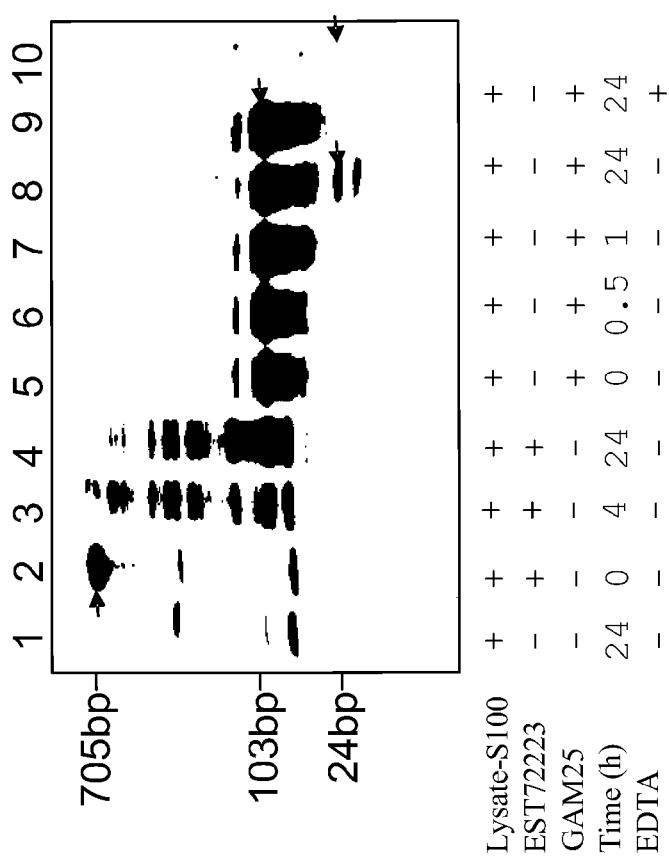

Reference is now made to FIGS. 24B, 24C and 24D that are pictures of laboratory results, which when taken together demonstrate laboratory confirmation of expression of the bioinformatically-detected novel oligonucleotide of FIG. 24A. In two parallel experiments, an enzymatically synthesized capped, EST72223 RNA transcript, was incubated with Hela S100 lysate for 0 minutes, 4 hours and 24 hours. RNA was subsequently harvested, run on a denaturing polyacrylamide gel, and reacted with either a 102 nt antisense MIR98 probe or a 145 nt antisenseGAM25 precursor transcript probe respectively. The Northern blot results of these experiments demonstrated processing of EST72223 RNA by Hela lysate (lanes 2-4, in FIGS. 24B and 24C), into ~80 bp and ~22 bp segments, which reacted with the MIR98 precursor probe (FIG. 24B), and into 100 bp and ~24 bp segments, which reacted with the GAM25 precursor probe (FIG. 24C). These results demonstrate the processing of EST72223 by Hela lysate into MIR98 precursor and GAM25 precursor. It is also appreciated from FIG. 24C (lane 1) that Hela lysate itself reacted with the GAM25 precursor probe, in a number of bands, including a ~100 bp band, indicating that GAM25-precursor is endogenously expressed in Hela cells. The presence of additional bands, higher than 100 bp in lanes 5-9 probably corresponds to the presence of nucleotide sequences in Hela lysate, which contain the GAM25 sequence.

In addition, in order to demonstrate the kinetics and specificity of the processing of MIR98 and GAM25 precursors into their respective mature, "diced" segments, transcripts of MIR98 and of the bioinformatically predicted GAM25 precursors were similarly incubated with Hela S100 lysate, for 0 minutes, 30 minutes, 1 hour and 24 hours, and for 24 hours with the addition of EDTA, added to inhibit Dicer activity, following which RNA was harvested, run on a polyacrylamide gel and reacted with MIR98 and GAM25 precursor probes. Capped transcripts were prepared for in-vitro RNA cleavage assays with T7 RNA polymerase, including a m7G (5')ppp(5')G-capping reaction using the T7-mMessage mMachine kit (Ambion). Purified PCR products were used as template for the reaction. These were amplified for each assay with specific primers containing a T7 promoter at the 5' end and a T3 RNA polymerase promoter at the 3' end. Capped RNA transcripts were incubated at 30 C in supplemented, dialysis concentrated, Hela S100 cytoplasmic extract (4 C Biotech, Seneffe, Belgium). The Hela S100 was supplemented by dialysis to a final concentration of 20 mM Hepes, 100 mM KCl, 2.5 mM MgCl2, 0.5 mM DTT, 20% glycerol and protease inhibitor cocktail tablets (Complete mini Roche Molecular Biochemicals). After addition of all components, final concentrations were 100 mM capped target RNA, 2 mM ATP, 0.2 mM GTP, 500 U/ml RNasin, 25 g/ml creatine kinase, 25 mM creatine phosphate, 2.5 mM DTT and 50% S100 extract. Proteinase K, used to enhance Dicer activity (Zhang et al., EMBO J. 21, 5875-5885 (2002)) was dissolved in 50 mM Tris-HCl pH 8, 5 mM CaCl2, and 50% glycerol, was added to a final concentration of 0.6 mg/ml. Cleavage reactions were stopped by the addition of 8 volumes of proteinase K buffer (200 Mm Tris-Hcl, pH 7.5, 25 mM EDTA, 300 mM NaCl, and 2% SDS) and incubated at 65 C for 15 min at different time points (0, 0.5, 1, 4, 24 h) and subjected to phenol/chloroform extraction. Pellets were dissolved in water and kept frozen. Samples were analyzed on a segmented half 6%, half 13% polyacrylamide 1×TBE-7M Urea gel.

The Northern blot results of these experiments demonstrated an accumulation of a ~22 bp segment which reacted with the MIR98 precursor probe, and of a ~24 bp segment which reacted with the GAM25 precursor probe, over time (lanes 5-8). Absence of these segments when incubated with EDTA (lane 9), which is known to inhibit Dicer enzyme (Zhang et al., 2002), supports the notion that the processing of MIR98 and GAM25 precursors into their "diced" segments is mediated by Dicer enzyme, found in Hela lysate. Other RNases do not utilize divalent cations and are thus not inhibited by EDTA. The molecular sizes of EST72223, MIR-98 and GAM25 and their corresponding precursors are indicated by arrows.

FIG. 24D present Northern blot results of same above experiments with GAM25 probe (24 nt). The results clearly demonstrated the accumulation of mature GAM25 oligonucleotide after 24 h.

To validate the identity of the band shown by the lower arrow in FIGS. 24C and 24D, a RNA band parallel to a marker of 24 base was excised from the gel and cloned as in Elbashir et al (2001) and sequenced. 90 clones corresponded to the sequence of mature GAM25 oligonucleotide, three corresponded to GAM25*(the opposite arm of the hairpin with a 1-3 nt 3' overhang) and two to the hairpin-loop.

GAM25 was also validated endogenously by sequencing from both sides from a HeLa YM100 total-RNA "ligation" libraries, utilizing hemispecific primers as described in FIG. 22.

Taken together, these results validate the presence and processing of a novel MIR-like oligonucleotide, GAM25, which was predicted bioinformatically. The processing of this novel GAM oligonucleotide product, by Hela lysate from EST72223, through its precursor, to its final form was similar to that observed for known miRNA oligonucleotide, MIR98.

Transcript products were 705 nt (EST72223), 102 nt (MIR98 precursor), 125 nt (GAM25 precursor) long. EST72223 was PCR amplified with T7-EST 72223 forward primer: 5'-TAATACGACTCACTATAGGCCCTTATTA-GAGGATTCTG CT-3' (SEQ ID NO: 10068178) and T3-EST72223 reverse primer:" AATTAACCCTCAC-TAAAGGTTTTTTTTTCCTGAGA CAGAGT-3' (SEQ ID NO: 10068179). MIR98 was PCR amplified using EST72223 as a template with T7MIR98 forward primer: 5'-TAATAC-GACTCACTATAGGGTGAGGTAGTAAG TTGTATTGTT-3' (SEQ ID NO: 10068180) and T3MIR98 reverse primer: 5'AATTAACCCTCACTAAAGGGAAAGTAGTAAGT TGTATAGTT-3' (SEQ ID NO: 10068181). GAM25 was PCR amplified using EST72223 as a template with GAM25 forward primer: 5' GAGGCAGGAGAATTGCTTGA-3' (SEQ ID NO: 10068182) and T3 EST72223 reverse primer: 5'-AATTAACCCTCACTAAAGGCCTGAGACA-GAGTCTTGCT C-3' (SEQ ID NO: 10068183).

It is appreciated that the data presented in FIGS. 24A, 24B, 24C and 24D when taken together validate the function of the bioinformatic oligonucleotide detection engine 100 of FIG. 9. FIG. 24A shows a novel GAM oligonucleotide bioinformatically-detected by the bioinformatic oligonucleotide detection engine 100, and FIGS. 24C and 24D show laboratory confirmation of the expression of this novel oligonucleotide. This is in accord with the engine training and validation methodology described hereinabove with reference to FIG. 9.

Figure 25A:
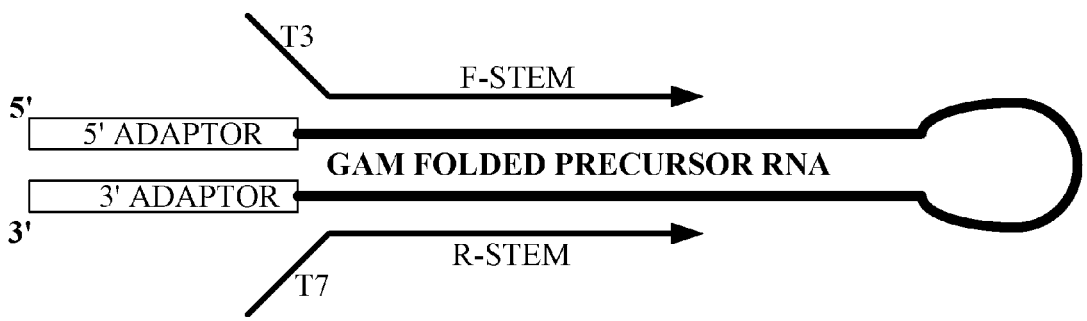
FIGS. 25A, 25B and 25C are schematic diagrams which, when taken together, represent methods of designing primers to identify specific hairpin oligonucleotides in accordance with a preferred embodiment of the present invention.
Figure 25B:
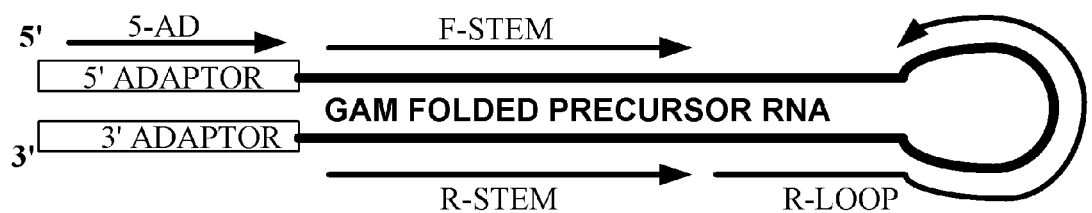
Figure 25C:
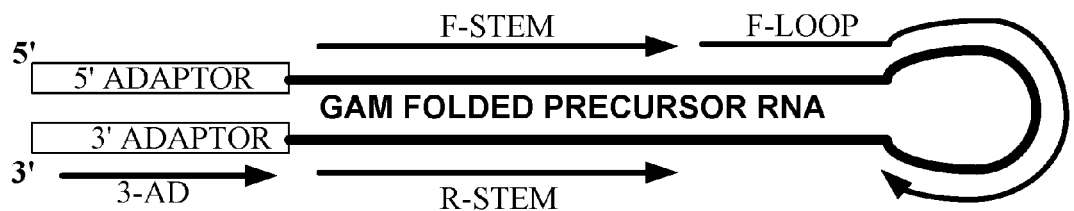

Reference is now made to FIGS. 25A-C, which schematically represent three methods that are employed to identify GAM FOLDED PRECURSOR RNA from libraries. Each method involves the design of specific primers for PCR amplification followed by sequencing. The libraries include hairpins as double-stranded DNA with two different adaptors ligated to their 5' and 3' ends.

Reference is now made to FIG. 25A, which depicts a first method that uses primers designed to the stems of the hairpins. Since the stem of the hairpins often has bulges, mismatches, as well as G-T pairing, which is less significant in DNA than is G-U pairing in the original RNA hairpin, the primer pairs were engineered to have the lowest possible match to the other strand of the stem. Thus, the F-Stem primer, derived from the 5' stem region of the hairpin, was chosen to have minimal match to the 3' stem region of the same hairpin. Similarly, the R-stem primer, derived from the 3' region of the hairpin (reverse complementary to its sequence), was chosen to have minimal match to the 5' stem region of the same hairpin. The F-Stem primer was extended in its 5' sequence with the T3 primer (5'-ATTAACCCTCAC-TAAAGGGA-3') and the R-Stem primer was extended in its 5' sequence with the T7 primer (5'-TAATACGACTCACTAT-AGGG). The extension is needed to obtain a large enough fragment for direct sequencing of the PCR product. Sequence data from the amplified hairpins is obtained in two ways. One way is the direct sequencing of the PCR products using the T3 primer that matches the extension of the F-Stem primer. Another way is the cloning of the PCR products into a plasmid, followed by PCR screening of individual bacterial colonies using a primer specific to the plasmid vector and either the R-Loop (FIG. 25B) or the F-Loop (FIG. 25C) primer. Positive PCR products are then sent for direct sequencing using the vector-specific primer.

Reference is now made to FIG. 25B, which depicts a second method in which R-Stem primer and R-Loop primers are used in a nested-PCR approach. First, PCR is performed with the R-Stem primer and the primer that matches the 5' adaptor sequence (5-ad primer). PCR products are then amplified in a second PCR using the R-Loop and 5-ad primers. As mentioned hereinabove, sequence data from the amplified hairpins is obtained in two ways. One way is the direct sequencing of the PCR products using the 5-ad primer. Another way is the cloning of the PCR products into a plasmid, followed by PCR screening of individual bacterial colonies using a primer specific to the plasmid vector and F-Stem primer. Positive PCR products are then sent for direct sequencing using the vector-specific primer. It should be noted that optionally an extended R-Loop primer is designed that includes a T7 sequence extension, as described hereinabove (FIG. 25A) for the R-Stem primer. This is important in the first sequencing option in cases where the PCR product is too short for sequencing.

Reference is now made to FIG. 25C, which depicts a third method, which is the exact reverse of the second method described hereinabove (FIG. 25B). F-Stem and F-Loop primers are used in a nested-PCR approach. First, PCR is performed with the F-Stem primer and the primer that matches the 3' adaptor sequence (3-ad primer). PCR products are then amplified in a second PCR using the F-Loop and 3-ad primers. As in the other two methods, sequence data from the amplified hairpins is obtained in two ways. One way is the direct sequencing of the PCR products using the F-Loop primer. Another way is the cloning of the PCR products into a plasmid, followed by PCR screening of individual bacterial colonies using a primer specific to the plasmid vector and R-Stem primer. Positive PCR products are then sent for direct sequencing using the vector-specific primer. It should be noted that optionally an extended F-Loop primer is designed that includes a T3 sequence extension, as described hereinabove (FIG. 25A) for the F-Stem primer. This is important in the first sequencing option in cases where the PCR product is too short for sequencing and also in order to enable the use of T3 primer.

In an embodiment of the present invention, the three methods mentioned hereinabove may be employed to validate the expression of GAM FOLDED PRECURSOR RNA.

Figure 26A:
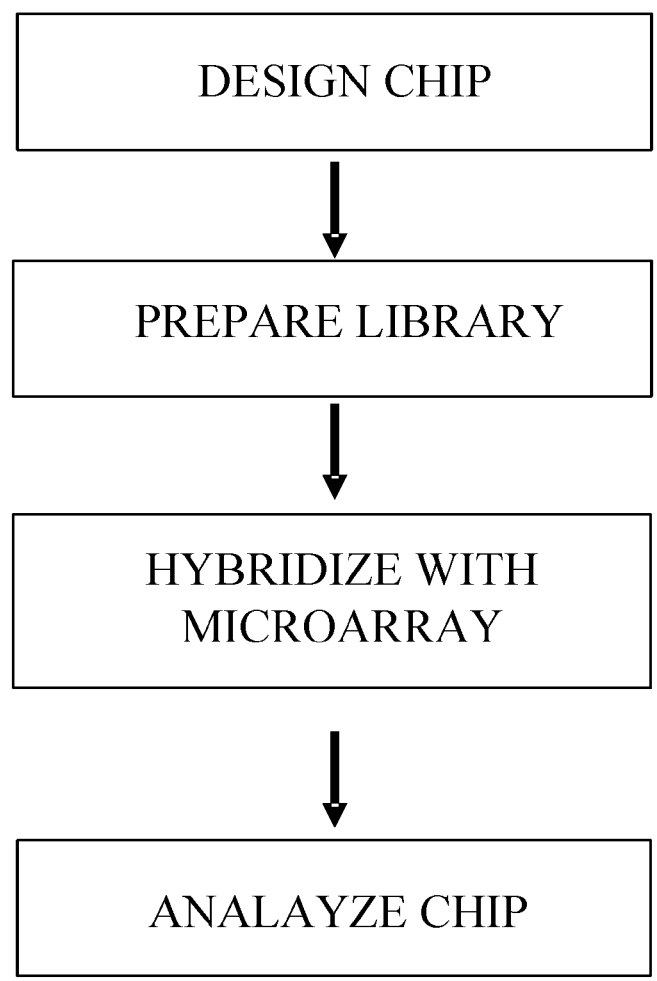
FIG. 26A is a simplified flowchart illustrating construction of a microarray constructed and operative to identify novel oligonucleotides of the present invention, in accordance with a preferred embodiment of the present invention.

Reference is now made to FIG. 26A, which is a flow chart with a general description of the design of the microarray to identify expression of published miRNA oligonucleotides, and of novel GAM oligonucleotides of the present invention.

Figure 26B:
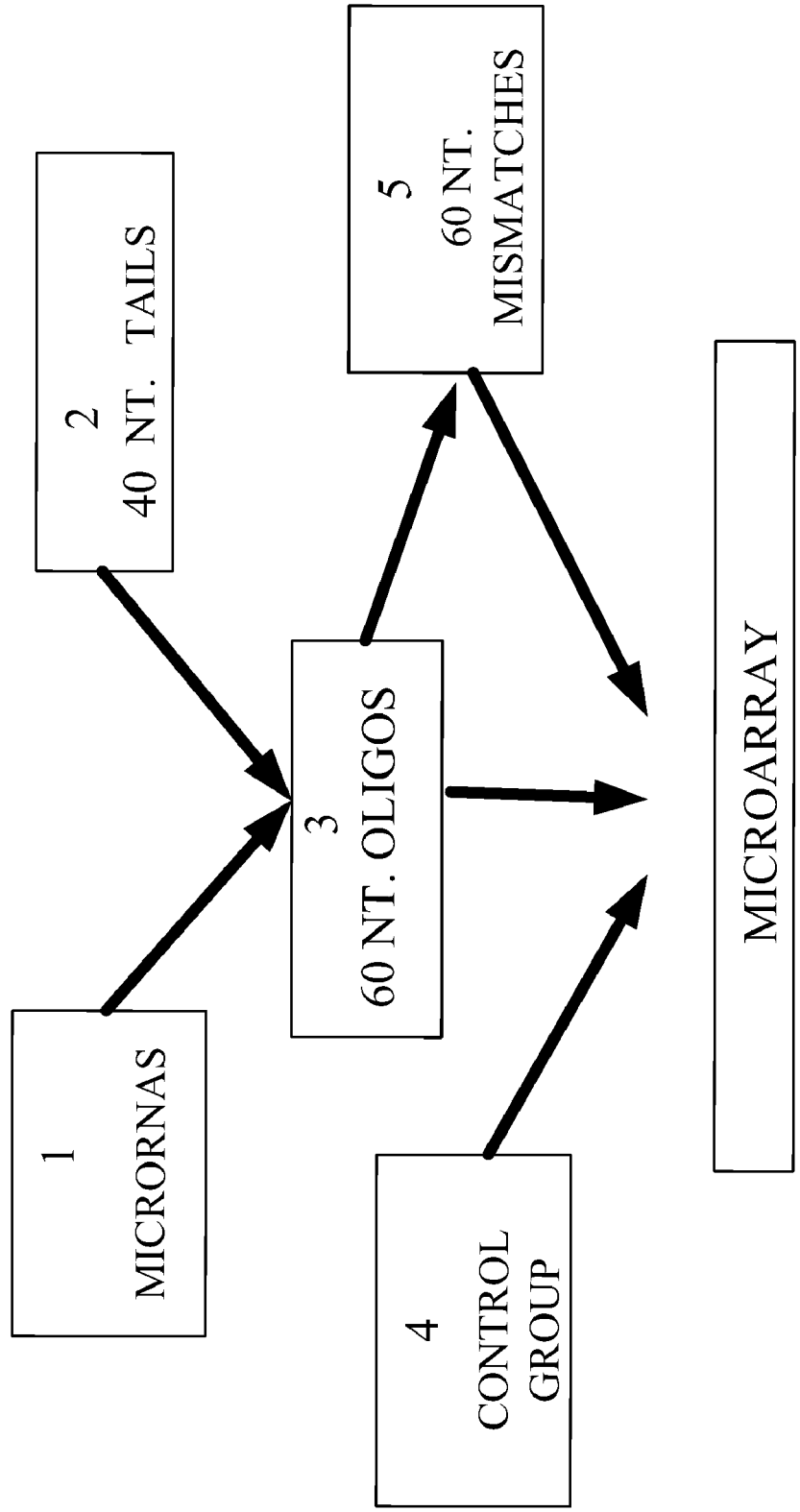
FIG. 26B is a simplified block diagram illustrating design of a microarray constructed and operative to identify novel oligonucleotides of the present invention, in accordance with a preferred embodiment of the present invention.
Figure 26C:
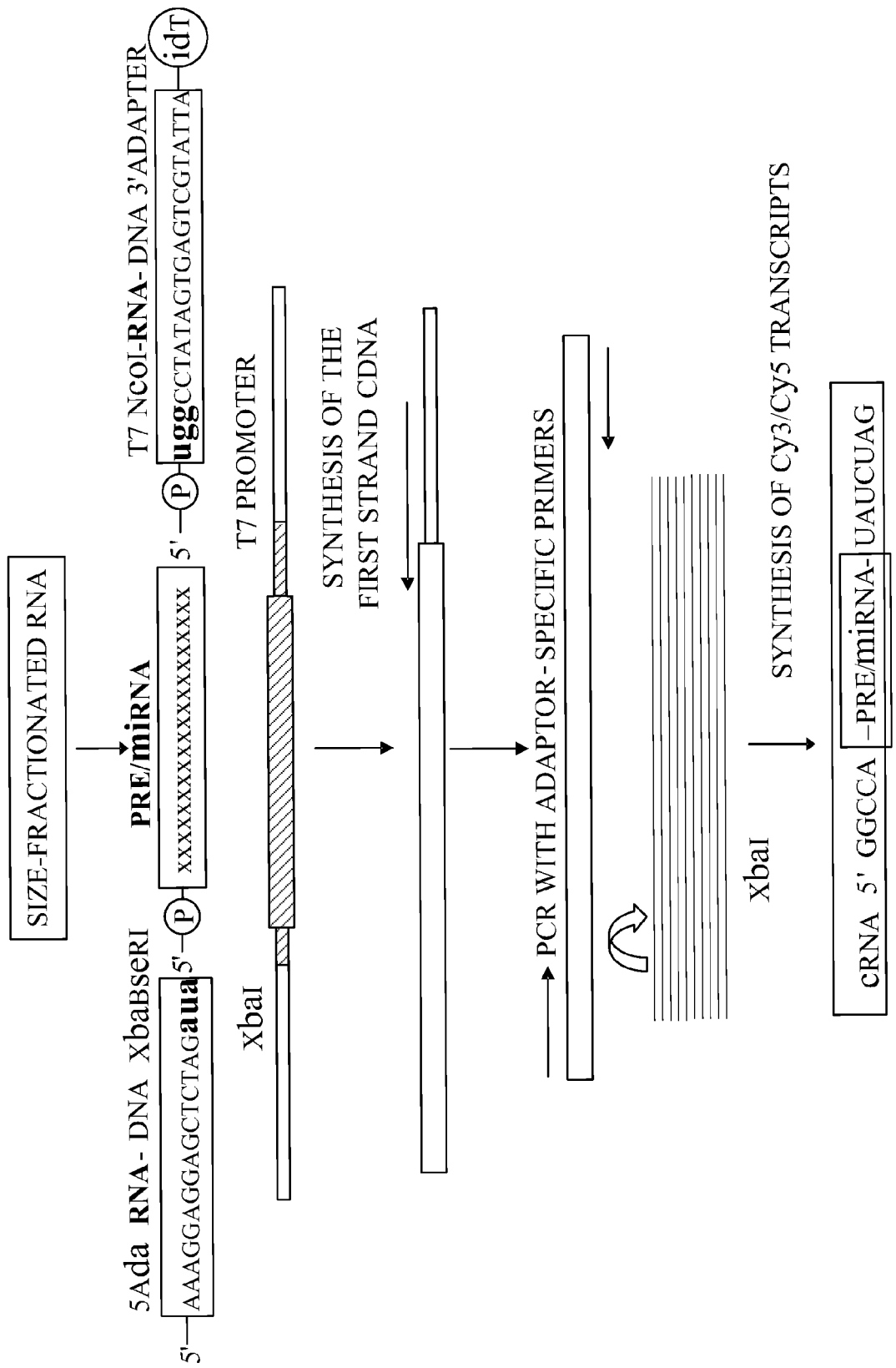
FIG. 26C is a flowchart illustrating a mode of preparation and amplification of a cDNA library in accordance with a preferred embodiment of the present invention.

A microarray that identifies miRNA oligonucleotides is designed (FIG. 26B). The DNA microarray is prepared by Agilent according to their SurePrint Procedure (reference describing their technology can be obtained from the Agilent website www.agilent.com). In this procedure, the oligonucleotide probes are synthesized on the glass surface. Other methods can also be used to prepare such microarray including the printing of pre-synthesized oligonucleotides on glass surface or using the photolithography method developed by Affymetrx (Lockhart D J et al., Nat Biotechnol. 14:1675-1680 (1996)). The 60-mer sequences from the design are synthesized on the DNA microarray. The oligonucleotides on the microarray, termed "probes" are of the exact sequence as the designed 60-mer sequences. Importantly, the 60-mer sequences and the probes are in the sense orientation with regards to the miRNA oligonucleotides. Next, a cDNA library is created from size-fractionated RNA, amplified, and converted back to RNA (FIG. 26C). The resulting RNA is termed "cRNA". The conversion to RNA is done using a T7 RNA polymerase promoter found on the 3' adaptor (FIG. 26C; T7 NcoI-RNA-DNA 3'Adaptor). Since the conversion to cRNA is done in the reverse direction compared to the orientation of the miRNA oligonucleotides, the cRNA is reverse complementary to the probes and is able to hybridize to it. This amplified RNA is hybridized with the microarray that identifies miRNA oligonucleotides, and the results are analyzed to indicate the relative level of miRNA oligonucleotides (and hairpins) that are present in the total RNA of the tissue (FIG. 27).

Reference is now made to FIG. 26B, which describes how the microarray to identify miRNA oligonucleotides is designed. miRNA oligonucleotide sequences or potential predicted miRNA oligonucleotides are generated by using known or predicted hairpins as input. Overlapping potential miRNA oligonucleotides are combined to form one larger sub-sequence within a hairpin.

To generate non-expressed sequences (tails), artificial sequences are generated that are 40 nts in length, which do not appear in the respective organism genome, do not have greater than 40% homology to sequences that appear in the genome, and with no 15-nucleotide window that has greater than 80% homology to sequences that appear in the genome.

To generate probe sequences, the most probable miRNA oligonucleotide sequences are placed at position 3 (from the 5' end) of the probe. Then, a tail sub-sequence to the miRNA oligonucleotide sequence was attached such that the combined sequence length will meet the required probe length (60 nts for Agilent microarrays).

The tails method provides better specificity compared to the triplet method. In the triplet method, it cannot be ascertained that the design sequence, and not an uncontrolled window from the triplet probe sequence, was responsible for hybridizing to the probe. Further the tails method allows the use of different lengths for the potential predicted miRNA oligonucleotide (of combined, overlapping miRNA oligonucleotides).

Hundreds of control probes were examined in order to ensure the specificity of the microarray. Negative controls contain probes which should have low intensity signal. For other control groups, the concentration of certain specific groups of interest in the library are monitored. Negative controls include tail sequences and non-hairpin sequences. Other controls include mRNA for coding genes, tRNA, and snoRNA.

For each probe that represents known or predicted miRNA oligonucleotides, additional mismatch probes were assigned in order to verify that the probe intensity is due to perfect match (or as close as possible to a perfect match) binding between the target miRNA oligonucleotide cRNA and its respective complementary sequence on the probe. Mismatches are generated by changing nucleotides in different positions on the probe with their respective complementary nucleotides (A< >T, G< >C, and vice versa). Mismatches in the tail region should not generate a significant change in the intensity of the probe signal, while mismatches in the miRNA oligonucleotide sequences should induce a drastic decrease in the probe intensity signal. Mismatches at various positions within the miRNA oligonucleotide sequence enable us to detect whether the binding of the probe is a result of perfect match or, alternatively, nearly perfect match binding.

Based on the above scheme, we designed a DNA microarray prepared by Agilent using their SurePrint technology. Table 11 is a detailed list of microarray chip probes Known miRNA Oligonucleotides:

The miRNA oligonucleotides and their respective precursor sequences are taken from Sanger Database to yield a total of 186 distinct miRNA oligonucleotide and precursor pairs. The following different probes are constructed:

1. Single miRNA Oligonucleotide Probes:

From each precursor, 26-mer containing the miRNA oligonucleotide were taken, then assigned 3 probes for each extended miRNA oligonucleotide sequence: 1. the 26-mer are at the 5' of the 60-mer probe, 2. the 26-mer are at the 3' of the 60-mer probe, 3. the 26-mer are in the middle of the 60-mer probe. Two different 34-mer subsequences from the design tails are attached to the 26-mer to accomplish 60-mer probe. For a subset of 32 of Single miRNA oligonucleotide probes, six additional mismatches mutations probes were designed: 4 block mismatches at 5' end of the miRNA oligonucleotide;

6 block mismatches at 3' end of the miRNA oligonucleotide;

1 mismatch at position 10 of the miRNA oligonucleotide;

2 mismatches at positions 8 and 17 of the miRNA oligonucleotide;

3 mismatches at positions 6, 12 and 18 of the miRNA oligonucleotide; and 6 mismatches at different positions out of the miRNA oligonucleotide.

2. Duplex miRNA Oligonucleotide Probes:

From each precursor, a 30-mer containing the miRNA oligonucleotide was taken, then duplicated to obtain 60-mer probe. For a subset of 32 of probes, three additional mismatch mutation probes were designed:

2 mismatches on the first miRNA oligonucleotide;

2 mismatches on the second miRNA oligonucleotide; and 2 mismatches on each of the miRNA oligonucleotides.

3. Triplet miRNA Oligonucleotide Probes:

Following Krichevsky's work (Krichevsky et al., RNA 9:1274-1281 (2003)), head to tail ~22-mer length miRNA oligonucleotide sequences were attached to obtain 60-mer probes containing up to three repeats of the same miRNA oligonucleotide sequence. For a subset of 32 probes, three additional mismatch mutation probes were designed:

2 mismatches on the first miRNA oligonucleotide;

2 mismatches on the second miRNA oligonucleotide; and 2 mismatches on each of the miRNA oligonucleotides.

4. Precursor with miRNA Oligonucleotide Probes:

For each precursor, 60-mer containing the miRNA oligonucleotide were taken.

5. Precursor without miRNA Oligonucleotide Probes:

For each precursor, a 60-mer containing no more then 16-mer of the miRNA oligonucleotide was taken. For a subset of 32 probes, additional mismatch probes containing four mismatches were designed.

Control Groups:

1. 100 60-mer sequences from representative ribosomal RNAs.

2. 85 60-mer sequences from representatives tRNAs.

3. 19 60-mer sequences from representative snoRNA.

4. 294 random 26-mer sequences from human genome not contained in published or predicted precursor sequences, placing them at the probe's 5' and attached 34-mer tail described above.

5. Negative Control: 182 different 60-mer probes contained different combinations of 10 nt-long sequences, in which each 10 nt-long sequence is very rare in the human genome, and the 60-mer combination is extremely rare.

Predicted GAM RNAs:

There are 8642 pairs of predicted GAM RNA and their respective precursors. From each precursor, a 26-mer containing the GAM RNA was placed at the 5' of the 60-mer probe and a 34-mer tail was attached to it. For each predicted probe, a mutation probes with 2 mismatches at positions 10 and 15 of the GAM RNA were added.

For a subset of 661 predicted precursors, up to 2 probes each containing one side of the precursor including any possible GAM RNA in it were added.

Microarray Analysis:

Based on known miRNA oligonucleotide probes, a preferred position of the miRNA oligonucleotide on the probe was evaluated, and hybridization conditions adjusted and the amount of cRNA to optimize microarray sensitivity and specificity ascertained. Negative controls are used to calculate background signal mean and standard deviation. Different probes of the same miRNA oligonucleotide are used to calculate signal standard deviation as a function of the signal.

For each probe, BG_Z_Score=(log(probe signal)−mean of log(negative control signal))/(log(negative control signal) standard deviation) were calculated.

For a probe with a reference probe with 2 mismatches on the miRNA oligonucleotide, MM_Z_Score MM_Z_Score= (log(perfect match signal)−log(reference mismatch signal))/ (standard deviation of log(signals) as the reference mismatch log(signal)) were calculated.

BG_Z_Score and MM_Z_Score are used to decide whether the probe is on and its reliability.

Reference is now made to FIG. 26C, which is a flowchart describing how the cDNA library was prepared from RNA and amplified. The general procedure was performed as described previously (Elbashir S M, Lendeckel W, Tuschl T. RNA interference is mediated by 21- and 22-nucleotide RNAs. Genes Dev. 2001 15:188-200) with several modifications which will be described hereinbelow.

First, the starting material is prepared. Instead of starting with standard total RNA, the total RNA was size-fractionated using an YM-100 Microcon column (Millipore Corporation, Billerica, Mass., USA) in the present protocol. Further, the present protocol uses human tissue or cell lines instead of a *Drosophila* in-vitro system as starting materials. Finally, 3 g of size-fractionated total RNA was used for the ligation of adaptor sequences.

Libraries used for microarray hybridization are listed hereinbelow: "A" library is composed of a mix of libraries from Total HeLa YM100 RNA and Nuclear HeLa YM100 RNA; "B" library is composed of a mix of libraries from Total HEK293 YM100 RNA and Nuclear HEK293 YM100 RNA; "C" library is composed of a mix of YM100 RNA libraries from Total PC3, Nuclear PC3 and from PC3 cells in which Dicer expression was transiently silenced by Dicer specific siRNA; "D" library is prepared from YM100 RNA from Total Human Brain (Ambion Cat#7962); "E" library is prepared from YM100 RNA from Total Human Liver (Ambion Cat#7960); "F" library is prepared from YM100 RNA from Total Human Thymus (Ambion Cat#7964); "G" library is prepared from YM100 RNA from Total Human Testis (Ambion Cat#7972); and "H" library is prepared from YM100 RNA from Total Human Placenta (Ambion Cat#7950).

Library letters appended by a numeral "1" or "2" are digested by XbaI (NEB); Library letters affixed by a numeral "3" are digested by Xba1 and SpeI (NEB); Library letters appended by a numeral "4" are digested by Xba1 and the transcribed cRNA is then size-fractionated by YM30, retaining the upper fraction consisting of 60 nts and longer; Library letters affixed by a numeral "5" are digested by Xba1 and the transcribed cRNA is then size-fractionated by YM30 retaining the flow-through fraction consequently concentrated with YM10 consisting of 30 nts-60 nts; Library letters affixed by a numeral "6" are digested by Xba1 and the DNA is fractionated on a 13% native acrylamide gel from 40-60 nt, electroeluted on a GeBaFlex Maxi column (GeBa Israel), and lyophilized; Library letters affixed by a numeral "7" are digested by Xba1 and the DNA is fractionated on a 13% native acrylamide gel from 80-160 nt, electroeluted and lyophilized.

Next, unique RNA-DNA hybrid adaptor sequences with a T7 promoter were designed. This step is also different than other protocols that create libraries for microarrays. Most protocols use complements to the polyA tails of mRNA with a T7 promoter to amplify only mRNA. However, in the present invention, adaptors are used to amplify all of the RNA within the size-fractionated starting material. The adaptor sequences are ligated to the size-fractionated RNA as described in FIG. 22, with subsequent gel-fractionation steps. The RNA is then converted to first strand cDNA using reverse transcription.

Next, the cDNA is amplified using PCR with adaptor-specific primers. At this point, there is the optional step of removing the tRNA, which is likely to be present because of its low molecular weight, but may add background noise in the present experiments. All tRNA contain the sequence ACC at their 3' end, and the adaptor contains GGT at its 5' end. This sequence together (GGTACC) is the target site for NcoI restriction digestion. Thus, adding the restriction enzyme NcoI either before or during PCR amplification will effectively prevent the exponential amplification of the cDNA sequences that are complements of the tRNAs.

The amplified DNA is restriction enzyme-digested with Xba1 (and, optionally, with Pst or SpeI) to remove the majority of the adaptor sequences that were initially added to the RNA. Using the first set of RNA-DNA hybrid adaptors listed below, the first two sets of primers listed below, and Xba1 restriction digest yields the following cRNA products: 5'GGCCA-pallindrome/microRNA-UAUCUAG. Using the second set of RNA-DNA hybrid adaptors listed below, the second set of primers listed below, and Xba1 and Pst restriction digest yields the following, smaller cRNA products: 5'GG-pallindrome/microRNA-C*.

Then, cDNA is transcribed to cRNA utilizing an RNA polymerase e.g. T7 dictated by the promoter incorporated in the adaptor. cRNA may be labeled in the course of transcription with aminoallyl or fluorescent nucleotides such as Cy3- or Cy5-UTP and CTP among other labels, and cRNA sequences thus transcribed and labeled are hybridized with the microarray.

The following RNA-DNA hybrid adaptors are included in the present invention:

Name: T7 NcoI-RNA-DNA 3'Adapter

Sequence: 5'(5phos)rUrGrGCCTATAGTGAGTCG-TATTA(3I nvdT)3' (SEQ ID NO: 10068186)

2. Name: 5Ada RNA-DNA XbaBseRI

Sequence: 5'AAAGGAGGAGCTCTAGrArUrA 3' (SEQ ID NO: 10068187) or optionally:

3. Name: 5Ada MC RNA-DNA PstAtaBser

Sequence: 5'CCTAGGAGGAGGACGTCTGrCrArG 3' (SEQ ID NO: 10068188)

4. Name: 3'Ada nT7 MC RNA-DNA

Sequence: 5'(5phos)rCrCrUATAGTGAGTCGTATTATCT (3InvdT)3' (SEQ ID NO: 10068189)

The following DNA primers are included in the present invention:

1. Name: T7 NcoI-RT-PCR primer

Sequence: 5'TAATACGACTCACTATAGGCCA 3' (SEQ ID NO: 10068308)

2. Name: T7NheI SpeI-RT-PCR primer

Sequence: 5'GCTAGCACTAGTTAATACGACTCACTAT-AGGC CA 3' (SEQ ID NO: 10068309)

3. Name: 5Ada XbaBseRI Fwd

Sequence: 5'AAAGGAGGAGCTCTAGATA 3' (SEQ ID NO: 10068192)

4. Name: Pst-5Ada XbaBseRI Fwd

Sequence: 5'TGACCTGCAGAAAGGAGGAGCTCTA-GATA 3' (SEQ ID NO: 10068193) or optionally:

5. Name: 5Ada MC PstAtaBser fwd

Sequence: 5'ATCCTAGGAGGAGGACGTCTGCAG 3' (SEQ ID NO: 10068306)

6. Name: RT nT7 MC XbaI

Sequence: 5'GCTCTAGGATAATACGACTCACTATAGG 3' (SEQ ID NO: 10068307)

Figure 27A:
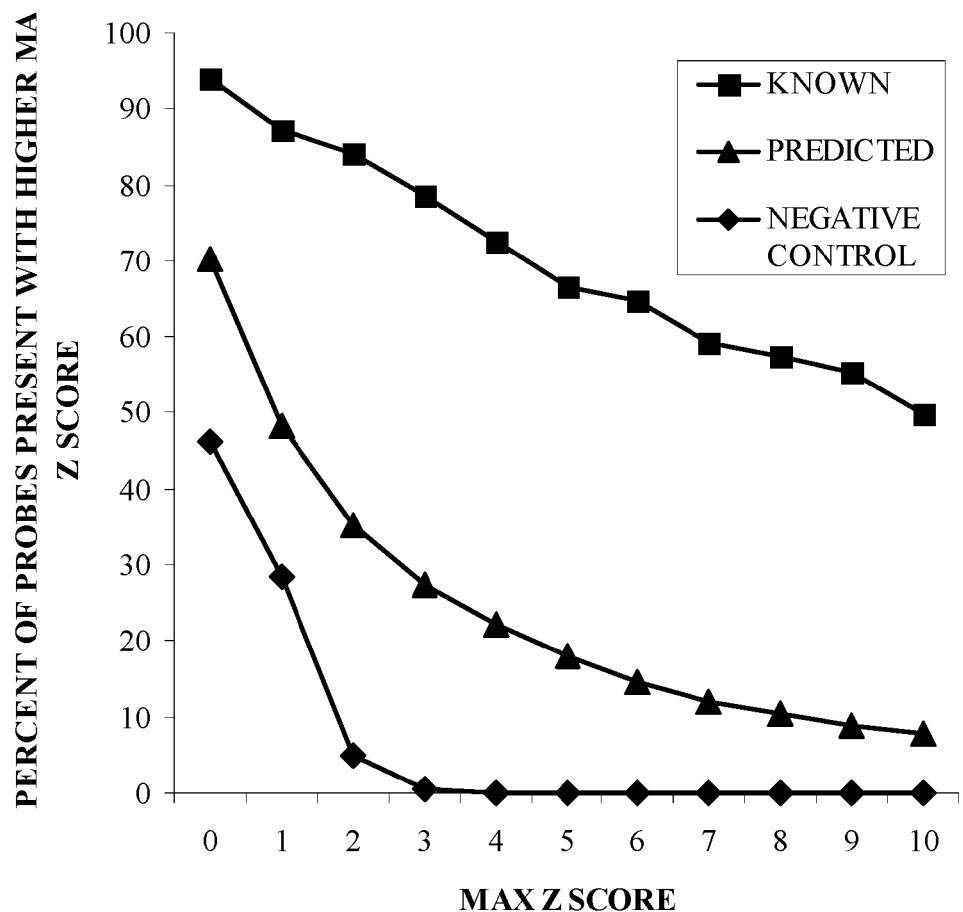
FIG. 27A is a line graph showing results of detection of known microRNA oligonucleotides and of novel GAM oligonucleotides, using a microarray constructed and operative in accordance with a preferred embodiment of the present invention.

Reference is now made to FIG. 27A, which demonstrates the detection of known miRNA oligonucleotides and of novel GAM oligonucleotides, using a microarray constructed and operative in accordance with a preferred embodiment of the present invention. Based on negative control probe intensity signals, we evaluated the background, non-specific, logarithmic intensity distribution, and extracted its mean, designated BG_mean, and standard deviation, designated BG_std. In order to normalize intensity signals between different microarray experiments, a Z score, which is a statistical measure that quantifies the distance (measured in standard deviations) that a data point is from the mean of a data set, was calculated for each probe with respect to the negative control using the following Z score formula: Z=(logarithm of probe signal BG_mean)/BG_std. We performed microarray experiments using RNA extracted from several different tissues and we calculated each probes maximum Z score. FIG. 27A shows the percentages of known, predicted and negative control groups that have a higher max Z score than a specified threshold as a function of max Z score threshold. The negative control group plot, included as a reference, considers probe with a max Z score greater then 4 as a reliable probe with meaningful signals. The sensitivity of our method was demonstrated by the detection of almost 80% of the known published miRNA oligonucleotides in at least one of the examined tissues. At a threshold of 4 for the max Z score, 28% of the predicted GAMs are present in at least one of the examined tissues.

Figure 27B:
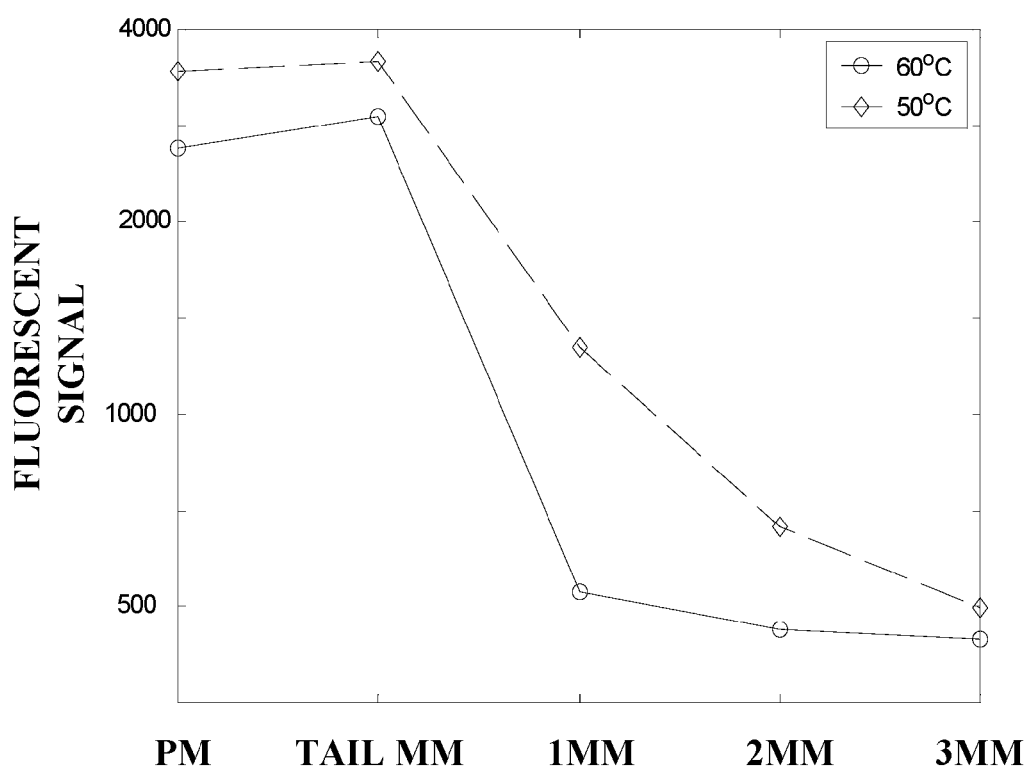
FIG. 27B is a line graph showing specificity of hybridization of a microarray constructed and operative in accordance with a preferred embodiment of the present invention.

Reference is now made to FIG. 27B, which is a line graph showing specificity of hybridization of a microarray constructed and operative in accordance with a preferred embodiment of the present invention and described hereinabove with reference to FIGS. 26A-26C. The average signal of known miRNA oligonucleotides in Library A2 is presented on a logarithmic scale as a function of the following probe types under two different hybridization conditions: 50 C and 60 C: perfect match (PM), six mismatches on the tail (TAIL MM), one mismatch on the miRNA oligonucleotide (1 mM), two separate mismatches on the miRNA oligonucleotide (2 mM), three separate mismatches on the miRNA oligonucleotide (3 mM). The relative equality of perfect match probes and probes with the same miRNA oligonucleotide but many mismatches over the tail attest to the independence between the tail and the probe signal. At a hybridization temperature of 60?C, one mismatch in the middle of the miRNA oligonucleotide is enough to dramatically reduce the probe signal. Conducting chip hybridization at 60 C ensures that a probe has a very high specificity.

It is appreciated that these results demonstrate the specificity of the microarray of the present invention in detecting expression of microRNA oligonucleotides.

Reference is now made to FIG. 27C, which is a summary table demonstrating detection of known microRNA oligonucleotides using a microarray constructed and operative in accordance with a preferred embodiment of the present invention and described hereinabove with reference to FIGS. 26A-26C.

Labeled cRNA from HeLa cells and Human Liver, Brain, Thymus, Placenta, and Testes was used for 6 different hybridizations. The table contains the quantitative values obtained for each miRNA oligonucleotide probe. For each miRNA oligonucleotide, the highest value (or values) is given in bolded font while lower values are given in regular font size. Results for MIR-124A, MIR-9 and MIR-122A are exactly as expected from previous studies. The References column contains the relevant references in the published literature for each case. In addition to these miRNA oligonucleotides, the table shows other known miRNA oligonucleotides that are expressed in a tissue-specific manner. We show that MIR-128A, MIR-129 and MIR-128B are highly enriched in Brain; MIR-194, MIR-148 and MIR-192 are highly enriched in Liver; mIR-96, MIR-150, MIR-205, MIR-182 and MIR-183 are highly enriched in Thy-mus; MIR-204, MIR-10B, MIR-154 and MIR134 are highly enriched in Testes; and MIR-122, MIR-210, MIR-221, MIR-141, MIR-23A, MIR-200 C and MIR-136 are highly enriched in Placenta. In most cases, low but significant levels are observed in the other tissues. However, in some cases, miRNA oligonucleotides are also expressed at relative high levels in an additional tissue.

It is appreciated that these results reproduce previously published studies of expression of known microRNA oligonucleotides. These results demonstrate the reliability of the microarray of the present invention in detecting expression of published microRNA oligonucleotides, and of novel GAM oligonucleotides of the present invention.

Reference is now made to

Figure 28A:
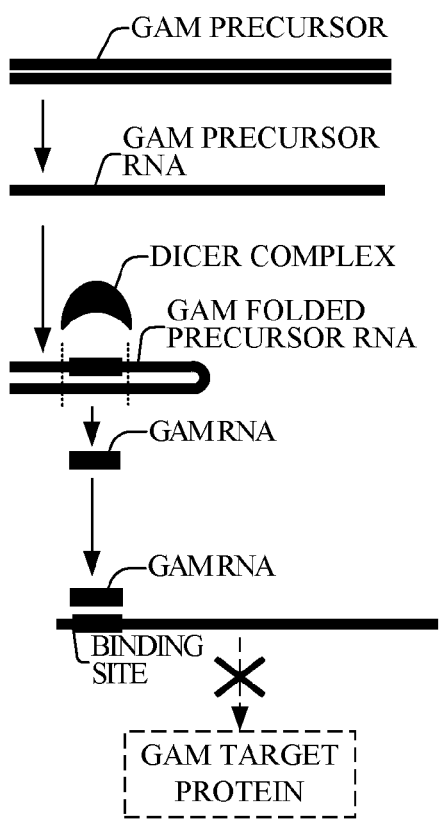

Reference is now made to FIGS. 28A-28D, simplified diagrams which when taken together illustrate different modes by which small molecules may be uses as therapeutic agents related to microRNA oligonucleotides. The present invention describes a novel approach whereby small molecules may be used to modulate activity of GAM oligonucleotides. This mode of therapy allows inter alia up regulation of a disease-related target gene of a novel GAM of the present invention, by lowering levels of the novel GAM which naturally inhibits expression of that target gene. Reference is now made to FIG. 28A. FIG. 28A which shows a normal GAM inhibiting translation of a target gene by binding of GAM RNA to a BINDING SITE found in an untranslated region of GAM TARGET RNA, as described hereinabove with reference to FIG. 8.

Figure 28B:
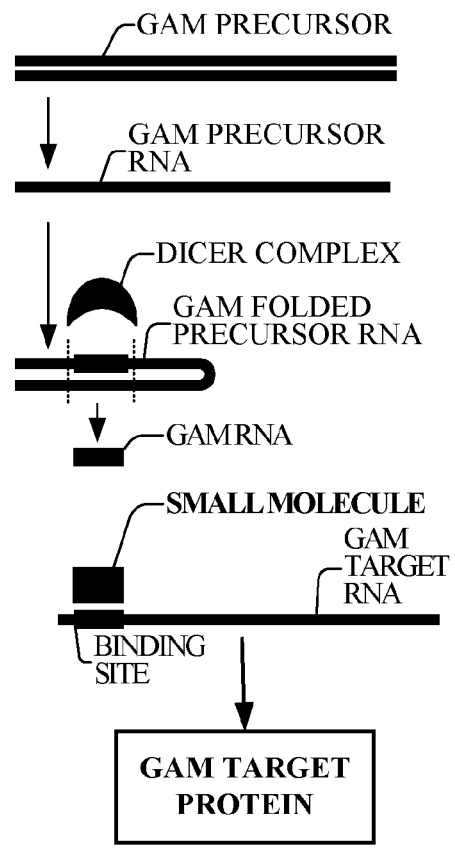

Reference is now made to FIG. 28B which shows an example of anti-GAM therapy, using a small molecule. SMALL MOLECULE is a small molecule that is capable of binding a binding site of GAM-RNA, such that this binding poses a competitive inhibition for the GAM RNA, which is therefore unable to bind the BINDING SITE, and therefore unable to repress translation of the TARGET PROTEIN. This causes de-facto an up-regulation of the target protein, since it counters the normal endogenous baseline inhibition of translation of GAM RNA on the target protein.

Reference is now made to FIG. 28C which shows an example of anti-GAM therapy, using a small molecule that binds the GAM RNA. In this case a small molecule is shown, which is capable of binding GAM-RNA itself, thereby inhibiting the translation inhibition activity of the GAM RNA. This too causes de-facto an up-regulation of the target protein, since it counters the normal endogenous baseline inhibition of translation of GAM RNA on the target protein.

It is appreciated that small molecule based anti-GAM therapy as illustrated hereinabove with reference to FIGS. 28A-28C is particularly useful with respect to disease states in which proteins associated with the disease are known to be under-expressed in association with a specific and are target genes of GAM oligonucleotides.

Reference is now made to FIG. 28D which shows an example of a GAM agonist therapy, using a small molecule. In this case a small molecule is shown which is capable of binding the binding site, but in which this binding causes an effect similar to the binding of the GAM RNA: it inhibits translation of the target protein.

Figure 29:
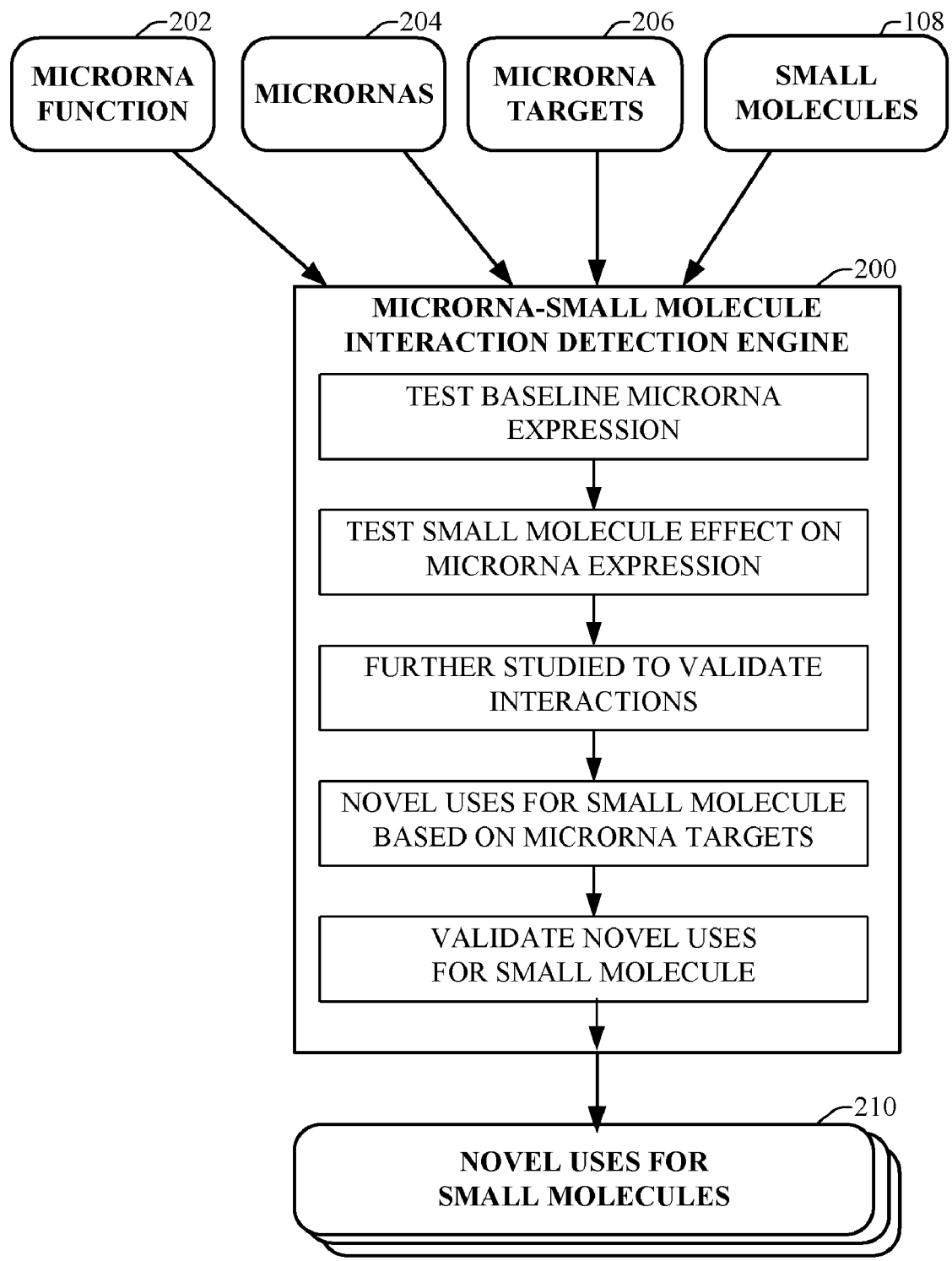
FIG. 29 is a block diagram of a microRNA-small molecule interaction detection engine constructed and operative in accordance with a preferred embodiment of the present invention.

Reference is now made to FIG. 29 which is a block diagram of a microRNA-small molecule interaction detection engine, constructed and operative in accordance with a preferred embodiment of the present invention.

A central element in the present invention is a microRNA small molecule interaction detection engine 200. The microRNA small molecule interaction detection engine 200 receives as input several types of data: one or more microRNAs 204, microRNA function 202 of the microRNAs 204, microRNA targets 206 of the microRNA 204, and one or more small molecules 108.

It is appreciated that the bioinformatic oligonucleotide detection engine 100 (FIG. 9) of the present invention is operative to detect novel microRNAs 204, and microRNA function 202 and microRNA targets 206 thereof, as described hereinabove with reference to FIGS. 1-27C. It is further appreciated that the present invention describes 122,764 novel microRNA like GAM oligonucleotides, described in Tables 1-14. These GAM oligonucleotides may serve as input for the microRNA small molecule interaction detection engine 200.

Table 15 lists 1,234 such known small molecules 108 that are used as pharmaceutical agents, and are FDA licensed, and therefore may be used as input for the microRNA small molecule interaction detection engine 200.

In a preferred embodiment of the present invention, the microRNA small molecule interaction detection engine 200 first tests baseline expression of one or more microRNAs in one or more tissues, in one or more clinical settings.

Next, the microRNA small molecule interaction detection engine 200 tests expression of microRNAs after introduction of a small molecule into the tissue tested, and therefrom assesses the effect of the small molecule on each of the microRNAs being tested.

Further biological and chemical studies are carried out in order to validate the suspected interaction between the small molecule and the microRNA.

The knowledge of the microRNA targets 206 of the microRNA and its microRNA function may then be used to evaluate potential novel uses for the small molecule, and estimate potential side-effects. The knowledge of the microRNA, and of its various targets allows an elaborate understanding of the web of activities and physiological actions that it may have, rather than blindly trying the small molecule in different clinical settings in order to see which will succeed, and which will produce side effects.

Finally, further biological studies are preferably performed to validate the novel uses of the small molecule.

The output of the microRNA small molecule interaction detection engine 200 is one or more novel uses for small molecules 210.

DETAILED DESCRIPTION OF TABLES

Table 1 comprises data relating the SEQ ID NO of oligonucleotides of the present invention to their corresponding GAM NAME, and contains the following fields: GAM SEQ-ID: GAM SEQ ID NO, as in the Sequence Listing; GAM NAME: Rosetta Genomics Ltd. nomenclature (see below); GAM RNA SEQUENCE: Sequence (5' to 3') of the mature, "diced" GAM RNA; GAM ORGANISM: identity of the organism encoding the GAM oligonucleotide; GAM POS: Dicer cut location (see below); and Table 2 comprises detailed textual description according to the description of FIG. 8 of each of a plurality of novel GAM oligonucleotides of the present invention, and contains the following fields: GAM NAME: Rosetta Genomics Ltd. nomenclature (see below); GAM ORGANISM: identity of the organism encoding the GAM oligonucleotide; PRE-CUR SEQ-ID:GAM precursor Seq-ID, as in the Sequence Listing; PRECURSOR SEQUENCE: Sequence (5' to 3') of the GAM precursor; GAM DESCRIPTION: Detailed description of GAM oligonucleotide with reference to FIG. 8; and Table 3 comprises data relating to the source and location of novel GAM oligonucleotides of the present invention, and contains the following fields: GAM NAME: Rosetta Genomics Ltd. nomenclature (see below); PRECUR SEQ-ID: GAM precursor SEQ ID NO, as in the Sequence Listing; GAM ORGANISM: identity of the organism encodes the GAM oligonucleotide; SOURCE: Chromosome encoding a human GAM oligonucleotide; STRAND: Orientation of the strand, "+" for the plus strand, "−" for the minus strand; SRC-START OFFSET: Start offset of GAM precursor sequence relative to the SOURCE; SRC-END OFFSET: End offset of GAM precursor sequence relative to the SOURCE; and Table 4 comprises data relating to GAM precursors of novel GAM oligonucleotides of the present invention, and contains the following fields: GAM NAME: Rosetta Genomics Ltd. nomenclature (see below); PRECUR SEQ-ID: GAM precursor Seq-ID, as in the Sequence Listing; GAM ORGANISM: identity of the organism encoding the GAM oligonucleotide; PRECURSOR-SEQUENCE: GAM precursor nucleotide sequence (5' to 3'); GAM FOLDED PRECURSOR RNA: Schematic representation of the GAM folded precursor, beginning 5' end (beginning of upper row) to 3' end (beginning of lower row), where the hairpin loop is positioned at the right part of the draw; and Table 5 comprises data relating to GAM oligonucleotides of the present invention, and contains the following fields: GAM NAME: Rosetta Genomics Ltd. nomenclature (see below); GAM ORGANISM: identity of the organism encoding the GAM oligonucleotide; GAM RNA SEQUENCE: Sequence (5' to 3') of the mature, "diced" GAM RNA; PRECUR SEQ-ID: GAM precursor Seq-ID, as in the Sequence Listing; GAM POS: Dicer cut location (see below); and Table 6 comprises data relating SEQ ID NO of the GAM target gene binding site sequence to TARGET gene name and target binding site sequence, and contains the following fields: TARGET BINDING SITE SEQ-ID: Target binding site SEQ ID NO, as in the Sequence Listing; TARGET ORGANISM: identity of organism encode the TARGET gene; TARGET: GAM target gene name; TARGET BINDING SITE SEQUENCE: Nucleotide sequence (5' to 3') of the target binding site; and Table 7 comprises data relating to target-genes and binding sites of GAM oligonucleotides of the present invention, and contains the following fields: GAM NAME: Rosetta Genomics Ltd. nomenclature (see below); GAM ORGANISM: identity of the organism encoding the GAM oligonucleotide; GAM RNA SEQUENCE: Sequence (5' to 3') of the mature, "diced" GAM RNA; TARGET: GAM target gene name; TARGET REF-ID: Target accession number (GenBank); TARGET ORGANISM: identity of organism encode the TARGET gene; UTR: Untranslated region of binding site/s (3' or 5'); TARGET BS-SEQ: Nucleotide sequence (5' to 3') of the target binding site; BINDING SITE-DRAW: Schematic representation of the binding site, upper row represent 5' to 3' sequence of the GAM, Lower row represent 3' to 5' Sequence of the target; GAM POS: Dicer cut location (see below); and Table 8 comprises data relating to functions and utilities of novel GAM oligonucleotides of the present invention, and contains the following fields: GAM NAME: Rosetta Genomics Ltd. nomenclature (see below); GAM RNA SEQUENCE: Sequence (5' to 3') of the mature, "diced" GAM RNA; GAM ORGANISM: identity of the organism encoding the GAM oligonucleotide; TARGET:GAM target gene name; TARGET ORGANISM: identity of organism encode the TARGET gene; GAM FUNCTION: Description of the GAM functions and utilities; GAM POS: Dicer cut location (see below); and Table 9 comprises references of GAMs target genes and contains the following fields: TARGET: Target gene name; TARGET ORGANISM: identity of organism encode the TARGET gene; REFERENCES: reference relating to the target gene; and Table 10 comprises data relating to novel GR (Genomic Record) polynucleotides of the present invention, and contains the following fields: GR NAME: Rosetta Genomics Ltd.nomenclature (see below); GR ORGANISM: identity of the organism encoding the GR polynucleotide; GR DESCRIPTION: Detailed description of a GR polynucleotide, with reference to FIG. 16; and Table 11 comprises data of all sequences printed on the chip experiment as described herein above with reference to FIG. 26 and include the following fields: PROBE SEQUENCE: the sequence that was printed on the chip PROBE TYPE: as described in details in FIG. 26 in chip design section and summarized as following: a. Known—published miR, Known_mis1—published miR with 1 mismatch mutation on miR sequence. Known_mis2—published miR with 2 mismatches mutation on miR sequenced. Known_mis3—published miR with 3 mismatches mutation on miR sequence, Known_mis4—published miR with 6 mismatches mutation not on miR sequence, Predicted—GAM-Rosetta Genomics Ltd. Mismatch—GAM-Rosetta Genomics Ltd. with 2 mismatches, Edges1—left half of GAM-Rosetta Genomics Ltd, Edges2—right half of GAM-Rosetta Genomics Ltd extended with its palindrom, Control1—negative control, Control2—random sequences, I. Control3—tRNA, m. Control4—snoRNA, Control5—mRNA, Control6—other; GAM RNA SEQ ID/MIR NAME: for GAM-Rosetta Genomics Ltd. Nomenclature (see below); GAM RNA SEQUENCE: Sequence (5' to 3') of the mature, "diced" GAM RNA; LIBRARY: the library name as defined in FIG. 26C; SIGNAL: Raw signal data for library; BACKGROUND Z-SCORE: Z score of probe signal with respect to background, negative control signals; MISMATCH Z-SCORE: Z-score of probe signal with respect to its mismatch probe signal;

Table 12 comprises data relating to diseases that GAM oligonucleotides are predicted to regulate the disease-associated genes. Each row is referred to a specific disease, and lists the GAM target genes related to the disease. The first row is a summary of ALL diseases containing in the present invention, thus listing ALL GAM target genes relating to theses diseases. The table contains the following fields: ROW#: index of the row number; DISEASE NAME: name of the disease; TARGET-GENES ASSOCIATED WITH DISEASE: list of GAM target genes that are associated with the specified disease; and Table 13 comprises data related to the GAM RNA SEQUENCEs included in the present invention that were validated by laboratory means. If the validated sequence appeared in more than one GAM precursor, the GAM RNA SEQ-ID indicated may be arbitrarily chosen. The VALIDATION METHOD indicates the type of validation performed on the sequence: "Mir Sequencing" refers to miRNA oligonucleotide sequences that were sequenced, as described hereinabove with reference to FIG. 22. Other validations are from microarray experiments as described hereinabove with reference to FIGS. 26A-C and 27A-C. The SIGNAL indicates a raw signal data; BACKGROUND Z-SCORE indicates a Z score of probe signal with respect to background, negative control signals; MISMATCH Z-SCORE: indicates a Z-score of probe signal with respect to its mismatch probe signal. The microarray validations are divided into two groups: a) "Chip strong" refers to miRNA oligonucleotide sequences whose intensity (SIGNAL) on the microarray "chip" was more than 6 standard deviations above the background intensity, and the differential to the corresponding mismatch intensity was more than 2 standard deviations, where in this case the standard deviation is of the intensity of identical probes and b) "Chip" refers to miRNA oligonucleotide sequences, whose intensity was more than 4 standard deviations above the background intensity.

Table 14 comprises sequence data of GAMs associated with different diseases. Each row refers to a specific disease, and lists the SEQ ID NOs of GAMs that target genes associated with that disease. The table contains the following fields: ROW#: index of the row number; DISEASE NAME: name of the disease; SEQ ID NOs OF GAMS ASSOCIATED WITH DISEASE: list of sequence listing IDs of GAMs targeting genes that are associated with the specified disease.

Table 15 comprises a list of pharmaceutical chemicals that have been licensed by the FDA for various indications, and their respective chemical formulas. The table contains the following fields: CHEMICAL NAME, and CHEMICAL FORMULA.

The following conventions and abbreviations are used in the tables: The nucleotide "U" is represented as "T" in the tables, and;

GAM NAME or GR NAME are names for nucleotide sequences of the present invention given by RosettaGenomics Ltd. nomenclature method. All GAMs/GRs are designated by GAMx/GRx where x is a unique ID.

GAM POS is a position of the GAM RNA on the GAM PRECURSOR RNA sequence. This position is the Dicer cut location: A indicates a probable Dicer cut location; B indicates an alternative Dicer cut location.

All human nucleotide sequences of the present invention as well as their chromosomal location and strand orientation are derived from sequence records of UCSC-hg16 version, which is based on NCBI, Build34 database (April, 2003).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07687616B1). An electronic copy of the "Sequence Listing" will also be available from the USPTO upon request and payment of the fee set forth in 37 CFR 1.19(b)(3).

The invention claimed is:

1. An isolated nucleic acid, wherein the nucleic acid consists of a sequence selected from the group consisting of:
   (a) SEQ ID NO: 7002375;
   (b) an RNA encoded by (a);
   (c) a sequence at least 80% identical to (a) or (b) wherein the sequence is 19-24 nucleotides; and
   (d) the complement of any one of (a)-(c), wherein the complement is identical in length to (a).

2. An isolated nucleic acid, wherein the nucleic acid consists of a sequence selected from the group consisting of:
   (a) SEQ ID NO:6816665;
   (b) an RNA encoded by (a);
   (c) the complement of (a) or (b), wherein the complement is identical in length to (a).

3. A vector comprising a human insert, wherein the human insert consists of the nucleic acid of claim 1 or claim 2, and wherein the vector comprises no insert other than the nucleic acid of claim 1 or claim 2.

4. A probe comprising a human insert, wherein the human insert consists of the nucleic acid of claim 1 or claim 2, and wherein the probe comprises no insert other than the nucleic acid of claim 1 or claim 2.

* * * * *